US008173769B2

(12) United States Patent
Li et al.

(10) Patent No.: US 8,173,769 B2
(45) Date of Patent: May 8, 2012

(54) TASTE RECEPTORS OF THE T1R FAMILY FROM DOMESTIC CAT

(75) Inventors: Xia Li, Havertown, PA (US); Weihua Li, Broomall, PA (US); Danielle R. Reed, Glenside, PA (US); Alexander A. Bachmanov, Philadelphia, PA (US); Joseph G. Brand, Wayne, PA (US)

(73) Assignee: Monell Chemical Senses Center, Philadelphia, PA (US)

( * ) Notice: Subject to any disclaimer, the term of this patent is extended or adjusted under 35 U.S.C. 154(b) by 163 days.

(21) Appl. No.: 12/406,334

(22) Filed: Mar. 18, 2009

(65) Prior Publication Data

US 2009/0205061 A1 Aug. 13, 2009

Related U.S. Application Data

(62) Division of application No. 10/591,360, filed as application No. PCT/US2004/015136 on May 13, 2004, now Pat. No. 7,527,944.

(60) Provisional application No. 60/482,992, filed on Jun. 27, 2003, provisional application No. 60/554,751, filed on Mar. 19, 2004.

(51) Int. Cl.
*C07K 14/705* (2006.01)
*C07K 19/00* (2006.01)

(52) U.S. Cl. ........................ 530/324; 530/350; 435/69.7

(58) Field of Classification Search ........................ None
See application file for complete search history.

(56) References Cited

FOREIGN PATENT DOCUMENTS

| | | | |
|---|---|---|---|
| GB | 2 364 058 | A | 1/2002 |
| WO | 91/09955 | A1 | 7/1991 |
| WO | 92/20808 | A1 | 11/1992 |
| WO | 94/12650 | A2 | 6/1994 |
| WO | 00/06592 | A1 | 2/2000 |
| WO | 00/06593 | A1 | 2/2000 |
| WO | 02/30981 | A1 | 4/2002 |
| WO | 02/064631 | A2 | 8/2002 |

OTHER PUBLICATIONS

Bachmanov, A. A. et al., "Positional Cloning of the Mouse Saccharin Preference (Sac) Locus," *Chem. Senses*, 2001, 26(7), 925-933.

Buck, L. & Axel, R., "A Novel Multigene Family May Encode Odorant Receptors: A Molecular Basis for Odor Recognition," *Cell*, 1991, 65, 175-187.

Hill, "Trends in Development of High-Throughput Screening Technologies for Rapid Discovery of Novel Drugs," *Cur. Opinion Drug Disc. Dev.*, 1998, 1, 92-97.

Hoon, M. A. et al., "Putative Mammalian Taste Receptors: A Class of Taste-Specific Gpcrs With Distinct Topographic Selectivity," *Cell*, 1999, 96(4), 541-551.

Kitagawa, M. et al., "Molecular Genetic Identification of a Candidate Receptor Gene for Sweet Taste," *Bioch. Bioph. Res. Comm.*, 2001, 283, 236-242.

Lehninger, *Biochemistry*, Second Edition, 1975, pp. 71-77, Worth Publishers, Inc., NY, NY.

Li, X. et al., "High-Resolution Genetic Mapping of the Saccharin Preference Locus (Sac) and the Putative Sweet Taste Receptor (T1R1) Gene (Gpr70) to Mouse Distal Chromosome 4," *Mamm. Genome*, 2001, 12(1), 13-16.

Li, X. et al., "Genetic, Physical, and Comparative Map of the Subtelomeric Region of Mouse Chromosome 4," *Mamm. Genome*, 2002, 13(1), 5-19.

Montmayeur, J. P. et al., "Receptors for Bitter and Sweet Taste," *Curr. Opin. Neurobiol.*, 2002, 12(4), 366-371.

Verma, I. M., "Gene Therapy," *Scientific American*, 1990, 263(5) 68-72, 81-84.

Zhao, G. Q. et al., "The Receptors for Mammalian Sweet and Umami Taste," *Cell*, 2003, 115(3), 255-266.

Li, X. et al., "Pseudogenization of a Sweet-Receptor Gene Accounts for Cats' Indifference toward Sugar," PLoS Genetics, Jul. 2005, 1(1), 0027-0035.

*Primary Examiner* — John Ulm
(74) *Attorney, Agent, or Firm* — Woodcock Washburn LLP

(57) ABSTRACT

The present invention relates to the discovery of several genes of the domestic cat (*Felis catus*) associated with taste perception. The invention provides, inter alia, the nucleotide sequence of the feline Tas1r1, Tas1r2, and Tas1r3 receptor genes, the amino acid sequences of the polypeptides encoded thereby, and antibodies to the polypeptides. The present invention also relates to methods for screening for compounds that modify the genes' function or activity, the compounds identified by such screens, and mimetics of the identified compounds. The invention further provides methods for modifying the taste preferences, ingestive responses, or general behavior of a mammal, such as a cat, by administering compounds that affect the function or activity of the gene or the polypeptide encoded thereby.

11 Claims, 25 Drawing Sheets

Figure 1A CLUSTAL W (1.82) multiple nucleotide sequence alignment of T1Rs

```
mouseTas1r2     ATGGGACCCCAGGCGAG------GACACTCCATTTGCTGTTTCTCCTGCTGCATGCTCTG 54
ratTas1r2       ATGGGTCCCCAGGCAAG------GACACTCTGCTTGCTGTCTCTCCTGCTGCATGTTCTG 54
humanTAS1R2     ATGGGGCCCAGGGCAAA------GACCATCTGCTCCCTGTTCTTCCTCCTATGGGTCCTG 54
catTas1r2       ATGGGACCCCGGGCCAG------GGAAGTCTGCTGCTTCATCATCCTGCCGCGGCTCCTG 54
mouseTas1r1     ATGCTTTTCTGGGCAGCTCACCTGCTGCTCAGCCTGCAGCTGGCCGTTGCTTACTGCTGG 60
ratTas1r1       ATGCTCTTCTGGGCTGCTCACCTGCTGCTCAGCCTGCAGTTGGTC------TACTGCTGG 54
humanTAS1R1     ATGCTGCTCTGCACGGCTCGCCTGGT---CGGCCTGCAGCTTCTCATTTCCTGCTGCTGG 57
catTas1r1       ATGTCACTCCCGGCGGCTCACCTGGT---CGGCCTGCAGCTCTCCCTCTCCTGCTGCTGG 57
mouseTas1r3     ATGCCAGCTTTGGCTAT---CATGGGTCTCA------------GCCTGGCTGCTTTCCTG 45
ratTas1r3       ATGCCGGGTTTGGCTAT---CTTGGGCCTCA------------GTCTGGCTGCTTTCCTG 45
catTas1r3       ATGCCCGGCCTCGCTCT---CCTGGGCCTCACGGCTCTCCTGGGCCTCACGGCTCTCTTG 57
humanTAS1R3     ATGCTGGGCCCTGCTGT---CCTGGGCCTCA------------GCCTCTGGGCTCTCCTG 45
                ***          *         *     *                             *

mouseTas1r2     C--CTAAGCCAGTCATGCTGGTAGGGAAC-TC---CGACTTTCACCTGGCTGGGGACTAC 108
ratTas1r2       C--CTAAGCCAGGCAAGCTGGTAGAGAAC-TC---TGACTTCCACCTGGCCGGGGACTAC 108
humanTAS1R2     G--CTGAGCC---------GGCTGAGAAC-TC---GGACTTCTACCTGCCTGGGGATTAC 99
catTas1r2       G--CTGAGCC---------GGCTGAGAAC-TC---AGACTTCTACTTGGCTGGGGATTAC 99
mouseTas1r1     G--CTTTCAGCTGCCAAAGGACAGAATCC-TCTCCAGGTTTCAGCCTCCCTGGGGACTTC 117
ratTas1r1       G--CTTTCAGCTGCCAAAGGACAGAGTCC-TCTCCAGGCTTCAGCCTTCCTGGGGACTTC 111
humanTAS1R1     G--CCTTTGCCTGCCATAGCACGGAGTCT-TCTCCTGACTTCACCCTCCCCGGAGATTAC 114
catTas1r1       G--CTCTCAGCTGCCACAGCACAGAGACG-TCTGCCGACTTCAGCCTCCCTGGGGATTAC 114
mouseTas1r3     GACCTTGGGATGGGGGCCTCTTTGTGTCTGTCACAGCAATTCAAGGCACAAGGGGACTAC 105
ratTas1r3       GACCTTGGGATGGGGTCCTCTTTGTGTCTGTCACAGCAATTCAAGGCACAAGGGGACTAT 105
catTas1r3       GACCACGGGGAGGGCGCAACGTCCTGCTTGTCACAGCAGCTCAGGATGCAGGGGGACTAT 117
humanTAS1R3     CACCCTGGGACGGGGGCCCCATTGTGCCTGTCACAGCAACTTAGGATGAAGGGGGACTAC 105
                   *                          **        *          ** ** *

mouseTas1r2     CTCCTGGGTGGCCTCTTTACCCTCCATGCCAACGTGAAGAGCGTCTCTCACCTCAGCTAC 168
ratTas1r2       CTCCTGGGTGGCCTCTTTACCCTCCATGCCAACGTGAAGAGCATCTCCCACCTCAGCTAC 168
humanTAS1R2     CTCCTGGGTGGCCTCTTCTCCCTCCATGCCAACATGAAGGGCATTGTTCACCTTAACTTC 159
catTas1r2       TTCCTCGGCGGCCTCTTCACCCTCCATGCCAACGTGAAGGGCATCGTCCACCTCAACCTC 159
mouseTas1r1     CTCCTGGCAGGCCTGTTCTCCCTCCATGCTGACTGTCTGCAGGTGAGACACA--GACCTC 175
ratTas1r1       CTCCTTGCAGGTCTGTTCTCCCTCCATGGTGACTGTCTGCAGGTGAGACACA--GACCTC 169
humanTAS1R1     CTCCTGGCAGGCCTGTTCCCTCTCCATTCTGGCTGTCTGCAGGTGAGGCACA--GACCCG 172
catTas1r1       CTCCTCGCAGGTCTGTTCCCTCTGCACTCTGACTGTCCGGGCGTGAGGCACC--GGCCCA 172
mouseTas1r3     ATACTGGGCGGCTATTTCCCCTGGGCTCAACCGAGGAGGCCACTCTCAACCAGAGAACA 165
ratTas1r3       ATATTGGGTGGACTATTTCCCCTGGGCACAACTGAGGAGGCCACTCTCAACCAGAGAACA 165
catTas1r3       GTGCTGGGTGGGCTCTTCCCTCTGGCTCTGCCGAGGGTACAGGTCTTGGCGACGGGCTG 177
humanTAS1R3     GTGCTGGGGGGGCTGTTCCCCCTGGGCGAGGCCGAGGAGGCTGGCCTCCGCAGCCGGACA 165
                 *  * *  ** ** **  * **                           *

mouseTas1r2     CTGCAGGTGCCCAAGTGCAATGAGTACAACA---TGAAGGTCTTGGGCTACAACCTCATG 225
ratTas1r2       CTGCAGGTGCCCAAGTGCAATGAGTTCACCA---TGAAGGTGTTGGGCTACAACCTCATG 225
humanTAS1R2     CTGCAGGTGCCCATGTGCAAGGAGTATGAAG---TGAAGGTGATAGGCTACAACCTCATG 216
catTas1r2       CTGCAGGTGCCCCAGTGCAAGGAGTATGAAA---TAAAGGTGTTGGGCTACGATCTCATG 216
mouseTas1r1     T----GGTGACAAGTTGTGACAGGTCTGACAGCTTCAACGGCCATGGCTATCACCTCTTC 231
ratTas1r1       T----GGTGACAAGTTGTGACAGGCCCGACAGCTTCAACGGCCATGGCTACCACCTCTTC 225
humanTAS1R1     A----GGTGACCCTGTGTGACAGGTCTTGTAGCTTCAATGAGCATGGCTACCACCTCTTC 228
catTas1r1       C----GGTGACCCTCTGTGACAGGCCCGACAGCTTCAACGGTCACGGCTACCACCTCTTC 228
mouseTas1r3     C------AACCCAACAGCATCCCGTGCAACAGGTTCTCACCCCTTGGTTTGTTCCTGGCC 219
ratTas1r3       C------AGCCCAACGGCATCCTATGTACCAGGTTCTCGCCCCTTGGTTTGTTCCTGGCC 219
catTas1r3       C------AGCCCAATGCCACCGTGTGCACCAGGTTCTCGTCTCTGGGCCTGCTCTGGGCG 231
humanTAS1R3     C------GGCCCAGCAGCCCTGTGTGCACCAGGTTCTCCTCAAACGGCCTGCTCTGGGCA 219
                          *                       *          **

mouseTas1r2     CAGGCCATGCGATTCGCCGTGGAGGAAATCAACAACTGTAGCTCTCTGCTGCCCGGCGTG 285
ratTas1r2       CAGGCCATGCGTTTCGCTGTGGAGGAGATCAACAACTGTAGCTCCCTGCTACCCGGCGTG 285
humanTAS1R2     CAGGCCATGCGCTTCGCGGTGGAGGAGATCAACAATGACAGCAGCCTGCTGCCTGGTGTG 276
catTas1r2       CAGGCCATGTGCTTTGCAGGGGAGGAGATCAATAGCCAGAGCAGCCTGCTGCCTGGCGTG 276
mouseTas1r1     CAAGCCATGCGGTTCACCGTTGAGGAGATAAACAACTCCACAGCTCTGCTTCCCAACATC 291
ratTas1r1       CAAGCCATGCGGTTCACTGTTGAGGAGATAAACAACTCCTCGGCCCTGCTTCCCAACATC 285
humanTAS1R1     CAGGCTATGCGGCTTGGGGTTGAGGAGATAAACAACTCCACGGCCCTGCTGCCCAACATC 288
catTas1r1       CAGGCCATGCGGTTTGGCATCGAGGAGATAAACAACTCCACGGCCCTCCTGCCGAACGTC 288
mouseTas1r3     ATGGCTATGAAGATGGCTGTGGAGGAGATCAACAATGGATCTGCCTTGCTCCCTGGGCTG 279
ratTas1r3       ATGGCTATGAAGATGGCTGTAGAGGAGATCAACAATGGATCTGCCTTGCTCCCTGGGCTG 279
catTas1r3       CTGGCCGTGAAGATGGCGGTGGAGGAGATCAACAACGGGTCGGCCCTGCTGCCCGGGCTG 291
humanTAS1R3     CTGGCCATGAAAATGGCCGTGGAGGAGATCAACAACAAGTCGGATCTGCTGCCCGGGCTG 279
                   **  **    *       ***** ** ** *            * ** **     *
```

Figure 1B

```
mouseTas1r2     CTGCTCGGCTACGAGATGGTGGATGTCTGCTACCTCTCC---AACAATATCCAGCCTGGG 342
ratTas1r2       CTGCTCGGCTACGAGATGGTGGATGTCTGTTACCTCTCC---AACAATATCCACCCTGGG 342
humanTAS1R2     CTGCTGGGCTATGAGATCGTGGATGTGTGCTACATCTCC---AACAATGTCCAGCCGGTG 333
catTas1r2       CTGCTGGGCTACAAAATGGTGGATGTCAGCTACATCTCC---AACAATGTCCAGCCCGTG 333
mouseTas1r1     ACCCTGGGGTATGAACTGTATGACGTGTGCTCAGAGTCT---TCCAATGTCTATGCCACC 348
ratTas1r1       ACCCTGGGGTATGAGCTGTACGACGTGTGCTCAGAATCT---GCCAATGTGTATGCCACC 342
humanTAS1R1     ACCCTGGGGTACCAGCTGTATGATGTGTGTTCTGACTCT---GCCAATGTGTATGCCACG 345
catTas1r1       ACCCTGGGATACCAGCTGTACGACGTGTGCTCGGAGTCT---GCCAACGTGTATGCCACA 345
mouseTas1r3     CGGCTGGGCTATGACCTATTTGACACATGCTCCGAGCCAGTGGTCACCATGAAATCCAGT 339
ratTas1r3       CGACTGGGCTATGACCTGTTTGACACATGCTCAGAGCCAGTGGTCACCATGAAGCCCAGC 339
catTas1r3       CACCTGGGCTATGACCTCTTTGACACGTGTTCAGAGCCCATGGTGGCCATGAAGCCCAGC 351
humanTAS1R3     CGCCTGGGCTACGACCTCTTTGATACGTGCTCGGAGCCTGTGGTGGCCATGAAGCCCAGC 339
                   ** ** **  *  *    **     * *      *           *  *  *

mouseTas1r2     CTCTACTTCCTGTC---ACAGATAGATGACTTCCTGCCCATCCTCAAAGACTACAGCCAG 399
ratTas1r2       CTCTACTTCCTGGC---ACAGGACGACGACCTCCTGCCCATCCTCAAAGACTACAGCCAG 399
humanTAS1R2     CTCTACTTCCTGGC---ACACGAGGACAACCTCCTTCCCATCCAAGAGGACTACAGTAAC 390
catTas1r2       CTCCACTTCCCGGC---AAAGGAGGACTGTTCCTTGCCCATCCAGGAGGACTACAGCCAC 390
mouseTas1r1     CTGAGGGTGCTCGCCCAGCAAGGGACAGGCCACCTAGAGATGCAGAGAGATCTTCGCAAC 408
ratTas1r1       CTGAGGGTGCTTGCCCTGCAAGGGCCCCGCCACATAGAGATACAGAAAGACCTTCGCAAC 402
humanTAS1R1     CTGAGAGTGCTCTCCCTGCCAGGGCAACACCACATAGAGCTCCAAGGAGACCTTCTCCAC 405
catTas1r1       CTAAACGTGCTCTCCCTGCTGGGGACACATCACGTAGAGATCCGAGCAGACCCTTCCCAC 405
mouseTas1r3     CTCATGTTCCTGGCCAAGGTGGGCAGTCAAAGCATTGCTGCCTACTGCAACTACACACAG 399
ratTas1r3       CTCATGTTCATGGCCAAGGTGGGAAGTCAAAGCATTGCTGCCTACTGCAACTACACACAG 399
catTas1r3       CTCGTGTTCATGGCCAAAGCAGGCAGCTGCAGCATTGCCGCCTACTGCAATTACACACAG 411
humanTAS1R3     CTCATGTTCCTGGCCAAGGCAGGCAGCCGCGACATCGCCGCCTACTGCAACTACACGCAG 399
                **     *     *                  * *              *        *

mouseTas1r2     TACAGGCCCCAAGTGGTGGCCGTCATTGGCCCAGACAACTCTGAGTCCGCCATCACCGTG 459
ratTas1r2       TACATGCCCCACGTGGTGGCTGTCATTGGCCCCGACAACTCTGAGTCCGCCATTACCGTG 459
humanTAS1R2     TACATTTCCCGTGTGGTGGCTGTCATTGGCCCTGACAACTCCGAGTCTGTCATGACTGTG 450
catTas1r2       TGTGTGCCCCGTGTGGTGGCTGTCATTGGTCCTGGCAACTCTGAGTCCACTGTGACTGTG 450
mouseTas1r1     CACTCCTCCAAGGTGGTGGCACTCATTGGGCCTGATAACACTGACCACGCTGTCACCACT 468
ratTas1r1       CACTCCTCCAAGGTGGTGGCCTTCATCGGGCCTGACAACACTGACCACGCTGTCACTACC 462
humanTAS1R1     TATTCCCCTACGGTGCTGGCAGTGATTGGGCCTGACAGCACCAACCGTGCTGCCACCACA 465
catTas1r1       TATTCGCCTGCCGCCCTGGCTGTCATTGGGCCTGACACCACCAACCACGCAGCCACCACT 465
mouseTas1r3     TACCAACCCCGTGTGCTGGCTGTCATCGGCCCCCACTCATCAGAGCTTGCCCTCATTACA 459
ratTas1r3       TACCAACCCCGTGTGCTGGCTGTCATTGGTCCCCACTCATCAGAGCTTGCCCTCATTACA 459
catTas1r3       TACCAGCCCCGCGTGCTGGCCGTCATCGGGCCCCACTCGTCTGAGCTCGCCCTCGTCACC 471
humanTAS1R3     TACCAGCCCCGTGTGCTGGCTGTCATCGGGCCCCACTCGTCAGAGCTCGCCATGGTCACC 459
                       *    *   ****  * ** ** **        *  *

mouseTas1r2     TCCAACATTCTCTCCTACTTCCTCGTGCCACAGGTCACATATAGCGCCATCACCGACAAG 519
ratTas1r2       TCCAACATTCTCTCTCATTTCCTCATCCCACAGATCACATACAGCGCCATCTCCGACAAG 519
humanTAS1R2     GCCAACTTCCTCTCCCTATTTCTCCTTCCACAGATCACCTACAGCGCCATCAGCGATGAG 510
catTas1r2       GCCCGCTTCCTCTCTCTCTTCCTCCTTCCACAGATCACCTACAGCGCCATCAGTGACGAG 510
mouseTas1r1     GCTGCCCTGCTGAGCCCTTTTCTGATGCCCCTGGTCAGCTATGAGGCGAGCAGCGTGATC 528
ratTas1r1       GCTGCCTTGCTGGGTCCTTTCCTGATGCCCCTGGTCAGCTATGAGGCAAGCAGCGTGGTA 522
humanTAS1R1     GCCGCCCTGCTGAGCCCTTTCCTGGTGCCCATGATTAGCTATGCGGCCAGCAGCGAGACG 525
catTas1r1       GCAGCCCTGCTGAGCCCCTTCCTGGTGCCCCTGATCAGCTACGAGGCCAGCAGCGTGACG 525
mouseTas1r3     GGCAAGTTCTTCAGCTTCTTCCTCATGCCACAGGTCAGCTATAGTGCCAGCATGGATCGG 519
ratTas1r3       GGCAAGTTCTTCAGCTTCTTCCTCATGCCACAGGTCAGCTATAGTGCCAGCATGGATCGG 519
catTas1r3       GGCAAGTTCTTCAGCTTCTTCCTTGTGCCTCAGGTCAGCTACGGCGCCAGCACCGACCGG 531
humanTAS1R3     GGCAAGTTCTTCAGCTTCTTCCTCATGCCCCAGGTCAGCTACGGTGCTAGCATGGAGCTG 519
                       *  *       ** **  * **   * * *  **    ** * *   *

mouseTas1r2     CTGCGAGACAAGCGGCGCTTCCCTGCCATGCTGCGCACTGTGCCCAGCGCCACCCACCAC 579
ratTas1r2       CTGCGGGACAAGCGGCACTTCCCTAGCATGCTACGCACAGTGCCCAGCGCCACCCACCAC 579
humanTAS1R2     CTGCGAGACAAGGTGCGCTTCCCGGCTTTGCTGCGTACCACACCCAGCGCCGACCACCAC 570
catTas1r2       CTACGGGACAAGCAGCGCTTCCCGGCCCTTCTGCCCACAGCGCCGGGCGCCGATCACCAG 570
mouseTas1r1     CTCAGTGGGAAGCGCAAGTTCCCGTCCTTCTTGCGCACCATCCCCAGCGATAAGTACCAG 588
ratTas1r1       CTCAGTGCCAAGCGCAAGTTCCCGTCTTTCCTTCGTACCGTCCCCAGTGACCGGCACCAG 582
humanTAS1R1     CTCAGCGTGAAGCGGCAGTATCCCTCTTTCCTGCGCACCATCCCCAATGACAAGTACCAG 585
catTas1r1       CTCGGAGTGAAGCGGCATTACCCCTCGTTTCTGCGCACCATCCCCAGCGACAAGCACCAG 585
mouseTas1r3     CTAAGTGACCGGGAAACGTTTCCATCCTTCTTCCGCACAGTGCCCAGTGACCGGGTGCAG 579
ratTas1r3       CTAAGTGACCGGGAAACATTTCCATCCTTCTTCCGCACAGTGCCCAGTGACCGGGTGCAG 579
catTas1r3       CTGAGCAACCGGGAGATCTTCCCGTCCTTCTTCCGCACGGTGCCCAGCGACCAGGTGCAG 591
humanTAS1R3     CTGAGCGCCCGGGAGACCTTCCCCTCCTTCTTCCGCACCGTGCCCAGCGACCGTGTGCAG 579
                **  *      *      *  **     *  * *  **    **    *        **
```

Figure 1C

```
mouseTas1r2     ATCGAGGCCATGGTGCAACTGATGGTTCACTTCCAGTGGAACTGGATCGTGGTGCTGGTG 639
ratTas1r2       ATCGAGGCCATGGTGCAGCTGATGGTTCACTTCCAATGGAACTGGATTGTGGTGCTGGTG 639
humanTAS1R2     GTCGAGGCCATGGTGCAGCTGATGCTGCACTTCCGCTGGAACTGGATCATTGTGCTGGTG 630
catTas1r2       ATCGAGGCCATGGTGCAGCTGATGTTGTACTTCCGCCGGAACTGGATCATCGCGCTGGTG 630
mouseTas1r1     GTGGAAGTCATAGTGCGGCTGCTGCAGAGCTTCGGCTGGGTCTGGATCTCGCTCGTTGGC 648
ratTas1r1       GTGGAGGTCATGGTGCAGCTGCTGCAGAGTTTTGGGTGGGTGTGGATCTCGCTCATTGGC 642
humanTAS1R1     GTGGAGACCATGGTGCTGCTGCTGCAGAAGTTCGGGTGGACCTGGATCTCTCTGGTTGGC 645
catTas1r1       GTGGAGGCCATGGTGCTGCTGCTGCAGAGCTTCGGGTGGGTCTGGATCTCGGTGGTCGGC 645
mouseTas1r3     CTGCAGGCAGTTGTGACTCTGTTGCAGAACTTCAGCTGGAACTGGGTGGCCGCCTTAGGG 639
ratTas1r3       CTGCAGGCCGTTGTGACACTGTTGCAGAATTTCAGCTGGAACTGGGTGGCTGCCTTAGGT 639
catTas1r3       GTGGCGGCCATGGTGGAGCTGCTGGAGGAGCTCGGCTGGAACTGGGTGGCGGCGGTGGGT 651
humanTAS1R3     CTGACGGCCGCCGCGGAGCTGCTGCAGGAGTTCGGCTGGAACTGGGTGGCCGCCCTGGGC 639
                 *          * *   *** **       *     **   *** *        * *

mouseTas1r2     AGCGATGACGATTATGGCCGAGAGAACAGCCACCTGCTGAGCCAGCGTCTGACCAACACT 699
ratTas1r2       AGCGACGACGATTACGGCCGCGAGAACAGCCACCTGTTGAGCCAGCGTCTGACCAAAACG 699
humanTAS1R2     AGCAGCGACACCTATGGCCGCGACAATGGCCAGCTGCTTGGCGAGCGCGTGGCCCGG--- 687
catTas1r2       AGCAGCGGCGACTGCGGCCGCGACGACAGCCAGCTGCTCAGCGATCGCCCGGCCGGC--- 687
mouseTas1r1     AGCTATGGTGACTACGGGCAGCTGGGCGTACAGGCGCTGGAGGAGC---TGGCCACTCCA 705
ratTas1r1       AGCTACGGTGATTACGGGCAGCTGGGTGTGCAGGCGCTGGAGGAGC---TGGCCGTGCCC 699
humanTAS1R1     AGCAGTGACGACTATGGGCAGCTAGGGGTGCAGGCACTGGAGAACC---AGGCCACTGGT 702
catTas1r1       AGCGACGGCGACTACGGGCAGCTGGGGGTGCAGGCGCTGGAGGAGC---AGGCCACCCAG 702
mouseTas1r3     AGTGATGATGACTATGGCCGGGAAGGTCTGAGCATCTTTTCTAGTC---TGGCCAATGCA 696
ratTas1r3       AGTGATGATGACTATGGCCGGGAAGGTCTGAGCATCTTTTCTGGTC---TGGCCAACTCA 696
catTas1r3       AGTGACGACGAGTATGGCCGGCAGGGCCTGAGCCTCTTCTCCGGCC---TGGCCAGCGCC 708
humanTAS1R3     AGCGACGACGAGTACGGCCGGCAGGGCCTGAGCATCTTCTCGGCCC---TGGCCGCGGCA 696
                **    *     *  ** *                  *       *    * **

mouseTas1r2     GGCGATATCTGCATTGCCTTCCAGGAGGTTCTGCCTGTACCAGAACCCAACCAGGCCGTG 759
ratTas1r2       AGCGACATCTGCATTGCCTTCCAGGAGGTTCTGCCCATACCTGAGTCCAGCCAGGTCATG 759
humanTAS1R2     CGCGACATCTGCATCGCCTTCCAGGAGACGCTGCCCACACTGCAGCCCAACCAGAACATG 747
catTas1r2       GGCGACACCTGCATCGCCTTCCGGGAGACGCTGCCCATGCCCCAGCCCAACCAGGCGGTG 747
mouseTas1r1     CGGGGCATCTGCGTCGCCTTCAAGGACGTGGTGCCTCT--CTCCGCCCAGGCGGGTGACC 763
ratTas1r1       CGGGGCATCTGCGTCGCCTTCAAGGACATCGTGCCTTT--CTCTGCCCGGGTGGGTGACC 757
humanTAS1R1     CAGGGGATCTGCATTGCTTTCAAGGACATCATGCCCTT--CTCTGCCCAGGTGGGCGATG 760
catTas1r1       CAGGGCATCTGCGTTGCCTTCAAGGACATCATCCCCTT--CTCTGCCCGGCCGGGCGACG 760
mouseTas1r3     CGAGGTATCTGCATCGCACATGAGGGCCTGGTGCCACAA-CATGACACTAGTGGCCAACA 755
ratTas1r3       CGAGGTATCTGCATTGCACACGAGGGCCTGGTGCCACAA-CATGACACTAGTGGCCAACA 755
catTas1r3       AGGGGCATCTGCATCGCGCATGAGGGCCTGGTGCCACTG-C-CGCCA--GGCAGCCTGCG 764
humanTAS1R3     CGCGGCATCTGCATCGCGCACGAGGGCCTGGTGCCGCTG-CCCCGTGCCGATGACTCGCG 755
                   *  *  **** *  **      **      * **

mouseTas1r2     AGGCCTGAGGAGCAGGACCAACTGGACAACATCCTGGACAAGCTGCGGC---GGACCTCG 816
ratTas1r2       AGGTCCGAGGAGCAGAGACAACTGGACAACATCCTGGACAAGCTGCGGC---GGACCTCG 816
humanTAS1R2     ACGTCAGAGGAGCGCCAGCGCCTGGTGACCATTGTGGACAAGCTGCAGC---AGAGCACA 804
catTas1r2       ACGCAGTGGGAGCGCCGGCGCCTGAAGGCCATCGTGGACGAGCAGCAGCGGCAGAGCTCT 807
mouseTas1r1     C------AAGGATGCAGCGCATGATGCTGCGTCTGGCTCGAGCCA-------GGACCACC 810
ratTas1r1       C------GAGGATGCAGAGCATGATGCAGCATCTGGCTCAGGCCA-------GGACCACC 804
humanTAS1R1     A------GAGGATGCAGTGCCTCATGCGCCACCTGGCCCAGGCCG-------GGGCCACC 807
catTas1r1       A------GAGGATGCAGAGCATCATGCACCACCTGGCCCGAGCGA-------GGACCACC 807
mouseTas1r3     G------TTGGGCAAGGTGCTGGATGTACTACGCCAAGTGAACCA--------AAGTAAA 801
ratTas1r3       A------TTGGGCAAGGTGGTGGATGTGCTACGCCAAGTGAACCA--------AAGCAAA 801
catTas1r3       G------CTGGGCGCCCTACAGGGCCTGCTGCGCCAGGTGAACCA--------GAGCAGC 810
humanTAS1R3     G------CTGGGGAAGGTGCAGGACGTCCTGCACCAGGTGAACCA--------GAGCAGC 801
                         *                                *

mouseTas1r2     GCGCGTGTGGTGGTGATATTCTCGCCAGAGCTGAGCCTGCACAACTTCTTCCGCGAGGTG 876
ratTas1r2       GCGCGCGTCGTGGTGGTGTTCTCGCCCGAGCTGAGCCTGTATAGCTTCTTTCACGAGGTG 876
humanTAS1R2     GCGCGCGTCGTGGTCGTGTTCTCGCCCGACCTGACCCTGTACCACTTCTTCAATGAGGTG 864
catTas1r2       CCGCGCGTCGTGGTCCTGCTGTCGCCAAAGCTGGTCCTGCACAACTTCTTCCGCGAGGTG 867
mouseTas1r1     GTG---GTCGTGGTCTT-CTCTAACCGGCACCTGGCTGGAGTG--TTCTTCAGGTCTGTG 864
ratTas1r1       GTG---GTTGTGGTCTT-CTCTAACCGGCACCTGGCTAGAGTG--TTCTTCAGGTCCGTG 858
humanTAS1R1     GTC---GTGGTTGTTTT-TTCCAGCCGGCAGTTGGCCAGGGTG--TTTTTCGAGTCCGTG 861
catTas1r1       GTT---GTGGTCGTTTT-CTCCAGCAGGCAGCTGGCCAGGGTG--TTCTTTGAGTCGGTG 861
mouseTas1r3     GTACAAGTGGTGGTGCTGTTTGCCTCTGCCCGTGCTGTCTACTCCCTTTTTAGTTACAGC 861
ratTas1r3       GTACAGGTGGTGGTGCTGTTTGCATCTGCCCGTGCTGTCTACTCCCTTTTTAGCTACAGC 861
catTas1r3       GTGCAGGTGGTGGTGCTGTTCTCCTCCGCCCACGCGGCCCGCACCCTCTTCAGCTACAGC 870
humanTAS1R3     GTGCAGGTGGTGCTGCTGTTCGCCTCCGTGCACGCCGCCCACGCCCTCTTCAACTACAGC 861
                *     ** **  *  *  *                          * **
```

Figure 1D

```
mouseTas1r2     CTGCGCTGGAACTTCACAGGCTTTGTGTGGATTGCCTCTGAGTCCTGGGCCATCGACCCT 936
ratTas1r2       CTCCGCTGGAACTTCACGGGTTTTGTGTGGATCGCCTCTGAGTCCTGGGCTATCGACCCA 936
humanTAS1R2     CTGCGCCAGAACTTCACGGGCGCCGTGTGGATCGCCTCCGAGTCCTGGGCCATCGACCCG 924
catTas1r2       CTCCGCCAGAACCTCACGGGCGTCGTGCGGATCGCCTCCGAGTCCTGGGCCATCGACCCG 927
mouseTas1r1     GTGCTGGCCAACCTGACTGGCAAAGTGTGGATCGCCTCCGAAGACTGGGCCATCT-CCAC 923
ratTas1r1       GTGCTGGCCAACCTGACTGGCAAAGTGTGGGTCGCCTCAGAAGACTGGGCCATCT-CCAC 917
humanTAS1R1     GTGCTGACCAACCTGACTGGCAAGGTGTGGGTCGCCTCAGAAGCCTGGGCCCTCT-CCAG 920
catTas1r1       GTGCTGGCCAACCTGACTGCCAAGGTGTGGATCGCCTCAGAAGACTGGGCCATCT-CTAG 920
mouseTas1r3     ATCCATCATGGCCTCTCACCCAAGGTATGGGTGGCCAGTGAGTCTTGGCTGACAT-CTGA 920
ratTas1r3       ATCCTTCATGACCTCTCACCCAAGGTATGGGTGGCCAGTGAGTCCTGGCTGACCT-CTGA 920
catTas1r3       ATCCGCTGCAAGCTCTCACCCAAGGTGTGGGTGGCCAGCGAGGCCTGGCTGACCT-CAGA 929
humanTAS1R3     ATCAGCAGCAGGCTCTCGCCCAAGGTGTGGGTGGCCAGCGAGGCCTGGCTGACCT-CTGA 920
                 *           *  *       **  ** * ***   **    ***        *

mouseTas1r2     GTTCTACACAAC-----CTCACAGAGCTGCGCCACACGGGCACTTTCCTGGGCGTCACCA 991
ratTas1r2       GTTCTGCATAAC-----CTCACGGAGCTGCGCCACACGGGTACTTTTCTGGGCGTCACCA 991
humanTAS1R2     GTCCTGCACAAC-----CTCACGGAGCTGGGCCACTTGGGCACCTTCCTGGGCATCACCA 979
catTas1r2       GTCCTGCACGACAGGCCCACGCGCTGCACAGCCTCCTGGGCTGCACCCAGACCAGCAGC- 986
mouseTas1r1     GTACATCACCAA----TGTGCCCGGGATCCAGGGCATTGGGACGGTGCTGGGGGTGGCCA 979
ratTas1r1       GTACATCACCAG----CGTGACTGGGATCCAAGGCATTGGGACGGTGCTCGGTGTGGCCG 973
humanTAS1R1     GCACATCACTGG----GGTGCCCGGGATCCAGCGCATTGGGATGGTGCTGGGCGTGGCCA 976
catTas1r1       ACACATCAGCAA----TGTGCCCGGGATCCAGGGCATTGGCACGGTGCTGGGTGTGGCCA 976
mouseTas1r3     CCTGGTCATGAC----ACTTCCCAATATTGCCCGTGTGGGCACTGTGCTTGGGTTTTTGC 976
ratTas1r3       CCTGGTCATGAC----ACTTCCCAATATTGCCCGTGTGGGCACTGTTCTTGGGTTTCTGC 976
catTas1r3       CCTGGTCATGAC----GCTGCCCGGCATGCCTGGGGTGGGCACCGTGCTGGGCTTCCTGC 985
humanTAS1R3     CCTGGTCATGGG----GCTGCCCGGCATGGCCCAGATGGGCACGGTGCTTGGCTTCCTCC 976
                      **             *                **       *

mouseTas1r2     TCCAGAGGGTGTCCATCCCTGGCTTCAGCCAGTTCCGAGTGCGCCAC---GACAAGCCAG 1048
ratTas1r2       TCCAGAGGGTGTCCATCCCTGGCTTCAGTCAGTTCCGAGTGCGCCGT---GACAAGCCAG 1048
humanTAS1R2     TCCAGAGCGTGCCCATCCCGGGCTTCAGTGAGTTCCGCGAGTGGGGC---CCACAGGCTG 1036
catTas1r2       TCCGGGTCGT--CTATCCCTGGCA--GGTGAGGCCC--------CAC---CCACGGA--G 1029
mouseTas1r1     TCCAGCAGAGACAAGTCCCTGGCCTGAAGGAGTTTGAAGAGTCCTAT---GTCCAGGCAG 1036
ratTas1r1       TCCAGCAGAGACAAGTCCCTGGGCTGAAGGAGTTTGAGGAGTCTTAT---GTCAGGGCTG 1030
humanTAS1R1     TCCAGAAGAGGGCTGTCCCTGGCCTGAAGGCGTTTGAAGAAGCCTAT---GCCCGGGCAG 1033
catTas1r1       TCCAGCAGAGGCTTGTCCCTGGCCTGAAGGAGTTTGAAGAGGCCTAT---GTCCAGGCAG 1033
mouseTas1r3     AGCGGGGTGCCCTACTGCCTGAATTTTCCCATTATGTGGAGACTCACCTTGCCCTGGCCG 1036
ratTas1r3       AGCGCGGTGCCCTACTGCCTGAATTTTCCCATTATGTGGAGACTCGCCTTGCCCTAGCTG 1036
catTas1r3       AGCAGGGCGCCCCGATGCCGGAGTTCCCATCCTACGTGCGGACCCGCCTGGCCCTGGCCG 1045
humanTAS1R3     AGAGGGGTGCCCAGCTGCACGAGTTCCCCCAGTACGTGAAGACGCACCTGGCCCTGGCCA 1036
                               * *  *

mouseTas1r2     AGTATCCCATGCCTA--ACGAGACCAGCCTG----------AGGACTACCTG-TAACCAG 1095
ratTas1r2       GGTATCCCGTGCCTA--ACACGACCAACCTG----------CGGACGACCTG-CAACCAG 1095
humanTAS1R2     GGCCGCCACCCCTCA--GCAGGACCAGCCAG----------AGCTATACCTG-CAACCAG 1083
catTas1r2       AGTCGGGGCCACACAC-GCAGGCGCCGCCAC----------AGCCCTGAGTGGTTGCCAT 1078
mouseTas1r1     TGATGGGTGCTCCCAGAACTTGCCCAGAGGG----------GTCCTGGTGCGGCACTAAC 1086
ratTas1r1       TAACAGCTGCTCCCAGCGCTTGCCCGGAGGG----------GTCCTGGTGCAGCACTAAC 1080
humanTAS1R1     ACAAGAAGGCCCCTAGGCCTTGCCACAAGGG----------CTCCTGGTGCAGCAGCAAT 1083
catTas1r1       ATAAGGGGGCCCCTGGGCCTTGCTCCAGGAC----------CTCCGAGTGCAGCAGCAAC 1083
mouseTas1r3     CTGACCCAGCATTCTGTGCCTCACTGAATGCGGA---GTTGGATCTGGAGGAACATGTGA 1093
ratTas1r3       CTGACCCAACATTCTGTGCCTCCCTGAAAGCTGA---GTTGGATCTGGAGGAGCGCGTGA 1093
catTas1r3       CTGACCCTGCCTTCTGCGCCTCGCTGGACGCTGAACAGCCAGGCCTGGAGGAGCACGTGG 1105
humanTAS1R3     CCGACCCGGCCTTCTGCTCTGCCCTGGGCGAGAGGGAGCAGGGTCTGGAGGAGGACGTGG 1096
                                  *

mouseTas1r2     ---GACTGTGACGCC--TGCATGAACATCACCGAGTCCTTTAACAACGTTCTCATGCTTT 1150
ratTas1r2       ---GACTGTGACGCC--TGCTTGAACACCACCAAGTCCTTCAACAACATCCTTATACTTT 1150
humanTAS1R2     ---GAGTGCGACAAC--TGCCTGAACGCCACCTTGTCCTTCAACACCATTCTCAGGCTCT 1138
catTas1r2       ---GGAGACCACTGCCCTGCTCTAGCGTCCCCCTCTCTGGCCGGGTCCTGGGCAAACTGG 1135
mouseTas1r1     C--AGCTGTGCAGGGAGTGTCACGCTTTCACGACATGGAACATGCCCGAGCTTGGAGCCT 1144
ratTas1r1       C--AGCTGTGCCGGGAGTGCCACACGTTCACGACTCGTAACATGCCCACGCTTGGAGCCT 1138
humanTAS1R1     C--AGCTCTGCAGAGAATGCCAAGCTTTCATGGCACACACGATGCCCAAGCTCAAAGCCT 1141
catTas1r1       C--AGCTCTGTAGAGAGTGTCGGGCTTTCACGGCAGAGCAGATGCCCACGCTCGGGGCAT 1141
mouseTas1r3     TGGGGCAACGCTGTCCACGGTGTGACGACATCATGCTGCAGAACCTATCATCTGGGCTGT 1153
ratTas1r3       TGGGGCCACGCTGTTCACAATGTGACTACATCATGCTACAGAACCTGTCATCTGGGCTGA 1153
catTas1r3       TGGGGCCACGCTGCCCCCAATGTGACCACGTCACGCTAGAGAACCTATCTGCGGGGCTG- 1164
humanTAS1R3     TGGGCCAGCGCTGCCCGCAGTGTGACTGCATCACGCTGCAGAACGTGAGCGCAGGGCTAA 1156
                                            *
```

Figure 1E

```
                                                                          Stop codon in cat T1R2 ▼
mouseTas1r2     CG---------------------GGGGAGCGTGTGGTCTACAGTGTGTACTCGGCCGTCT 1189
ratTas1r2       CG---------------------GGGGAGCGCGTGGTCTACAGCGTGTACTCGGCAGTTT 1189
humanTAS1R2     CT---------------------GGGGAGCGTGTCGTCTACAGCGTGTACTCTGCGGTCT 1177
catTas1r2       CG---------------------GGAGAGGCCAGGGGACGTACCCTGTCCCCAGACACAT 1174
mouseTas1r1     TC---------------------TCCATGAGCGCTGCCTACAATGTGTATGAGGCTGTGT 1183
ratTas1r1       TC---------------------TCCATGAGTGCCGCCTACAGAGTGTATGAGGCTGTGT 1177
humanTAS1R1     TC---------------------TCCATGAGTTCTGCCTACAACGCATACCGGGCTGTGT 1180
catTas1r1       TC---------------------TCCATGAGCTCTGCTTATAACGCCTACCGGGCAGTCT 1180
mouseTas1r3     TGCAGAACCTATCAGCTGGGCAATTGCACCACCAAATATTTGCAACCTATGCAGCTGTGT 1213
ratTas1r3       TGCAGAACCTATCAGCTGGGCAGTTGCACCACCAAATATTTGCAACCTATGCAGCTGTGT 1213
catTas1r3       -----------------------CTGCACCACCAGACCTTCGCTGCCTACGCGGCTGTGT 1201
humanTAS1R3     ------------------------ATCACCACCAGACGTTCTCTGTCTACGCAGCTGTGT 1192
                                                               *     *     *

                ▼▼
mouseTas1r2     ACGCGGTAGCCCACACCCTCCACAGACTCCTCCACTGCAACCAGGTCCGCTGCACCA--- 1246
ratTas1r2       ACGCGGTGGCCCATGCCCTCCACAGACTCCTCGGCTGTAACCGGGTCCGCTGCACCA--- 1246
humanTAS1R2     ATGCTGTGGCCCATGCCCTGCACAGCCTCCTCGGCTGTGACAAAAGCACCTGCACCA--- 1234
catTas1r2       AA---------------------------------------------------------- 1176
mouseTas1r1     ATGCTGTGGCCCACGGCCTCCACCAGCTCCTGGGATGTACCTCTGGGACCTGTGCCA--- 1240
ratTas1r1       ACGCTGTGGCCCACGGCCTCCACCAGCTCCTGGGATGTACTTCTGAGATCTGTTCCA--- 1234
humanTAS1R1     ATGCGGTGGCCCATGGCCTCCACCAGCTCCTGGGCTGTGCCTCTGGAGCTTGTTCCA--- 1237
catTas1r1       ACGCAGTGGCCCATGGCCTCCACCAGCTCCTGGGCTGTGCCTCTGGAGCCTGTTCCA--- 1237
mouseTas1r3     ACAGTGTGGCTCAAGCCCTTCACAACACCCTACAGTGCAATGTCTCACATTGCCACGTAT 1273
ratTas1r3       ACAGTGTGGCTCAGGCCCTTCACAACACCCTGCAGTGCAATGTCTCACATTGCCACACAT 1273
catTas1r3       ATGGCGTGGCCCAAGCCCTTCACAACACACTGCGCTGCAATGCCTCGGGCTGCCCCAGGC 1261
humanTAS1R3     ATAGCGTGGCCCAGGCCCTGCACAACACTCTTCAGTGCAACGCCTCAGGCTGCCCCGCGC 1252
                *

mouseTas1r2     AGCAAATCGTCTATCCATGGCAGCTACTCAGGGAGATCTGGCATGTCAACTTCACGCTCC 1306
ratTas1r2       AGCAAAAGGTCTACCCGTGGCAGCTACTCAGGGAGATCTGGCACGTCAACTTCACGCTCC 1306
humanTAS1R2     AGAGGGTGGTCTACCCCTGGCAGCTGCTTGAGGAGATCTGGAAGGTCAACTTCACTCTCC 1294
catTas1r2       ------------------------------------------------------------
mouseTas1r1     GAGGCCCAGTCTACCCCTGGCAGCTTCTTCAGCAGATCTACAAGGTGAATTTCCTTCTAC 1300
ratTas1r1       GAGGCCCAGTCTACCCCTGGCAGCTTCTTCAGCAGATCTACAAGGTGAATTTTCTTCTAC 1294
humanTAS1R1     GGGGCCGAGTCTACCCCTGGCAGCTTTTGGAGCAGATCCACAAGGTGCATTTCCTTCTAC 1297
catTas1r1       GGGACCGAGTCTACCCCTGGCAGCTTCTGGAGCAGATCCGCAAGGTGAATTTCCTCCTAC 1297
mouseTas1r3     CAGAACATGTTCTACCCTGGCAGCTCCTGGAGAACATGTACAATATGAGTTTCCATGCTC 1333
ratTas1r3       CAGAGCCTGTTCAACCCTGGCAGCTCCTGGAGAACATGTACAATATGAGTTTCCGTGCTC 1333
catTas1r3       GGGAGCCTGTGCGGCCCTGGCAGCTCCTAGAGAACATGTACAACGTGAGCTTCCGTGCTC 1321
humanTAS1R3     AGGACCCCGTGAAGCCCTGGCAGCTCCTGGAGAACATGTACAACCTGACCTTCCACGTGG 1312

mouseTas1r2     TGGGCAACCAGCTCTTCTTCGACGAACAAGGGGACATGCCGATGCTCCTGGACATCATCC 1366
ratTas1r2       TGGGTAACCGGCTCTTCTTTGACCAACAAGGGGACATGCCGATGCTCTTGGACATCATCC 1366
humanTAS1R2     TGGACCACCAAATCTTCTTCGACCCGCAAGGGGACGTGGCTCTGCACTTGGAGATTGTCC 1354
catTas1r2       ------------------------------------------------------------
mouseTas1r1     ATAAGAAGACTGTAGCATTCGATGACAAGGGGGACCCTCTAGGTTATTATGACATCATCG 1360
ratTas1r1       ATGAGAATACTGTGGCATTTGATGACAACGGGGACACTCTAGGTTACTACGACATCATCG 1354
humanTAS1R1     ACAAGGACACTGTGGCGTTTAATGACAACAGAGATCCCCTCAGTAGCTATAACATAATTG 1357
catTas1r1       ACAAGGACACCGTGAGGTTTAATGACAACGGGGACCCTCTCAGTGGCTACGACATAATTG 1357
mouseTas1r3     GAGACTTGACACTACAGTTTGATGCTGAAGGGAATGTAGACATGGAATATGACCTGAAGA 1393
ratTas1r3       GAGACTTGACACTGCAGTTTGATGCCAAAGGGAGTGTAGACATGGAATATGACCTGAAGA 1393
catTas1r3       GCGGCCTGGCACTGCAGTTCGACGCCAGCGGGAACGTGAACGTGGATTACGACCTGAAAC 1381
humanTAS1R3     GCGGGCTGCCGCTGCGGTTCGACAGCAGCGGAAACGTGGACATGGAGTACGACCTGAAGC 1372

mouseTas1r2     AGTGGCAATGGGGCCTGAGCCAGAACCCCTTCCAAAGCATCGCCTCCTACTCCCCCACCG 1426
ratTas1r2       AGTGGCAGTGGGACCTGAGCCAGAATCCCTTCCAAAGCATCGCCTCCTATTCTCCCACCA 1426
humanTAS1R2     AGTGGCAATGGGACCGGAGCCAGAATCCCTTCCAGAGCGTCGCCTCCTACTACCCCCTGC 1414
catTas1r2       ------------------------------------------------------------
mouseTas1r1     CCTGGGACTGGAATGGACCTGAATGGACCTTTGAGGTCATTGGTTCTGCCTCACTGTCTC 1420
ratTas1r1       CCTGGGACTGGAATGGACCTGAATGGACCTTTGAGATCATTGGCTCTGCCTCACTGTCTC 1414
humanTAS1R1     CCTGGGACTGGAATGGACCCAAGTGGACCTTCACGGTCCTCGGTTCCTCCACATGGTCTC 1417
catTas1r1       CCTGGGACTGGAGTGGCCCCAAGTGGAACTTCAGGGTCATTGGCTCCTCCATGTGGCCTC 1417
mouseTas1r3     TGTGGGTGTGGCAGAGCCCTACACCTGTATTACATACTGTGGGCACCTTCAACGGCACCC 1453
ratTas1r3       TGTGGGTGTGGCAGAGCCCTACACCTGTACTACATACTGTAGGCACCTTCAACGGCACCC 1453
catTas1r3       TGTGGGTGTGGCAGGACCCGACGCCCGAGCTGCGCACCGTAGGCACCTTCAAGGGCCGCC 1441
humanTAS1R3     TGTGGGTGTGGCAGGGCTCAGTGCCCAGGCTCCACGACGTGGGCAGGTTCAACGGCAGCC 1432
```

Figure 1F

```
mouseTas1r2    AGACGAGGCTGACCTACATTAG---CAATGTGTCCTGGTACACCCCCAACAACACGGTCC 1483
ratTas1r2      GCAAGAGGCTAACCTACATTAA---CAATGTGTCCTGGTACACCCCCAACAACACGGTCC 1483
humanTAS1R2    AGCGACAGCTGAAGAACATCCA---AGACATCTCCTGGCACACCGTCAACAACACGATCC 1471
catTas1r2      ------------------------------------------------------------
mouseTas1r1    CAGTTCATCTAGACATAAATAAGACAAAAATCCAGTGGCACGGGAAGAACAATCAGGTGC 1480
ratTas1r1      CAGTTCATCTGGACATAAATAAGACAAAAATCCAGTGGCACGGGAAGAACAATCAGGTGC 1474
humanTAS1R1    CAGTTCAGCTAAACATAAATGAGACCAAAATCCAGTGGCACGGAAAGGACAACCAGGTGC 1477
catTas1r1      CAGTTCAGCTGGACATAAATAAAACCAAAATCCGGTGGCACGGGAAGGACAACCAGGTGC 1477
mouseTas1r3    ---TTCAGCTGCAGCAGTCTAA------AATGTACTGGC------CAGGCAACCAGGTGC 1498
ratTas1r3      ---TTCAGCTGCAGCACTCGAA------AATGTATTGGC------CAGGCAACCAGGTGC 1498
catTas1r3      ---TGGAGCTCTGGCGCTCTCA------GATGTGCTGGCACACGCCGGGGAAGCAGCAGC 1492
humanTAS1R3    ---TCAGGACAGAGCGCCTGAA------GATCCGCTGGCACACGTCTGACAACCAGAAGC 1483

mouseTas1r2    CCATATCCATGTGTTCTAAGAGTTGCCAGCCTGGGCAAATGAAAAAACCCATAGGCCTCC 1543
ratTas1r2      CTGTCTCCATGTGTTCCAAGAGCTGCCAGCCAGGGCAAATGAAAAAGTCTGTGGCCTCC 1543
humanTAS1R2    CTATGTCCATGTGTTCCAAGAGGTGCCAGTCAGGGCAAAAGAAGAAGCCTGTGGGCATCC 1531
catTas1r2      ------------------------------------------------------------
mouseTas1r1    CTGTGTCAGTGTGTACCAGGGACTGTCTCGAAGGGCACCACAGGTTGGTCATGGGTTCCC 1540
ratTas1r1      CTGTGTCAGTGTGTACCACGGACTGTCTGGCAGGGCACCACAGGGTGGTTGTGGGTTCCC 1534
humanTAS1R1    CTAAGTCTGTGTGTTCCAGCGACTGTCTTGAAGGGCACCAGCGAGTGGTTACGGGTTTCC 1537
catTas1r1      CAAAGTCTGTGTGCTCCAGCGACTGCCTCGAAGGGCACCAGCGAGTGATTTCGGGTTTCT 1537
mouseTas1r3    CAGTCTCCCAGTGTTCCCGCCAGTGCAAAGATGGCCAGGTTCGCCGAGTAAAGGGCTTTC 1558
ratTas1r3      CAGTCTCCCAGTGCTCCCGGCAGTGCAAAGATGGCCAGGTGCGCAGAGTAAAGGGCTTTC 1558
catTas1r3      CCGTGTCCCAGTGCTCCCGGCAGTGCAAGGAAGGCCAGGTGCGCCGCGTGAAGGGCTTCC 1552
humanTAS1R3    CCGTGTCCCGGTGCTCGCGGCAGTGCCAGGAGGGCCAGGTGCGCCGGGTCAAGGGGTTCC 1543

mouseTas1r2    ACCCGTGCTGCTTCGAGTGTGTGGACTGTCCGCCGGGCACCTACCTCAACCGATCAGTAG 1603
ratTas1r2      ACCCTTGTTGCTTCGAGTGCTTGGATTGTATGCCAGGCACCTACCTCAACCGCTCAGCAG 1603
humanTAS1R2    ACGTCTGCTGCTTCGAGTGCATCGACTGCCTTCCCGGCACCTTCCTCAACCACACTGAAG 1591
catTas1r2      ------------------------------------------------------------
mouseTas1r1    ACCACTGCTGCTTCGAGTGCATGCCCTGTGAAGCTGGGACATTTCTCAAC---ACGAGTG 1597
ratTas1r1      ACCACTGCTGCTTTGAGTGTGTGCCCTGCGAAGCTGGGACCTTTCTCAAC---ATGAGTG 1591
humanTAS1R1    ATCACTGCTGCTTTGAGTGTGTGCCCTGTGGGGCTGGGACCTTCCTCAAC---AAGAGTG 1594
catTas1r1      ACCACTGTTGCTTTGAGTGTGTGCCCTGTGAGGCCGGGAGCTTCCTCAAC---AAGAGCG 1594
mouseTas1r3    ATTCCTGCTGCTATGACTGCGTGGACTGCAAGGCGGGCAGCTACCGGAAG---CATCCAG 1615
ratTas1r3      ATTCCTGCTGCTATGACTGTGTGGACTGCAAGGCAGGGAGCTACCGGAAG---CATCCAG 1615
catTas1r3      ACTCTTGCTGTTACAACTGCGTGGACTGCAAGGCGGGCAGTTATCAGCGC---AACCCAG 1609
humanTAS1R3    ACTCCTGCTGCTACGACTGTGTGGACTGCGAGGCGGGCAGCTACCGGCAA---AACCCAG 1600

mouseTas1r2    ATGAGTTTAACTGTCTGTCCTGCCCGGGTTCCATGTGGTCTTACAAGAACAACATCGCTT 1663
ratTas1r2      ATGAGTTTAACTGTCTGTCCTGCCCGGGTTCCATGTGGTCCTACAAGAACGACATCACTT 1663
humanTAS1R2    ATGAATATGAATGCCAGGCCTGCCCGAATAACGAGTGGTCCTACCAGAGTGAGACCTCCT 1651
catTas1r2      ------------------------------------------------------------
mouseTas1r1    AGCTTCACACCTGCCAGCCTTGTGGAACAGAAGAATGGGCCCCTGAGGGGAGCTCAGCCT 1657
ratTas1r1      AGCTTCACATCTGCCAGCCTTGTGGAACAGAAGAATGGGCACCCAAGGAGAGCACTACTT 1651
humanTAS1R1    ACCTCTACAGATGCCAGCCTTGTGGGAAAGAAGAGTGGGCACCTGAGGGAAGCCAGACCT 1654
catTas1r1      ACCTCCACAGCTGCCAGCCTTGTGGGAAAGAAAAGTGGGCACCCGCGGGAAGTGAAACCT 1654
mouseTas1r3    ATGACTTCACCTGTACTCCATGTAACCAGGACCAGTGGTCCCCAGAGAAAAGCACAGCCT 1675
ratTas1r3      ATGACTTCACCTGTACTCCATGTGGCAAGGATCAGTGGTCCCCAGAAAAAAGCACAACCT 1675
catTas1r3      ATGACCTCCTCTGCACCCAGTGTGACCAGGACCAGTGGTCCCCAGACCGGAGCACACGCT 1669
humanTAS1R3    ACGACATCGCCTGCACCTTTTGTGGCCAGGATGAGTGGTCCCCGGAGCGAAGCACACGCT 1660

mouseTas1r2    GCTTCAAGCGGCGGCTGGCCTTCCTGGAGTGGCACCAAGTGCCCACTATCGTGGTGACCA 1723
ratTas1r2      GCTTCCAGCGGCGGCCTACCTTCCTGGAGTGGCACGAAGTGCCCACCATCGTGGTGGCCA 1723
humanTAS1R2    GCTTCAAGCGGCAGCTGGTCTTCCTGGAATGGCATGAGGCACCCACCATCGCTGTGGCCC 1711
catTas1r2      ------------------------------------------------------------
mouseTas1r1    GCTTCTCACGCACCGTGGAGTTCTTGGGGTGGCATGAACCCATCTCTTTGGTGCTATTAG 1717
ratTas1r1      GCTTCCCACGCACGGTGGAGTTCTTGGCTTGGCATGAACCCATCTCTTTGGTGCTAATAG 1711
humanTAS1R1    GCTTCCCGCGCACTGTGGTGTTTTTGGCTTTGCGTGAGCACACCTCTTGGGTGCTGCTGG 1714
catTas1r1      GCTTTCCACGCACCGTGGTGTTTTTGACTTGGCACGAGACCATCTCTTGGGTGCTGCTGG 1714
mouseTas1r3    GCTTACCTCGCAGGCCCAAGTTTCTGGCTTGGGGGGAGCCAGTTGTGCTGTCACTCCTCC 1735
ratTas1r3      GCTTACCTCGCAGGCCCAAGTTTCTGGCTTGGGGGGAGCCAGCTGTGCTGTCACTTCTCC 1735
catTas1r3      GCTTCGCCCGCAAGCCCATGTTCCTGGCATGGGGGGAGCCAGCTGTGCTGCTACTGCTCG 1729
humanTAS1R3    GCTTCCGCCGCAGGTCTCGGTTCCTGGCATGGGGCGAGCCGGCTGTGCTGCTGCTGCTCC 1720
```

Figure 1G

```
mouseTas1r2     TCCTGGCCGCCCTGGGCTTCATCAGTACGCTGGCCATTCTGCTCATCTTCTGGAGACATT 1783
ratTas1r2       TACTGGCTGCCCTGGGCTTCTTCAGTACACTGGCCATTCTTTTCATCTTCTGGAGACATT 1783
humanTAS1R2     TGCTGGCCGCCCTGGGCTTCCTCAGCACCCTGGCCATCCTGGTGATATTCTGGAGGCACT 1771
catTas1r2       ------------------------------------------------------------
mouseTas1r1     CAGCTAACACGCTATTGCTGCTGCTGCTGATTGGGACTGCTGGCCTGTTTGCCTGGCGTC 1777
ratTas1r1       CAGCTAACACGCTATTGCTGCTGCTGCTGGTTGGGACTGCTGGCCTGTTTGCCTGGCATT 1771
humanTAS1R1     CAGCTAACACGCTGCTGCTGCTGCTGCTGCTTGGGACTGCTGGCCTGTTTGCCTGGCACC 1774
catTas1r1       CAGCTAATACGTTGCTGCTGCTGCTGGTGACTGGGACTGCTGGCCTGTTTGCCTGGCACT 1774
mouseTas1r3     TGCTGCTTTGCCTGGTGCTGGGTCTAGCACTGGCTGCTCTGGGGCTCTCTGTCCACCACT 1795
ratTas1r3       TGCTGCTTTGCCTGGTGCTGGGCCTGACACTGGCTGCCCTGGGGCTCTTTGTCCACTACT 1795
catTas1r3       CGCTGCTGGCTCTGGCGCTGGGCCTGGCGCTGGCAGCCCTGGGGCTCTTCCTCTGGCACT 1789
humanTAS1R3     TGCTGCTGAGCCTGGCGCTGGGCCTTGTGCTGGCTGCTTTGGGGCTGTTCGTTCACCATC 1780

mouseTas1r2     TCCAGACGCCCATGGTGCGCTCGGCGGGCGGCCCCATGTGCTTCCTGATGCTGGTGCCCC 1843
ratTas1r2       TCCAGACACCCATGGTGCGCTCGGCCGGTGGCCCCATGTGCTTCCTGATGCTCGTGCCCC 1843
humanTAS1R2     TCCAGACACCCATAGTTCGCTCGGCTGGGGGCCCCATGTGCTTCCTGATGCTGACACTGC 1831
catTas1r2       ------------------------------------------------------------
mouseTas1r1     TTCACACGCCTGTTGTGAGGTCAGCTGGGGGTAGGCTGTGCTTCCTCATGCTGGGTTCCT 1837
ratTas1r1       TTCACACACCTGTAGTGAGGTCAGCTGGGGGTAGGCTGTGCTTCCTCATGCTGGGTTCCC 1831
humanTAS1R1     TAGACACCCCTGTGGTGAGGTCAGCAGGGGGCCGCCTGTGCTTTCTTATGCTGGGCTCCC 1834
catTas1r1       TAGACACCCCTGTGGTGAAGTCCGCTGGGGGCCGACTGTGCTTCTTCATGCTAGGCTCCC 1834
mouseTas1r3     GGGACAGCCCTCTTGTCCAGGCCTCAGGTGGCTCACAGTTCTGCTTTGGCCTGATCTGCC 1855
ratTas1r3       GGGACAGCCCTCTTGTTCAGGCCTCAGGTGGGTCACTGTTCTGCTTTGGCCTGATCTGCC 1855
catTas1r3       CGGACAGCCCGCTGGTTCAGGCCTCAGGTGGGCCACGGGCCTGCTTTGGCCTGGCTTGCC 1849
humanTAS1R3     GGGACAGCCCACTGGTTCAGGCCTCGGGGGGGCCCCTGGCCTGCTTTGGCCTGGTGTGCC 1840

mouseTas1r2     TGCTGCTGGCGTTCGGGATGGTCCCCGTGTATGTGGGCCCCCCCACGGTCTTCTCCTGTT 1903
ratTas1r2       TGCTGCTGGCGTTTGGGATGGTGCCCGTGTATGTGGGGCCCCCCACGGTCTTCTCATGCT 1903
humanTAS1R2     TGCTGGTGGCATACATGGTGGTCCCGGTGTACGTGGGGCCGCCCAAGGTCTCCACCTGCC 1891
catTas1r2       ------------------------------------------------------------
mouseTas1r1     TGGTAGCTGGGAGTTGCAGCCTCTACAGCTTCTTCGGGAAGCCCACGGTGCCCGCGTGCT 1897
ratTas1r1       TGGTGGCCGGAAGTTGCAGCTTCTATAGCTTCTTCGGGGAGCCCACGGTGCCCGCGTGCT 1891
humanTAS1R1     TGGCAGCAGGTAGTGGCAGCCTCTATGGCTTCTTTGGGGAACCCACAAGGCCTGCGTGCT 1894
catTas1r1       TGGCAGGGGGCAGCTGTGGGCTCTACGGCTTTTTTGGGGAGCCCACGCTGCCCACATGCT 1894
mouseTas1r3     TAGGCCTCTTCTGCCTCAGTGTCCTTCTGTTCCCAGGGCGGCCAAGCTCTGCCAGCTGCC 1915
ratTas1r3       TAGGCCTCTTCTGCCTCAGTGTCCTTCTGTTCCCAGGACGACCACGCTCTGCCAGCTGCC 1915
catTas1r3       TGGGCCTGGTCTGCCTCAGTGTCCTCCTGTTCCCTGGCCAGCCAGGCCCTGCCAGCTGCC 1909
humanTAS1R3     TGGGCCTGGTCTGCCTCAGCGTCCTCCTGTTCCCTGGCCAGCCCAGCCCTGCCCGATGCC 1900

mouseTas1r2     TCTGCCGCCAGGCTTTCTTCACCGTTTGCTTCTCCGTCTGCCTCTCCTGCATCACGGTGC 1963
ratTas1r2       TCTGCCGACAGGCTTTCTTCACCGTCTGCTTCTCCATCTGCCTATCCTGCATCACCGTGC 1963
humanTAS1R2     TCTGCCGCCAGGCCCTCTTTCCCCTCTGCTTCACAATTTGCATCTCCTGTATCGCCGTGC 1951
catTas1r2       ------------------------------------------------------------
mouseTas1r1     TGCTGCGTCAGCCCCTCTTTTCTCTCGGGTTTGCCATTTTCCTCTCCTGTCTGACAATCC 1957
ratTas1r1       TGCTGCGTCAGCCCCTCTTTTCTCTCGGGTTTGCCATCTTCCTCTCCTGCCTGACAATCC 1951
humanTAS1R1     TGCTACGCCAGGCCCTCTTTGCCCTTGGTTTCACCATCTTCCTGTCCTGCCTGACAGTTC 1954
catTas1r1       TGTTGCGCCAAAGCCTCCTTGCCCTGGGTTTTGCCATCTTCCTGTCCTGCCTGACCATCC 1954
mouseTas1r3     TTGCACAACAACCAATGGCTCACCTCCCTCTCACAGGCTGCCTGAGCACACTCTTCCTGC 1975
ratTas1r3       TTGCCCAACAACCAATGGCTCACCTCCCTCTCACAGGCTGCCTGAGCACACTCTTCCTGC 1975
catTas1r3       TGGCCCAGCAGCCACTGTTCCACCTCCCACTCACTGGCTGCCTGAGCACGTTTTTCCTGC 1969
humanTAS1R3     TGGCCCAGCAGCCCTTGTCCCACCTCCCGCTCACGGGCTGCCTGAGCACACTCTTCCTGC 1960

mouseTas1r2     GCTCCTTCCAGATTGTGTGCGTCTTCAAGATGGCCAGACGCCTGCCAAGCGCCTACGGTT 2023
ratTas1r2       GCTCCTTCCAGATCGTGTGTGTCTTCAAGATGGCCAGACGCCTGCCAAGTGCCTACAGTT 2023
humanTAS1R2     GTTCTTTCCAGATCGTCTGCGCCTTCAAGATGGCCAGCCGCTTCCCACGCGCCTACAGCT 2011
catTas1r2       ------------------------------------------------------------
mouseTas1r1     GCTCCTTCCAACTGGTCATCATCTTCAAGTTTTCTACCAAGGTACCCACATTCTACCACA 2017
ratTas1r1       GCTCCTTCCAACTGGTCATCATCTTCAAGTTTTCTACCAAGGTGCCCACATTCTACCGTA 2011
humanTAS1R1     GCTCATTCCAACTAATCATCATCTTCAAGTTTTCCACCAAGGTACCTACATTCTACCACG 2014
catTas1r1       GCTCCTTCCAACTGGTCTTCATCTTCAAGTTTTCTGCCAAGGTACCCACCTTCTACCGTG 2014
mouseTas1r3     AAGCAGCTGAGACCTTTGTGGAGTCTGAGCTGCCACTGAGCTGGGCAAACTGGCTATGCA 2035
ratTas1r3       AAGCAGCCGAGATCTTTGTGGAGTCTGAGCTGCCACTGAGTTGGGCAAACTGGCTCTGCA 2035
catTas1r3       AAGCGGCCGAGATATTTGTGGGGTCGGAGCTGCCACCAAGCTGGGCTGAGAAGATGCGTG 2029
humanTAS1R3     AGGCGGCCGAGATCTTCGTGGAGTCAGAACTGCCTCTGAGCTGGGCAGACCGGCTGAGTG 2020
```

Figure 1H

```
mouseTas1r2    TCTGGATGCGTTACCACGGGCCCTACGTCTTTGTGGCCTTCATCACGGCCGTCAAGGTGG 2083
ratTas1r2      TTTGGATGCGTTACCACGGGCCCTATGTCTTCGTGGCCTTCATCACGGCCATCAAGGTGG 2083
humanTAS1R2    ACTGGGTCCGCTACCAGGGGCCCTACGTCTCTATGGCATTTATCACGGTACTCAAAATGG 2071
catTas1r2      ------------------------------------------------------------
mouseTas1r1    CTTGGGCCCAAAACCATGGTGCCGGAATATTCGTCATTGTCAGCTCCACGGTCCATTTGT 2077
ratTas1r1      CCTGGGCCCAAAACCATGGTGCAGGTCTATTCGTCATTGTCAGCTCCACGGTCCATTTGC 2071
humanTAS1R1    CCTGGGTCCAAAACCACGGTGCTGGCCTGTTTGTGATGATCAGCTCAGCGGCCCAGCTGC 2074
catTas1r1      CCTGGGTCCAAAACCACGGTCCTGGCCTATTTGTGGTGATCAGCTCAATGGCCCAGCTGC 2074
mouseTas1r3    GCTACCTTCGGGGACTCTGGGCCTGGCTAGTGGTACTGTTGGCCACTTTTGTGGAGGCAG 2095
ratTas1r3      GCTACCTTCGGGGCCCCTGGGCTTGGCTGGTGGTACTGCTGGCCACTCTTGTGGAGGCTG 2095
catTas1r3      GCCGCCTGCGGGGGCCCTGGGCCTGGCTGGTGGTGCTGCTTGCTATGCTGGCAGAAGCCG 2089
humanTAS1R3    GCTGCCTGCGGGGGCCCTGGGCCTGGCTGGTGGTGCTGCTGGCCATGCTGGTGGAGGTCG 2080

mouseTas1r2    CCCTGGTGGCAGGCAACATGCTGGCCACCACCATCAACCCCATTGGCCGGACCGACCCCG 2143
ratTas1r2      CCCTGGTGCTGGGCAACATGCTGGCCACCACCATCAACCCCATTGGCCGGACCGACCCGG 2143
humanTAS1R2    TCATTGTGGTAATTGGCATCCTGGCCACGGGCCTCAGTCCCACCACCCGTACTGACCCCG 2131
catTas1r2      ------------------------------------------------------------
mouseTas1r1    TCCTCTGTCTCCACGTGGCTTGCAATGTGGACCCCACGGCCCACCA---GGGAGTACCAGC 2134
ratTas1r1      TCATCTGTCTCACATGGCTTGTAATGTGGACCCCACGACCCACCA---GGGAATACCAGC 2128
humanTAS1R1    TTATCTGTCTAACTTGGCTGGTGGTGTGGACCCCACTGCCTGCTA---GGGAATACCAGC 2131
catTas1r1      TCATCTGTCTAACTTGGCTGGCGGTGTGGACCCCACTGCCCACCA---GGGAGTACCAGC 2131
mouseTas1r3    CACTATGTGCCTGGTATTTGATCGCTTTCCCACCAGAGGTGGTGA--CAGACTGGTCAGT 2153
ratTas1r3      CACTATGTGCCTGGTACTTGATGGCTTTCCCTCCAGAGGTGGTGA--CAGATTGGCAGGT 2153
catTas1r3      CATTGTGTGCCTGGTACCTGGTAGCCTTCCCGCCAGAGGTGGTGA--CGGACTGGCGGGT 2147
humanTAS1R3    CACTGTGCACCTGGTACCTGGTGGCCTTCCCGCCGGAGGTGGTGA--CGGACTGGCACAT 2138

mouseTas1r2    ATGACCCCAATATCATAATCCTCTCCTGCCACCCTAACTACCGCAACGGGCTACTCTTCA 2203
ratTas1r2      ATGACCCCAACATCATGATCCTCTCGTGCCACCCTAACTACCGCAACGGGCTACTGTTCA 2203
humanTAS1R2    ATGACCCCAAGATCACAATTGTCTCCTGTAACCCCAACTACCGCAACAGCCTGCTGTTCA 2191
catTas1r2      ------------------------------------------------------------
mouseTas1r1    GCTTCCCCCATCTGGTGATTCTTGAGTGCACAGAGGTCAACTCTGTGGGCTTCCTGGTGG 2194
ratTas1r1      GCTTCCCCCATCTGGTGATTCTCGAGTGCACAGAGGTCAACTCTGTACGCTTCCTGTTGG 2188
humanTAS1R1    GCTTCCCCCATCTGGTGATGCTTGAGTGCACAGAGACCAACTCCCTGGGCTTCATACTGG 2191
catTas1r1      GCTTCCCTCAGCTGGTGGTGCTTGATTGCACAGAGGCCAACTCACCGGGCTTCATGTTGG 2191
mouseTas1r3    GCTGCCCACAGA-GGTACTGGAGCACTGCCACGTGCGTTCCTGGGTCAGCCTGGGCTTGG 2212
ratTas1r3      GCTGCCCACGGA-GGTACTGGAACACTGCCGCATGCGTTCCTGGGTCAGCCTGGGCTTGG 2212
catTas1r3      ACTGCCCACAGA-GGCGCTGGTGCACTGCCACGTGCACTCCTGGATCAGCTTCGGCCTGG 2206
humanTAS1R3    GCTGCCCACGGA-GGCGCTGGTGCACTGCCGCACACGCTCCTGGGTCAGCTTCGGCCTAG 2197

mouseTas1r2    ACACCAGCATGGACTTGCTGCTGTCCGTGCTGGGTTTCAGCTTCGCGTACGTGGGCAAGG 2263
ratTas1r2      ACACCAGCATGGACTTGCTGCTGTCTGTGCTGGGTTTCAGCTTCGCTTACATGGGCAAGG 2263
humanTAS1R2    ACACCAGCCTGGACCTGCTGCTCTCAGTGGTGGGTTTCAGCTTCGCCTACATGGGCAAAG 2251
catTas1r2      ------------------------------------------------------------
mouseTas1r1    CTTTCGCACACAACATCCTCCTCTCCATCAGCACCTTTGTCTGCAGCTACCTGGGTAAGG 2254
ratTas1r1      CTTTCACCCACAACATTCTCCTCTCCATCAGTACCTTCGTCTGCAGCTACCTGGGTAAGG 2248
humanTAS1R1    CCTTCCTCTACAATGGCCTCCTCTCCATCAGTGCCTTTGCCTGCAGCTACCTGGGTAAGG 2251
catTas1r1      CTTTCGCCTACAATGGCCTCCTGTCCGTCAGCGCCTTTGCCTGCAGCTACCTGGGCAAGG 2251
mouseTas1r3    TGCACATCACCAATGCAATGTTAGCTTTCCTCTGCTTTCTGGGCACTTTCCTGGTACAGA 2272
ratTas1r3      TGCACATCACCAATGCAGTGTTAGCTTTCCTCTGCTTTCTGGGCACTTTCCTGGTACAGA 2272
catTas1r3      TGCATGCCACTAACGCCATGCTGGCCTTTCTCTGCTTCCTGGGCACTTTCCTGGTGCAGA 2266
humanTAS1R3    CGCACGCCACCAATGCCACGCTGGCCTTTCTCTGCTTCCTGGGCACTTTCCTGGTGCGGA 2257

mouseTas1r2    AACTGCCCACCAACTACAACGAAGCCAAGTTCATCACCCTCAGCATGACCTTCTCCTTCA 2323
ratTas1r2      AGCTGCCCACCAACTACAACGAAGCCAAGTTCATCACTCTCAGCATGACCTTCTCCTTCA 2323
humanTAS1R2    AGCTGCCCACCAACTACAACGAGGCCAAGTTCATCACCCTCAGCATGACCTTCTATTTCA 2311
catTas1r2      ------------------------------------------------------------
mouseTas1r1    AACTGCCGGAGAACTATAACGAAGCCAAATGTGTCACCTTCAGCCTGCTCCTCCACTTCG 2314
ratTas1r1      AACTGCCAGAGAACTATAATGAAGCCAAATGTGTCACCTTCAGCCTGCTCCTCAACTTCG 2308
humanTAS1R1    ACTTGCCAGAGAACTACAACGAGGCCAAATGTGTCACCTTCAGCCTGCTCTTCAACTTCG 2311
catTas1r1      ACCTGCCAGAGAACTACAACGAGGCCAAATGTGTCACTTTTAGTCTGCTGCTCAACTTCG 2311
mouseTas1r3    GCCAGCCTGGCCGCTACAACCGTGCCCGTGGCCTCACCTTCGCCATGCTAGCTTATTTCA 2332
ratTas1r3      GCCAGCCTGGTCGCTATAACCGTGCCCGTGGCCTCACCTTCGCCATGCTAGCTTATTTCA 2332
catTas1r3      GCCGGCCAGGCCGCTACAATGGTGCCCGCGGCCTCACCTTTGCCATGCTGGCCTACTTCA 2326
humanTAS1R3    GCCAGCCGGGCCGCTACAACCGTGCCCGTGGCCTCACCTTTGCCATGCTGGCCTACTTCA 2317
```

Figure 1I

```
mouseTas1r2     CCTCCTCCATCTCCCTCTGCACGTTCATGTCTGTCCACGATGGCGTGCTGGTCACCATCA 2383
ratTas1r2       CCTCCTCCATCTCCCTCTGCACCTTCATGTCTGTGCACGACGGCGTGCTGGTCACCATCA 2383
humanTAS1R2     CCTCATCCGTCTCCCTCTGCACCTTCATGTCTGCCTACAGCGGGGTGCTGGTCACCATCG 2371
catTas1r2       ------------------------------------------------------------
mouseTas1r1     TATCCTGGATCGCTTTCTTCACCATGTCCAGCATTTACCAGGGCAGCTACCTACCCGCGG 2374
ratTas1r1       TATCCTGGATCGCCTTCTTCACCATGGCCAGCATTTACCAGGGCAGCTACCTGCCTGCGG 2368
humanTAS1R1     TGTCCTGGATCGCCTTCTTCACCACGGCCAGCGTCTACGACGGCAAGTACCTGCCTGCGG 2371
catTas1r1       TGTCCTGGATTGCCTTCTTCACCACGGCCAGCGTCTACCAGGGCAAGTACTTGCCCGCGG 2371
mouseTas1r3     TCACCTGGGTCTCTTTTGTGCCCCTCCTGGCCAATGTGCAGGTGGCCTACCAGCCAGCTG 2392
ratTas1r3       TCATCTGGGTCTCTTTTGTGCCCCTCCTGGCTAATGTGCAGGTGGCCTACCAGCCAGCTG 2392
catTas1r3       TCACCTGGATCTCCTTTGTGCCCCTCTTTGCCAATGTGCACGTGGCCTACCAGCCTGCCG 2386
humanTAS1R3     TCACCTGGGTCTCCTTTGTGCCCCTCCTGGCCAATGTGCAGGTGGTCCTCAGGCCCGCCG 2377

mouseTas1r2     TGGATCTCCTGGTCACTGTGCTCAACTTTCTGGCCATCGGCTTGGGGTACTTTGGCCCCA 2443
ratTas1r2       TGGACCTCCTGGTCACTGTGCTCAACTTCCTGGCCATCGGCTTGGGATACTTTGGCCCCA 2443
humanTAS1R2     TGGACCTCTTGGTCACTGTGCTCAACCTCCTGGCCATCAGCCTGGGCTACTTCGGCCCCA 2431
catTas1r2       ------------------------------------------------------------
mouseTas1r1     TCAATGTGCTGGCAGGGCTGGCCACTCTGAGTGGCGGCTTCAGCGGCTATTTCCTCCCTA 2434
ratTas1r1       TCAATGTGCTGGCAGGGCTGACCACACTGAGCGGCGGCTTCAGCGGTTACTTCCTCCCCA 2428
humanTAS1R1     CCAACATGATGGCTGGGCTGAGCAGCCTGAGCAGCGGCTTCGGTGGGTATTTTCTGCCTA 2431
catTas1r1       TCAACGTGCTGGCGGCGCTGAGCAGCCTGAGTGGCGGCTTCAGCGCTTATTTCCTCCCCA 2431
mouseTas1r3     TGCAGATGGGTGCTATCCTAGTCTGTGCCCTGGGCATCCTGGTCACCTTCCACCTGCCCA 2452
ratTas1r3       TGCAGATGGGTGCTATCTTATTCTGTGCCCTGGGCATCCTGGCCACCTTCCACCTGCCCA 2452
catTas1r3       TGCAGATGGGCACCATCCTCCTCTGTGCCCTGGGTATCCTAGCCACCTTCCACCTGCCCA 2446
humanTAS1R3     TGCAGATGGGCGCCCTCCTGCTCTGTGTCCTGGGCATCCTGGCTGCCTTCCACCTGCCCA 2437

mouseTas1r2     AGTGTTACATGATCCTTTTCTACCCGGAGCGCAACACTTCAGCTTATTTCAATAGCATGA 2503
ratTas1r2       AGTGTTACATGATCCTTTTCTACCCGGAGCGCAACACCTCAGCCTATTTCAATAGCATGA 2503
humanTAS1R2     AGTGCTACATGATCCTCTTCTACCCGGAGCGCAACACGCCCGCCTACTTCAACAGCATGA 2491
catTas1r2       ------------------------------------------------------------
mouseTas1r1     AATGCTACGTGATTCTCTGCCGTCCAGAACTCAACAACACAGAACACTTTCAGGCCTCCA 2494
ratTas1r1       AGTGCTATGTGATTCTCTGCCGTCCAGAACTCAACAATACAGAACACTTTCAGGCCTCCA 2488
humanTAS1R1     AGTGCTACGTGATCCTCTGCCGCCCAGACCTCAACAGCACAGAGCACTTCCAGGCCTCCA 2491
catTas1r1       AGTGCTACGTGATCCTGTGCCGCCCAAAATTTAACAGCACACAGCACTTCCAGGCCTCCA 2491
mouseTas1r3     AGTGCTATGTGCTTCTTTGGCTGCCAAAGCTCAACACCCAGGAGTTCTTCCTGGGAAGGA 2512
ratTas1r3       AATGCTATGTACTTCTGTGGCTGCCAGAGCTCAACACCCAGGAGTTCTTCCTGGGAAGGA 2512
catTas1r3       AGTGCTACCTGCTGCTGCAGCGGCCGGAGCTCAACACCCCTGAGTTCTTCCTGGAAGACA 2506
humanTAS1R3     GGTGTTACCTGCTCATGCGGCAGCCAGGGCTCAACACCCCCGAGTTCTTCCTGGGAGGGG 2497

mouseTas1r2     TTCAGGGCTACACGATGAGGAAGAGCTAG------------------------------- 2532
ratTas1r2       TCCAGGGCTACACCATGAGGAAGAGC---------------------------------- 2529
humanTAS1R2     TCCAGGGCTACACCATGAGGAGGGACTAG------------------------------- 2520
catTas1r2       ------------------------------------------------------------
mouseTas1r1     TCCAGGACTACACGAGGCGCTGCGGCACTACCTGA------------------------- 2529
ratTas1r1       TCCAGGACTACACGAGGCGCTGCGGCACTACC---------------------------- 2520
humanTAS1R1     TTCAGGACTACACGAGGCGCTGCGGCTCCACCTGA------------------------- 2526
catTas1r1       TCCAGGAGTACACGAGGCGCTGCGGCTCCACCTGA------------------------- 2526
mouseTas1r3     ATGCCAAGAAAGCAGCAGATGAGAAC-AGTGGCGGTGGTGAGGCAGCTCAGGGACACAAT 2571
ratTas1r3       GCCCCAAGGAAGCATCAGATGGGAAT-AGTGGTAGTACTGACGCAACTCGGGGACACAGT 2571
catTas1r3       ATGCCA---GAGCACAGGGCAGCAGTTGGGGGCAGGGCAGCGGAGAATCGGGGCAAAAAC 2563
humanTAS1R3     GCCCTGGGGATGCCCAAGGCCAGAAT----GACGGGAACACAGGAAATCAGGGGAAACAT 2553

mouseTas1r2     -----------------------------------
ratTas1r2       -----------------------------------
humanTAS1R2     -----------------------------------
catTas1r2       -----------------------------------
mouseTas1r1     -----------------------------------
ratTas1r1       -----------------------------------
humanTAS1R1     -----------------------------------
catTas1r1       -----------------------------------
mouseTas1r3     GAATGA----------------------------- 2577
ratTas1r3       GAATGA----------------------------- 2577
catTas1r3       AAGTGACACCCGATCCAGTGACCTCACCGCAGTGA 2598
humanTAS1R3     GAGTGA----------------------------- 2559
```

Figure 2A CLUSTAL W (1.82) multiple amino acid sequence alignment of T1Rs:

```
mouseT1R2   MGPQARTLHLLFLLLLHALPKPVML---VGNSDFHLAGDYLLGGLFTLHANVKSVSHLSYL 57
ratT1R2     MGPQARTLCLLSLLLLHVLPKPGKL---VENSDFHLAGDYLLGGLFTLHANVKSISHLSYL 57
humanT1R2   MGPRAKTICSLFFLLWVLAEP------AENSDFYLPGDYLLGGLFSLHANMKGIVHLNFL 54
catT1R2     MGPRAREVCCFIILPRLLAEP------AENSDFYLACDYFLGGLFTLHANVKGIVHLNLL 54
mouseT1R1   MLFWAAHLLLSLQLAVAYCWAFSCQRTESSPGFSLPGDFLLAGLFSLHADCLQVRHRPLV 60
ratT1R1     MLFWAAHLLLSLQL--VYCWAFSCQRTESSPGFSLPGDFLLAGLFSLHGDCLQVRHRPLV 58
humanT1R1   MLLCTARLVG-LQLLISCCWAFACHSTESSPDFTLPGDYLLAGLFPLHSGCLQVRHRPEV 59
catT1R1     MSLPAAHLVG-LQLSLSCCWALSCHSTETSADFSLPGDYLLAGLFPLHSDCPGVRHRPTV 59
mouseT1R3   MPALAIMGLS----LAAFLELGMGASLCLSQQFKAQGDYILGGLFPLG-STEEATLNQRT 55
ratT1R3     MPGLAILGLS----LAAFLELGMGSSLCLSQQFKAQGDYILGGLFPLG-TTEEATLNQRT 55
humanT1R3   MLGPAVLGLS----LWALLHPGTGAPLCLSQQLRMKGDYVLGGLFPLG-EAEEAGLRSRT 55
catT1R3     MPGLALLGLTALLGLTALLDHGEGATSCLSQQLRMQGDYVLGGLFPLG-SAEGTGLGDGL 59
                                                **:.*.***.*

mouseT1R2   QVPKCNEYNMKVLGYNLMQAMRFAVEEINNCSSLLPGVLLGYEMVDVCYL-SNNIQPGLY 116
ratT1R2     QVPKCNEFTMKVLGYNLMQAMRFAVEEINNCSSLLPGVLLGYEMVDVCYL-SNNIHPGLY 116
humanT1R2   QVPMCKEYEVKVIGYNLMQAMRFAVEEINNDSSLLPGVLLGYEIVDVCYI-SNNVQPVLY 113
catT1R2     QVPQCKEYEIKVLGYDLMQAMCFAGEEINSQSSLLPGVLLGYKMVDVSYI-SNNVQPVLH 113
mouseT1R1   TSCDR-SDSFNGHGYHLFQAMRFTVEEINNSTALLPNITLGYELYDVCSE-SSNVYATLR 118
ratT1R1     TSCDR-PDSFNGHGYHLFQAMRFTVEEINNSSALLPNITLGYELYDVCSE-SANVYATLR 116
humanT1R1   TLCDR-SCSFNEHGYHLFQAMRLGVEEINNSTALLPNITLGYQLYDVCSD-SANVYATLR 117
catT1R1     TLCDR-PDSFNGHGYHLFQAMRFGIEEINNSTALLPNVTLGYQLYDVCSE-SANVYATLN 117
mouseT1R3   QPNSIPCNRFSPLGLFLAMAMKMAVEEINNGSALLPGLRLGYDLFDTCSEPVVTMKSSLM 115
ratT1R3     QPNGILCTRFSPLGLFLAMAMKMAVEEINNGSALLPGLRLGYDLFDTCSEPVVTMKPSLM 115
humanT1R3   RPSSPVCTRFSSNGLLWALAMKMAVEEINNKSDLLPGLRLGYDLFDTCSEPVVAMKPSLM 115
catT1R3     QPNATVCTRFSSLGLLWALAVKMAVEEINNGSALLPGLHLGYDLFDTCSEPMVAMKPSLV 119
                ..  *     *: :  ****. : ***.: ***.: *..       : . *

mouseT1R2   FLSQID-DFLPILKDYSQYRPQVVAVIGPDNSESAITVSNILSYFLVPQVTYSAITDKLR 175
ratT1R2     FLAQDD-DLLPILKDYSQYMPHVVAVIGPDNSESAITVSNILSHFLIPQITYSAISDKLR 175
humanT1R2   FLAHED-NLLPIQEDYSNYISRVVAVIGPDNSESVMTVANFLSLFLLPQITYSAISDELR 172
catT1R2     FPAKED-CSLPIQEDYSHCVPRVVAVIGPGNSESTVTVARFLSLFLLPQITYSAISDELR 172
mouseT1R1   VLAQQGTGHLEMQRDLRNHSSKVVALIGPDNTDHAVTTAALLSPFLMPLVSYEASSVILS 178
ratT1R1     VLALQGPRHIEIQKDLRNHSSKVVAFIGPDNTDHAVTTAALLGPFLMPLVSYEASSVVLS 176
humanT1R1   VLSLPGQHHIELQGDLLHYSPTVLAVIGPDSTNRAATTAALLSPFLVPMISYAASSETLS 177
catT1R1     VLSLLGTHHVEIRADPSHYSPAALAVIGPDTTNHAATTAALLSPFLVPLISYEASSVTLG 177
mouseT1R3   FLAKVGSQSIAAYCNYTQYQPRVLAVIGPHSSELALITGKFFSFFLMPQVSYSASMDRLS 175
ratT1R3     FMAKVGSQSIAAYCNYTQYQPRVLAVIGPHSSELALITGKFFSFFLMPQVSYSASMDRLS 175
humanT1R3   FLAKAGSRDIAAYCNYTQYQPRVLAVIGPHSSELAMVTGKFFSFFLMPQVSYGASMELLS 175
catT1R3     FMAKAGSCSIAAYCNYTQYQPRVLAVIGPHSSELALVTGKFFSFFLVPQVSYGASTDRLS 179
            . :  .   :     :  :  . .:*.*** .:: .  .. ::. **:* ::* *    *

mouseT1R2   DKRRFPAMLRTVPSATHHIEAMVQLMVHFQWNWIVVLVSDDDYGRENSHLLSQRLTNTGD 235
ratT1R2     DKRHFPSMLRTVPSATHHIEAMVQLMVHFQWNWIVVLVSDDDYGRENSHLLSQRLTKTSD 235
humanT1R2   DKVRFPALLRTTPSADHHVEAMVQLMLHFRWNWIIVLVSSDTYGRDNGQLLGERVARR-D 231
catT1R2     DKQRFPALLPTAPGADHQIEAMVQLMLYFRRNWIIALVSSGDCGRDDSQLLSDRPAGG-D 231
mouseT1R1   GKRKFPSFLRTIPSDKYQVEVIVRLLQSFGWVWISLVGSYGDYGQLGVQALEELATPR-G 237
ratT1R1     AKRKFPSFLRTVPSDRHQVEVMVQLLQSFGWVWISLIGSYGDYGQLGVQALEELAVPR-G 235
humanT1R1   VKRQYPSFLRTIPNDKYQVETMVLLLQKFGWTWISLVGSSDDYGQLGVQALENQATGQ-G 236
catT1R1     VKRHYPSFLRTIPSDKHQVEAMVLLLQSFGWVWISVVGSDGDYGQLGVQALEEQATQQ-G 236
mouseT1R3   DRETFPSFFRTVPSDRVQLQAVVTLLQNFSWNWVAALGSDDDYGREGLSIFSSLANAR-G 234
ratT1R3     DRETFPSFFRTVPSDRVQLQAVVTLLQNFSWNWVAALGSDDDYGREGLSIFSGLANSR-G 234
humanT1R3   ARETFPSFFRTVPSDRVQLTAAAELLQEFGWNWVAALGSDDEYGRQGLSIFSALAAAR-G 234
catT1R3     NREIFPSFFRTVPSDQVQVAAMVELLEELGWNWVAAVGSDDEYGRQGLSLFSGLASAR-G 238
              :  :*::: * *.   :: . . *:  :    *:  : * .  *: .  :        .
```

Figure 2B

```
mouseT1R2         ICIAFQEVLPVPEPNQAVRPEEQDQLDNILDKLRR-TSARVVVIFSPELSLHNFFREVLR 294
ratT1R2           ICIAFQEVLPIPESSQVMRSEEQRQLDNILDKLRR-TSARVVVVFSPELSLYSFFHEVLR 294
humanT1R2         ICIAFQETLPTLQPNQNMTSEERQRLVTIVDKLQQ-STARVVVVFSPDLTLYHFFNEVLR 290
catT1R2           TCIAFRETLPMPQPNQAVTQWERRRLKAIVDEQQRQSSARVVVLLSPKLVLHNFFREVLR 291
mouseT1R1         ICVAFKDVVPLS------AQAGDPRMQRMMLRLAR-ARTTVVVVFSNRHLAGVFFRSVVL 290
ratT1R1           ICVAFKDIVPFS------ARVGDPRMQSMMQHLAQ-ARTTVVVVFSNRHLARVFFRSVVL 288
humanT1R1         ICIAFKDIMPFS------AQVGDERMQCLMRHLAQ-AGATVVVVFSSRQLARVFFESVVL 289
catT1R1           ICVAFKDIIPFS------ARPGDERMQSIMHHLAR-ARTTVVVVFSSRQLARVFFESVVL 289
mouseT1R3         ICIAHEGLVPQHD----TSGQQLGKVLDVLRQVNQ-SKVQVVVLFASARAVYSLFSYSIH 289
ratT1R3           ICIAHEGLVPQHD----TSGQQLGKVVDVLRQVNQ-SKVQVVVLFASARAVYSLFSYSIL 289
humanT1R3         ICIAHEGLVPLPR----ADDSRLGKVQDVLHQVNQ-SSVQVVLLFASVHAAHALFNYSIS 289
catT1R3           ICIAHEGLVPLP-----PGSLRLGALQGLLRQVNQ-SSVQVVVLFSSAHAARTLFSYSIR 292
                   *:*..   :*                     :  ::  .   : :  . **::::          :*    :

mouseT1R2         WNFTGFVWIASESWAIDPVLHNLTELRHTGTFLGVTIQRVSIPGFSQFRVRHDKPEYPMP 354
ratT1R2           WNFTGFVWIASESWAIDPVLHNLTELRHTGTFLGVTIQRVSIPGFSQFRVRRDKPGYPVP 354
humanT1R2         QNFTGAVWIASESWAIDPVLHNLTELGHLGTFLGITIQSVPIPGFSEFREWGPQAGPPPL 350
catT1R2           QNLTGVVRIASESWAIDPVLHDRPTRCTASWAAPRPAAPGRLSLAGEAPPTESRGHTRRR 351
mouseT1R1         ANLTGKVWIASEDWAISTYITNVPGIQGIGTVLGVAIQQRQVPGLKEFEESYVQAVMGAP 350
ratT1R1           ANLTGKVWVASEDWAISTYITSVTGIQGIGTVLGVAVQQRQVPGLKEFEESYVRAVTAAP 348
humanT1R1         TNLTGKVWVASEAWALSRHITGVPGIQRIGMVLGVAIQKRAVPGLKAFEEAYARADKKAP 349
catT1R1           ANLTAKVWIASEDWAISRHISNVPGIQGIGTVLGVAIQQRLVPGLKEFEEAYVQADKGAP 349
mouseT1R3         HGLSPKVWVASESWLTSDLVMTLPNIARVGTVLGFLQRGALLPEFSHYVETHLALAADPA 349
ratT1R3           HDLSPKVWVASESWLTSDLVMTLPNIARVGTVLGFLQRGALLPEFSHYVETRLALAADPT 349
humanT1R3         SRLSPKVWVASEAWLTSDLVMGLPGMAQMGTVLGFLQRGAQLHEFPQYVKTHLALATDPA 349
catT1R3           CKLSPKVWVASEAWLTSDLVMTLPGMPGVGTVLGFLQQGAPMPEFPSYVRTRLALAADPA 352
                     ::   * :*** *    .    ;

mouseT1R2         NETSLRTTC--NQDCDACMNITESFNNVLMLSG------------ERVVYSVYSAVYAVA 400
ratT1R2           NTTNLRTTC--NQDCDACLNTTKSFNNILILSG------------ERVVYSVYSAVYAVA 400
humanT1R2         SRTSQSYTC--NQECDNCLNATLSFNTILRLSG------------ERVVYSVYSAVYAVA 396
catT1R2           RHSPEWLPWRPLPCSSVPLSGRVLGKLAGEARGRTLSPDT---------------------391
mouseT1R1         RTCPEGSWCGTNQLCRECHAFTTWNMPELGAFS------------MSAAYNVYEAVYAVA 398
ratT1R1           SACPEGSWCSTNQLCRECHTFTTRNMPTLGAFS------------MSAAYRVYEAVYAVA 396
humanT1R1         RPCHKGSWCSSNQLCRECQAFMAHTMPKLKAFS------------MSSAYNAYRAVYAVA 397
catT1R1           GPCSRTSECSSNQLCRECRAFTAEQMPTLGAFS------------MSSAYNAYRAVYAVA 397
mouseT1R3         FCASLN-AELDLEEHVMGQRCPRCDDIMLQNLSSGLLQNLSAGQLHHQIFATYAAVYSVA 408
ratT1R3           FCASLK-AELDLEERVMGPRCSQCDYIMLQNLSSGLMQNLSAGQLHHQIFATYAAVYSVA 408
humanT1R3         FCSALGEREQGLEEDVVGQRCPQCDCITLQNVS---------AGLNHHQTFSVYAAVYSVA 401
catT1R3           FCASLDAEQPGLEEHVVGPRCPQCDHVTLENLS---------AGLLHHQTFAAYAAVYGVA 404

mouseT1R2         HTLHRLLHCNQVRCTK-QIVYPWQLLREIWHVNFTLLGNQLFFDEQGDMPMLLDIIQWQW 459
ratT1R2           HALHRLLGCNRVRCTK-QKVYPWQLLREIWHVNFTLLGNRLFFDQQGDMPMLLDIIQWQW 459
humanT1R2         HALHSLLGCDKSTCTK-RVVYPWQLLEEIWKVNFTLLDHQIFFDPQGDVALHLEIVQWQW 455
catT1R2           ----------- ------------------------------------------------ 391
mouseT1R1         HGLHQLLGCTSGTCAR-GPVYPWQLLQQIYKVNFLLHKKTVAFDDKGDPLGYYDIIAWDW 457
ratT1R1           HGLHQLLGCTSEICSR-GPVYPWQLLQQIYKVNFLLHENTVAFDDNGDTLGYYDIIAWDW 455
humanT1R1         HGLHQLLGCASGACSR-GRVYPWQLLEQIHKVHFLLHKDTVAFNDNRDPLSSYNIIAWDW 456
catT1R1           HGLHQLLGCASGACSR-DRVYPWQLLEQIRKVNFLLHKDTVRFNDNGDPLSGYDIIAWDW 456
mouseT1R3         QALHNTLQCNVSHCHVSEHVLPWQLLENMYNMSFHARDLTLQFDAEGNVDMEYDLKMWVW 468
ratT1R3           QALHNTLQCNVSHCHTSEPVQPWQLLENMYNMSFRARDLTLQFDAKGSVDMEYDLKMWVW 468
humanT1R3         QALHNTLQCNASGCPAQDPVKPWQLLENMYNLTFHVGGLPLRFDSSGNVDMEYDLKLWVW 461
catT1R3           QALHNTLRCNASGCPRREPVRPWQLLENMYNVSFRARGLALQFDASGNVNVDYDLKLWVW 464
                               *

mouseT1R2         GLSQNPFQSIASYSPTETRLTY-ISNVSWYTPNNTVPISMCSKSCQPGQMKKPIGLHPCC 518
ratT1R2           DLSQNPFQSIASYSPTSKRLTY-INNVSWYTPNNTVPVSMCSKSCQPGQMKKSVGLHPCC 518
humanT1R2         DRSQNPFQSVASYYPLQRQLKN-IQDISWHTVNNTIPMSMCSKRCQSGQKKKPVGIHVCC 514
catT1R2           --------------------------- ---------------------------------
mouseT1R1         NGPEWTFEVIGSASLSPVHLDINKTKIQWHGKNNQVPVSVCTRDCLEGHHRLVMGSHHCC 517
ratT1R1           NGPEWTFEIIGSASLSPVHLDINKTKIQWHGKNNQVPVSVCTTDCLAGHHRVVVGSHHCC 515
humanT1R1         NGPKWTFTVLGSSTWSPVQLNINETKIQWHGKDNQVPKSVCSSDCLEGHQRVVTGFHHCC 516
catT1R1           SGPKWNFRVIGSSMWPPVQLDINKTKIRWHGKDNQVPKSVCSSDCLEGHQRVISGFYHCC 516
mouseT1R3         QSPTPVLHTVGTFNG---TLQLQQSKMYWP--GNQVPVSQCSRQCKDGQVRRVKGFHSCC 523
ratT1R3           QSPTPVLHTVGTFNG---TLQLQHSKMYWP--GNQVPVSQCSRQCKDGQVRRVKGFHSCC 523
humanT1R3         QGSVPRLHDVGRFNG---SLRTERLKIRWHTSDNQKPVSRCSRQCQEGQVRRVKGFHSCC 518
catT1R3           QDPTPELRTVGTFKG---RLELWRSQMCWHTPGKQQPVSQCSRQCKEGQVRRVKGFHSCC 521
                                              *                .  *:
```

Figure 2C

```
mouseT1R2   FECVDCPPGTYLNRSVDEFNCLSCPGSMWSYKNNIACFKRRLAFLEWHEVPTIVVTILAA 578
ratT1R2     FECLDCMPGTYLNRSADEFNCLSCPGSMWSYKNDITCFQRRPTFLEWHEVPTIVVAILAA 578
humanT1R2   FECIDCLPGTFLNHTEDEYECQACPNNEWSYQSETSCFKRQLVFLEWHEAPTIAVALLAA 574
catT1R2     ------------------------------------------------------------
mouseT1R1   FECMPCEAGTFLNTS-ELHTCQPCGTEEWAPEGSSACFSRTVEFLGWHEPISLVLLAANT 576
ratT1R1     FECVPCEAGTFLNMS-ELHICQPCGTEEWAPKESTTCFPRTVEFLAWHEPISLVLIAANT 574
humanT1R1   FECVPCGAGTFLNKS-DLYRCQPCGKEEWAPEGSQTCFPRTVVFLALREHTSWVLLAANT 575
catT1R1     FECVPCEAGSFLNKS-DLHSCQPCGKEKWAPAGSETCFPRTVVFLTWHETISWVLLAANT 575
mouseT1R3   YDCVDCKAGSYRKHP-DDFTCTPCNQDQWSPEKSTACLPRRPKFLAWGEPVVLSLLLLLC 582
ratT1R3     YDCVDCKAGSYRKHP-DDFTCTPCGKDQWSPEKSTTCLPRRPKFLAWGEPAVLSLLLLLC 582
humanT1R3   YDCVDCEAGSYRQNP-DDIACTFCGQDEWSPERSTRCFRRRSRFLAWGEPAVLLLLLLLS 577
catT1R3     YNCVDCKAGSYQRNP-DDLLCTQCDQDQWSPDRSTRCFARKPMFLAWGEPAVLLLLALLA 580
                                                        :    :*

mouseT1R2   LGFISTLAILLIFWRHFQTPMVRSAGGPMCFLMLVPLLLAFGMVPVYVGPPTVFSCFCRQ 638
ratT1R2     LGFFSTLAILFIFWRHFQTPMVRSAGGPMCFLMLVPLLLAFGMVPVYVGPPTVFSCFCRQ 638
humanT1R2   LGFLSTLAILVIFWRHFQTPIVRSAGGPMCFLMLTLLLVAYMVVPVYVGPPKVSTCLCRQ 634
catT1R2     ------------------------------------------------------------
mouseT1R1   LLLLLLIGTAGLFAWRLHTPVVRSAGGRLCFLMLGSLVAGSCSLYSFFGKPTVPACLLRQ 636
ratT1R1     LLLLLLVGTAGLFAWHFHTPVVRSAGGRLCFLMLGSLVAGSCSFYSFFGEPTVPACLLRQ 634
humanT1R1   LLLLLLLGTAGLFAWHLDTPVVRSAGGRLCFLMLGSLAAGSGSLYGFFGEPTRPACLLRQ 635
catT1R1     LLLLLVTGTAGLFAWHLDTPVVKSAGGRLCFFMLGSLAGGSCGLYGFFGEPTLPTCLLRQ 635
mouseT1R3   LVLGLALAALGLSVHHWDSPLVQASGGSQFCFGLICLGLFCLSVLLFPGRPSSASCLAQQ 642
ratT1R3     LVLGLTLAALGLFVHYWDSPLVQASGGSLFCFGLICLGLFCLSVLLFPGRPRSASCLAQQ 642
humanT1R3   LALGLVLAALGLFVHHRDSPLVQASGGPLACFGLVCLGLVCLSVLLFPGQPSPARCLAQQ 637
catT1R3     LALGLALAALGLFLWHSDSPLVQASGGPRACFGLACLGLVCLSVLLFPGQPGPASCLAQQ 640

mouseT1R2   AFFTVCFSVCLSCITVRSFQIVCVFKMARRLPSAYGFWMRYHGPYVFVAFITAVKVALVA 698
ratT1R2     AFFTVCFSICLSCITVRSFQIVCVFKMARRLPSAYSFWMRYHGPYVFVAFITAIKVALVV 698
humanT1R2   ALFPLCFTICISCIAVRSFQIVCAFKMASRFPRAYSYWVRYQGPYVSMAFITVLKMVIVV 694
catT1R2     ----- ------------------------------------------------------
mouseT1R1   PLFSLGFAIFLSCLTIRSFQLVIIFKFSTKVPTFYHTWAQNHGAG-IFVIVSSTVHLFLC 695
ratT1R1     PLFSLGFAIFLSCLTIRSFQLVIIFKFSTKVPTFYRTWAQNHGAG-LFVIVSSTVHLLIC 693
humanT1R1   ALFALGFTIFLSCLTVRSFQLIIIFKFSTKVPTFYHAWVQNHGAG-LFVMISSAAQLLIC 694
catT1R1     SLLALGFAIFLSCLTIRSFQLVFIFKFSAKVPTFYRAWVQNHGPG-LFVVISSMAQLLIC 694
mouseT1R3   PMAHLPLTGCLSTLFLQAAETFVESELPLSWANWLCSYLRGLWAW-LVVLLATFVEAALC 701
ratT1R3     PMAHLPLTGCLSTLFLQAAEIFVESELPLSWANWLCSYLRGPWAW-LVVLLATLVEAALC 701
humanT1R3   PLSHLPLTGCLSTLFLQAAEIFVESELPLSWADRLSGCLRGPWAW-LVVLLAMLVEVALC 696
catT1R3     PLFHLPLTGCLSTFFLQAAEIFVGSELPPSWAEKMRGRLRGPWAW-LVVLLAMLAEAALC 699
                      :  :*    :           ::.

mouseT1R2   GNMLATTINPIGRTDPDDPNIIILSCHPNYRNGLLFNTSMDLLLSVLGFSFAYVGKELPT 758
ratT1R2     GNMLATTINPIGRTDPDDPNIMILSCHPNYRNGLLFNTSMDLLLSVLGFSFAYMGKELPT 758
humanT1R2   IGMLATGLSPTTRTDPDDPKITIVSCNPNYRNSLLFNTSLDLLLSVVGFSFAYMGKELPT 754
catT1R2     -------- ---------------------------------------------------
mouseT1R1   LTWLAMWTPRPTREYQRFPHLVILECTEVNSVGFLVAFAHNILLSISTFVCSYLGKELPE 755
ratT1R1     LTWLVMWTPRPTREYQRFPHLVILECTEVNSVGFLLAFTHNILLSISTFVCSYLGKELPE 753
humanT1R1   LTWLVVWTPLPAREYQRFPHLVMLECTETNSLGFILAFLYNGLLSISAFACSYLGKDLPE 754
catT1R1     LTWLAVWTPLPTREYQRFPQLVVLDCTEANSPGFMLAFAYNGLLSVSAFACSYLGKDLPE 754
mouseT1R3   AWYLIAFPPEVVTDWSVLPTEVLEHCHVRSWVSLGLVHITNAMLAFLCFLGTFLVQSQPG 761
ratT1R3     AWYLMAFPPEVVTDWQVLPTEVLEHCRMRSWVSLGLVHITNAVLAFLCFLGTFLVQSQPG 761
humanT1R3   TWYLVAFPPEVVTDWHMLPTEALVHCRTRSWVSFGLAHATNATLAFLCFLGTFLVRSQPG 756
catT1R3     AWYLVAFPPEVVTDWRVLPTEALVHCHVHSWISFGLVHATNAMLAFLCFLGTFLVQSRPG 759

mouseT1R2   NYNEAKFITLSMTFSFTSSISLCTFMSVHDGVLVTIMDLLVTVLNFLAIGLGYFGPKCYM 818
ratT1R2     NYNEAKFITLSMTFSFTSSISLCTFMSVHDGVLVTIMDLLVTVLNFLAIGLGYFGPKCYM 818
humanT1R2   NYNEAKFITLSMTFYFTSSVSLCTFMSAYSGVLVTIVDLLVTVLNLLAISLGYFGPKCYM 814
catT1R2     ------------------------------------------------------------
mouseT1R1   NYNEAKCVTFSLLLHFVSWIAFFTMSSIYQGSYLPAVNVLAGLATLSGGFSGYFLPKCYV 815
ratT1R1     NYNEAKCVTFSLLLNFVSWIAFFTMASIYQGSYLPAVNVLAGLTTLSGGFSGYFLPKCYV 813
humanT1R1   NYNEAKCVTFSLLFNFVSWIAFFTTASVYDGKYLPAANMMAGLSSLSSGFGGYFLPKCYV 814
catT1R1     NYNEAKCVTFSLLLNFVSWIAFFTTASVYQGKYLPAVNVLAALSSLSGGFSGYFLPKCYV 814
mouseT1R3   RYNRARGLTFAMLAYFITWVSFVPLLANVQVAYQPAVQMGAILVCALGILVTFHLPKCYV 821
ratT1R3     RYNRARGLTFAMLAYFIIWVSFVPLLANVQVAYQPAVQMGAILFCALGILATFHLPKCYV 821
humanT1R3   RYNRARGLTFAMLAYFITWVSFVPLLANVQVVLRPAVQMGALLLCVLGILAAFHLPRCYL 816
catT1R3     RYNGARGLTFAMLAYFITWISFVPLFANVHVAYQPAVQMGTILLCALGILATFHLPKCYL 819
```

Figure 2D

| | | |
|---|---|---|
| mouseT1R2 | ILFYPERNTSAYFNSMIQGYTMRKS--------------------- | 843 |
| ratT1R2 | ILFYPERNTSAYFNSMIQGYTMRKS--------------------- | 843 |
| humanT1R2 | ILFYPERNTPAYFNSMIQGYTMRRD--------------------- | 839 |
| catT1R2 | ---------------------------------------------- | |
| mouseT1R1 | ILCRPELNNTEHFQASIQDYTRRCGTT------------------- | 842 |
| ratT1R1 | ILCRPELNNTEHFQASIQDYTRRCGTT------------------- | 840 |
| humanT1R1 | ILCRPDLNSTEHFQASIQDYTRRCGST------------------- | 841 |
| catT1R1 | ILCRPKFNSTQHFQASIQEYTRRCGST------------------- | 841 |
| mouseT1R3 | LLWLPKLNTQEFFLGRN--AKKAADENSGGGEAAQGHNE------- | 858 |
| ratT1R3 | LLWLPELNTQEFFLGRS--PKEASDGNSGSSEATRGHSE------- | 858 |
| humanT1R3 | LMRQPGLNTPEFFLGG---GPGDAQGQNDGNTGNQGKHE------- | 852 |
| catT1R3 | LLQRPELNTPEFFLEDNARAQGSSWGQGRGESGQKQVTPDPVTSPQ | 865 |

Phylogenetic Tree of T1Rs:

Predicted conformation of the 7TM T1R3 protein sequence from cat.
Arrow points to region of possible functional amino acid substitution.

Figure 5A Predicted conformation of the 7TM T1R1 protein sequence from cat.
Figure 5B Predicted conformation of the cat T1R2 protein sequence.
A
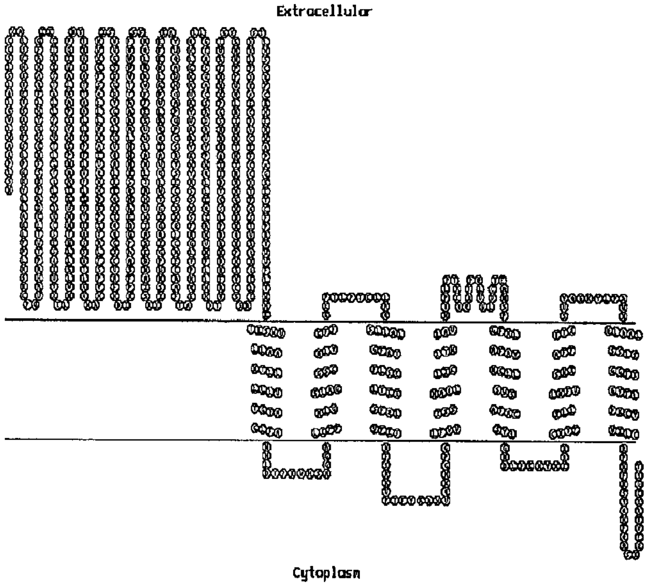
B
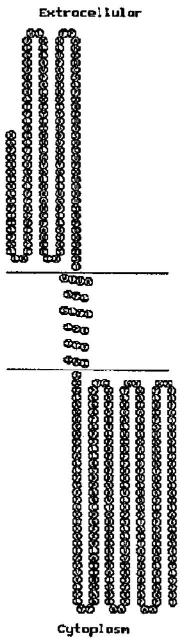

Figure 6A Genomic sequences of cat T1R1 obtained from BAC sequencing

CTGGAAAAAAAGGNGAACCCAGGATGATTCACCCCAAAATTTCAGTNTCAGAAAANTGAGGACTGGNA
GGAGGTCAACTTAAAGTCAGTTTCATTTGGTAAACTGAGGCCCAGGTAAAAAGTTCTAAAACCCACAG
CTCCCTTCCATATTCTGTCCCCCAGAGAAGCAGTGTCCCTGCCTTCCTCTGACCCCTGCCCCTCAAGA
CGCCTGGGCTCCCTTTCTGAGCCGGGTGAAGCCGCAGGCACCAGAGCGAGAACAGAACCCACAACCAT
CCAGAGGGAGGGGCAGCGGCCACCACCTGGCTTGCACCTGTGCCTTCACCCTGCCCAGTTCCTGAGTA
GGACCGCAGGCCCGGAAGGCCAAGGCAAACAGCCTGGTTCCTACGACTGGGTTCCAGCCCCACCCCTG
GCACAGGCGTGAAGTTGGGAAGCATCTGGGCAGCCGCTGTCTATTCTATTTAAACAGCCGAGCTGGTC
AGAGGGTGCCTGGCTGGCCATGCCAGGCACAGGACGGACTGGCCAGCATGTCACTCCCGGCGGCTCACC
TGGTCGGCCTGCAGCTCTCCCTCTCCTGCTGCTGGGCTCTCAGCTGCCACAGCACAGAGACGTCTGCC
GACTTCAGCCTCCCTGGGGATTACCTCCTCGCAGGTCTGTTCCCTCTGCACTCTGACTGTCCGGGCGT
GAGGCACCGGCCCACGGTGACCCTCTGTGACAGGTGAGTGAGGGGTCCCGTGCCTCTAGGACCTCTGC
CCATCCTCTGTCCTCCTCAGTGAGGATCCTTGGGTTGTTGATTGAGTGGAGTTAGGGCCTTTTAGAGA
GCTGAGACTCTAGAAGCTAAACCACGTGTTGCTTTACCTGTCTTCCACCCTGAGGATCACACGTTAAG
TGTTCTTACCAGTCAAAATTGAATATGTATCAAACAAAAATAAATGGCCTTCCATGCTGAAATAACAA
AAAACAGACACGCATGGAGAACCTACTTTGTGGGGCGCCTGGGTGGCCCAGTCGGTTAAGTGTCTGCC
TCTTCGTTTTGGCTCAGGTCATGACCTCGGGGTTCATGAGTTCGAGCCCCGCGTCAGCTCCGTGATGA
GCCTGGAGCCCGCTTGGAATTCCCTCCCCACCCCCACCCCCCGCTCATGCCAGCTCGAGCTCTCGCTC
ACTCTCTCAAAATAAACTTAAGAGGGGCGCCTGGGTGGCGCAGTCAGTTAAGCGTCCGACTTCAGCCA
GGTCACGATCAGCACATTATTTCCTGGACCTTCCATTCTCCTTTCGCTGTACAGAGCTTAACGTAAAC
TCCCTGGCAAGACCTCCTTTCTGATTTTAGAAAGGCCAGCTTATTGGTTTGGTTCCTGTAATAGCTTA
AAAATAGAATCCAGCTGTATCAGGAAACATTTAAAAAATGTATCAAGGAAGACCTATAACAGTAAAAA
TATTTTTAAATCCCAGAGTGTTTTCATAAAGACACAGGATTACATTACTCAATTATTTTTAAAGGGTT
TTTGAAAAGCCGTGTTTCACTTGCCATGGCTAATGATTATAGGCATCCGAATGAGCCTGTGGCTATGA
CTTCAGTCTGTTCGGTGGAAATGACTCTGATGTCATAAACTGACTCGGCTTCGCTGACAGGAAAGTCG
TACAGAAGAAAAGCTGTTCGAGCCCATATGTTGGTTGCGCTCAATGTCAGGAAGGGGCGACGTAATGT
GTGCAGAAATGGGCAGCTGTCGAGAGTGAAGAAATTGGGAAGTTGGCACGGAAGAGGGGACCGAGTCC
GAGAAGGCTGCTGGATAAAGCAGAGCTTTTGCAGAAGAGAAGGGCCGGCTGCTGTCCCTATCCTGGTG
GCGGAACCACTTAGAAACAAGGCGTCAGAATTAGAGACTTCGGTTCATGCAGGGAGGGCGGCCCAGGG
GGGTGGCGTCCTTGGAAACTCTGGTAAGTTTGAGATTGATCCCAGGGGTCGTGGGATGGAGCCTCGCA
TGAGACTCTACACTGATCGATGAGAAGCAGAAGCCCCTTGTCTGTGAGGAAGGGGACACGAGCAGTTG
GCACACTAAAACGCAAGGACACGTTTCTACGAGAAAACGGTACATCTGTCTGCGACACAGAAAGATCC
CCGGNACCAGTCNTCGNNNNNNNNNTTCCGNTGGGATTCCAGTCAGCAGTTCCCGAGAGGCACTGAGGA
ACACAGGCCCTCACCACGTTCACAAGTGTCCTGATGAGAGGGATACTAGGTAAACGAGGTTCGA:CAG
GTGTGGTGGTTAATTTTATACATCAACCTGGCTAGGGTACGGTGCCCAGTTGTTTGGCCAAACACCAG
TCTAGATGGGGCTGTGAAGGTTAACATTTAAACCAACAGGGTGAGTAAAGCAGATCGCTTTCCATTGT

Figure 6B

GTGGGTGGGCCTCATCCAATCAGTTGAAGACCTTAAAAGAAAAGATTGAGGTCCCCCCAAAAAGGAAG
AAATTCTGCCTTCGAACTCAACACTGCAGCTTTGACCACTGAGAGCATTTCCAGCCTGCCCTGCAAAC
GCCAGACTCACCAGCCCCACAATCATGTGAACCAATTCCTTAAAATAAACTTCTCTTTCTCTCTCTCT
ATCCAACTGGTTCTGTTTCTCTGCAGAACCCTGACTCACGCAGCAGGTTTCCCTGCTACAGGACTTCA
TCAGCCTTTCAACCCTAATATGCTCATCCAGGGAGGAATGGTTTGTGGTTTCTCCAAGTTGTAACCGC
CCCTCCCCCCCCGCCCCCGCCCCCCCAAAGGCCTGTTAACACAGCTGAGTGTATGGTACAGGGCCCAC
AGTGAGGTCATGGTGGTAGGGGACGGGACAGATGCCCTCAGAGTTTCCTTTCTACCCTTCCCCCCACC
CCCGACGCCAAGAGGGTCTCGGCAAGGCCTTGCTCCTCTGAGCTCTCAGCTGGGCTTTCTCTACAGGC
CCGACAGCTTCAACGGTCACGGCTACCACCTCTTCCAGGCCATGCGGTTTGGCATCGAGGAGATAAAC
AACTCCACGGCCCTCCTGCCGAACGTCACCCTGGGATACCAGCTGTACGACGTGTGCTCGGAGTCTGC
CAACGTGTATGCCACACTAAACGTGCTCTCCCTGCTGGGACACATCACGTAGAGATCCGAGCAGACC
CTTCCCACTATTCGCCTGCCGCCCTGGCTGTCATTGGGCCTGACACCACCAACCACGCAGCCACCACT
GCAGCCCTGCTGAGCCCCTTCCTGGTGCCCCTGGTGAGCTGGAGCCCGGGGGCCTGTCCATCTCCCCT
GCCGGCAGGTCCAGTGTGGGCTGAGGGGGTGGGGGGGTGGGCAAGAGCTGCCATGCCCACTCTGAGTC
TCCTGGGTGGTCACATTGCAGGGGGCCCTGCCCCCTTCACAGTCCCCGCCCCAGCATCCCTTCCTCCC
CAAGTGCTGCATCCAGACCTCCCTGCCTCAATGTCCTGAGAAAAACCGTCTCCTTTGAAACTGCTGCC
CTTTGCTCTGCCCCCTCCATTCCATCTCCTCTGTGAAGAACGGAACACCCTTTGTTTCCCACCTCACA
CACTTGTCCACTTCTCCCCGCCCTCCTCCTTCCGGTCTTCCTTCCCTCCCTCCCAGCTCAGGCTCAGA
GGTGTGGTCCCCCTCCCCCTCCAATGCCGTCCTCCTGGGCCTCACCCTCTCCTCTGCTCGTAGGCCTG
TCCTAGGCTTCCTCCTCCGCCTATAAGCTGGCTTTACCCCTCTCTGTCTTCCAGGCACCTGTGGTCTT
AGCGCTGCCCTCTCTCTGAACCTCGTTCCGTGGAAACTTGTGCACTGAGCTCTCTCTTCTTGTTTGCT
TCTCCCTCTCATCACTTGCTTCCCGGGCCCCTGCCCTGACTGCTGCACCACCACTCCTGCTCTTGTGA
TCTCCAGGGCTTTCTAGATCTCCAGGTCCAGCAAATGCTTTTCAGCCCTTCTTTGCTTGACATGACGA
CTTTGTGACAAATTTGACCAGTCCTTCAGTGACGCTCTTGCCTCGGCATTTATGACCTGCCACCTCCC
TCTCACTTGTGGTACCTCCTTCTCAGTCTCCTTTGGAGAATCTCCTCCCCCCCTCTTCTGAAAAAGTG
GATGATTCCCCGAGTGCAGGACCACTCCCTTTCCCAGGCAGGTGCTGGGAGCAAACAACTTTCCCTAC
TCTTCAAGAATCTTTCTGGCTGGTCTAAAAATAAGTTGATGTGACACAGANAAAAGGAAAAGTCAAAT
CACGTATGTACAGGGANCTACNAAACACGAAAGGTCAAGANAGGAAAGNGAGGCTANCTGCTATCTGA
ACTATGAACAAGGGNAGGGGTAAATTCAAGGAAAGAAGAAATCANAGAAAGAAGAGGNANGGTATAAA
AGNTGCTGGCCATCAAAAATGGAAGGAAGAATTANAANNGATTGGAGNNNNNNNNNNNNNNNNNNNNNNN
NNNNNNNNNNNNNNNNNNNNNNNNNNNNNNNNNNNNNNNCTTTTTCCCGTCACCGGTGGCCAGGGTTAAA
TTCAGGCTGCCAAGCTGTTTTTTGGGATGACTCCAGCAGTCTCCTAGGGAGTTCTTCCTGACTCTGGT
CTTGAGCCTTTTCTAACACATTCTTCACTGAAATCAGATACACCCCTGAAACACAAGTCTGGGCAGAT
TACCTCTCTGCCTAGACATTTAAGGGGCTCCCCAGGGCCTGCAGATAAAGACCAAGTATCTTAGCTAT
CTTGGTGCCAGGAGTAAGGCCTCCTGCCCTGACCAGACACGCCTACTTTTGTGCTCCTTCTTCCGGCT

Figure 6C

TCCAACCTCCTGGGTCAGTTCTCTCACTGGGTGTAGCTTTTGTTCTCTTCCCCTTCTTCTCCCACAAA
CCTCCCCCTGGGTTTCTGCCTCTTCTTTAGATGTAGCTGGTCGGCCTCCTAGTCCACCAGAGCTGTCC
TTGAGAGCCAGGGCTGGGACCATGTCTCCCTCCTCCTCGGGTCCCCGCGCCCAGCACAGGGCCAGCAC
TTGGAGGCTCTGAGTTGAGGCCAAGGCCACTGAAGTCGCTGAACTGAACCCCCCCCCCGGCCCCCCTC
CGCAGATCAGCTACGAGGCCAGCAGCGTGACGCTCGGAGTGAAGCGGCATTACCCCTCGTTTCTGCGC
ACCATCCCCAGCGACAAGCACCAGGTGGAGGCCATGGTGCTGCTGCTGCAGAGCTTCGGGTGGGTCTG
GATCTCGGTGGTCGGCAGCGACGGCGACTACGGGCAGCTGGGGGTGCAGGCGCTGGAGGAGCAGGCCA
CCCAGCAGGGCATCTGCGTTGCCTTCAAGGACATCATCCCCTTCTCTGCCCGGCCGGGCGACGAGAGG
ATGCAGAGCATCATGCACCACCTGGCCCGAGCGAGGACCACCGTTGTGGTCGTTTTCTCCAGCAGGCA
GCTGGCCAGGGTGTTCTTTGAGTCGGTGGTGCTGGCCAACCTGACTGCCAAGGTGTGGATCGCCTCAG
AAGACTGGGCCATCTCTAGACACATCAGCAATGTGCCCGGGATCCAGGGCATTGGCACGGTGCTGGGT
GTGGCCATCCAGCAGAGGCTTGTCCCTGGCCTGAAGGAGTTTGAAGAGGCCTATGTCCAGGCAGATAA
GGGGGCCCCTGGGCCTTGCTCCAGGACCTCCGAGTGCAGCAGCAACCAGCTCTGTAGAGAGTGTCGGG
CTTTCACGGCAGAGCAGATGCCCACGCTCGGGGCATTCTCCATGAGCTCTGCTTATAACGCCTACCGG
GCAGTCTACGCAGTGGCCCATGGCCTCCACCAGCTCCTGGGCTGTGCCTCTGGAGCCTGTTCCAGGGA
CCGAGTCTACCCCTGGCAGGTAAGGTAGCCCAGACCCCGGCACCCTGAAACGGGGTGCTTTCCTAAGG
CAAACAGAGTGATCCCTCTCTGGCCAACTGAGTGCTGGGGGTGGGGGACAAAGGCCACCCATCAGAAG
GCTAATTCCTTCTCTTGGGCTTCACTTCTCTGACCTCGGCCCCTCCCACCACCATGCTCCAGACCCAG
GGCTAAAAATCTCTGGGAAACGGGCCTTTTTAGAAGCTTCCTCTCACTCAGGAGGCCAGTTGGGAGGG
TCGAGGGGCTTCCTTGGAAGGGAGGGGGCTCTGAATTTCCAGACAGACTGAAACCACCCAAATAGAAG
CATTTGCTTCCTAAGCCTTCCGGGTCTGGGAGAGTTGAGGAGGAGCAGCCTGCGTCATCTGTGGCTGC
TCCATGATCCCCGTTTATCTCAGCTTCTGGAGCAGATCCGCAAGGTGAATTTCCTCCTACACAAGGAC
ACCGTGAGGTTTAATGACAACGGGGACCCTCTCAGTGGCTACGACATAATTGCCTGGGACTGGAGTGG
CCCCAAGTGGAACTTCAGGGTCATTGGCTCCTCCATGTGGCCTCCAGTTCAGCTGGACATAAATAAAA
CCAAAATCCGGTGGCACGGGAAGGACAACCAGGTAATGGAGCCATGGTCACTCACCAAGTCACCGCCT
TACGGGCAGCCTGGAGCCTGAAGTCACTGTCGACACAGCTCACACGGAGCAGGAGGGGGCCCCGGGTG
CCAGGCCAACGTGGCTCTATCCAGCCCTGCCAGGGAAGCCCCACAGACCGCACCCAGATGGCCGGCTG
CAGCTGGTATACACAACCAGGGGCTGTGCCCTGGGAGTGAGCTGTGAGGGCAGATGCACGGAGACTCC
CATTCGCCATGTGAGCATCCCTTGACTTGGGCCACTCCATGTGGTTCCAGAACACCTGTGGCTTCTTG
CAGGTGCCAAAGTCTGTGTGCTCCAGCGACTGCCTCGAAGGGCACCAGCGAGTGATTTCGGGTTTCTA
CCACTGTTGCTTTGAGTGTGTGCCCTGTGAGGCCGGGAGCTTCCTCAACAAGAGCGGTGAGTGTCCAA
ATGAGTGGGAGAATGACTGGGCACTCCCAGGGTCTGTATGGCAGATGAGGGGATCTCCCTTGGGCCAC
GCACGTGCAGAACCAGAGCCTTGCTCCCTCTGTTGCCAGTTGAGGTACAGGTTGTAGAATATTTGCCA
CCAGACTGAGTTCTGATGAAGCAGAAACCAACAACCAGTTGAAATCCTCAGGTCCCCTACGTCTTTTA
CTAGAGGGCTCCTGATGCAATCCCTGCAGATGCAATCTTATCCTAAATTCAACCTTTTTATGCGAACA

Figure 6D

```
GATGTAGTTATGTTCCCTTGTCCCCTCCCATGCTGTCTGTGTGAAGTCCCTTCCGTCGCCCCTGCCAA
AGACAGCCAGCACCTTGGACAGCTTGGCCTTGATGCAGATACTATTGTATCCGCAGACAAGAAACATA
GCATACTCCACCCAGTGATGGTGCAAGGTCAAGATCAGAGAGCAAACTCAGGTAGCTAAGGGCTCAGC
CCAGAGCTGGACTCTGTGAGCCACGTTCTTTCCTTTTACTATCTCTGTGGGCGTGAGAACACATCTCT
TCTGTTCTCAGAGAGTCAGAGAAACCACAGAATGGCAGCACAGATAGGGGGCTTTGGGTAATGGAAGC
GCTGGGGAGATGAAAATGCCCTTCCTTTGGGGCTGGTTGCTCCTGTTGGATCATAGCCTCACTGGCAT
GTGGGCAGAGCTACCAGAGTAAGGCCCTCTCTAAGGATCTCTCGGTTTGCAAGCCCCTTCTGGGATCA
TAAGCCATACAGAACCTACCCAAGGGTCTCCAGAATCTGCAATTAACACAGGCATCTGGAGGAAACAC
TTGGCCGCGGGGCCCCACTCAGGGCTACCCCCTATCTCGCTGTGTGCAGTAGGAGCCCGGCTTCTGGG
GTACAGCGCTCCCAGCACCTTGCAGGCCTACATGGCTTCCCTTCCTCATTCCTGCTCTGCTCATCTAG
GCTCTCAGGAGCCCCCTCCACCTTTTTCTTCCAGACCTCCACAGCTGCCAGCCTTGTGGGAAAGAAGA
GTGGGCACCCGCGGGAAGTGAAACCTGCTTTCCACGCACCGTGGTGTTTTTGACTTGGCACGAGACCA
TCTCTTGGGTGCTGCTGGCAGCTAATACGTTGCTGCTGCTGCTGGTGACTGGGACTGCTGGCCTGTTT
GCCTGGCACTTAGACACCCCTGTGGTGAAGTCCGCTGGGGGCCGACTGTGCTTCTTCATGCTAGGCTC
CCTGGCAGGGGCAGCTGTGGGCTCTACGGCTTTTTTGGGGAGCCCACGCTGCCCACATGCTTGTTGC
GCCAAAGCCTCCTTGCCCTGGGTTTTGCCATCTTCCTGTCCTGCCTGACCATCCGCTCCTTCCAACTG
GTCTTCATCTTCAAGTTTTCTGCCAAGGTACCCACCTTCTACCGTGCCTGGGTCCAAAACCACGGTCC
TGGCCTATTTGTGGTGATCAGCTCAATGGCCCAGCTGCTCATCTGTCTAACTTGGCTGGCGGTGTGGA
CCCCACTGCCCACCAGGGAGTACCAGCGCTTCCCTCAGCTGGTGGTGCTTGATTGCACAGAGGCCAAC
TCACCGGGCTTCATGTTGGCTTTCGCCTACAATGGCCTCCTGTCCGTCAGCGCCTTTGCCTGCAGCTA
CCTGGGCAAGGACCTGCCAGAGAACTACAACGAGGCCAAATGTGTCACTTTTAGTCTGCTGCTCAACT
TCGTGTCCTGGATTGCCTTCTTCACCACGGCCAGCGTCTACCAGGGCAAGTACTTGCCCGCGGTCAAC
GTGCTGGCGGCGCTGAGCAGCCTGAGTGGCGGCTTCAGCGGTTATTTCCTCCCCAAGTGCTACGTGAT
CCTGTGCCGCCCAAAATTTAACAGCACACAGCACTTCCAGGCCTCCATCCAGGAGTACACGAGGCGCT
GCGGCTCCACCTGACCAGTGGGGCGGGCAGGGCCTAGCCGGGGAGGTGGGGGGTGGGGGGTGAAGGGG
TAGAAGGTGGGGTAGGGGCGCCTCCCCTGCCCTGAGGGTCGAAGGTCGAGCGAGGCGAGCGGGCCCCG
CGCCCTCCGGGAGGCCTTTTGGACTCCTGTCTTGGCTCGGGTAGTGTACGCTCACGGGAGTCCAGTCC
AGGCTCCGAGCTGCCAATAAAGCGGTGAAACATGCGTCCTGGCTGCTCTAGCTGTCTGAACCGAGGGT
GGGGCG
```

Figure 7A Genomic sequences of cat T1R2 obtained from BAC sequencing

TTAGCTGCTGAAACGCTGCTTTTTAGCAAAAGGCCGTGACCTCATGATGTTATACGTCGTGGAGATTGA
GAACCAGGTCCTAGCATCTGACTATGTGCTTTGAGTCCCCACTTTTGCTGGTTGTGCAACCCAGGGTGA
GCTTCGTAAGCTTCTCTGTGCCTCAGTTTTCTCATCTGTGGAATGGGGCCGGTCATAGTCCCCGTTATT
GTGATCATCGAGCAAGATGGTGAATGGCGAGCACACAGCATGATGCCTAGTTCTTACTGGAACACCTGT
CCTGGGTCAGGGGCTGTATATAAAGTACTACCTGCCAGGATCAACTTGATCCGGTTCTATTCTGTCTCC
TGGGTGAGTATCTGTGCCCTTTACTCCCAGATGTTGGAAATGTCAGGGGCATGAGACCTGTCCTTAACC
GAGTGGCAGAAGGTTAAGTTTGTGTCCGAGATAGCAGGACATGCTTTCTCTACCTCCGCAGGGCGTTCT
CCCAGACCCCCCAGGGCCCACCATGCCCTGCTAGGAAGGGATCATCCTAATTCTAGCCTCTTCTTCCGC
CCCAGAGTTCTGAAGCTTCTCCACCTGTCCAGGTGTTTCCCCACCCCTTCAGCCACGGCAAGACCGTCA
CTATGTAAATGTCTGTGCAAATCCCCTGGTGTCAAGCTGCCAGCTCTCTGATGAGGCAGGGCCACCTCC
GGGGACCCCTCACTTCCCAGCCATGGGACCCCGGGCCAGGGAAGTCTGCTGCTTCATCATCCTGCCGCG
GCTCCTGGCTGAGCCGGCTGAGAACTCAGACTTCTACTTGGCTGGGGATTACTTCCTCGGCGGCCTCTT
CACCCTCCATGCCAACGTGAAGGGCATCGTCCACCTCAACCTCCTGCAGGTGCCCCAGTGCAAGGAGTG
AGTCGCCAATGTGGGGCTGGAAGTGGCGACGGGGGCGGAGTGGGAAGCCTGGGCTGGTCCTGTGCTCCT
CAGGGGACCACGCCAGGACCAAGGGCTCAAAATGCTCTTCCTCATTCATTGCCAACCTCTCATCCCGCA
TTATCCCCACCGGCCTGCAGGGAGACCCCATGCAGTTCATGTTACCAAAATCTTTGGCAATTGTATTCT
GAAATATGGAGAGCTGGTTGTCCCGCCGTGTGTCTTAATAAATAAAGAGTTACAGGGTACTTGAGCCTG
GAGGGGTTGTAGAGACCACCCCCACCTACTTTGTCAAGTGGGGAACTCCTACTGAGTCCGTGTCAAGTC
CAAGTCTAGACACCGGGGGTTATGCCTTTGGAAGGCAGAAATGTGGTTTTTCGGTAGCAGGTTCTCAGA
CTGGAGGGGAAGGTTTGCATTTCTCTAGGGCTGTGGTTAGGTGGGAAGGGGTGCTTCCAGGACCAGAAG
GGATTTCCTCCACTCACCTTGTCCCCTGTGAGCCCTGGGGGTGGCTGCATCACTCAAGGTTGGGTGAGA
CACCTTTGTGCAAGTGCGAAGGCTGGGATGGCGGACCCAGCGTGGGATGATGAGATAGTGACTTGCTGC
AGAGAGGGTGAAGGCGTCCTGTGAGAGAGGGAGAGAAAAAAGTCTGTGACGTCGGGGAAGATCACATGC
TGGCTTGAGAATGACGNNNNNNNNNNNNNNNNNNNNNNNNNNNNNNNNNNNNNNNNNNNNNNNNNNNNN
NNNNNNNNNNNNNNNNNNNNNNNNNNNNNNNGATGTGGAGGTGATRGTGATGGCGGTGATTGTGACGGTGGTA
TCGGTGATGGTGGTCACAGACAACGCAGTTATAGTGATGGCAGTGGTGATAGGAATAGTAGGTGGTGAT
GGTCATTCTGGAGATGTGGCAGGTGACAACGATGAGATGAAAATGCCAGAATCTTCTGGAGTGGCTCCT
TCTTGAGCCACTCCTCGGCTTTCCTATGGCAGGCAGAGGGGACTCCCCGGCTCTCCTGTCCCTTCCCCC
TCTCACTCTGGACCTGCCTCTCACCCCACCCCACATGGCTCCCCCAGGTATGAAATAAAGGTGTTGGGC
TACGATCTCATGCAGGCCATGTGCTTTGCAGGGGAGGAGATCAATAGCCAGAGCAGCCTGCTGCCTGGC
GTGCTGCTGGGCTACAAAATGGTGGATGTCAGCTACATCTCCAACAATGTCCAGCCCGTGCTCCACTTC
CCGGCAAAGGAGGACTGTTCCTTGCCCATCCAGGAGGACTACAGCCACTGTGTGCCCCGTGTGGTGGCT
GTCATTGGTCCTGGCAACTCTGAGTCCACTGTGACTGTGGCCCGCTTCCTCTCTCTCTTCCTCCTTCCA
CAGGGGAGGCCCCTGGGTCCTGGGGTAAGGAGCTGGGGGGCAGAGGAGTGGTTATCCAGGGGGCTCACT
TCCCCCCACCGGTCCTGGGGGTAGGAGGAGGCAGGAAGTAGGGTCAGAATGTCAACCCCAATCCTRGGA
AGGCAGCCCAGCCACGTGGTTAAGAGCTCAGGCTTGGAGGCAGACAGACCKGGGNNNNNNNNNNNNNNN
NNNNNNNNNNNNNNNNNNNNNNNNNNNNNNNNNNGCCTTCAGAGAGATCATCCTNTCAAGGGGGCCCTTAT
TCCTTTNCCCCTGGGAGCCCNTCAGTNCCCACCACTTTCTGCAGCNCCCATTCGGGTCTCCGATTCCTC

Figure 7B

CAATCCACTCACTCGCTGTGTGGCTCTGGATAAGTGACTGTCCCTCTCTGAACCTCAGCGTCCTCATCT
GCAAAGTGGAGACATAACAGCACATCAGAAGGTCGCGAGAATAGGGGCGCCTGGGAGGCTCAGTCGGTT
AAGCATCCGATTCTGGGTCGCGGCTCAGGTCATGATCTCCCGGTTCGTGAGTTCAAGCCCCGCATCGGG
CTGTGTGCTGACAGCACAGANCCTGCTTGGGATTCTGTCTTCCCTTCTCTCTGCCCCTCACCTGCTTTT
GCTCTCTCTCTCTCAAAATAAATAAATAAACTTTTTAAAAAAAAGGAAGGTAGTGAGAAAAAAGCGGGT
GACAGAGATGGAGAGGGCTCCACGCGGTACCTGGCATGCTGCGAGCCCTCAGAACCCGTTAGCGACGGA
AGTGACCTGTGTGCGTCGTCACCACCATCCCAGCAGGCCTTGAGGCTTCGACCCTGCCTCCCCCGCAAA
GCTCACAGTCTCCGAGGCTCCGGGCCACGTCCCCCGGGCGTCCTGTCTGTGTCCCTCGAACCCCGCCCA
GCCCTGCCGCACCGTGAGCTAGTCAGCGCCTGCTGGGTTCGTGACTCTCTCCGCCATTGTGCACCCTGG
GGCTGGGGCCACACCCAGGGGCTCCGGTTAATTTAGATGCTTTCTTTCTCTGCCATCTGCTTACCCCCG
AGCTTGGTTAGAGAGCCTGACTTTGCTGGGAGTCTCCAGAACGTCCCGGGACCTCCCAGCAACCAGCAT
CTTTATTCTCCCTCCTTAGAACTGATGTGTGCAGTCGCTGTGCCTCTGCAGCTCAGAGCAGGGGTGGTT
CCTGTGAACTGGGGCCAGGGGTGGTTTCCTGGAGGGGGCAAGGCACCGACTAGCCCTCGAAGAAGGAGC
CGGGCTTGGCTGAGGTGGGACAGGGGGAGAGCATGAGGTTTTCGGCCAGCTTTCTGTGCCTGGGAACCC
CCTCTCCCCACAACCCTGGATCCCAGAGGCCTTAACGGGCCCCAGCTGTAACAGACTCGTCTGTGTCGA
GCATTCCACAGTAGGTGTCCCCAGGCTCCCTCGGGGCCACCAAAGGACCACAACGACATTACGCGGACA
GGGTCTCAGATTCCGATGGGTCCCCTGTTTGCTGGAACCATCTCCCTTTGGAAATTTACAGCTCTCTTT
TCTGGCAGTAACCCCGCCCCTTGGTGCTGGGTACGAAGGGGGCACCCAGAGCGGGGCTCACCCAGCAGC
GCTGACTGCTGCGTTGTCGGGCTAACGGGTATTAACCGCCTCCCTCGCCGCTCCCATTCTCTTAGCTGC
TGAAACGCTGCTTTTTAGCAAAGGCCGTGACCTCATGATGTTATACGTCGTGGAGATTGAGAACCAGGT
CCTAGCATCTGACTATGTGCTTTGAGTCCCCACTTTTGCTGGTTGTGCAACCCAGGGTGAGCTTCGTAA
GCTTCTCTGTGCCTCAGTTTTCTCATCTGTGGAATGTGTGAGGGGCAGACCTCACTTTCAAGCGGGGTG
GCCAGGAGGGCCTTTCTGACAACTGGACAACGACCTGAGGGAGAGGAAGGAGTGAGGGAGCTATGTGGG
TGCCTAGAAGAGCGCTCCGGAAGAGGGGGCAGCGAATGCAGAGGCCGGCAGGAGCCTGGTGCGTTGGCT
GAACCGGTGAGCAGCCCCGGGACCAGGCGGGACAGTAGGAGAAGATGAAGCCAGAGAGGTGAGGGCCGG
GGTCAGTGGTGGAGCCCCTTGGGGGCCACTGAAGGACTCTGGCTGTCCTCGAGTGACATTAGGAGCTGT
TGGGGAGTTTTGAGCTGAGGAGTAAGGTGACGGACAAGTGGTCGCAGAGGCCACCCGGCTGCCACGAAC
AGCAGCAGAGACAGCCAAGGGGAAGGGTGGGGGGCTGTGGTGACCCCGGGAGGGTGGTGATGGTGGCCC
GGTGAGGCCCTAGCTCACGCTGGCGGCCCTCCGCTCTCCGGCAGATCACCTACAGCGCCATCAGTGACG
AGCTACGGGACAAGCAGCGCTTCCCGGCCCTTCTGCCCACAGCGCCGGGCGCCGATCACCAGATCGAGG
CCATGGTGCAGCTGATGTTGTACTTCCGCCGGAACTGGATCATCGCGCTGGTGAGCAGCGGCGACTGCG
GCCGCGACGACAGCCAGCTGCTCAGCGATCGCCCGGCCGGCGGCGACACCTGCATCGCCTTCCGGGAGA
CGCTGCCCATGCCCCAGCCCAACCAGGCGGTGACGCAGTGGGAGCGCCGGCGCCTGAAGGCCATCGTGG
ACGAGCAGCAGCGGCAGAGCTCTGCGCGCGTCGTGGTCCTGCTGTCGCCAAAGCTGGTCCTGCACAACT
TCTTCCGCGAGGTGCTCCGCCAGAACCTCACGGGCGTCGTGCGGATCGCCTCCGAGTCCTGGGCCATCG
ACCCGGTCCTGCACGACAGGCCCACGCGCTGCACAGCCTCCTGGGCTGCACCCAGACCAGCAGCTCCGG
GTCGTCTATCCCTGGCAGGTGAGGCCCCACCCACGGAGAGTCGGGGCCACACACGCAGGCGCCGCCACA

Figure 7C

GCCCTGAGTGGTTGCCATGGAGACCACTGCCCTGCTCTAGCGTCCCCCTCTCTGGCCGGGTCCTGGGCA
AACTGGCGGGAGAGGCCAGGGGACGTACCCTGTCCCCAGACACATAAAGCCAGAAGTGCTTCATGGTGA
CAAAACTCCTTTTTTTACATTAATGTAATCCTCGCCATCCAAGATAGCCTGTCCCGGCAGGAGATTTGG
GTGAAGTTTCCTGGAAGGAGGCCTGGCAGGCAGTGGGCCCCCTGGCCCCCCTGCCGTTTCTCCAGGGTG
GCGGCCTTGGGGGAGGACTTCTGTGTTCAGCTCTCTGAGGCTCTGCTTTGGGTTTATGCATCTTCTCTC
GTCCCAGGTCTGGACGATTCAGAGGAGTAAGGAGGCAAGGAGTCGCCTGGATTCAGACCTGGAATTTAA
ATCTGTATTTTTCTGATCTGCGTGCACACCCGCGCGTGCACACACACACACCTAACCACGAAGTTTATG
TAGGTAGAAGATTTTACTGAGGGGGCGCCTGGGTGGCTCAGTCGGTTAAGCGTCCGACTTCAGCCAGGT
CACGATCTCGCGGTCTGTGAGTTCGAGCCCCGCGTCAGGCTCTGGGCTGATGGCTCNNNNNNNNNNNNN
NNNNNNNNNNNNNNNNNNNNNNNNNNNNNNNNNNNNNAGCACCCCGAGGGCCCGGGGGAGGGCACCTGAGCC
CGTAAAGGGAAACAGGAGTGGCCTCTGAACCCAGGTGATAGGTCTCCGCTGGATGGCAGACGTGACTCC
CACGGGAGCAGGAATAATGTCGACACATCGGCCGGAAGGGGAGCACTTCCTGGTGTGCAGTCATTGTGC
TAAGCTCCCAACATTGGGAAACTCATGCGTTGCTTCAGAGCCCGGGAGACAGGGTTTTTGTTGTCCTAC
TTTACAGAAGAGGAGACTGGAGCTCACGGGGGTTGGGCGACAGGCCCGAGGCTCAGAGCAGGTGGCAGA
GCTGGTGCCTGAACCCAGGTGTGTCTGACTACAGAGCCGGGGCTCCCAGCCGCTGCCTCCCGGGTGACC
ACATCTGCGGTCTCATTGCCCCCTTGTAGGGATGTGGACACCCAGTCTCGTGGGGTAGTCACTCTCCCC
CGGATCGAGCCCGACTTCTTTTTTTTTTTTTAATTTTTTTTCAACGTTTATTTATTTTTGGGACAGAG
AGAGACAGAGCATGAATGGGCGAGGGGCAGAGAGAGAGGGAGACACAGAATCGGAAACAGGCTCCAGGC
TCCGAGCCATCAGCCCAGAGCCTGATGCGGGGCTCGAACTCACGGACCGCGAGATCGTGACCTGGCTGA
AGTCGGACACTTACCCGAATGCGCCACCCAGGGGCCCAGATCGAGCCCGACTTCTGACGCCAGCGTCGC
TTCCTTTCCCTGTGGCCTCCCAGCTGCTTCAGGAAATCTGGAAGGTCAACTTCACCCTCCTGGGCCACC
AGATCTTTTTTGACCAGCGAGGGGACCTACTCATGCGCCTGGAGATCATCCAGGGACGGTGGGACCTGA
GCCAGAACCTTTCTGGAGCGTCGCCTCCTACTGCCCGGTGCTACGACGGCTGAGGGCCATCCGTGACGT
CTCCTGGCACACGGCCAACAACACGGTCAGCTCTCGGAGGGCTGGTGGGGGGCTGGGACCTGGGTCTGG
GCACTGGCTCGTGCAGGGGTGGCAAGGGCCCTGTGGACCTGAGATCCATTATCGAGCACTGATGTCATC
CCTATTTGTGGGTGTCCCTCCTCCCATTGACTAAGCACTGTGGAAGTCTAGAGCTTTCTGGATCCTCAG
GACCCAGGGGCTCAGGGGGCTGCACAAAGTGAACGTTAGGTGGACACGTGTGTGCTAAGGACTTCAATT
CTCATGTCAACCCTAGGAAATAGAGAGTACTGTTCCTCCTGTCTTTGGGGTTGGGAAACTGGAGGCACA
GAGGGGGTCGCGTGACCCATAAAAGGCCACACAGCTTTCGCATGTCTCTATACACAGCATTCAGTCTAC
ATCCCATCGATTAGTACTCGCGTTTTGGGGACAGTAGCTGTGCCTTCACCTGTGTCTGACATCTGTCAG
TCTGAAAGCTCCTTTGTTTTACCCTCTTAGCTTACAAGCTGTCAGAATGGCCGCGATGTGGGGAAGGTA
GAGACTCAGCCTCGTGGGGAAGGGGGGAGGTGGGGGGACCTAAAAGTTCAAAGAGCCAGGGCACCTGGG
TGGCTCAGTCAGTTAAGCATCCGACTCTGGATCTCAGCTCAGTCTTGATCTCAGGTCGTGAGTTTAGAC
CCCTGTGTAGGGCTCCGTGCTGGGCGCGCAGCCTACTTAAAAATAATAAAAACAAAAGCNNNNNNNNNN
NNNNNNNNNNNNNNNNNNNNNNNNNNNNNNNNNGATCCCCGTGTCCATGTGTTCCAAGGACTGCCAGCCT
GGGCAAAGGAAGAAGCCCGTGGGTATTCATCCCTGCTGCTTCGAGTGTCTCGACTGCCTTCCGGGCACC
TTCCTCAACCAAACTGCAGATGGGACTCACAGACCCACACCCCTGCCCTGCCCTGCCCTGCCCCGCCCT

Figure 7D

GGGGCTCCCAGGGCCCTTCATCTTTGGCAGGGTCTCTGGAGTCTCATCCAGGGGACACAGGTGTCCAAA
GGCCAGGGACCATGTTTTGACTCCGCTTGTATCTCCCTAACCGCTGGTGTAAGAAAAATCTTCAATGCT
GTGAGGGCGTGGGGGTGGGAGAAGGAACAGCCCTCAACCAGGCGAGGCTGTAACTGATCCCCTCTGCAC
ACACATGTAGCTGAGGGCCCAGGGGGGTCAGGCCAGAGAATGTCCACCGGATGAACGAACGAATGAATG
AATGAACGAACGAACAAACACACAAATGAATGAATGTCTCTGTCCGTAGAAGAAATGTTTCTGGCAGAC
AGGGCTAGGATCTAATTTCTCTCTGTGGCCTCCCGAGTGCCTCGTGTAGTTCGGAGCATATAATGTTTG
CTCAGTGAATGTTTATTGAGTGACATCCTTGATGAGAAGAATTGACATCTCCCCCTATAGATCATAAAC
TCCAGGAAAGGGGGGACAATGTCATCCCTCCAGTGTTTACCACAGTTCACCGTTGGGGCCGAATTATTT
TTTTTTCATGACTTCACAGATTAGTAACTAAGCGGTTCTGTACATCTACCGATCAGAGTACTTACGACG
TGCCCAGCAGAGCCCAGGGCACAGGGTAGGTGCTCAACAAAAGTTTGTTTGCAATTGATCAGTAGCCGG
AAGTCAGGGGGCTCGGTTTTATCCACGTCTGTGCTCTCCATCTCAGATGCCTATCACAGTGGGTGGCGC
TCAAAAAGAAACTTGAATAAACGGTCGAATGTCCATCTCACCAGAGGGTACGGTCTTGGAAGGGAGGCA
TTACGGTTGCCAGGCTCTGAGTCAAGGGGACCTTGGACCACATCCTGCCTCTGTAACTGGTTTTGTAAC
NGCCTGGAGGAGCCTCAGATGCCACATCTGTGAAATGGGGTTGCAGTGAGGATCTGATGGGCCGGTGGA
TACGAGGGACGCAGTGAGAGGTGCTACGACCGCAGGCATCGCCCTTGGCTCGCCCCCTCCCTACCCCTA
CAGCCGGCCGGGTGCAGGTGCAGAGGATGTGGGTGCCGGGAAGGTGGGTGTATCTGATGGAACTGCTGT
GGGCTCTTGCAGACGAGTTTGGCTGCCGGCCCTGCCCGAGTTGCGGGTGGTCCCGGAGGAACGACGCTT
CGTGCTTCAAGCGGCGGCTGGCCTCCCTTGAATGACGCGAGGCACCCGCCGTCGCTGTGGCCGTGCTGT
CCATCCTGGGCTCCCTCTGCACCCTGGCCATCCTGGTGATCTTCTGGAGGCACCGCCACGCGCCCATGG
TTCGCTCGGCCGGGGGCCCCAGGTGCTTCCCGATGCCGATGCCCCTGCTGTATAGGTGACGGTCTCCAT
GTACATCGGGCAGCCCGCGTTTTTCATGTGCCTCGGCCACCAGACCCTCTTCACCCTCTGCTTCACCGT
CTGTATCTCCCGTGTCACCGTGCGCTCTTTCCAGATCGTCCGCGTCTTCAACATGGCCAGGCGCCTCCC
GCGTGCCTACGGCTACTGGGTCCGCTACCACGGGCCCTGTGTCTTCGTGGCGTCCTTCACGGTGCTCAA
GATGGTCATCGTGGCGGGCAACGTGCTGGCCGCGACCGCCGAGCCCGCCGCCCGCCCCGACCCCGATGA
CCCCAAGATCCGCGGTTCTCGCCTGCAACTACCACAACGTGCTCCTGTTCGACACCAGCCTGGACCCGCT
TCTGTCCGTGGCGGGCTTCGGCTTCGCCTACGTGGGCAAGGAGCTGCCCACCACCCACAACGAGGCCAA
GTTCTTCACCTTCCGCATGACCTTCTACTTCACCTCTTCCATCTCCCTCTGTACCTTCATGTCTGTCTA
CGAGGGGGTCCTGGTCACCATCCTGCACCTCGTGGTGGCAGTGCTCAACCTTCTGGGCGCTTTGGCCCC
TGGGCTACTTCGGCCCCAAGTGCTGCGTGGTCCTCTTCTACCCGGATCACAACACGCCCGTCTACTTCA
GCAGCATGATTCAGGGCTACACCACCGGGAAGGACTAGCACTGCCCCCTGGCTGCCCAGGGGGCCAGAG
GGCTCGGTACTGGGAGATGGAGACCAGGGGTGGGGCTGGGGGTGGTGGTGACTCATTCAGCCCCTGCTG
GGAGCAGGGACACCACCCCGCCCTACTCTCTGATTTGGCCTCCCCCTCCAGGTTCTCTGCACCCTGGCC
GTTTTTACCCACCCGCTGGTGGATGCCTAAAAATACGCTTTCCCTGCAGCCGTTTGGCTTGCCAGGCAC
TGCCACCCATGCTAGGGAAAGGAGCCGGGGTGACCTCCCTATGGGTCTCCAAGACAGAGATGGAGCGAA
GCAGCCCACAGTCGCCATCTGGTGGTCACAGCGGGTGTCCGCAGGTTCCGGCTCCGGGCAGCCATGCTG
GAAGGCTGGGCTGGGGCTGGTGTTGGGGGACATCTGCCCGGCATCATTCACTCCCTGCCCACGTGTCTG
CGCCTCACCTCCCAGACTCCCCCGCCCCCCAGCTTGGGACCCAGCTTGGGACCCAGCTTCTCTGAGTCA

Figure 7E

TGGCTGCGCATAGGGGCTGCTTCATAAATGCTTATGAATAAACCTCCCTTGGGTGAAACGAAGGCGTTT
CCTTCTTGTTTCCAGAGGTTTCCCCCCTCCCCCCCCCGTCGCCCCAAGAAAGAAGACTGGGATCAGAGA
CCTCAGCTTCCATTTCCGCGTTGCCACTTCTGANCCGTGTACTTTGGGCCAATTCTATTTACTGTTTCG
GANCCTACACGGNCCCTTTCCTNAAATAGGAACAATAAACCAGGGGCACCTTTGACNCACTGTGTAGTA
NCCAATTTGACGATAANTTTTTTTAAAAGATTAAATTAATCNGATAAATT

TASTE RECEPTORS OF THE T1R FAMILY FROM DOMESTIC CAT

CROSS REFERENCE TO RELATED APPLICATIONS

This application is a divisional of U.S. application Ser. No. 10/591,360, which is the U.S. National Stage of International Application No. PCT/US2004/015136, filed May 13, 2004, which claims the benefit of U.S. Provisional Application Ser. No. 60/482,992, filed Jun. 27, 2003 and of U.S. Provisional Application Ser. No. 60/554,751, filed Mar. 19, 2004. The contents of each of these applications is incorporated herein by reference in its entirety.

FIELD OF THE INVENTION

The present invention relates to the field of sensory mechanisms of the domestic cat, *Felis catus*. The invention relates, for example, to the discovery of several genes of *Felis catus* encoding taste receptors of the T1R family, Tas1r1, Tas1r2, and Tas1r3, the polypeptides encoded thereby (T1R1, T1R2, and T1R3), and methods and uses of the same.

BACKGROUND OF THE INVENTION

The sense of taste is important for determining food choice, for regulating food intake, and for ensuring efficient use of ingested nutrients. Taste can act as a warning system for the presence of potentially harmful foods, by, for example, the aversive sensations of sourness or bitterness, and as an attractant to potentially nutrient-rich foods, by, for example, the appealing sensations of sweetness, saltiness, and umami.

Taste stimuli are received by taste receptor cells assembled into taste buds that are located in the epithelium of taste papillae of the tongue (Kitagawa et al., *Bioch. Bioph. Res. Comm.,* 283:236-242 (2001)). The stimuli are believed to be transduced by taste receptors at the surface of the taste receptor cells (Id.). The taste receptors encoded by the genes of a given species are reflective of that species' food choices. For example, the "sweet receptors" of an herbivorous species are expected to be different from those of a carnivorous species, since the two consume completely different diets whose foods contain different primary stimuli. Since taste receptor specificity likely reflects food choice, it follows that receptor sequence homology among species may be as predictive or more predictive of food preferences of a given species as phylogenetic relatedness among species.

The behavior of the domestic cat (*Felis catus*), a carnivore, towards stimuli such as sweet carbohydrates, which it generally cannot taste, and towards L-amino acids, which it generally can taste, should be explicable by the specificity of taste receptors of other carnivores. Direct knowledge of taste receptor genes will allow insight into an animal's sensory world and may be useful for identifying modulators of the taste receptors encoded thereby to influence an animal's taste preferences.

Molecular receptors for the taste element of sweetness have been identified from human, mouse, and rat. Thus far, there are three known members of the T1R taste receptor family: T1R1, T1R2, and T1R3 (Montmayeur & Matsunami, *Curr. Opin. NeurobioL,* 12(4):366-371 (2002)). The T1R3 receptor gene is located within the Sac locus, the primary genetic locus controlling preference for sweet-tasting stimuli in mice (Li et al., *Mamm. Genome,* 12(1):13-16 (2001); Li et al., *Mamm. Genome,* 13(1):5-19 (2002)). The human syntenic region for mouse T1R3 gene is on 1p36.33 (1162-1186 kb). The gene for T1R1 is located on human 1p36.23 (6324-6349 kb), which is ~5 Mb from T1R3, and that for T1R2 is located on human 1p36.13 (18483-18729 kb), which is ~12 Mb from T1R1.

Most of the T1Rs are G-protein coupled receptors with long N-terminal extracellular domains believed to be involved in ligand binding (Montmayeur & Matsunami, *Curr. Opin. Neurobiol.,* 12(4):366-371 (2002)). The T1R receptors have been shown to dimerize. For example, homodimerization of T1Rs has been detected (Zhao et al., *Cell,* 115:255-266 (2003)). The taste receptors also heterodimerize. For example, coupling of T1R3 with T1R1 or T1R2 has been detected. In mouse, the T1R1/T1R3 heterodimer functions as a receptor for selected amino acids. The T1R2/T1R3 heterodimer functions as a receptor for stimuli considered sweet by humans. Current data indicate that the T1R3 component of the T1R dimer couples the taste receptor to cellular signal transduction processes, thereby ensuring that the stimulus-binding event is transduced to a neural signal. Thus, knowledge of the T1R receptors will lead to better understanding of species-specific reactions to sapid stimuli.

Currently, mechanisms for identifying novel taste stimuli for the domestic cat are limited, for example, to exhaustive and difficult feeding studies in which a novel ingredient is paired with a control ingredient and intake of the two are compared. Considerable time, effort, and expense can be expended in the discovery of a single stimulus. Furthermore, feline illnesses often are exacerbated by a cat's refusal to eat. Additionally, the molecular features that define acceptable taste stimuli for domestic cat remain largely unknown, making rational computational design approaches for taste stimuli difficult. As a result, knowledge of the feline taste receptor and its ligands may lead to a better understanding of cat taste perception and modulation thereof.

The present invention provides novel genes encoding the feline taste receptors T1R1, T1R2, and T1R3, the polypeptides encoded thereby, and methods of use of the receptors to identify compounds that can stimulate, inhibit, or modify the ingestive responses or general behavior of a cat. The screening methods of the invention allow the rapid screening of binding partners, agonists, antagonists, and modulators of the T1R receptors of the domestic cat. The results of the feline T1R receptor studies reflect the unique taste profile of the domestic cat.

SUMMARY OF THE INVENTION

Certain embodiments of the present invention relate to polynucleotides encoding a T1R receptor, including, but not limited to polynucleotides having the nucleotide sequence of SEQ ID NO:1, SEQ ID NO:99, SEQ ID NO:59, SEQ ID NO:60, SEQ ID NO:62, SEQ ID NO:63, fragments of the polynucleotide of SEQ ID NO:1, SEQ ID NO:99, SEQ ID NO:59, SEQ ID NO:60, SEQ ID NO:62, or SEQ ID NO:63 encoding a polypeptide having substantially the same biological activity as a polypeptide encoded by the nucleotide sequence of SEQ ID NO:1, SEQ ID NO:99, SEQ ID NO:59, SEQ ID NO:60, SEQ ID NO:62, or SEQ ID NO:63, respectively; variants of the polynucleotide of SEQ ID NO:1 or SEQ ID NO:99 having at least 80% homology to the polynucleotide of SEQ ID NO:1 or SEQ ID NO:99; variants of the polynucleotide of SEQ ID NO:59 or SEQ ID NO:60 having at least 85% homology to the polynucleotide of SEQ ID NO:59 or SEQ ID NO:60; variants of the polynucleotide of SEQ ID NO:62 or SEQ ID NO:63 having at least 75% homology to SEQ ID NO:62 or SEQ ID NO:63; polynucleotide variants of SEQ ID NO:1, SEQ ID NO:99, SEQ ID NO:59, SEQ ID NO:60, SEQ ID NO:62, or SEQ ID NO:63 encoding a polypeptide having substantially the same biological activity as a polypeptide encoded by the nucleotide sequence of SEQ ID NO:1, SEQ ID NO:99, SEQ ID NO:59, SEQ ID NO:60, SEQ ID NO:62, or SEQ ID NO:63, respectively; variants of the polynucleotide of SEQ ID NO:1, SEQ ID NO:99, SEQ ID NO:59, SEQ ID NO:60, SEQ ID NO:62, or SEQ ID NO:63 encoding a polypeptide conferring modified taste perception to one or more taste stimuli relative to a polypeptide encoded by the polynucleotide of SEQ ID NO:1, SEQ ID NO:99, SEQ ID NO:59, SEQ ID NO:60, SEQ ID NO:62, or SEQ ID NO:63, respectively; nucleotide sequences encoding the amino acid sequence of SEQ ID NO:2, SEQ ID NO:61, or SEQ ID NO:64; nucleotide sequences substantially complementary to the nucleotide sequence of SEQ ID NO:1, SEQ ID NO:99, SEQ ID NO:59, SEQ ID NO:60, SEQ ID NO:62, or SEQ ID NO:63; and nucleotide sequences that hybridize to the complement of the polynucleotide having SEQ ID NO:1, SEQ ID NO:99, SEQ ID NO:59, SEQ ID NO:60, SEQ ID NO:62, or SEQ ID NO:63 under high stringency conditions. The biological activity of the polypeptides encoded by the polynucleotides of the invention may be determined, for example, by an in vitro binding assay, such as but not limited to assessing the level of binding of the polypeptide to a T1R dimerization partner. The polynucleotides of the invention may be DNA or RNA and may be single- or double-stranded. In some embodiments of the invention, the polynucleotide fragments have at least about 42 nucleotides. The polynucleotide fragments of the invention encode, for example, an extracellular domain of the polypeptide of SEQ ID NO:2, SEQ ID NO:61, or SEQ ID NO:64; a transmembrane domain of the polypeptide of SEQ ID NO:2, SEQ ID NO:61, or SEQ ID NO:64; or an intracellular domain of the polypeptide of SEQ ID NO:2, SEQ ID NO:61, or SEQ ID NO:64. For example, the polynucleotides of the invention encoding extracellular domains of feline T1R receptors include nucleotides 1-1689, 1870-1905, 2101-2178, and 2341-2376 of SEQ ID NO:60; nucleotides 1-441 of SEQ ID NO:63; and nucleotides 1-1713, 1882-1923, 2113-2193, and 2359-2382 of SEQ ID NO:1 or SEQ ID NO:99. The polynucleotides of the invention encoding transmembrane domains of feline T1R receptors include nucleotides 1690-1767, 1810-1869, 1906-1980, 2041-2100, 2179-2244, 2281-2340, and 2379-2451 of SEQ ID NO:60; nucleotides 442-501 of SEQ ID NO:63; and nucleotides 1714-1782, 1828-1881, 1924-1992, 2041-2112, 2191-2262, 2299-2358, and 2383-2436 of SEQ ID NO:1 or SEQ ID NO:99. The polynucleotides of the invention encoding intracellular domains of feline T1R receptors include nucleotides 1768-1809, 1981-2040, 2245-2280, and 2452-2523 of SEQ ID NO:60; nucleotides 502-1173 of SEQ ID NO:63; nucleotides 1783-1827, 1993-2040, 2263-2298, and 2437-2566 of SEQ ID NO:1; and nucleotides 1783-1827, 1993-2040, 2263-2298, and 2437-2595 of SEQ ID NO:99. The polynucleotides of the invention also include any combination of the polynucleotides encoding the functional domains of the invention, such as combinations of the polynucleotides encoding the extracellular, transmembrane, and/or intracellular domains of the same or different feline T1R receptors. In other embodiments of the invention, the polynucleotide variants of the polynucleotide of SEQ ID NO:1 or SEQ ID NO:99 encoding an amino acid sequence of SEQ ID NO:2 have a nonconserved amino acid substitution, for example, at residue 59 and/or residue 64.

The invention also encompasses expression vectors containing the polynucleotides of the invention operably linked to a promoter. Another embodiment of the invention provides host cells containing the expression vector. The host cells may be prokaryotic, such as bacterial cells, or eukaryotic, such as yeast or mammalian cells, including human, murine, porcine, bovine, canine, or feline cells. The invention further encompasses cell cultures of the host cells. The invention also encompasses methods of producing a feline T1R receptor by culturing the host cells and recovering receptor therefrom.

Another embodiment of the invention includes T1R receptor polypeptides, including polypeptides encoded by the polynucleotides of the invention. The polypeptides of the invention include, for example, those having the amino acid sequence of SEQ ID NO:2, SEQ ID NO:61, or SEQ ID NO:64, fragments of at least 30 contiguous amino acids of SEQ ID NO:2, SEQ ID NO:61, or SEQ ID NO:64, and variants thereof having substantially the same biological activity as the polypeptide of SEQ ID NO:2, SEQ ID NO:61, or SEQ ID NO:64, respectively. The biological activity of the polypeptides of the invention may be determined, for example, by an in vitro binding assay, such as but not limited to assessing the level of binding of the polypeptide to a T1R dimerization partner. Biological activity of the polypeptides of the invention also may be determined by measuring ion conductance; ion flow; calcium imaging including with fura-2, green dextran activity, or aquorin activity; voltage measurement and/or voltage imaging with dyes or reporter genes such as β-luciferase, alkaline phosphatase, β-galactosidase, or β-lactamase; second messenger measurement, for example, $IP_3$, cAMP, G-protein activation-based assays; or receptor phosphorylation. The variant polypeptides of the invention may have an amino acid sequence having at least one sequence variation of SEQ ID NO:2, SEQ ID NO:61, or SEQ ID NO:64 that confers modified taste perception to one or more taste stimuli relative to a polypeptide of SEQ ID NO:2, SEQ ID NO:61, or SEQ ID NO:64, respectively. The polypeptides of the invention further comprise functional domains of the T1R receptors of the invention, for example, extracellular, transmembrane, and intracellular domains of the receptors, and combinations thereof. Examples of functional domains of the T1R1 polypeptide of SEQ ID NO:61 include extracellular domains corresponding to residues 1-563, 624-635, 701-726, and 781-792; transmembrane domains corresponding to residues 564-589, 604-623, 636-660, 681-700, 727-748, 761-780, and 793-817; and intracellular domains corresponding to residues 590-603, 661-680, 749-760, and 818-841. Examples of functional domains of the T1R2 receptor of SEQ ID NO:64 include an extracellular domain corresponding to residues 1-147; a transmembrane domain corresponding to residues 148-167; and an intracellular domain corresponding to residues 168-391. Examples of functional domains of the T1R3 polypeptide of SEQ ID NO:2 include the extracellular domains (residues 1-571, 628-641, 705-730, and 787-794 of SEQ ID NO:2), the transmembrane domains (residues 572-594, 610-627, 642-664, 681-704, 731-754, 767-780, and 795-812 of SEQ ID NO:2), and the intracellular domains (residues 595-609, 665-680, 755-766, and 813-865 of SEQ ID NO:2). The polypeptides of the invention also include any combination of the functional domains of the polypeptides of the invention, such as combinations of the extracellular, transmembrane, and/or intracellular domains of the same or different feline T1R receptors.

The invention provides methods of identifying a feline T1R receptor variant that confers modified taste perception by expressing a variant of the polynucleotide of SEQ ID NO:1, SEQ ID NO:99, SEQ ID NO:59, SEQ ID NO:60, SEQ ID NO:62, or SEQ ID NO:63 homologous to the polynucleotide of SEQ ID NO:1, SEQ ID NO:99, SEQ ID NO:59, SEQ ID NO:60, SEQ ID NO:62, or SEQ ID NO:63, respectively, and detecting an increase or a decrease in the biological activity of the polypeptide encoded by the variant relative to the biological activity of the polypeptide encoded by SEQ ID NO:1, SEQ ID NO:99, SEQ ID NO:59, SEQ ID NO:60, SEQ ID NO:62, or SEQ ID NO:63, respectively.

The invention further provides kits for the detection of polynucleotides encoding a feline T1R receptor including a polynucleotide that specifically hybridizes to a polynucleotide encoding a polypeptide having an amino acid sequence of SEQ ID NO:2, SEQ ID NO:61, or SEQ ID NO:64, and instructions relating to detection thereof.

Also provided by the invention are antibodies that immunoreact specifically with at least one epitope of a polypeptide of the invention. The invention also includes kits for the detection of polypeptides encoding a feline T1R receptor including antibodies of the invention and instructions relating to detection.

Further provided by the invention are methods for identifying a compound that interacts with a feline T1R receptor by expressing a polynucleotide of the invention in the presence of a test compound, and detecting direct or indirect interaction between a polypeptide produced by the expression step with the compound. Also provided are methods for identifying compounds that interact with a feline T1R receptor by contacting a feline T1R receptor with a test compound, and detecting interaction between the receptor and the compound. The methods for detecting such interaction may be cell-based or cell-free assays. For example, a polynucleotide of the invention may be expressed in a heterologous expression system or in a cellular extract. The receptor may be bound to a solid support. In one aspect of the invention, the recognition sites of the receptor are coupled with a monitoring system, either electrical or optical. In another embodiment, the solid support is formulated into a feline-specific electronic tongue or biosensor.

The invention also provides methods for identifying agonists and antagonists of a feline T1R receptor. For example, the methods of the invention include identification of an agonist of a feline T1R receptor by expressing a polynucleotide of the invention in the presence of a test compound, and detecting increased transcription of said polynucleotide or increased biological activity of a polypeptide produced by the expression step in the presence of the compound relative to the rate of transcription or biological activity of the polypeptide in the absence of the compound. The biological activity detected may be an increase or decrease in the interaction between the T1R receptor and its T1R dimerization partner. For example, the T1R dimerization partner of a T1R1 or a T1R2 receptor may be T1R3 and vice versa. (In addition, T1R receptors may form homodimers which may have unique ligand binding properties. The T1R dimerization partner thus also may be a homodomerization partner. Also included are methods for identifying agonists of a feline T1R receptor by contacting a polypeptide of the invention with a test compound, and detecting an increase in biological activity of the polypeptide in the presence of the compound relative to biological activity of the polypeptide in the absence of the compound. The methods for identifying agonists of the cat T1R receptors may be cell-based or cell-free assays. For example, a polynucleotide of the invention may be expressed in a heterologous expression system or in a cellular extract. The receptor may be bound to a solid support. In one aspect of the invention, the recognition sites of the receptor are coupled with a monitoring system, either electrical or optical. In another embodiment, the solid support is formulated into a feline-specific electronic tongue or biosensor.

Methods for identifying antagonists of the polypeptides of the invention also are provided. For example, the invention provides methods for identifying antagonists of a feline T1R receptor by expressing a polynucleotide of the invention in the presence of a test compound, and detecting decreased transcription of said polynucleotide or decreased biological activity of a polypeptide produced by the expression step in the presence of the compound relative to the rate of transcription or biological activity of the polypeptide in the absence of the compound. Another example of methods for identifying an antagonist of a feline T1R receptor involves contacting a polypeptide of the invention with a test compound, and detecting a decrease in biological activity of the polypeptide in the presence of the compound relative to biological activity of the polypeptide in the absence of the compound. The methods for identifying the antagonists may be cell-based or cell-free assays. For example, a polynucleotide of the invention may be expressed in a heterologous expression system or in a cellular extract. The receptor may be bound to a solid support. In one aspect of the invention, the recognition sites of the receptor are coupled with a monitoring system, either electrical or optical. In another embodiment, the solid support is formulated into a feline-specific electronic tongue or biosensor.

Also encompassed by the invention are methods for predicting the taste perception of an organism such as a mammal, including but not limited to a cat. The methods may involve detection of a nucleotide sequence or amino acid sequence of the invention in a biological sample of the organism. For example, an organism having a polynucleotide or polypeptide of the invention may be attracted to one or more amino acids. An organism having a polynucleotide or polypeptide of the invention may show no preference for one or more carbohydrates or high-intensity sweeteners. An organism having a polynucleotide or polypeptide of the invention may be attracted to one or more amino acids and may exhibit no preference for one or more carbohydrates or high-intensity sweeteners.

Another embodiment of the invention includes compounds and compositions for modifying the taste perception of a mammal, such as a cat. The compounds and compositions may contain at least one of the polynucleotides of the invention, polypeptides of the invention, or compounds identified by the methods of the invention. Examples of the compositions of the invention include veterinary foods and drinks and pharmaceutical compositions. The compositions of the invention may include a pharmaceutically acceptable excipient. The compositions of the invention may be breed-specific. Methods for modifying the taste perception of a mammal (e.g., a cat) by administering to the mammal a polynucleotide of the invention, a polypeptide of the invention, and/or a compound identified according to the methods of the invention also are provided.

The invention further contemplates transgenic animals comprising a polynucleotide of the invention.

The materials, methods, and examples provided herein are illustrative only and are not intended to be limiting. Other features and advantages of the invention will be apparent from the following detailed description and claims.

BRIEF DESCRIPTION OF THE DRAWINGS

FIGS. 1A-1I show the multiple sequence alignment of the cDNAs encoding T1R receptors of domestic cat (Tas1r1, SEQ ID NO:60; Tas1r2, SEQ ID NO:63; and Tas1r3, SEQ ID NO:99) with known nucleotide sequences of receptors of the T1R family from human (Tas1r1, SEQ ID NO:8; Tas1r2, SEQ ID NO:5; Tas1r3, SEQ ID NO:11), mouse (Tas1r1, SEQ ID NO:6; Tas1r2, SEQ ID NO:3; Tas1r3, SEQ ID NO:9), and rat (Tas1r1, SEQ ID NO:7; Tas1r2, SEQ ID NO:4; Tas1r3, SEQ ID NO:10). An asterisk (*) indicates a conserved nucleotide position among the sequences. A heart (♥) indicates the stop codon of feline T1R2.

FIGS. 2A-D show the deduced amino acid sequences of the feline T1R taste receptors (T1R1, SEQ ID NO:61; T1R2, SEQ ID NO:64; and T1R3, SEQ ID NO:2) aligned with the amino acid sequences of members of the T1R receptor family from human (T1R1, SEQ ID NO:17; T1R2, SEQ ID NO:20; T1R3, SEQ ID NO:12), rat (T1R1, SEQ ID NO:16; T1R2, SEQ ID NO:19; T1R3, SEQ ID NO:14), and mouse (T1R1, SEQ ID NO:15; T1R2, SEQ ID NO:18; T1R3, SEQ ID NO:13). An asterisk (*) indicates a conserved nucleotide position among the sequences. A colon (:) indicates an observed conserved amino acid substitution. A period (.) indicates an observed semi-conserved amino acid substitution. The deduced amino acid sequence for cat T1R3 (SEQ ID NO:2) contains four additional amino acids at positions 11-14 relative to the T1R3 receptors of mouse (SEQ ID NO:13), human (SEQ ID NO:12), and rat (SEQ ID NO:14). The deduced sequence for cat reveals a threonine in position 64, a position equivalent to amino acid 60 in mouse, and a leucine at position 59, a position equivalent to position 55 in mouse. In mouse, amino acid substitutions of a threonine at position 60 and an alanine at position 55, both positions located within the putative extracellular N-terminal domain of the polypeptide, are present in strains of mice demonstrating low preference for the sweet stimulus saccharin (Bachmanov et al., *Chem. Senses,* 26:925-933 (2001)). Leucine is a conservative substitution for alanine. Accordingly, the amino acid sequence differences of cat and mouse T1R3 receptor may account for functional differences that lead to different taste preferences between the two species.

FIG. 5A shows the predicted conformation of cat T1R1 (SEQ ID NO: 61), indicating that the receptor is a 7-transmembrane-type receptor. FIG. 5B illustrates the predicted conformation of cat T1R2 (SEQ ID NO: 64). Since feline T1R2 is a short protein (391 amino acids), a 7-transmembrane domain protein is not predicted. Without seven transmembrane domains, the cat T1R2 receptor may not interact appropriately with its dimerization partner, such as T1R3, and/or the plasma membrane, which may result in the cat's indifference toward sweet carbohydrates. The cat T1R2 may have another function.

FIGS. 6A-D show the genomic sequence of cat Tas1r1 (SEQ ID NO:59) obtained from BAC sequencing. The letter "N" denotes gaps between exons or unknown sequences.

FIGS. 7A-E show the genomic sequence of cat Tas1r2 (SEQ ID NO:62) obtained from BAC sequencing. The letter "N" denotes gaps between exons or unknown sequences.

DETAILED DESCRIPTION OF ILLUSTRATIVE EMBODIMENTS

Figure 3:
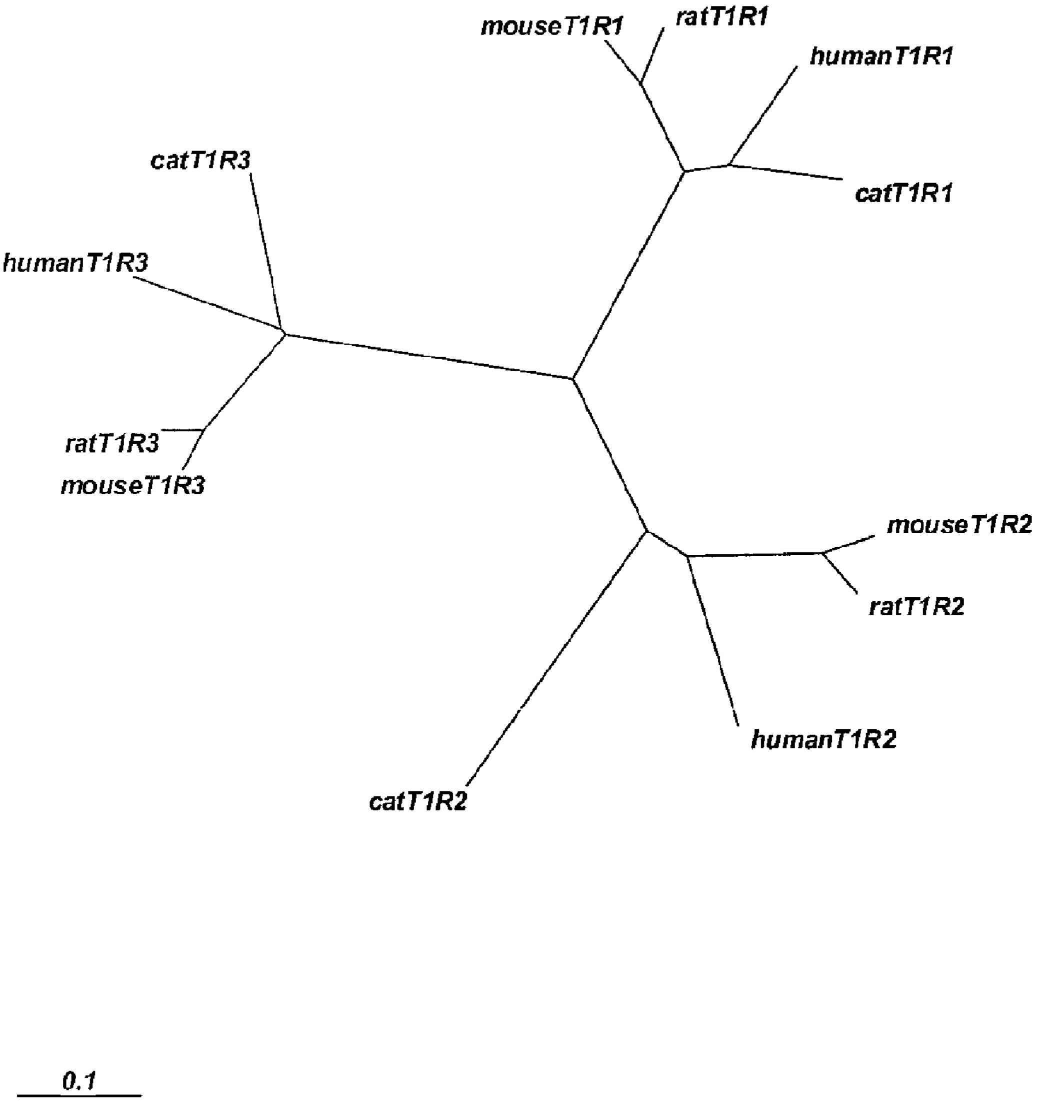
FIG. 3 illustrates a phylogenetic tree showing the relatedness of the domestic cat T1R receptor family to the T1R family of receptors including human, rat, and mouse T1R1, T1R2, and T1R3. The T1R receptors of the rat and mouse are closely related, while the T1R receptors of human and cat diverge from rat and mouse. Interestingly, the sweet stimuli to which the rat and mouse respond are very similar, whereas those that stimulate the human and those that stimulate the cat differ from one another and from those for rat and mouse. For example, humans are unique in their ability to taste most high-intensity sweeteners, while cats find many amino acids attractive but are unable to taste most carbohydrate and high-intensity sweeteners. The cat T1R2 diverges from that of human, mouse, and rat, which is consistent with the fact that cat does not show a preference for carbohydrate sweeteners.

The reference works, patents, patent applications, and scientific literature that are referred to herein reflect in part the knowledge of those with skill in the art and are hereby incorporated by reference in their entirety to the same extent as if each was specifically and individually indicated to be incorporated by reference. Any conflict between any reference cited herein and the specific teachings of this specification shall be resolved in favor of the latter. Likewise, any conflict between an art-understood definition of a word or phrase and a definition of the word or phrase as specifically taught in this specification shall be resolved in favor of the latter.

Standard reference works setting forth the general principles of recombinant DNA technology are known to those of skill in the art (Ausubel et al., Current Protocols In Molecular Biology, John Wiley & Sons, New York, 1998; Sambrook et al., Molecular Cloning: A Laboratory Manual, 2d Ed., Cold Spring Harbor Laboratory Press, Plainview, N.Y., 1989; Kaufman et al., Eds., Handbook of Molecular and Cellular Methods in Biology and Medicine, CRC Press, Boca Raton, 1995; McPherson, Ed., Directed Mutagenesis: A Practical Approach, IRL Press, Oxford, 1991).

As used herein, "T1R receptor" encompasses the taste receptors of the T1R1, T1R2, and T1R3 types, for example, the feline T1R1, T1R2, and T1R3 taste receptors of the invention.

As used herein, "taste perception" refers to a response (e.g., biochemical, behavioral) or sensitivity of a T1R receptor of the invention to a taste stimulus. "Taste stimulus" as used herein refers to any compound that elicits, for example at the biochemical level (e.g., activation or inhibition of a taste receptor) or behavioral level (e.g., preference, indifference, or distaste), a taste response which would be perceived by a mammal as at least one of the five taste elements, including sweet, salty, sour, bitter, and umami. "Taste perception" or "taste stimulus," or variants thereof, does not require, though it does include, transmission of a neural signal resulting in in vivo sensation of taste by a mammal. Modification of taste perception includes an alteration of (enhancement of, reduction to, or change to) a biochemical response, an ingestive response, a taste preference, or general behavior of a mammal in response to a compound.

As used herein "polynucleotide" refers to a nucleic acid molecule and includes genomic DNA, cDNA, RNA, mRNA, mixed polymers, recombinant nucleic acids, fragments and variants thereof, and the like. Polynucleotide fragments of the invention comprise at least 10, and preferably at least 12, 14, 16, 18, 20, 25, 30, 35, 40, 45, 50, 75, or 100 consecutive nucleotides of a reference polynucleotide. The polynucleotides of the invention include sense and antisense strands. The polynucleotides of the invention may be naturally occurring or non-naturally occurring polynucleotides. A "synthesized polynucleotide" as used herein refers to polynucleotides produced by purely chemical, as opposed to enzymatic, methods. "Wholly" synthesized DNA sequences are therefore produced entirely by chemical means, and "partially" synthesized DNAs embrace those wherein only portions of the resulting DNA were produced by chemical means. The polynucleotides of the invention may be single- or double-stranded. The polynucleotides of the invention may be chemically modified and may contain non-natural or derivatized nucleotide bases as will be readily appreciated by those skilled in the art. Such modifications include, for example, labels, methylation, substitution of one or more nucleotides with an analog, internucleotide modifications such as uncharged linkages (e.g., methyl phosphonates, phosphotriesters, phosphoramidates, carbamates, etc.), charged linkages (e.g., phosphorothioates, phosphorodithioates, etc.), pendent moieties (e.g., polypeptides, etc.), intercalators (e.g., acridine, psoralen, etc.), chelators, alkylators, and modified linkages (e.g., alpha anomeric nucleic acids, etc.). Also included are synthetic molecules that mimic polynucleotides in their ability to bind to a designated sequence via hydrogen bonding and other chemical interactions. Such molecules are known in the art and include, for example, those in which peptide linkages substitute for phosphate linkages in the backbone of the molecule.

"Recombinant nucleic acid" is a nucleic acid generated by combination of two segments of nucleotide sequence. The combination may be, for example, by chemical means or by genetic engineering.

As used herein, "polynucleotide amplification" refers to a broad range of techniques for increasing the number of copies of specific polynucleotide sequences. Typically, amplification of either or both strand(s) of the target nucleic acid comprises the use of one or more nucleic acid-modifying enzymes, such as a DNA polymerase, ligase, RNA polymerase, or RNA-dependent reverse transcriptase. Examples of polynucleotide amplification include, but are not limited to, polymerase chain reaction (PCR), nucleic acid sequence based amplification (NASB), self-sustained sequence replication (3SR), strand displacement activation (SDA), ligase chain reaction, Qβ replicase system, and the like. A wide variety of alternative cloning and in vitro amplification methodologies are well known to those skilled in the art. Examples of these techniques are found in, for example, Berger et al., *Guide to Molecular Cloning Techniques*, METHODS IN ENZYMOLOGY 152, Academic Press, Inc., San Diego, Calif. (Berger), which is incorporated herein by reference in its entirety.

As used herein, the term "oligonucleotide" or "primer" refers to a series of linked nucleotide residues which has a sufficient number of bases to be used in a polymerase chain reaction (PCR). This short sequence is based on (or designed from) a genomic or cDNA sequence and is used to amplify, confirm, or reveal the presence of an identical, similar, or complementary DNA or RNA in a particular cell or tissue. Oligonucleotides comprise portions of a nucleic acid sequence having at least about 10 nucleotides and as many as about 50 nucleotides, often about 12 or 15 to about 30 nucleotides. They are chemically synthesized and may be used as probes. "Primer pair" refers to a set of primers including a 5' upstream primer that hybridizes with the 5' end of a target sequence to be amplified and a 3' downstream primer that hybridizes with the complement of the 3' end of the target sequence to be amplified.

As used herein, the term "probe" refers to nucleic acid sequences of variable length, for example between at least about 10 and as many as about 6,000 nucleotides, depending on use. Probes are used in the detection of identical, similar, or complementary target nucleic acid sequences, which target sequences may be single- or double-stranded. Longer probes are usually obtained from a natural or recombinant source, are highly specific, and are much slower to hybridize than oligomers, or shorter probes. They may be single- or double-stranded and are carefully designed to have specificity in PCR, hybridization membrane-based, or ELISA-like technologies. An "overgo probe" is a DNA probe comprising two short, overlapping DNA sequences (e.g., 10-50 nucleotides each) with a complementary overlapping region (e.g., 5-15 nucleotides) that is used in an overgo hybridization strategy. For example, an overgo probe may be two 22 mers with an 8 bp complementary overlap, resulting in a 36 mer overgo probe. As another example, an overgo probe may be two 24 mers with an 8 bp complementary overlap, resulting in a 40 mer overgo probe.

As used herein, the phrase "stringent hybridization conditions" or "high stringency conditions" refers to conditions under which a probe, primer, or oligonucleotide will hybridize to its target sequence, but to a minimal number of or no other sequences. Stringent conditions are sequence-dependent and will be different in different circumstances. Longer sequences will hybridize with specificity to their proper complements at higher temperatures. Generally, stringent conditions are selected to be about 5° C. lower than the thermal melting point ($T_m$) for the specific sequence at a defined ionic strength and pH. The $T_m$ is the temperature (under defined ionic strength, pH and nucleic acid concentration) at which 50% of the probes complementary to the target sequence hybridize to the target sequence at equilibrium. Since the target sequences are generally present in excess, at $T_m$, 50% of the probes are hybridized to their complements at equilibrium. Stringent temperature conditions will generally include temperatures in excess of 30° C., typically in excess of 37° C., and may be in excess of 45° C. Stringent salt conditions will ordinarily be less than 1.0 M, typically less than 0.5 M, and may be less than 0.2 M. Typically, stringent conditions will be those in which the salt concentration is less than about 1.0 M sodium ion, typically about 0.01 to 1.0 M sodium ion (or other salts) at pH 7.0 to 8.3 and the temperature is at least about 30° C. for short probes, primers, or oligonucleotides (e.g., 10 to 50 nucleotides) and at least about 60° C. for longer probes, primers, or oligonucleotides. Stringent conditions may also be achieved with the addition of destabilizing agents, such as formamide.

As used herein "antisense oligonucleotide" refers to a nucleic acid molecule that is complementary to at least a portion of a target nucleotide sequence of interest and specifically hybridizes to the target nucleotide sequence under physiological conditions. The term "double stranded RNA" or "dsRNA" as used herein refers to a double-stranded RNA molecule capable of RNA interference, including short interfering RNA (siRNA) (see for example, Bass, *Nature*, 411, 428-429 (2001); Elbashir et al., *Nature*, 411, 494-498 (2001)).

As used herein, the term "complementary" refers to Watson-Crick basepairing between nucleotide units of a nucleic acid molecule.

The term "marker gene" or "reporter gene" refers to a gene encoding a product that, when expressed, confers a phenotype at the physical, morphologic, or biochemical level on a transformed cell that is easily identifiable, either directly or indirectly, by standard techniques and includes, but is not limited to, genes encoding proteins that confer resistance to toxins or antibiotics such as ampicillin, neomycin, and methotroxate; genes encoding proteins that complement auxotrophic deficiencies; and genes encoding proteins that supply critical components not available from complex media. Examples of marker genes include green fluorescent protein (GFP), red fluorescent protein (DsRed), alkaline phosphatase (AP), β-lactamase, chloramphenicol acetyltransferase (CAT), adenosine deaminase (ADA), aminoglycoside phosphotransferase (neor, G418r) dihydrofolate reductase (DHFR), hygromycin-B-phosphotransferase (HPH), thymidine kinase (TK), lacZ (encoding β-galactosidase), β-lactamase, luciferase (luc), and xanthine guanine phosphoribosyltransferase (XGPRT). As with many of the standard procedures associated with the practice of the invention, skilled artisans will be aware of additional sequences that can serve the function of a marker or reporter. Thus, this list is merely meant to show examples of what can be used and is not meant to limit the invention.

As used herein, the term "promoter" refers to a regulatory element that regulates, controls, or drives expression of a nucleic acid molecule of interest and can be derived from sources such as from adenovirus, SV40, parvoviruses, vaccinia virus, cytomegalovirus, or mammalian genomic DNA. Examples of suitable promoters include, but are not limited to, CMV, MSH2, trp, lac, phage, and TRNA promoters. Suitable promoters that can be used in yeast include, but are not limited to, such constitutive promoters as 3-phosphoglycerate kinase and various other glycolytic enzyme gene promoters such as enolase or glyceraldehydes-3-phosphate dehydrogenase, or such inducible promoters as the alcohol dehydrogenase 2 promoter or metallothionine promoter. Again, as with many of the standard procedures associated with the practice of the invention, skilled artisans will be aware of additional promoters that can serve the function of directing the expression of a marker or reporter. Thus, the list is merely meant to show examples of what can be used and is not meant to limit the invention.

"Operably linked" refers to juxtaposition wherein the components are in a functional relationship. For example, a promoter is operably linked or connected to a coding sequence if it controls the transcription or expression of the sequence.

The terms "polypeptide," "peptide," and "protein" are used interchangeably herein. "Polypeptide" refers to a polymer of amino acids without referring to a specific length. Polypeptides of the invention include peptide fragments, derivatives, and fusion proteins. Peptide fragments preferably have at least about 10, 15, 20, 25, 30, 35, 40, 45, 50, 60, 70, 80, 90, or 100 amino acids. Some peptide fragments of the invention are biologically active. Biological activities include immunogenicity, ligand binding, dimerization. and activity associated with the reference peptide. Immunogenic peptides and fragments of the invention generate an epitope-specific immune response, wherein "epitope" refers to an immunogenic determinant of a peptide and preferably contains at least three, five, eight, nine, ten, fifteen, twenty, thirty, forty, forty-five, or fifty amino acids. Some immunogenic peptides of the invention generate an immune response specific to that peptide. Polypeptides of the invention include naturally occurring and non-naturally occurring peptides. The term includes modified polypeptides (wherein examples of such modifications include glycosylation, acetylation, phosphorylation, carboxylation, ubiquitination, labeling, etc.), analogs (such as non-naturally occurring amino acids, substituted linkages, etc.), and functional mimetics. A variety of methods for labeling polypeptides are well known in the art and include radioactive isotopes such as $^{32}P$ or $^{35}S$, ligands that bind to labeled antiligands (e.g., antibodies), fluorophores, chemiluminescent agents, enzymes, and antligands.

As used herein, the term "amino acid" denotes a molecule containing both an amino group and a carboxyl group. In some embodiments, the amino acids are α-, β-, γ- or δ-amino acids, including their stereoisomers and racemates. As used herein the term "L-amino acid" denotes an α-amino acid having the L configuration around the α-carbon, that is, a carboxylic acid of general formula $CH(COOH)(NH_2)$-(side chain), having the L-configuration. The term "D-amino acid" similarly denotes a carboxylic acid of general formula $CH(COOH)(NH_2)$-(side chain), having the D-configuration around the α-carbon. Side chains of L-amino acids include naturally occurring and non-naturally occurring moieties. Non-naturally occurring (i.e., unnatural) amino acid side chains are moieties that are used in place of naturally occurring amino acid side chains in, for example, amino acid analogs. Amino acid substituents may be attached, for example, through their carbonyl groups through the oxygen or carbonyl carbon thereof, or through their amino groups, or through functionalities residing on their side chain portions.

The amino acid sequences are presented in the amino (N) to carboxy (C) direction, from left to right. The N-terminal α-amino group and the C-terminal β-carboxy groups are not depicted in the sequence. The nucleotide sequences are presented by single strands only, in the 5' to 3' direction, from left to right. Nucleotides and amino acids are represented in the manner recommended by the IUPAC-IUB Biochemical Nomenclature Commission, or amino acids are represented by their three letters code designations.

As used herein, the term "antibody" is meant to refer to complete, intact antibodies, and Fab, Fab', $F(ab)_2$, $F_v$, and other fragments thereof. Complete, intact antibodies include antibodies such as polyclonal antibodies, monoclonal antibodies, chimeric antibodies, and humanized antibodies, felinized antibodies, and immunologic binding equivalents thereof. The antibodies of the invention may be labeled or unlabeled. Examples of labels of antibodies include, but are not limited to, radionuclides, enzymes, substrates, cofactors, inhibitors, fluorescent agents, chemiluminescent agents, magnetic particles, and the like. Recombinant immunoglobulins are included in the invention.

As used herein, the term "binding" means the physical or chemical interaction between two proteins or compounds or associated proteins or compounds or combinations thereof. Binding includes ionic, non-ionic, Hydrogen bonds, Van der Waals, hydrophobic interactions, etc. The physical interaction, the binding, can be either direct or indirect, indirect being through or due to the effects of another protein or compound. Direct binding refers to interactions that do not take place through or due to the effect of another protein or compound but instead are without other substantial chemical intermediates. Binding may be detected in many different manners. As a non-limiting example, the physical binding interaction between two molecules can be detected using a labeled compound. Other methods of detecting binding are well-known to those of skill in the art.

As used herein, the term "contacting" means bringing together, either directly or indirectly, a compound into physical proximity to a molecule of interest. Contacting may occur, for example, in any number of buffers, salts, solutions, or in a cell or cell extract.

As used herein, the terms "modulates" or "modifies" means an increase or decrease in the amount, quality, or effect of a particular activity or protein. "Modulators" refer to any inhibitory or activating molecules identified using in vitro and in vivo assays for, e.g., agonists, antagonists, and their homologs, including fragments, variants, and mimetics, as defined herein, that exert substantially the same biological activity as the molecule. "Inhibitors" or "antagonists" are modulating compounds that reduce, decrease, block, prevent, delay activation, inactivate, desensitize, or downregulate the biological activity or expression of a molecule or pathway of interest. "Inducers," "activators," or "agonists" are modulating compounds that increase, induce, stimulate, open, activate, facilitate, enhance activation, sensitize, or upregulate a molecule or pathway of interest. In some preferred embodiments of the invention, the level of inhibition or upregulation of the expression or biological activity of a molecule or pathway of interest refers to a decrease (inhibition or downregulation) or increase (upregulation) of greater than about 50%, 60%, 70%, 75%, 80%, 85%, 90%, 91%, 92%, 93%, 94%, 95%, 96%, 97%, 98%, or 99%. The inhibition or upregulation may be direct, i.e., operate on the molecule or pathway of interest itself, or indirect, i.e., operate on a molecule or pathway that affects the molecule or pathway of interest.

A "purified" or "substantially purified" polynucleotide or polypeptide is substantially separated from other cellular components that naturally accompany a native (or wild-type) nucleic acid or polypeptide and/or from other impurities (e.g., agarose gel). A purified polypeptide or protein will comprise about 60% to more than 99% w/w of a sample, and may be about 90%, about 95%, or about 98% pure. As used herein, the term "isolated" refers to a molecule that has been removed from its native environment. Examples of isolated nucleic acid molecules include, but are not limited to, recombinant DNA molecules contained in a vector, recombinant DNA molecules maintained in a heterologous host cell, partially or substantially purified nucleic acid molecules, and synthetic DNA or RNA molecules.

"About" as used herein refers to +/−10% of the reference value.

As used herein, "variant" nucleotide or amino acid sequences refer to homologs, including, for example, isoforms, species variants, allelic variants, and fragments of the sequence of interest. "Homologous nucleotide sequence" or "homologous amino acid sequence," or variations thereof, refers to sequences characterized by a homology, at the nucleotide level or amino acid level, of at least about 60%, at least about 70%, at least about 75%, at least about 80%, at least about 81%, at least about 82%, at least about 83%, at least about 84%, at least about 85%, preferably at least about 90%, at least about 95%, at least about 98%, or at least about 99%, and more preferably 100%, to a reference sequence, or portion or fragment thereof encoding or having a functional domain. The reference sequence may include, for example, but is not limited to the nucleic acid sequence of SEQ ID NO:1, SEQ ID NO:99, SEQ ID NO:59, SEQ ID NO:60, SEQ ID NO:62, and SEQ ID NO:63, or portions thereof which encode a functional domain of the encoded polypeptide, SEQ ID NO:2, SEQ ID NO:61, or SEQ ID NO:64, or the polypeptide having amino acid sequence SEQ ID NO:2, SEQ ID NO:61, or SEQ ID NO:64, or fragments thereof having functional domains of the full-length polypeptide. Functional domains of the T1R receptors of the invention include extracellular domains, transmembrane domains, and intracellular domains. Examples of functional domains of the T1R1 polypeptide of SEQ ID NO:61 include extracellular domains corresponding to residues 1-563, 624-635, 701-726, and 781-792; transmembrane domains corresponding to residues 564-589, 604-623, 636-660, 681-700, 727-748, 761-780, and 793-817; and intracellular domains corresponding to residues 590-603, 661-680, 749-760, and 818-841. Examples of functional domains of the T1R2 receptor of SEQ ID NO:64 include an extracellular domain corresponding to residues 1-147; a transmembrane domain corresponding to residues 148-167; and an intracellular domain corresponding to residues 168-391. Examples of functional domains of the T1R3 polypeptide of SEQ ID NO:2 include the extracellular domains (residues 1-571, 628-641, 705-730, and 787-794 of SEQ ID NO:2), the transmembrane domains (residues 572-594, 610-627, 642-664, 681-704, 731-754, 767-780, and 795-812 of SEQ ID NO:2), and the intracellular domains (residues 595-609, 665-680, 755-766, and 813-865 of SEQ ID NO:2). Isoforms can be expressed in different tissues of the same organism as a result of, for example, alternative splicing of RNA. Alternatively, isoforms can be encoded by different genes. Homologous nucleotide sequences include nucleotide sequences encoding for a species variant of a protein. Homologous nucleotide sequences also include, but are not limited to, naturally occurring allelic variations and mutations of the nucleotide sequences set forth herein. Study of mutations and polymorphisms of the T1R receptor polynucleotide sequences may explain breed-specific and/or individual taste preferences of a mammal such as a cat. Additionally, sequence variants of the T1R receptors may be associated with specific disease states, such that knowledge of the genes allows diagnosis and treatment of T1R-associated disorders (e.g., obesity, diabetes). Homologous amino acid sequences include those amino acid sequences which encode conservative amino acid substitutions in polypeptides having an amino acid sequence of SEQ ID NO:2, SEQ ID NO:61, or SEQ ID NO:64, as well as in polypeptides identified according to the methods of the invention. Percent homology may be determined by, for example, the Gap program (Wisconsin Sequence Analysis Package, Version 8 for Unix, Genetics Computer Group, University Research Park, Madison Wis.), using the default settings, which uses the algorithm of Smith and Waterman (Smith and Waterman, *Adv. Appl. Math.,* 2: 482-489, 1981). Nucleic acid fragments of the invention preferably have at least about 5, at least about 10, at least about 15, at least about 20, at least about 25, at least about 50, or at least about 100 nucleotides of the reference nucleotide sequence. The nucleic acid fragments of the invention may encode a polypeptide having at least one biological property, or function, that is substantially similar to a biological property of the polypeptide encoded by the full-length nucleic acid sequence.

As is well known in the art, because of the degeneracy of the genetic code, there are numerous DNA and RNA molecules that can code for the same polypeptide as that encoded by a nucleotide sequence of interest. The present invention, therefore, contemplates those other DNA and RNA molecules which, on expression, encode a polypeptide encoded by the nucleic acid molecule of interest. For example, nucleotide "insertions", "substitutions" or "deletions" are changes to or within a nucleotide sequence. Such polynucleotide variants are within the scope of the invention. DNA and RNA molecules other than those specifically disclosed herein characterized simply by a change in a codon for a particular amino acid, are within the scope of this invention.

Amino acid "insertions", "substitutions" or "deletions" are changes to or within an amino acid sequence. The variation allowed in a particular amino acid sequence may be experimentally determined by producing the peptide synthetically or by systematically making insertions, deletions, or substitutions of nucleotides in the nucleic acid sequence using recombinant DNA techniques. Alterations of the naturally occurring amino acid sequence can be accomplished by any of a number of known techniques. For example, mutations can be introduced into the polynucleotide encoding a polypeptide at particular locations by procedures well known to the skilled artisan, such as oligonucleotide-directed mutagenesis.

A polypeptide variant of the present invention may exhibit substantially the biological activity of a naturally occurring reference polypeptide. "Biological activity" as used herein refers to the level of a particular function (for example, enzymatic activity) of a molecule or pathway of interest in a biological system. "Wild-type biological activity" refers to the normal level of function of a molecule or pathway of interest. "Reduced biological activity" refers to a decreased level of function of a molecule or pathway of interest relative to a reference level of biological activity of that molecule or pathway. For example, reduced biological activity may refer to a decreased level of biological activity relative to the wild-type biological activity of a molecule or pathway of interest. "Increased biological activity" refers to an increased level of function of a molecule or pathway of interest relative to a reference level of biological activity of that molecule or pathway. For example, increased biological activity may refer to an increased level of biological activity relative to the wild-type biological activity of a molecule or pathway of interest. Reference to exhibiting "substantially the biological activity of a naturally occurring polypeptide" indicates that variants within the scope of the invention can comprise conservatively substituted sequences, meaning that one or more amino acid residues of a polypeptide are replaced by different residues that do not alter the secondary and/or tertiary structure of the polypeptide. Such substitutions may include the replacement of an amino acid by a residue having similar physicochemical properties, such as substituting one aliphatic residue (Ile, Val, Leu or Ala) for another, or substitution between basic residues Lys and Arg, acidic residues Glu and Asp, amide residues Gln and Asn, hydroxyl residues Ser and Tyr, or aromatic residues Phe and Tyr. Further information regarding making phenotypically silent amino acid exchanges are known in the art (Bowie et al., *Science,* 247: 1306-1310, 1990). Other polypeptide homologs which might retain substantially the biological activities of the reference polypeptide are those where amino acid substitutions have been made in areas outside functional regions of the protein. The biological activity may be assessed by, for example, measuring binding of a T1R receptor of the invention to a dimerization partner. Biological activity of the polypeptides of the invention also may be determined by measuring ion conductance; ion flow; calcium imaging including with fura-2, green dextran activity, or aquorin activity; voltage measurement and/or voltage imaging with dyes or reporter genes such as β-luciferase, alkaline phosphatase, β-galactosidase, or β-lactamase; second messenger measurement, for example, $IP_3$, cAMP, G-protein activation-based assays; or receptor phosphorylation.

A nucleotide and/or amino acid sequence of a nucleic acid molecule or polypeptide employed in the invention or of a compound identified by the screening method of the invention may be used to search a nucleotide and amino acid sequence databank for regions of similarity using Gapped BLAST (Altschul et al., *Nuc. Acids Res.,* 25: 3389, 1997). Briefly, the BLAST algorithm, which stands for Basic Local Alignment Search Tool is suitable for determining sequence similarity (Altschul et al., *J Mol. Biol.,* 215: 403-410, 1990). Software for performing BLAST analyses is publicly available through the National Center for Biotechnology Information. This algorithm involves first identifying high scoring sequence pair (HSPs) by identifying short words of length W in the query sequence that either match or satisfy some positive-valued threshold score T when aligned with a word of the same length in a database sequence. T is referred to as the neighborhood word score threshold (Altschul et al., *J Mol. Biol.,* 215: 403-410, 1990). These initial neighborhood word hits act as seeds for initiating searches to find HSPs containing them. The word hits are extended in both directions along each sequence for as far as the cumulative alignment score can be increased. Extension for the word hits in each direction are halted when: 1) the cumulative alignment score falls off by the quantity X from its maximum achieved value; 2) the cumulative score goes to zero or below, due to the accumulation of one or more negative-scoring residue alignments; or 3) the end of either sequence is reached. The BLAST algorithm parameters W, T, and X determine the sensitivity and speed of the alignment. The BLAST program uses as defaults a word length (W) of 11, the BLOSUM62 scoring matrix (Henikoff et al., *Proc. Natl. Acad. Sci. USA,* 89: 10915-10919, 1992) alignments (B) of 50, expectation (E) of 10, M=5, N=4, and a comparison of both strands. The BLAST algorithm (Karlin et al., *Proc. Natl. Acad. Sci. USA,* 90: 5873-5787, 1993) and Gapped BLAST perform a statistical analysis of the similarity between two sequences. One measure of similarity provided by the BLAST algorithm is the smallest sum probability (P(N)), which provides an indication of the probability by which a match between two nucleotide or amino acid sequences would occur by chance. For example, a nucleic acid is considered similar to a gene or cDNA if the smallest sum probability in comparison of the test nucleic acid to the reference nucleic acid is less than about 1, preferably less than about 0.1, more preferably less than about 0.01, and most preferably less than about 0.001.

The term "mimetic" as used herein refers to a compound that is sterically similar to a reference compound. Mimetics are structural and functional equivalents to the reference compounds.

The terms "patient" and "subject" are used interchangeably herein and include, but are not limited to, avians, felines, canines, bovines, ovines, porcines, equines, rodents, simians, and humans. "Host cell" includes, for example, a prokaryotic cell, such as a bacterial cell, or eukaryotic cell, such as a mammalian cell (e.g., human, rodent, canine, feline), a yeast cell, or a plant cell. "Rodents" include, for example, rats and mice.

The term "treatment" as used herein refers to any indicia of success of prevention, treatment, or amelioration of a disease or condition. Treatment includes any objective or subjective parameter, such as, but not limited to, abatement, remission, normalization of receptor activity, reduction in the number or severity of symptoms or side effects, or slowing of the rate of degeneration or decline of the patient. Treatment also includes a prevention of the onset of symptoms in a patient that may be at increased risk for or is suspected of having a disease or condition but does not yet experience or exhibit symptoms thereof.

As used herein, the term "compound" means any identifiable chemical or molecule, including, but not limited to a small molecule, peptide, protein, sugar, nucleotide, or nucleic acid. Such compound can be natural or synthetic.

Topologically, sensory GPCRs have various domains including one or more of an "N-terminal domain," an "extracellular domain," "transmembrane domain," cytoplasmic and extracellular loops, "intracellular domain," and a "C-terminal domain" (see, e.g., Hoon et al., *Cell* 96:541-551 (1999); Buck & Axel, *Cell* 65:175-187 (1991)). These domains can be structurally identified using methods known to those of skill in the art, such as sequence analysis programs that identify hydrophobic and hydrophilic domains (see, e.g., Stryer, Biochemistry (3rd ed. 1988). Such domains are useful for making chimeric proteins and for in vitro assays of the invention, e.g., ligand binding assays. In the polypeptides of the invention, the N-terminal domain is believed to be extracellular, while the C-terminal domain is believed to be cytoplasmic or intracellular.

Polynucleotides

The invention provides purified and isolated polynucleotides (e.g., cDNA, genomic DNA, synthetic DNA, RNA, or combinations thereof, whether single- or double-stranded) that comprise a nucleotide sequence encoding the amino acid sequence of the polypeptides of the invention. Such polynucleotides are useful for recombinantly expressing the receptor and also for detecting expression of the receptor in cells (e.g., using Northern hybridization and in situ hybridization assays). Such polynucleotides also are useful in the design of antisense and other molecules for the suppression of the expression of a T1R receptor in a cultured cell, a tissue, or an animal; for therapeutic purposes; or to provide a model for diseases or conditions characterized by aberrant T1R expression. Specifically excluded from the definition of polynucleotides of the invention are entire isolated, non-recombinant native chromosomes of host cells. Polynucleotides of the invention include the nucleotide sequence of SEQ ID NO:1, SEQ ID NO:99, SEQ ID NO:59, SEQ ID NO:60, SEQ ID NO:62, and SEQ ID NO:63. It will be appreciated that numerous other polynucleotide sequences exist that also encode the T1R receptors of the invention due to the well-known degeneracy of the universal genetic code. Such polynucleotides are included within the scope of the invention.

The invention also provides a purified and isolated polynucleotide comprising a nucleotide sequence that encodes a mammalian (e.g., feline) polypeptide, wherein the polynucleotide hybridizes to a polynucleotide having a sequence of SEQ ID NO:1, SEQ ID NO:99, SEQ ID NO:59, SEQ ID NO:60, SEQ ID NO:62, or SEQ ID NO:63 or the non-coding strand complementary thereto, under high stringency conditions.

Genomic DNA of the invention comprises the protein-coding region for a polypeptide of the invention and is also intended to include allelic variants thereof. It is widely understood that, for many genes, genomic DNA is transcribed into RNA transcripts that undergo one or more splicing events wherein introns (i.e., non-coding regions) of the transcripts are removed, or "spliced out." RNA transcripts that can be spliced by alternative mechanisms, and therefore be subject to removal of different RNA sequences but still encode a T1R polypeptide, are referred to in the art as splice variants which are embraced by the invention. Splice variants comprehended by the invention therefore are encoded by the same original genomic DNA sequences but arise from distinct mRNA transcripts. Allelic variants are modified forms of a wild-type gene sequence, the modification resulting from recombination during chromosomal segregation or exposure to conditions which give rise to genetic mutation. Allelic variants, like wild type genes, are naturally occurring sequences (as opposed to non-naturally occurring variants that arise from in vitro manipulation).

The invention also comprehends cDNA that is obtained through reverse transcription of an RNA polynucleotide encoding a T1R receptor (conventionally followed by second strand synthesis of a complementary strand to provide a double-stranded DNA).

One embodiment of the DNA of the invention comprises a double-stranded molecule along with the complementary molecule (the "non-coding strand" or "complement") having a sequence unambiguously deducible from the coding strand according to Watson-Crick base-pairing rules for DNA.

The present invention includes fragments of nucleotide sequences encoding a T1R receptor comprising at least 10, and preferably at least 12, 14, 16, 18, 20, 25, 30, 35, 40, 45, 50, 75, or 100 consecutive nucleotides of a polynucleotide encoding a T1R receptor. Fragment polynucleotides of the invention may comprise sequences unique to the T1R-encoding polynucleotide sequence or sequences shared only by the feline T1R-encoding polynucleotide sequences of the invention, and therefore hybridize under highly stringent or moderately stringent conditions only (i.e., "specifically") to polynucleotides encoding a feline T1R receptor (or fragments thereof). Polynucleotide fragments of genomic sequences of the invention comprise not only sequences unique to the coding region, but also include fragments of the full-length sequence derived from introns, regulatory regions, and/or other non-translated sequences. Sequences unique to polynucleotides of the invention are recognizable through sequence comparison to other known polynucleotides, and can be identified through use of alignment programs routinely utilized in the art, e.g., those made available in public sequence databases. Such sequences also are recognizable from Southern hybridization analyses to determine the number of fragments of genomic DNA to which a polynucleotide will hybridize. Polynucleotides of the invention can be labeled in a manner that permits their detection, including radioactive, fluorescent, and enzymatic labeling. Polynucleotide fragments of the invention also include nucleotide sequences encoding functional domains of the polypeptides of the invention. For example, the polynucleotides of the invention encoding extracellular domains of feline T1R receptors include nucleotides 1-1689, 1870-1905, 2101-2178, and 2341-2376 of SEQ ID NO:60; nucleotides 1-441 of SEQ ID NO:63; and nucleotides 1-1713, 1882-1923, 2113-2193, and 2359-2382 of SEQ ID NO:1 or SEQ ID NO:99. The polynucleotides of the invention encoding transmembrane domains of feline T1R receptors include nucleotides 1690-1767, 1810-1869, 1906-1980, 2041-2100, 2179-2244, 2281-2340, and 2379-2451 of SEQ ID NO:60; nucleotides 442-501 of SEQ ID NO:63; and nucleotides 1714-1782, 1828-1881, 1924-1992, 2041-2112, 2191-2262, 2299-2358, and 2383-2436 of SEQ ID NO:1 or 99. The polynucleotides of the invention encoding intracellular domains of feline T1R receptors include nucleotides 1768-1809, 1981-2040, 2245-2280, and 2452-2523 of SEQ ID NO:60; nucleotides 502-1173 of SEQ ID NO:63; nucleotides 1783-1827, 1993-2040, 2263-2298, and 2437-2566 of SEQ ID NO:1; and nucleotides 1783-1827, 1993-2040, 2263-2298, and 2437-2595 of SEQ ID NO:99. The polynucleotides of the invention also include any combination of the polynucleotides encoding the functional domains of the invention, such as combinations of the polynucleotides encoding the extracellular, transmembrane, and/or intracellular domains of the same or different feline T1R receptors.

Fragment polynucleotides are particularly useful as probes for detection of full-length or fragments of T1R polynucleotides. One or more polynucleotides can be included in kits that are used to detect the presence of a polynucleotide encoding a T1R receptor, or used to detect variations in a polynucleotide sequence encoding a T1R receptor, for example a feline T1R receptor.

The invention also embraces DNAs encoding T1R polypeptides that hybridize under high stringency conditions to the non-coding strand, or complement, of the polynucleotides.

Exemplary highly stringent hybridization conditions are as follows: hybridization at 42° C. in a hybridization solution comprising 50% formamide, 1% SDS, 1 M NaCl, 10% Dextran sulfate, and washing twice for 30 minutes at 60° C. in a wash solution comprising 0.1×SSC and 1% SDS. It is understood in the art that conditions of equivalent stringency can be achieved through variation of temperature and buffer, or salt concentration as described, for example, in Ausubel et al. (Eds.), Protocols in Molecular Biology, John Wiley & Sons (1994), pp. 6.0.3 to 6.4.10. Modifications in hybridization conditions can be empirically determined or precisely calculated based on the length and the percentage of guanosine/cytosine (GC) base pairing of the probe. The hybridization conditions can be calculated as described, for example, in Sambrook et al., (Eds.), MOLECULAR CLONING: A LABORATORY MANUAL, Cold Spring Harbor Laboratory Press: Cold Spring Harbor, N.Y. (1989), pp. 9.47 to 9.51.

With the knowledge of the nucleotide sequence information disclosed in the present invention, one skilled in the art can identify and obtain nucleotide sequences which encode T1R receptors from different sources (i.e., different tissues or different organisms) through a variety of means well known to the skilled artisan and as disclosed by, for example, Sambrook et al., MOLECULAR CLONING: A LABORATORY MANUAL, Second Edition, Cold Spring Harbor Press, Cold Spring Harbor, N.Y. (1989).

For example, DNA that encodes a T1R receptor may be obtained by screening mRNA, cDNA, or genomic DNA with oligonucleotide probes generated from the T1R gene sequence information provided herein. Probes may be labeled with a detectable group, such as a fluorescent group, a radioactive atom or a chemiluminescent group in accordance with procedures known to the skilled artisan and used in conventional hybridization assays, as described by, for example, Sambrook et al.

A nucleic acid molecule comprising a T1R nucleotide sequence can alternatively be synthesized by use of the polymerase chain reaction (PCR) procedure, with the PCR oligonucleotide primers produced from the nucleotide sequences provided herein. The PCR reaction provides a method for selectively increasing the concentration of a particular nucleic acid sequence even when that sequence has not been previously purified and is present only in a single copy in a particular sample. The method can be used to amplify either single- or double-stranded DNA. The essence of the method involves the use of two oligonucleotide probes to serve as primers for the template-dependent, polymerase mediated replication of a desired nucleic acid molecule.

A wide variety of alternative cloning and in vitro amplification methodologies are well known to those skilled in the art. Examples of these techniques are found in, for example, Berger et al., *Guide to Molecular Cloning Techniques*, METHODS IN ENZYMOLOGY 152, Academic Press, Inc., San Diego, Calif. (Berger), which is incorporated herein by reference in its entirety.

The polynucleotides of the invention may be used in hybridization techniques known to those skilled in the art, including but not limited to, Northern and Southern blotting and overgo hybridization (see infra). For example, polynucleotide probes of the invention may be used in tissue distribution studies and diagnostic assays. The T1R receptors of the invention are likely to be present and active in tissues other than those involved in taste perception. It is therefore likely that the feline T1R receptors serve multiple functions in vivo, such as, for example, regulation of amino acid metabolism in addition to taste perception.

Automated sequencing methods can be used to obtain or verify the T1R receptor-encoding nucleotide sequence. The nucleotide sequences of the present invention are believed to be accurate. However, as is known in the art, nucleotide sequences obtained by automated methods may contain some errors. Nucleotide sequences determined by automation are typically at least about 90%, more typically at least about 95% to at least about 99.9% identical to the actual nucleotide sequence of a given nucleic acid molecule. The actual sequence may be more precisely determined using manual sequencing methods, which are well known in the art. An error in a sequence which results in an insertion or deletion of one or more nucleotides may result in a frame shift in translation such that the predicted amino acid sequence will differ from that which would be predicted from the actual nucleotide sequence of the nucleic acid molecule, starting at the point of the mutation.

The nucleic acid molecules of the present invention, and fragments derived therefrom, are useful for screening for restriction fragment length polymorphisms (RFLP) associated with certain disorders, for genetic mapping, and for methods for predicting the taste perception of an organism such as a mammal involving detection of a nucleotide sequence of the invention in a biological sample of the organism. For example, a mammal having a polynucleotide of the invention may be attracted to the taste of one or more amino acids and/or be insensitive or indifferent to one or more carbohydrate or high-intensity sweeteners.

The polynucleotide sequence information provided by the invention makes possible large-scale expression of the encoded polypeptide by techniques well known and routinely practiced in the art.

Vectors

Another aspect of the present invention is directed to vectors, or recombinant expression vectors, comprising any of the nucleic acid molecules described above. Vectors are used herein either to amplify DNA or RNA encoding a T1R receptor and/or to express DNA which encodes a T1R receptor. Examples of vectors include, but are not limited to, plasmids, phages, cosmids, episomes, viral particles or viruses, and integratable DNA fragments (i.e., fragments integratable into the host genome by homologous recombination). Examples of viral particles include, but are not limited to, adenoviruses, baculoviruses, parvoviruses, herpesviruses, poxviruses, adeno-associated viruses, Semliki Forest viruses, vaccinia viruses, and retroviruses. Examples of expression vectors include, but are not limited to, pcDNA3 (Invitrogen) and pSVL (Pharmacia Biotech). Other expression vectors include, but are not limited to, pSPORT™ vectors, pGEM™ vectors (Promega), pPROEXvectors™ (LTI, Bethesda, Md.), Bluescript™ vectors (Stratagene), pQE™ vectors (Qiagen), pSE420™ (Invitrogen), and pYES2™(Invitrogen).

Expression constructs may comprise T1R-encoding polynucleotides operably linked to an endogenous or exogenous expression control DNA sequence and a transcription terminator. Expression control DNA sequences include promoters, enhancers, operators, and regulatory element binding sites generally, and are typically selected based on the expression systems in which the expression construct is to be utilized. Promoter and enhancer sequences are generally selected for the ability to increase gene expression, while operator sequences are generally selected for the ability to regulate gene expression. Expression constructs of the invention may also include sequences encoding one or more selectable markers that permit identification of host cells bearing the construct. Expression constructs may also include sequences that facilitate, or promote, homologous recombination in a host cell. Constructs of the invention also may include sequences necessary for replication in a host cell.

Expression constructs may be utilized for production of an encoded protein, but may also be utilized simply to amplify a T1R-encoding polynucleotide sequence. In some embodiments, the vector is an expression vector wherein a polynucleotide of the invention is operably linked to a polynucleotide comprising an expression control sequence. Autonomously replicating recombinant expression constructs such as plasmid and viral DNA vectors incorporating polynucleotides of the invention are also provided. Some expression vectors are replicable DNA constructs in which a DNA sequence encoding a T1R receptor is operably linked or connected to suitable control sequence(s) capable of effecting the expression of the receptor in a suitable host. Amplification vectors do not require expression control domains, but rather need only the ability to replicate in a host, such as conferred by an origin of replication, and a selection gene to facilitate recognition of transformants. The need for control sequences in the expression vector will vary depending upon the host selected and the transformation method chosen. Control sequences include a transcriptional promoter, an optional operator sequence to control transcription, a sequence encoding suitable mRNA ribosomal binding, and sequences which control the termination of transcription and translation.

Vectors of the invention may contain a promoter that is recognized by the host organism. The promoter sequences of the present invention may be prokaryotic, eukaryotic, or viral. Examples of suitable prokaryotic sequences include the $P_R$ and $P_L$ promoters of bacteriophage lambda (The Bacteriophage Lambda, Hershey, A. D., Ed., Cold Spring Harbor Press, Cold Spring Harbor, N.Y. (1973), which is incorporated herein by reference in its entirety; Lambda II, Hendrix, R. W., Ed., Cold Spring Harbor Press, Cold Spring Harbor, N.Y. (1980), which is incorporated herein by reference in its entirety), the trp, recA, heat shock, and lacZ promoters of *E. coli* and the SV40 early promoter (Benoist et al. *Nature,* 1981, 290, 304-310), which is incorporated herein by reference in its entirety. Additional promoters include, but are not limited to, mouse mammary tumor virus, long terminal repeat of human immunodeficiency virus, maloney virus, cytomegalovirus immediate early promoter, Epstein Barr virus, Rous sarcoma virus, human actin, human myosin, human hemoglobin, human muscle creatine, and human metallothionein.

Additional regulatory sequences can also be included in vectors of the invention. Examples of suitable regulatory sequences are represented by the Shine-Dalgarno of the replicase gene of the phage MS-2 and of the gene cII of bacteriophage lambda. The Shine-Dalgarno sequence may be directly followed by DNA encoding a T1R receptor, resulting in the expression of the mature protein.

Moreover, suitable expression vectors can include an appropriate marker that allows the screening of transformed host cells. The transformation of the selected host is carried out using any one of the various techniques well known to the expert in the art and described in Sambrook et al., supra.

An origin of replication or autonomously replicating sequence (ARS) can also be provided either by construction of the vector to include an exogenous origin or may be provided by the host cell chromosomal replication mechanism. If the vector is integrated into the host cell chromosome, the latter may be sufficient. Alternatively, rather than using vectors which contain viral origins of replication, one skilled in the art can transform mammalian cells by the method of co-transformation with a selectable marker and T1R DNA. An example of a suitable marker is dihydrofolate reductase (DHFR) or thymidine kinase (see U.S. Pat. No. 4,399,216).

Additional regulatory sequences that may be included in the polynucleotides of the invention include secretion signals which allow the encoded polypeptide to cross and/or lodge in cell membranes, or be secreted from the cell.

Nucleotide sequences encoding a T1R receptor may be recombined with vector DNA in accordance with conventional techniques, including blunt-ended or staggered-ended termini for ligation, restriction enzyme digestion to provide appropriate termini, filling in of cohesive ends as appropriate, alkaline phosphatase treatment to avoid undesirable joining, and ligation with appropriate ligases. Techniques for such manipulation are disclosed by Sambrook et al., supra and are well known in the art. Methods for construction of mammalian expression vectors are disclosed in, for example, Okayama et al, *Mol. Cell. Biol.,* 1983, 3, 280, Cosman et al., *Mol. Immunol.,* 1986, 23, 935, Cosman et al., *Nature,* 1984, 312, 768, EP-A-0367566, and WO 91/18982, each of which is incorporated herein by reference in its entirety.

Vectors of the invention are useful for expressing T1Rs in various cell systems. Overexpression of a T1R may, for example, be useful in screening for antagonists of the receptor as described herein. Stimulation of transcription of T1R polynucleotides may be used to analyze the effect of T1R expression on the expression of other taste receptors. Vectors may also be used to produce antisense polynucleotides that inhibit endogenous T1R expression to analyze the effect of a loss of the T1R gene.

Host Cells

According to another aspect of the invention, host cells are provided, including prokaryotic and eukaryotic cells, comprising a polynucleotide of the invention (or vector of the invention) in a manner that permits expression of the encoded T1R polypeptide. Polynucleotides of the invention may be introduced into the host cell as part of a circular plasmid, or as linear DNA comprising an isolated protein-coding region or a viral vector. Methods for introducing DNA into the host cell that are well known and routinely practiced in the art include transformation, transfection, electroporation, nuclear injection, or fusion with carriers such as liposomes, micelles, ghost cells, and protoplasts. Expression systems of the invention include bacterial, yeast, fungal, plant, insect, invertebrate, vertebrate, and mammalian cell systems.

The invention provides host cells that are transformed or transfected (stably or transiently) with polynucleotides of the invention or vectors of the invention. As stated above, such host cells are useful for amplifying the polynucleotides and also for expressing a T1R polypeptide or fragment thereof encoded by the polynucleotide.

In still another related embodiment, the invention provides a method for producing a T1R polypeptide (or fragment thereof) comprising the steps of growing a host cell of the invention in a nutrient medium and isolating the polypeptide or variant thereof from the cell or the medium. Because the T1R receptor is a membrane-spanning polypeptide, it will be appreciated that, for some applications, such as certain activity assays, the preferable isolation may involve isolation of cell membranes containing the polypeptide embedded therein, whereas for other applications a more complete isolation may be preferable.

According to some aspects of the present invention, transformed host cells having an expression vector comprising any of the nucleic acid molecules described above are provided. Expression of the nucleotide sequence occurs when the expression vector is introduced into an appropriate host cell. Suitable host cells for expression of the polypeptides of the invention include, but are not limited to, prokaryotes, yeast, and eukaryotes. If a prokaryotic expression vector is employed, then the appropriate host cell would be any prokaryotic cell capable of expressing the cloned sequences. Suitable prokaryotic cells include, but are not limited to, bacteria of the genera *Escherichia, Bacillus, Salmonella, Pseudomonas, Streptomyces*, and *Staphylococcus.*

If a eukaryotic expression vector is employed, then the appropriate host cell would be any eukaryotic cell capable of expressing the cloned sequence. Eukaryotic cells may be cells of higher eukaryotes. Suitable eukaryotic cells include, but are not limited to, non-human mammalian tissue culture cells and human tissue culture cells. Host cells include, but are not limited to, insect cells, HeLa cells, Chinese hamster ovary cells (CHO cells), African green monkey kidney cells (COS cells), human HEK-293 cells, and murine 3T3 fibroblasts.

Propagation of such cells in cell culture has become a routine procedure (see, Tissue Culture, Academic Press, Kruse and Patterson, eds. (1973), which is incorporated herein by reference in its entirety).

In addition, a yeast host may be employed as a host cell. Yeast cells include, but are not limited to, the genera *Saccharomyces, Pichia*, and *Kluveromyces*. Yeast hosts may be *S. cerevisiae* and *P. pastoris*. Yeast vectors may contain an origin of replication sequence from a 2T yeast plasmid, an autonomously replication sequence (ARS), a promoter region, sequences for polyadenylation, sequences for transcription termination, and a selectable marker gene. Shuttle vectors for replication in both yeast and *E. coli* are also included herein.

Alternatively, insect cells may be used as host cells. In some embodiments, the polypeptides of the invention are expressed using a baculovirus expression system (see, Luckow et al., *Bio/Technology,* 1988, 6, 47; Baculovirus Expression Vectors: A Laboratory Manual, O'Reilly et al. (Eds.), W.H. Freeman and Company, New York, 1992; and U.S. Pat. No. 4,879,236, each of which is incorporated herein by reference in its entirety). In addition, the MAXBAC™ complete baculovirus expression system (Invitrogen) can, for example, be used for production in insect cells.

Host cells of the invention are a valuable source of immunogen for development of antibodies specifically immunoreactive with the T1R receptor. Host cells of the invention also are useful in methods for the large-scale production of T1R polypeptides wherein the cells are grown in a suitable culture medium and the desired polypeptide products are isolated from the cells, or from the medium in which the cells are grown, by purification methods known in the art, e.g., conventional chromatographic methods including immunoaffinity chromatography, receptor affinity chromatography, hydrophobic interaction chromatography, lectin affinity chromatography, size exclusion filtration, cation or anion exchange chromatography, high pressure liquid chromatography (HPLC), reverse phase HPLC, and the like. Still other methods of purification include those methods wherein the desired protein is expressed and purified as a fusion protein having a specific tag, label, or chelating moiety that is recognized by a specific binding partner or agent. The purified protein can be cleaved to yield the desired protein, or can be left as an intact fusion protein. Cleavage of the fusion component may produce a form of the desired protein having additional amino acid residues as a result of the cleavage process.

Knowledge of the feline T1R receptor-encoding nucleotide sequence allows for modification of cells to permit, or increase, expression of endogenous receptor. Cells can be modified (e.g., by homologous recombination) to provide increased expression by replacing, in whole or in part, the naturally occurring T1R promoter with all or part of a heterologous promoter so that the cells express the receptor at higher or lower levels. The heterologous promoter is inserted in such a manner that it is operably linked to endogenous T1R coding sequence. (See, for example, PCT International Publication No. WO 94/12650, PCT International Publication No. WO 92/20808, and PCT International Publication No. WO 91/09955.) It is also contemplated that, in addition to heterologous promoter DNA, amplifiable marker DNA (e.g., ada, dhfr, and the multifunctional CAD gene which encodes carbamoyl phosphate synthase, aspartate transcarbamylase, and dihydroorotase) and/or intron DNA may be inserted along with the heterologous promoter DNA. If linked to the T1R coding sequence, amplification of the marker DNA by standard selection methods results in co-amplification of the T1R coding sequences in the cells.

Knock-Out and Transplacement Animals

The DNA sequence information provided by the present invention also makes possible the development (e.g., by homologous recombination strategies; see Capecchi, *Science* 244:1288-1292 (1989), which is incorporated herein by reference) of transgenic or gene-targeted animals, including, for example, animals that fail to express functional T1R ("knock-out") or that express a variant thereof ("transplacement"). Such animals (especially small laboratory animals such as rats, rabbits, mice, and cats) are useful as models for studying the in vivo activities of T1R receptors and modulators of T1R receptors.

Antisense and siRNA

Also encompassed by the invention are antisense and short interfering polynucleotides that recognize and hybridize to polynucleotides encoding the T1R receptors of the invention. Full-length and fragment antisense polynucleotides are provided. Fragment antisense molecules of the invention include (i) those that specifically recognize and hybridize to T1R RNA (as determined by sequence comparison of DNA encoding T1R receptor to DNA encoding other known molecules). Identification of sequences unique to T1R-encoding polynucleotides can be deduced through use of any publicly available sequence database, and/or through use of commercially available sequence comparison programs. After identification of the desired sequences, isolation through restriction digestion or amplification using any of the various polymerase chain reaction techniques well known in the art can be performed. Antisense polynucleotides are particularly relevant to regulation of expression of T1R receptor by those cells expressing T1R mRNA.

Antisense nucleic acids (preferably 10 to 30 base-pair oligonucleotides) capable of specifically binding to T1R expression control sequences or T1R RNA are introduced into cells (e.g., by a viral vector or colloidal dispersion system such as a liposome). The antisense nucleic acid binds to the target nucleotide sequence in the cell and prevents transcription and/or translation of the target sequence. Phosphorothioate and methylphosphonate antisense oligonucleotides are specifically contemplated for therapeutic use by the invention. Locked nucleic acids are also specifically contemplated for therapeutic use by the present invention. (See, for example, Wahlestedt et al., *Proc. Natl. Acad. Sci. USA,* 97(10), 5633-5638 (2000), which is incorporated by reference in its entirety) The antisense oligonucleotides may be further modified by adding poly-L-lysine, transferrin polylysine, or cholesterol moieties at their 5' end. Suppression of T1R expression at either the transcriptional or translational level is useful to generate cellular or animal models for diseases/conditions characterized by aberrant T1R expression.

Antisense oligonucleotides to or fragments of nucleotide sequence of SEQ ID NO:1, SEQ ID NO:99, SEQ ID NO:59, SEQ ID NO:60, SEQ ID NO:62, or SEQ ID NO:63, or sequences complementary or homologous thereto, derived from the nucleotide sequences of the present invention encoding T1R receptors are useful as diagnostic tools for probing gene expression in various tissues. For example, tissue can be probed in situ with oligonucleotide probes carrying detectable groups by conventional autoradiography techniques to investigate native expression of this enzyme or pathological conditions relating thereto. Antisense oligonucleotides may be directed to regulatory regions of a T1R nucleotide sequence, or mRNA corresponding thereto, including, but not limited to, the initiation codon, TATA box, enhancer sequences, and the like.

Those of skill in the art recognize that the antisense oligonucleotides that inhibit the expression and/or biological activity of a T1R receptor of the invention may be predicted using any gene encoding a T1R receptor. Specifically, antisense nucleic acid molecules comprise a sequence preferably complementary to at least about 5, 10, 15, 20, 25, 30, 35, 40, 45, 50, 100, 250 or 500 nucleotides or an entire T1R receptor gene sequence. The antisense oligonucleotides may comprise a sequence complementary to about 15 consecutive nucleotides of the coding strand of the T1R receptor-encoding sequence.

In one embodiment, an antisense nucleic acid molecule is antisense to a "coding region" of the coding strand of a nucleotide sequence encoding a T1R protein. The coding strand may also include regulatory regions of the T1R sequence. The term "coding region" refers to the region of the nucleotide sequence comprising codons which are translated into amino acid residues. In another embodiment, the antisense nucleic acid molecule is antisense to a "noncoding region" of the coding strand of a nucleotide sequence encoding a T1R protein. The term "noncoding region" refers to 5' and 3' sequences which flank the coding region that are not translated into amino acids (i.e., also referred to as 5' and 3' untranslated regions (UTR)).

Antisense oligonucleotides may be directed to regulatory regions of a nucleotide sequence encoding a T1R protein, or mRNA corresponding thereto, including, but not limited to, the initiation codon, TATA box, enhancer sequences, and the like. Given the coding strand sequences provided herein, antisense nucleic acids of the invention can be designed according to the rules of Watson and Crick or Hoogsteen base pairing. The antisense nucleic acid molecule can be complementary to the entire coding region of a T1R mRNA, but also may be an oligonucleotide that is antisense to only a portion of the coding or noncoding region of the mRNA. For example, the antisense oligonucleotide can be complementary to the region surrounding the translation start site of an mRNA. An antisense oligonucleotide can be, for example, about 5, 10, 15, 20, 25, 30, 35, 40, 45 or 50 nucleotides in length.

Another means to inhibit the activity of a T1R receptor according to the invention is via RNA interference (RNAi) (see e.g., Elbashir et al., *Nature,* 411:494-498 (2001); Elbashir et al., *Genes Development,* 15:188-200 (2001)). RNAi is the process of sequence-specific, post-transcriptional gene silencing, initiated by double-stranded RNA (dsRNA) that is homologous in sequence to the silenced gene (e.g., is homologous in sequence to the sequence encoding a T1R receptor, for example but not limited to the sequence as set forth in SEQ ID NO:1, SEQ ID NO:99, SEQ ID NO:59, SEQ ID NO:60, SEQ ID NO:62, or SEQ ID NO:63). siRNA-mediated silencing is thought to occur post-transcriptionally and/or transcriptionally. For example, siRNA duplexes may mediate post-transcriptional gene silencing by reconstitution of siRNA-protein complexes (siRNPs), which guide mRNA recognition and targeted cleavage.

Accordingly, another form of a T1R inhibitory compound of the invention is a short interfering RNA (siRNA) directed against a T1R-encoding sequence. Exemplary siRNAs are siRNA duplexes (for example, 10-25, preferably 20, 21, 22, 23, 24, or 25 residues in length) having a sequence homologous or identical to a fragment of the T1R sequence set forth as SEQ ID NO:1, SEQ ID NO:99, SEQ ID NO:59, SEQ ID NO:60, SEQ ID NO:62, or SEQ ID NO:63 and having a symmetric 2-nucleotide 3'-overhang. The 2-nucleotide 3' overhang may be composed of (2'-deoxy) thymidine because it reduces costs of RNA synthesis and may enhance nuclease resistance of siRNAs in the cell culture medium and within transfected cells. Substitution of uridine by thymidine in the 3' overhang is also well tolerated in mammalian cells, and the sequence of the overhang appears not to contribute to target recognition.

Polypeptides

The invention also provides purified and isolated mammalian (e.g., feline) T1R receptor polypeptides and dimers. The T1R polypeptides of the invention may be encoded by a polynucleotide of the invention. Some embodiments include a feline T1R polypeptide comprising the amino acid sequence of SEQ ID NO:2, SEQ ID NO:61, or SEQ ID NO:64, or fragments thereof comprising an epitope specific to the polypeptide. T1R receptors may form homodimers or heterodimers in taste buds and other tissues to sense molecules. The invention further comprises homodimeric and heterodimeric forms of T1R receptors wherein one T1R receptor molecule associates with a molecule of T1R1, T1R2, or T1R3. A reference to "epitope specific to" or "polypeptide-specific epitope," or variations thereof, indicates that a portion of the T1R receptor, T1R receptor amino acid sequence, or T1R dimer is recognizable by an antibody that is specific for the T1R or amino acid sequence.

Included within the scope of the invention are polypeptides encoded by feline allelic variants of T1R. The allelic variants of the T1R receptor of the invention may modify the taste perception of a mammal, such as a cat, to a taste stimulus. Such functional amino acid sequence modifications may account for differences in intraspecies (e.g., breed-specific) taste perception.

Extracellular epitopes are useful for generating and screening for antibodies and other binding compounds that bind to a T1R receptor or dimer. Thus, in another embodiment, the invention provides a purified and isolated polypeptide comprising at least one extracellular domain of the T1R receptor or dimer. Also included is a polypeptide comprising a T1R receptor fragment selected from the group consisting of an extracellular domain of T1R3 (residues 1-571, 628-641, 705-730, and 787-794 of SEQ ID NO:2), a transmembrane domain of T1R3 (residues 572-594, 610-627, 642-664, 681-704, 731-754, 767-780, and 795-812 of SEQ ID NO:2), an intracellular domain of T1R3 (residues 595-609, 665-680, 755-766, and 813-865 of SEQ ID NO:2), an extracellular domain of the T1R1 receptor (residues 1-563, 624-635, 701-726, and 781-792 of SEQ ID NO:61), a transmembrane domain of the T1R1 receptor (residues 564-589, 604-623, 636-660, 681-700, 727-748, 761-780, and 793-817 of SEQ ID NO:61), an intracellular domain of the T1R1 receptor (residues 590-603, 661-680, 749-760, and 818-841 of SEQ ID NO:61), an extracellular domain of T1R2 (residues 1-147 of SEQ ID NO:64), a transmembrane domain of a T1R2 receptor (residues 148-167 of SEQ ID NO:64), and an intracellular domain of a T1R2 receptor (residues 168-391 of SEQ ID NO:64). Polypeptide fragments of the invention may be continuous portions of the native receptor. However, it will also be appreciated that knowledge of the T1R genes and protein sequences as provided herein permits recombination of various domains that are not contiguous in the native protein.

The invention embraces polypeptides that preferably have at least about 99%, at least about 95%, at least about 90%, at least about 85%, at least about 80%, at least about 75%, at least about 74%, at least about 73%, at least about 72%, at least about 71%, at least about 70%, at least about 65%, at least about 60%, at least about 55%, or at least about 50% identity and/or homology to the polypeptides of the invention.

Polypeptides of the invention may be isolated from natural cell sources or may be chemically synthesized, but are preferably produced by recombinant procedures involving host cells of the invention. Use of mammalian host cells is expected to provide for such post-translational modifications (e.g., glycosylation, truncation, lipidation, and phosphorylation) as may be needed to confer optimal biological activity on recombinant expression products of the invention.

The invention also embraces variant T1R polypeptides. In one example, insertion variants are provided wherein one or more amino acid residues supplement a T1R amino acid sequence such as SEQ ID NO:2, SEQ ID NO:61, or SEQ ID NO:64. Insertions may be located at either or both termini of the protein, or may be positioned within internal regions of the amino acid sequence. Insertional variants with additional residues at either or both termini can include, for example, fusion proteins and proteins including amino acid tags or labels.

Insertion variants include T1R polypeptides wherein one or more amino acid residues are added to a biologically active fragment thereof. For example, the insertion variants of the invention include chimeric T1R receptors wherein at least one functional domain of a feline T1R receptor of the invention is present.

The invention also embraces T1R variants having additional amino acid residues that result from use of specific expression systems. For example, use of commercially available vectors that express a desired polypeptide as part of a glutathione-S-transferase (GST) fusion product provides the desired polypeptide having an additional glycine residue at position −1 after cleavage of the GST component from the desired polypeptide. Variants that result from expression in other vector systems are also contemplated.

In another aspect, the invention provides deletion variants wherein one or more amino acid residues in a T1R polypeptide are removed. Deletions can be effected at one or both termini of the T1R polypeptide, or with removal of one or more non-terminal amino acid residues of T1R. Deletion variants, therefore, include all fragments of a T1R polypeptide.

The invention also embraces polypeptide fragments that maintain biological (e.g., ligand binding, dimerization, receptor activity) and/or immunological properties of a T1R polypeptide.

As used in the present invention, polypeptide fragments preferably comprise at least 10, 15, 20, 25, 30, 35, 40, 45, or 50 consecutive amino acids of SEQ ID NO:2, SEQ ID NO:61, or SEQ ID NO:64. Some polypeptide fragments display antigenic properties unique to, or specific for, a feline T1R receptor. Fragments of the invention having the desired biological and immunological properties can be prepared by any of the methods well known and routinely practiced in the art.

In still another aspect, the invention provides substitution variants of T1R polypeptides. Substitution variants include those polypeptides wherein one or more amino acid residues of a T1R polypeptide are removed and replaced with alternative residues. In one aspect, the substitutions are conservative in nature; however, the invention embraces substitutions that are also non-conservative. Conservative substitutions for this purpose may be defined as set out in Tables 1, 2, or 3 below.

Variant polypeptides include those wherein conservative substitutions have been introduced by modification of polynucleotides encoding polypeptides of the invention. Amino acids can be classified according to physical properties and contribution to secondary and tertiary protein structure. A conservative substitution is recognized in the art as a substitution of one amino acid for another amino acid that has similar properties. Exemplary conservative substitutions are set out in Table 1 (from WO 97/09433, page 10, published Mar. 13, 1997 (PCT/GB96/02197, filed Sep. 6, 1996), immediately below.

TABLE 1

Conservative Substitutions I

| SIDE CHAIN CHARACTERISTIC | AMINO ACID |
|---|---|
| Aliphatic | |
| Non-polar | G A P |
| | I L V |
| Polar - uncharged | C S T M |
| | N Q |
| Polar - charged | D E |
| | K R |
| Aromatic | H F W Y |
| Other | N Q D E |

Alternatively, conservative amino acids can be grouped as described in Lehninger, [Biochemistry, Second Edition; Worth Publishers, Inc. NY, N.Y. (1975), pp. 71-77] as set out in Table 2, below.

TABLE 2

Conservative Substitutions II

| SIDE CHAIN CHARACTERISTIC | AMINO ACID |
|---|---|
| Non-polar (hydrophobic) | |
| A. Aliphatic: | A L I V P |
| B. Aromatic: | F W |
| C. Sulfur-containing: | M |
| D. Borderline: | G |
| Uncharged-polar | |
| A. Hydroxyl: | STY |
| B. Amides: | N Q |
| C. Sulfhydryl: | C |
| D. Borderline: | G |
| Positively Charged (Basic): | K R H |
| Negatively Charged (Acidic): | D E |

As still another alternative, exemplary conservative substitutions are set out in Table 3, below.

TABLE 3

Conservative Substitutions III

| Original Residue | Exemplary Substitution |
|---|---|
| Ala (A) | Val, Leu, Ile |
| Arg (R) | Lys, Gln, Asn |
| Asn (N) | Gln, His, Lys, Arg |
| Asp (D) | Glu |
| Cys (C) | Ser |
| Gln (Q) | Asn |
| Glu (E) | Asp |
| His (H) | Asn, Gln, Lys, Arg |
| Ile (I) | Leu, Val, Met, Ala, Phe, |
| Leu (L) | Ile, Val, Met, Ala, Phe |
| Lys (K) | Arg, Gln, Asn |
| Met (M) | Leu, Phe, Ile |
| Phe (F) | Leu, Val, Ile, Ala |
| Pro (P) | Gly |
| Ser (S) | Thr |
| Thr (T) | Ser |
| Trp (W) | Tyr |
| Tyr (Y) | Trp, Phe, Thr, Ser |
| Val (V) | Ile, Leu, Met, Phe, Ala |

It should be understood that the definition of polypeptides of the invention is intended to include polypeptides bearing modifications other than insertion, deletion, or substitution of amino acid residues. By way of example, the modifications may be covalent in nature, and include for example, chemical bonding with polymers, lipids, other organic, and inorganic moieties. Such derivatives may be prepared to increase circulating half-life of a polypeptide, or may be designed to improve the targeting capacity of the polypeptide for desired cells, tissues, or organs. Similarly, the invention further embraces T1R polypeptides that have been covalently modified to include one or more water-soluble polymer attachments such as polyethylene glycol, polyoxyethylene glycol, or polypropylene glycol. Variants that display ligand binding properties of native T1R and are expressed at higher levels, as well as variants that provide for constitutively active receptors, are particularly useful in assays of the invention; the variants are also useful in providing cellular, tissue and animal models of diseases/conditions characterized by aberrant T1R activity.

In a related embodiment, the present invention provides compositions comprising purified polypeptides of the invention. Some compositions comprise, in addition to the polypeptide of the invention, a pharmaceutically acceptable (i.e., sterile and non-toxic) liquid, semisolid, or solid diluent that serves as a pharmaceutical vehicle, excipient, or medium. Any diluent known in the art may be used. Exemplary diluents include, but are not limited to, water, saline solutions, polyoxyethylene sorbitan monolaurate, magnesium stearate, methyl- and propylhydroxybenzoate, talc, alginates, starches, lactose, sucrose, dextrose, sorbitol, mannitol, glycerol, calcium phosphate, mineral oil, and cocoa butter.

Variants that display ligand-binding properties of native T1R and are expressed at higher levels, as well as variants that provide for constitutively active receptors, are particularly useful in assays of the invention; the variants are also useful in assays of the invention and in providing cellular, tissue and animal models of diseases/conditions characterized by aberrant T1R activity.

Antibodies

Also included in the present invention are antibodies (e.g., monoclonal and polyclonal antibodies, single chain antibodies, chimeric antibodies, bifunctional/bispecific antibodies, humanized antibodies, human antibodies, felinized antibodies, feline antibodies, and complementary determining region (CDR)-grafted antibodies, including compounds which include CDR sequences which specifically recognize a polypeptide of the invention) specific for a T1R receptor of the invention, a fragment thereof, or dimers of the T1R receptors of the invention (e.g., T1R1-T1R3; T1R2-T1R3; and T1R3-T1R3 dimers). Antibody fragments, including Fab, Fab', $F(ab')_2$, and $F_v$, are also provided by the invention. The term "specific for," when used to describe antibodies of the invention, indicates that the variable regions of the antibodies of the invention recognize and bind T1R polypeptides, preferably exclusively (i.e., are able to distinguish T1R polypeptides of the invention from other known polypeptides by virtue of measurable differences in binding affinity, despite the possible existence of localized sequence identity, homology, or similarity between T1R and such polypeptides). It will be understood that specific antibodies may also interact with other proteins (for example, *S. aureus* protein A or other antibodies in ELISA techniques) through interactions with sequences outside the variable region of the antibodies, and, in particular, in the constant region of the molecule. Screening assays to determine binding specificity of an antibody of the invention are well known and routinely practiced in the art. For a comprehensive discussion of such assays, see Harlow et al. (Eds.), ANTIBODIES A LABORATORY MANUAL; Cold Spring Harbor Laboratory; Cold Spring Harbor, N.Y. (1988), Chapter 6. Antibodies that recognize and bind fragments of the T1R polypeptides of the invention are also contemplated, provided that the antibodies are specific for T1R polypeptides. Antibodies of the invention can be produced using any method well known and routinely practiced in the art.

The invention provides an antibody that is specific for the feline T1R receptors of the invention. Antibodies that can be generated from polypeptides that have previously been described in the literature and that are capable of fortuitously cross-reacting with feline T1R receptor (e.g., due to the fortuitous existence of a similar epitope in both polypeptides) are considered "cross-reactive" antibodies. Such cross-reactive antibodies are not antibodies that are "specific" for a feline T1R receptor. The determination of whether an antibody is specific for a feline T1R receptor or is cross-reactive with another known receptor is made using any of several assays, such as Western blotting assays, that are well known in the art. For identifying cells that express a T1R receptor and also for modulating T1R-ligand binding activity, antibodies that specifically bind to an extracellular epitope of the T1R receptor may be used.

In some embodiments of the invention, the antibodies specifically bind T1R polypeptides, or block ligands or binding partners from binding to the T1R polypeptides. These antibodies may also block the biological activity of the T1R polypeptides. In other embodiments, the antibodies preferentially bind T1R polypeptides of a certain species or family of T1R polypeptides.

In some variations, the invention provides monoclonal antibodies. Hybridomas that produce such antibodies also are intended as aspects of the invention. In yet another variation, the invention provides a felinized antibody. Felinized antibodies are useful for in vivo therapeutic indications.

In another variation, the invention provides a cell-free composition comprising polyclonal antibodies, wherein at least one of the antibodies is an antibody of the invention specific for T1R receptor. Antisera isolated from an animal is an exemplary composition, as is a composition comprising an antibody fraction of an antisera that has been resuspended in water or in another diluent, excipient, or carrier.

In still another related embodiment, the invention provides an anti-idiotypic antibody specific for an antibody that is specific for T1R receptor of the invention.

It is well known that antibodies contain relatively small antigen binding domains that can be isolated chemically or by recombinant techniques. Such domains are useful T1R receptor binding molecules themselves, and also may be reintroduced into other antibodies or fused to toxins or other polypeptides. Thus, in still another embodiment, the invention provides a polypeptide comprising a fragment of a T1R-specific antibody, wherein the fragment and the polypeptide bind to the T1R receptor. By way of non-limiting example, the invention provides polypeptides that are single chain antibodies and CDR-grafted antibodies.

Non-feline antibodies may be felinized by any of the methods known in the art. In one method, the non-feline CDRs are inserted into a feline antibody or consensus antibody framework sequence. Similarly, non-human antibodies may be humanized by methods known in the art. In one embodiment, non-human CDRs are inserted into a human antibody or consensus antibody framework sequence. Further changes can then be introduced into the antibody framework to modulate affinity or immunogenicity.

Antibodies of the invention are useful for, e.g., therapeutic purposes (such as by modulating activity of T1R receptor), diagnostic purposes (such as detecting or quantitating T1R receptor activity), and also for purification of T1R receptor. Kits comprising an antibody of the invention for any of the purposes described herein are also included within the scope of the invention. In general, a kit of the invention preferably includes a control antigen for which the antibody is immunospecific.

Compositions

Mutations in the feline T1R gene that result in loss of normal function of the T1R gene product underlie some T1R-related disease states. The invention comprehends gene and peptide therapy, for example, to restore T1R activity to treat those disease states. Delivery of a functional T1R gene to appropriate cells is effected ex vivo, in situ, or in vivo by use of vectors, and more particularly viral vectors (e.g., adenovirus, adeno-associated virus, or a retrovirus), or ex vivo by use of physical DNA transfer methods (e.g., liposomes or chemical treatments). See, for example, Anderson, *Nature*, supplement to vol. 392, No. 6679, pp. 25-20 (1998). For additional reviews of gene therapy technology see Friedmann, *Science,* 244: 1275-1281 (1989); Verma, *Scientific American:* 68-84 (1990); and Miller, *Nature,* 357: 455-460 (1992). Alternatively, it is contemplated that in other disease states, preventing the expression of, or inhibiting the activity of, T1R receptor will be useful in treatment. It is contemplated that antisense therapy or gene therapy could be applied to negatively regulate the expression of T1R receptor.

Another aspect of the present invention is directed to compositions, including pharmaceutical compositions, comprising any of the nucleic acid molecules or recombinant expression vectors described above and an acceptable carrier or diluent. The carrier or diluent may be pharmaceutically acceptable. Suitable carriers are described in the most recent edition of *Remington's Pharmaceutical Sciences*, A. Osol, a standard reference text in this field, which is incorporated herein by reference in its entirety. Examples of such carriers or diluents include, but are not limited to, water, saline, Ringer's solution, dextrose solution, and 5% serum albumin. Liposomes and nonaqueous vehicles such as fixed oils may also be used. The formulations may be sterilized by commonly used techniques.

Also within the scope of the invention are compositions comprising polypeptides, polynucleotides, or antibodies of the invention that have been formulated with, e.g., a pharmaceutically acceptable carrier.

The invention also provides methods of using antibodies of the invention. For example, the invention provides a method for modulating ligand-binding of a T1R receptor comprising the step of contacting the receptor with an antibody specific for the T1R polypeptide, under conditions wherein the antibody binds the receptor.

Methods of Identifying Ligands and Modulators

The invention also provides assays to identify compounds that bind and/or modulate T1R receptor. A "T1R binding partner" is a compound that directly or indirectly binds a T1R polypeptide of the invention. One assay of the invention comprises the steps of: (a) contacting T1R receptor or T1R dimer of the invention with a compound suspected of binding T1R receptor or dimer (the test compound); and (b) measuring binding between the compound and the T1R receptor or dimer. In one variation, the composition comprises a cell expressing T1R receptor or dimer on its surface. In another variation, isolated T1R receptor or dimer or cell membranes comprising T1R receptor or dimer are employed. The binding may be measured directly, e.g., by using a labeled compound, or may be measured indirectly. Compounds identified as binding a T1R receptor or T1R dimer may be further tested in other assays including, but not limited to, T1R activity assays and/or in vivo models, in order to confirm or quantitate their activity.

Specific binding molecules, including natural ligands and synthetic compounds, can be identified or developed using isolated or recombinant T1R products, T1R variants, or preferably, cells expressing such products. Binding partners are useful for purifying T1R products and detection or quantification of T1R products in fluid and tissue samples using known immunological procedures. Binding molecules are also manifestly useful in modulating (i.e., blocking, inhibiting or stimulating) biological activities of T1R, especially those activities involved in signal transduction. Binding molecules also are useful in methods for predicting the taste perception of an organism such as a mammal by detecting a polypeptide of the invention in a biological sample of the organism. For example, an organism in which a polypeptide of the invention has been identified may be attracted to the taste of amino acids and/or indifferent to the taste of carbohydrate and high-intensity sweeteners.

The DNA and amino acid sequence information provided by the present invention also makes possible identification of binding partner compounds with which a T1R polypeptide or polynucleotide will interact. Methods to identify binding partner compounds include solution assays, in vitro assays wherein T1R polypeptides are immobilized, and cell-based assays. Identification of binding partner compounds of T1R polypeptides provides candidates for therapeutic or prophylactic intervention in pathologies associated with T1R normal and aberrant biological activity.

The invention includes several assay systems for identifying T1R-binding partners. In solution assays, methods of the invention comprise the steps of (a) contacting a T1R receptor or dimer with one or more candidate binding partner compounds and (b) identifying the compounds that bind to the T1R receptor or dimer. Identification of the compounds that bind the T1R receptor or dimer can be achieved by isolating the T1R polypeptide/binding partner complex, and separating the binding partner compound from the T1R polypeptide. An additional step of characterizing the physical, biological, and/or biochemical properties of the binding partner compound is also comprehended in another embodiment of the invention. In one aspect, the T1R polypeptide/binding partner complex is isolated using an antibody immunospecific for either the T1R receptor or dimer or the candidate binding partner compound.

In still other embodiments, either the T1R receptor or dimer or the candidate binding partner compound comprises a label or tag that facilitates its isolation, and methods of the invention to identify binding partner compounds include a step of isolating the T1R polypeptide/binding partner complex through interaction with the label or tag. An exemplary tag of this type is a poly-histidine sequence, generally around six histidine residues, that permits isolation of a compound so labeled using nickel chelation. Other labels and tags, such as the FLAG® tag (Eastman Kodak, Rochester, N.Y.), well known and routinely used in the art, are embraced by the invention.

In one variation of an in vitro assay, the invention provides a method comprising the steps of (a) contacting an immobilized T1R receptor or dimer with a candidate binding partner compound and (b) detecting binding of the candidate compound to the T1R receptor or dimer. In an alternative embodiment, the candidate binding partner compound is immobilized and binding of T1R receptor or dimer is detected. Immobilization is accomplished using any of the methods well known in the art, including covalent bonding to a support, a bead, or a chromatographic resin, as well as non-covalent, high affinity interactions such as antibody binding, or use of streptavidin/biotin binding wherein the immobilized compound includes a biotin moiety. The support may, for example, be formulated into a feline-specific electronic tongue or biosensor. Detection of binding can be accomplished (i) using a radioactive label on the compound that is not immobilized, (ii) using a fluorescent label on the non-immobilized compound, (iii) using an antibody immunospecific for the non-immobilized compound, (iv) using a label on the non-immobilized compound that excites a fluorescent support to which the immobilized compound is attached, as well as other techniques well known and routinely practiced in the art.

The invention also provides cell-based assays to identify binding partner compounds of a T1R receptor or dimer. In one embodiment, the invention provides a method comprising the steps of contacting a T1R receptor or dimer expressed on the surface of a cell with a candidate binding partner compound and detecting binding of the candidate binding partner compound to the T1R receptor or dimer. In some embodiments, the detection comprises detecting physiological event in the cell caused by the binding of the molecule.

Another aspect of the present invention is directed to methods of identifying compounds that bind to either T1R receptor or dimer or nucleic acid molecules encoding T1R receptor, comprising contacting T1R receptor or dimer, or a nucleic acid molecule encoding the same, with a compound, and determining whether the compound binds T1R receptor or dimer or a nucleic acid molecule encoding the same. Binding can be determined by binding assays which are well known to the skilled artisan, including, but not limited to, gel-shift assays, Western blots, radiolabeled competition assay, phage-based expression cloning, co-fractionation by chromatography, co-precipitation, cross-linking, interaction trap/two-hybrid analysis, southwestern analysis, ELISA, and the like, which are described in, for example, CURRENT PROTOCOLS IN MOLECULAR BIOLOGY, 1999, John Wiley & Sons, NY, which is incorporated herein by reference in its entirety. The compounds to be screened include (which may include compounds which are suspected to bind T1R receptor or dimer, or a nucleic acid molecule encoding the same), but are not limited to, extracellular, intracellular, biological, or chemical origin. The methods of the invention also embrace ligands that are attached to a label, such as a radiolabel (e.g., $^{125}I$, $^{35}S$, $^{32}P$, $^{33}P$, $^{3}H$), a fluorescence label, a chemiluminescent label, an enzymic label, and an immunogenic label. Modulators falling within the scope of the invention include, but are not limited to, non-peptide molecules such as non-peptide mimetics, non-peptide allosteric effectors, and peptides. The T1R polypeptide or dimer or polynucleotide employed in such a test may either be free in solution, attached to a solid support, borne on a cell surface or located intracellularly, or associated with a portion of a cell. One skilled in the art can, for example, measure the formation of complexes between T1R receptor, dimer, or polynucleotide- and the compound being tested. Alternatively, one skilled in the art can examine the diminution in complex formation between T1R receptor, dimer, or polynucleotide and its substrate caused by the compound being tested. In some embodiments of the invention, the recognition sites of the T1R receptor, dimer, or polypeptide are coupled with a monitoring system, either electrical or optical. An appropriate chemical stimulus can bind to the receptor's ligand binding domain, changing the receptor conformation to a degree that the coupled electronics or optical changes can be observed on a read-out. Such a device could be developed into a feline-specific electronic tongue, for example.

In another embodiment of the invention, high throughput screening for compounds having suitable binding affinity to T1R receptor or dimer is employed. Briefly, large numbers of different small peptide test compounds are synthesized on a solid substrate. The peptide test compounds are contacted with T1R receptor or dimer and washed. Bound T1R receptor or dimer is then detected by methods well known in the art. Purified polypeptides of the invention can also be coated directly onto plates for use in the aforementioned drug screening techniques. In addition, non-neutralizing antibodies can be used to capture the protein and immobilize it on the solid support.

Generally, an expressed T1R receptor can be used for HTS binding assays in conjunction with a ligand, such as an amino acid or carbohydrate. The identified peptide is labeled with a suitable radioisotope, including, but not limited to, $^{125}I$, $^{3}H$, $^{35}S$ or $^{32}P$, by methods that are well known to those skilled in the art. Alternatively, the peptides may be labeled by well-known methods with a suitable fluorescent derivative (Baindur et al., *Drug Dev. Res.*, 1994, 33, 373-398; Rogers, *Drug Discovery Today,* 1997, 2, 156-160). Radioactive ligand specifically bound to the receptor in membrane preparations made from the cell line expressing the recombinant protein can be detected in HTS assays in one of several standard ways, including filtration of the receptor-ligand complex to separate bound ligand from unbound ligand (Williams, *Med. Res. Rev.*, 1991, 11, 147-184; Sweetnam et al., *J. Natural Products,* 1993, 56, 441-455). Alternative methods include a scintillation proximity assay (SPA) or a FlashPlate format in which such separation is unnecessary (Nakayama, *Cur. Opinion Drug Disc. Dev.,* 1998, 1, 85-91; Bossé et al., *J. Biomolecular Screening,* 1998, 3, 285-292.). Binding of fluorescent ligands can be detected in various ways, including fluorescence energy transfer (FRET), direct spectrophotofluorometric analysis of bound ligand, or fluorescence polarization (Rogers, *Drug Discovery Today,* 1997, 2, 156-160; Hill, *Cur. Opinion Drug Disc. Dev.,* 1998, 1, 92-97).

Other assays may be used to identify specific ligands of a T1R receptor or dimer, including assays that identify ligands of the target protein through measuring direct binding of test ligands to the target, as well as assays that identify ligands of target proteins through affinity ultrafiltration with ion spray mass spectroscopy/HPLC methods or other physical and analytical methods. Alternatively, such binding interactions are evaluated indirectly using the yeast two-hybrid system described in Fields et al., *Nature,* 340:245-246 (1989), and Fields et al., *Trends in Genetics,* 10:286-292 (1994), both of which are incorporated herein by reference. The two-hybrid system is a genetic assay for detecting interactions between two proteins or polypeptides. It can be used to identify proteins that bind to a known protein of interest, or to delineate domains or residues critical for an interaction. Variations on this methodology have been developed to clone genes that encode DNA binding proteins, to identify peptides that bind to a protein, and to screen for drugs. The two-hybrid system exploits the ability of a pair of interacting proteins to bring a transcription activation domain into close proximity with a DNA binding domain that binds to an upstream activation sequence (UAS) of a reporter gene, and is generally performed in yeast. The assay requires the construction of two hybrid genes encoding (1) a DNA-binding domain that is fused to a first protein and (2) an activation domain fused to a second protein. The DNA-binding domain targets the first hybrid protein to the UAS of the reporter gene; however, because most proteins lack an activation domain, this DNA-binding hybrid protein does not activate transcription of the reporter gene. The second hybrid protein, which contains the activation domain, cannot by itself activate expression of the reporter gene because it does not bind the UAS. However, when both hybrid proteins are present, the noncovalent interaction of the first and second proteins tethers the activation domain to the UAS, activating transcription of the reporter gene. For example, when the first protein is a receptor, or fragment thereof, that is known to interact with another protein or nucleic acid, this assay can be used to detect agents that interfere with the binding interaction. Expression of the reporter gene is monitored as different test agents are added to the system. The presence of an inhibitory agent results in lack of a reporter signal.

The yeast two-hybrid assay can also be used to identify proteins that bind to the gene product. In an assay to identify proteins that bind to a T1R receptor, or fragment thereof, a fusion polynucleotide encoding both a T1R receptor (or fragment) and a UAS binding domain (i.e., a first protein) may be used. In addition, a large number of hybrid genes each encoding a different second protein fused to an activation domain are produced and screened in the assay. Typically, the second protein is encoded by one or more members of a total cDNA or genomic DNA fusion library, with each second protein-coding region being fused to the activation domain. This system is applicable to a wide variety of proteins, and it is not necessary to know the identity or function of the second binding protein. The system is highly sensitive and can detect interactions not revealed by other methods; even transient interactions may trigger transcription to produce a stable mRNA that can be repeatedly translated to yield the reporter protein.

Other assays may be used to search for agents that bind to the target protein. One such screening method to identify direct binding of test ligands to a target protein is described in U.S. Pat. No. 5,585,277, incorporated herein by reference. This method relies on the principle that proteins generally exist as a mixture of folded and unfolded states, and continually alternate between the two states. When a test ligand binds to the folded form of a target protein (i.e., when the test ligand is a ligand of the target protein), the target protein molecule bound by the ligand remains in its folded state. Thus, the folded target protein is present to a greater extent in the presence of a test ligand which binds the target protein, than in the absence of a ligand. Binding of the ligand to the target protein can be determined by any method that distinguishes between the folded and unfolded states of the target protein. The function of the target protein need not be known in order for this assay to be performed. Virtually any agent can be assessed by this method as a test ligand, including, but not limited to, metals, polypeptides, proteins, lipids, polysaccharides, polynucleotides and small organic molecules.

Another method for identifying ligands of a target protein is described in Wieboldt et al., *Anal. Chem.*, 69:1683-1691 (1997), incorporated herein by reference. This technique screens combinatorial libraries of 20-30 agents at a time in solution phase for binding to the target protein. Agents that bind to the target protein are separated from other library components by simple membrane washing. The specifically selected molecules that are retained on the filter are subsequently liberated from the target protein and analyzed by HPLC and pneumatically assisted electrospray (ion spray) ionization mass spectroscopy. This procedure selects library components with the greatest affinity for the target protein, and is particularly useful for small molecule libraries.

Other embodiments of the invention comprise using competitive screening assays in which neutralizing antibodies capable of binding a polypeptide of the invention specifically compete with a test compound for binding to the polypeptide. In this manner, the antibodies can be used to detect the presence of any peptide that shares one or more antigenic determinants with T1R receptor. Radiolabeled competitive binding studies are described in A. H. Lin et al., *Antimicrobial Agents and Chemotherapy,* 1997, 41(10): 2127-2131, the disclosure of which is incorporated herein by reference in its entirety.

Another aspect of the present invention is directed to methods of identifying compounds that modulate (i.e., increase or decrease) activity of T1R receptor or dimer comprising contacting T1R receptor or dimer with a compound, and determining whether the compound modifies activity of T1R receptor or dimer. The activity in the presence of the test compound is compared to the activity in the absence of the test compound. Where the activity of the sample containing the test compound is higher than the activity in the sample lacking the test compound, the compound is an agonist. Similarly, where the activity of the sample containing the test compound is lower than the activity in the sample lacking the test compound, the compound is an antagonist.

Agents that modulate (i.e., increase, decrease, or block) T1R receptor or dimer activity or expression also may be identified, for example, by incubating a putative modulator with a cell containing a T1R polypeptide, dimer, or polynucleotide and determining the effect of the putative modulator on T1R receptor activity or expression. The selectivity of a compound that modulates the activity of T1R receptor or dimer can be evaluated by comparing its effects on T1R receptor or dimer to its effect on other T1R receptors or dimers. Selective modulators may include, for example, antibodies and other proteins, peptides, or organic molecules that specifically bind to a T1R polypeptide or a T1R receptor-encoding nucleic acid. Modulators of T1R receptor activity will be therapeutically useful in treatment of diseases and physiological conditions in which normal or aberrant T1R receptor activity is involved. Compounds identified as modulating T1R receptor activity may be further tested in other assays including, but not limited to, in vivo models, in order to confirm or quantitate their activity.

The invention also provides methods for identifying a T1R receptor modulator by: (a) contacting a T1R receptor (or dimer) binding partner and a composition comprising a T1R receptor in the presence and in the absence of a putative modulator compound; (b) detecting binding between the binding partner and the T1R receptor; and (c) identifying a putative modulator compound or a modulator compound in view of decreased or increased binding between the binding partner and the T1R receptor in the presence of the putative modulator, as compared to binding in the absence of the putative modulator. Compounds identified as modulators of binding between T1R receptor and a T1R binding partner may be further tested in other assays including, but not limited to, in vivo models, in order to confirm or quantitate their activity.

The invention also includes within its scope high-throughput screening (HTS) assays to identify compounds that interact with, enhance, or inhibit biological activity (i.e., affect enzymatic activity, binding activity, etc.) of a T1R receptor or dimer. HTS assays permit screening of large numbers of compounds in an efficient manner. Cell-based HTS systems are contemplated to investigate T1R receptor-ligand interaction. HTS assays are designed to identify “hits” or “lead compounds” having the desired property, from which modifications can be designed to improve the desired property. Chemical modification of the “hit” or “lead compound” is often based on an identifiable structure/activity relationship between the “hit” and the T1R polypeptide.

For example, modulators of T1R receptor activity may be identified by expressing the T1R receptor in a heterologous cultured mammalian cell line, such as HEK cells, and detecting receptor activity in the presence and absence of a test compound by monitoring changes in intracellular calcium using a calcium-specific intracellular dye. In another embodiment, this process may be automated using a high-throughput screening device.

Candidate modulators contemplated by the invention include compounds selected from libraries of either potential activators or potential inhibitors. There are a number of different libraries used for the identification of small molecule modulators, including: (1) chemical libraries, (2) natural product libraries, and (3) combinatorial libraries comprised of random peptides, oligonucleotides, or organic molecules. Chemical libraries consist of random chemical structures, some of which are analogs of known compounds or analogs of compounds that have been identified as "hits" or "leads" in other drug discovery screens, some of which are derived from natural products, and some of which arise from non-directed synthetic organic chemistry. Natural product libraries are collections of microorganisms, animals, plants, or marine organisms that are used to create mixtures for screening by: (1) fermentation and extraction of broths from soil, plant, or marine microorganisms or (2) extraction of plants or marine organisms. Natural product libraries include polyketides, non-ribosomal peptides, and variants (non-naturally occurring) thereof. For a review, see *Science* 282:63-68 (1998). Combinatorial libraries are composed of large numbers of peptides, oligonucleotides, or organic compounds as a mixture. These libraries are relatively easy to prepare by traditional automated synthesis methods, PCR, cloning, or proprietary synthetic methods. Of particular interest are non-peptide combinatorial libraries. Still other libraries of interest include peptide, protein, peptidomimetic, multiparallel synthetic collection, recombinatorial, and polypeptide libraries. For a review of combinatorial chemistry and libraries created therefrom, see Myers, *Curr. Opin. Biotechnol.* 8:701-707 (1997). Identification of modulators through use of the various libraries described herein permits modification of the candidate "hit" (or "lead") to optimize the capacity of the "hit" to modulate activity.

T1R receptor binding partners that stimulate T1R receptor activity are useful as agonists in disease states or conditions characterized by insufficient T1R receptor signaling (e.g., as a result of insufficient activity of a T1R receptor ligand). T1R receptor binding partners that block ligand-mediated T1R receptor signaling are useful as T1R receptor antagonists to treat disease states or conditions characterized by excessive T1R receptor signaling. Thus, in another aspect, the invention provides methods for treating a disease or abnormal condition by administering to a patient in need of such treatment a substance that modulates the activity or expression of a polypeptide having a sequence of SEQ ID NO:2, SEQ ID NO:61, or SEQ ID NO:64, or exhibiting substantially the same biological activity as a polypeptide having a sequence of SEQ ID NO:2, SEQ ID NO:61, or SEQ ID NO:64, or dimers thereof.

In addition T1R receptor modulators in general, as well as T1R receptor encoding polynucleotides and polypeptides, are useful in diagnostic assays for such diseases or conditions.

The T1R polynucleotides of the invention may also be used to identify compounds for which an organism having the receptor exhibits a taste preference or indifference using cell signaling assays known in the art. In such assays, polynucleotide encoding a T1R is incorporated into an expression vector and transfected into a host cell. The expression of the T1R may be inducible or constitutive. The host cells expressing the T1R receptor are contacted with candidate compounds and the effect of each compound on the cells is assayed. Stimulation of a response is indicative of reactivity to the test compound and correlates with compounds associated with a taste preference. The assays that can be used to assess stimulation of T1R receptor include, but are not limited to assays measuring ion conductance, ion flow, calcium imaging (e.g., using fura-2, green dextran activity or aequorin activity), voltage measurement and or voltage imaging with dyes, expression of reporter genes (e.g., luciferase, alkaline phosphatase, beta-galactosidase, beta-lactamase, fluorescent binding protein), receptor binding assays, second messenger assays (e.g., IP3, cAMP), G-protein activation based assays (e.g., modulation of GTP-gamma-S binding), receptor phosphorylation measures, and the like. In some embodiments analysis of stimulation of T1R receptors and receptor dimers may be determined using a FLIPR® assay as described by the manufacturer (Molecular Devices, Corp.).

Screening of cells treated with dyes and fluorescent reagents is well known in the art. Genetic engineering of cells to produce fluorescent proteins, such as modified green fluorescent protein (GFP), as a reporter molecule is also well known in the art. Fluorescence-based reagents are useful for the assay of many cell functions including ion concentrations, membrane potential, specific translocations, enzyme activities, gene expression, as well as the presence, amounts and patterns of metabolites, proteins, lipids, carbohydrates, and nucleic acid sequences.

Cell signaling assays known in the art may also be used to identify T1R antagonists. Expression of G protein coupled receptors at very high concentration in a heterologous system has been shown to result in constitutive cell signaling. For example, but not by way of limitation, T1R receptor may be overexpressed in *Spodoptera frugiperda* (Sf9) cells. Alternatively, for example, T1R may be operably linked to a CMV promoter and expressed in COS or HEK293 cells. In the activated constitutive state, test compounds may be assayed for their ability to inhibit constitutive cell signaling activity. Suitable assays include, but are not limited to assays measuring ion conductance, ion flow, calcium imaging (e.g., using fura-2, green dextran activity or aequorin activity), voltage measurement and/or voltage imaging with dyes, expression of reporter genes (e.g., luciferase, alkaline phosphatase, beta-galactosidase, beta-lactamase, fluorescent binding protein), receptor binding assays, second messenger assays (e.g., IP3, cAMP), G-protein activation based assays (e.g., modulation of GTP-gamma-S binding), receptor phosphorylation measures, and the like.

Tissue Distribution

One skilled in the art may determine whether a T1R receptor is expressed in tissues other than taste bud tissues through routine experimentation following the guidance provided herein. Specifically, one may detect T1R RNA using Northern blots or reverse transcriptase polymerase chain reaction (rtPCR) and other methods known in the art. Protocols and procedures for such assays may be found, for example in Ausubel et al., Current Protocols In Molecular Biology, John Wiley & Sons, New York, 1998; Sambrook et al., Molecular Cloning: A Laboratory Manual, 2d Ed., Cold Spring Harbor Laboratory Press, Plainview, N.Y., 1989.

One may also detect T1R protein using specific antibodies and probing tissue sections. For example, but not by way of limitation, one may obtain paraffin-embedded sections of tissues of interest (from human or other species) or use fresh tissue. Tissue sections may be treated with 0.3% $H_2O_2$ in methanol for 30 minutes to eliminate endogenous peroxidase activity. The tissues may then be incubated in anti-T1R antibody (or an antisera raised against T1R) at 4° C. for hours to days. The tissues may then be treated with a secondary antibody that specifically binds to the primary antibody (such as a heterologous species' serum raised against the primary species immunoglobulin). The secondary antibody may be conjugated to biotin, for example. The tissue sections are further incubated with peroxidase-conjugated streptavidin at room temperature. After each step, tissue sections are rinsed in 0.01 M phosphate buffered saline (pH 7.2) containing 0.05% Tween 20. Immunoreaction products may be visualized through reaction with 0.0125% diaminobenzidine (DAB) and 0.002% $H_2O_2$ in 0.05M Tris-HCl buffer (pH 7.6). The sections are counterstained with hematoxylin and viewed with a light microscope. Other antibody-based assays to examine tissues for T1R expression may be used. Various protocols are known in the art and may be found, for example, in Harlow et al. (Eds.), Antibodies A Laboratory Manual; Cold Spring Harbor Laboratory; Cold Spring Harbor, N.Y. (1988).

The presence of T1R receptor in tissues outside of taste buds suggests a role for T1R receptors other than taste perception. The invention provides methods for modulating these functions by increasing or decreasing the expression of T1R.

As such, the invention encompasses a method of modulating a T1R receptor family member by modulating expression of another T1R family receptor. For example, the Tas1r gene may be expressed such that an increased level of Tas1r RNA results in feedback inhibition of expression of at least one of T1R1, T1R2, and T1R3. In other embodiments of the invention, the Tas1r gene may be expressed such that an increased level of T1R RNA results in an increase in the expression of at least one of T1R1, T1R2, and T1R3. In other embodiments, the Tas1r gene may be repressed such that a decreased level of Tas1r RNA results in an increase in the expression of at least one of T1R1, T1R2, and T1R3. In other embodiments, the Tas1r gene may be repressed such that a decreased level of Tas1r RNA results in a concomitant decrease in the expression of at least one of T1R1, T1R2, and T1R3. The gene modulation may be tissue- or species-specific. Thus, expression of Tas1r may be regulated using the expression vectors of the invention using inducible promoters and tissue-specific promoters, for example. Alternatively, expression of Tas1r may be repressed in cells that produce T1R using antisense RNA and other inhibitory strategies described herein and as are known in the art. The modulation of the T1R receptor family in patients may be useful for altering metabolism, nutrient uptake, neural function, and to treat disorders associated with an abnormally low or high level of T1R expression in cells.

Mimetics

Mimetics or mimics of compounds identified herein (sterically similar compounds formulated to mimic the key portions of the structure) may be designed for pharmaceutical use. Mimetics may be used in the same manner as the compounds identified by the present invention that modulate the T1R receptor and hence are also functional equivalents. The generation of a structural-functional equivalent may be achieved by the techniques of modeling and chemical design known to those of skill in the art. It will be understood that all such sterically similar constructs fall within the scope of the present invention.

The design of mimetics to a known pharmaceutically active compound is a known approach to the development of pharmaceuticals based on a "lead" compound. This is desirable where, for example, the active compound is difficult or expensive to synthesize, or where it is unsuitable for a particular method of administration, e.g., some peptides may be unsuitable active agents for oral compositions as they tend to be quickly degraded by proteases in the alimentary canal.

There are several steps commonly taken in the design of a mimetic. First, the particular parts of the compound that are critical and/or important in determining its T1R-modulating properties are determined. In the case of a polypeptide, this can be done by systematically varying the amino acid residues in the peptide, e.g. by substituting each residue in turn. Alanine scans of peptides are commonly used to refine such peptide motifs.

Once the active region of the compound has been identified, its structure is modeled according to its physical properties, e.g. stereochemistry, bonding, size, and/or charge, using data from a range of sources, such as, but not limited to, spectroscopic techniques, X-ray diffraction data, and NMR. Computational analysis, similarity mapping (which models the charge and/or volume of the active region, rather than the bonding between atoms), and other techniques known to those of skill in the art can be used in this modeling process.

In a variant of this approach, the three-dimensional structure of the compound that modulates a T1R receptor and the active region of the T1R receptor are modeled. This can be especially useful where either or both of these compounds change conformation upon binding. Knowledge of the structure of the ligand-binding domain (for example, residues 1-571 of SEQ ID NO:2) of the receptor also allows the design of high potency ligands and/or modulators.

A template molecule is then selected onto which chemical groups that mimic the T1R modulator can be grafted. The template molecule and the chemical groups grafted onto it can conveniently be selected so that the mimetic is easy to synthesize, is pharmacologically acceptable, and does not degrade in vivo, while retaining the biological activity of the lead compound. Alternatively, where the mimetic is peptide-based, further stability can be achieved by cyclizing the peptide, thereby increasing its rigidity. The mimetic or mimetics found by this approach can then be screened by the methods of the present invention to see whether they have the ability to modulate the T1R receptor. Further optimization or modification can then be performed to arrive at one or more final mimetics for in vivo or clinical testing.

Compositions of Binding and/or Modulating Compounds

Following identification of a compound that binds and/or or modulates a T1R receptor, the compound may be manufactured and/or used in preparation of compositions including, but not limited to, foods, drinks, and pharmaceutical compositions. The compositions are provided or administered to patients, including, but not limited to, avians, felines, canines, bovines, ovines, porcines, equines, rodents, simians, and humans.

Thus, the present invention extends, in various aspects, not only to compounds identified in accordance with the methods disclosed herein but also foods, drinks, pharmaceutical compositions, drugs, or other compositions comprising such a compound; methods comprising administration of such a composition to a patient, e.g. for treatment (which includes prophylactic treatment) of a T1R receptor-associated disorder (e.g., obesity, diabetes); uses of such a compound in the manufacture of a composition for administration to a patient; and methods of making a composition comprising admixing such a compound with a pharmaceutically acceptable excipient, vehicle or carrier, and optionally other ingredients.

Some compositions of the invention comprise a taste-modifying amount of at least one or more binding or modulating compounds. A "taste-modifying amount" is a quantity sufficient to increase or decrease the perception of a taste stimulus by a given mammal. The food and drink compositions of the invention are formulated by the addition of a binding or modulating compound to a food or drink of the mammal. Such compositions may be individualized or breed-specific. For example, feline veterinary specialty diets may thus be made more palatable.

The pharmaceutical compositions of the invention comprise a therapeutically effective amount of a compound identified according to the methods disclosed herein, or a pharmaceutically acceptable salt thereof, and a pharmaceutically acceptable carrier or excipient.

The compounds of the invention can be formulated as neutral or salt forms. Pharmaceutically acceptable salts include those formed with free amino groups such as those derived from hydrochloric, phosphoric, acetic, oxalic, tartaric acids, etc., and those formed with free carboxyl groups such as those derived from sodium, potassium, ammonium, calcium, ferric hydroxides, isopropylamine, triethylamine, 2-ethylamino ethanol, histidine, procaine, etc.

Pharmaceutically acceptable carriers include but are not limited to saline, buffered saline, dextrose, water, glycerol, ethanol, and combinations thereof. The carrier and composition can be sterile. The formulation should suit the mode of administration.

The composition, if desired, can also contain minor amounts of wetting or emulsifying agents or pH buffering agents. The composition can be a liquid solution, suspension, emulsion, tablet, pill, capsule, sustained release formulation, or powder. The composition can be formulated as a suppository, with traditional binders and carriers such as triglycerides. Oral formulations can include standard carriers such as pharmaceutical grades of mannitol, lactose, starch, magnesium stearate, sodium saccharine, cellulose, magnesium carbonate, etc.

The pharmaceutical compositions of the invention may further comprise a secondary compound for the treatment of a disorder unrelated to the T1R receptor, such as an antibiotic or other therapeutic agent, to improve the palatability of the pharmaceutical composition, thereby improving the ease of administration.

In one embodiment, the composition is formulated in accordance with routine procedures as a pharmaceutical composition adapted for oral (e.g., tablets, granules, syrups) or non-oral (e.g., ointments, injections) administration to the subject. Various delivery systems are known and can be used to administer a compound that modulates a T1R receptor, e.g., encapsulation in liposomes, microparticles, microcapsules, expression by recombinant cells, receptor-mediated endocytosis, construction of a therapeutic nucleic acid as part of a retroviral or other vector, etc. Methods of introduction include but are not limited to intradermal, intramuscular, intraperitoneal, intravenous, subcutaneous, intranasal, topical, and oral routes.

The compounds of the invention may be administered by any convenient route, for example by infusion or bolus injection, by absorption through epithelial or mucocutaneous linings (e.g., oral mucosa, rectal and intestinal mucosa, etc.), and may be administered together with other biologically active agents, for example in HAART therapy. Administration can be systemic or local. In addition, it may be desirable to introduce the pharmaceutical compositions of the invention into the central nervous system by any suitable route, including intraventricular and intrathecal injection; intraventricular injection may be facilitated by an intraventricular catheter, for example, attached to a reservoir, such as an Ommaya reservoir.

In a specific embodiment, it may be desirable to administer the pharmaceutical compositions of the invention locally to the area in need of treatment; this may be achieved by, for example, and not by way of limitation, local infusion during surgery; topical application, e.g., in conjunction with a wound dressing after surgery; by injection; by means of a catheter; by means of a suppository; or by means of an implant, said implant being of a porous, non-porous, or gelatinous material, including membranes, such as sialastic membranes, or fibers.

The composition can be administered in unit dosage form and may be prepared by any of the methods well known in the pharmaceutical art, for example, as described in REMINGTON'S PHARMACEUTICAL SCIENCES (Mack Publishing Co., Easton, Pa.). The amount of the compound of the invention that modulates a T1R receptor that is effective in the treatment of a particular disorder or condition will depend on factors including but not limited to the chemical characteristics of the compounds employed, the route of administration, the age, body weight, and symptoms of a patient, the nature of the disorder or condition, and can be determined by standard clinical techniques. Typically therapy is initiated at low levels of the compound and is increased until the desired therapeutic effect is achieved. In addition, in vitro assays may optionally be employed to help identify optimal dosage ranges. Suitable dosage ranges for intravenous administration are preferably generally about 20-500 micrograms of active compound per kilogram body weight. Suitable dosage ranges for intranasal administration are preferably generally about 0.01 pg/kg body weight to 1 mg/kg body weight. Suppositories preferably generally contain active ingredient in the range of 0.5% to 10% by weight; oral formulations preferably may contain 10% to 95% active ingredient. Effective doses may be extrapolated from dose-response curves derived from in vitro or animal model test systems.

Typically, compositions for intravenous administration are solutions in sterile isotonic aqueous buffer. Where necessary, the composition may also include a solubilizing agent and a local anesthetic such as lidocaine to ease pain at the site of the injection. Generally, the ingredients are supplied either separately or mixed together in unit dosage form, for example, as a dry-lyophilized powder or water-free concentrate in a hermetically sealed container such as an ampoule or sachette indicating the quantity of active agent. Where the composition is to be administered by infusion, it can be dispensed with an infusion bottle containing sterile pharmaceutical grade water or saline.

Where the composition is administered by injection, an ampoule of sterile water for injection or saline can be provided so that the ingredients may be mixed prior to administration.

Methods for Predicting and Representing Taste Perception of an Organism

Methods for predicting the taste perception of an organism, such as a mammal, include detection of a nucleotide sequence (e.g., nucleotide sequence of SEQ ID NO:1, SEQ ID NO:99, SEQ ID NO:59; SEQ ID NO:60, SEQ ID NO:62, or SEQ ID NO:63, or fragments, variants, or homologues thereof encoding a polypeptide having an equivalent, substantially the same, or same biological activity as the polypeptide encoded by the reference sequence) or amino acid sequence (e.g., SEQ ID NO:2, SEQ ID NO:61, or SEQ ID NO:64, or fragments, variants, or homologues thereof having the same or substantially the same biological activity of the reference polypeptide) of the invention in a biological sample of the organism. Methods for detecting a polynucleotide or polypeptide of the invention in a biological sample may comprise any method known to the skilled artisan, including but not limited to the methods of detection mentioned herein. An organism having a polynucleotide or polypeptide of the invention in its biological sample is predicted to exhibit characteristics of taste perception of a domestic cat. For example, an organism having a polynucleotide or polypeptide of the invention, such as a polynucleotide encoding a feline T1R1 receptor or the polypeptide encoded thereby, will be attracted to one or more amino acids. An organism having a polynucleotide or polypeptide of the invention may show no preference for one or more carbohydrates or high-intensity sweeteners. As an example, an organism having a polynucleotide encoding a single transmembrane domain T1R2 receptor, for example the feline T1R2 receptor of the invention, or the polypeptide encoded thereby, would be predicted to show a reduced or no response to sweet taste stimuli relative to an organism having a 7-transmembrane domain T1R2 receptor An organism having a polynucleotide or polypeptide of the invention may be attracted to one or more amino acids and may exhibit no preference for one or more carbohydrates or high-intensity sweeteners. For example, an organism having a polynucleotide or polypeptide of the invention, such as a polynucleotide encoding a feline T1R1 receptor or the polypeptide encoded thereby, and further having a polynucleotide encoding a single transmembrane domain T1R2 receptor, for example the feline T1R2 receptor of the invention, or the polypeptide encoded thereby, will be attracted to one or more amino acids and will exhibit no preference for one or more carbohydrates or high-intensity sweeteners.

Also contemplated by the invention is a method for representing taste perception of a particular taste in a mammal, for example a cat, by providing values $X_1$ to $X_n$ representative of the quantitative stimulation of each of n T1R receptors or dimers of the invention, where n is greater than or equal to 2, and generating from the values a quantitative representation of taste perception of the mammal. The representation may constitute a point or a volume in n-dimensional space, may constitute a graph or a spectrum, and/or may constitute a matrix of quantitative representations. Also, the providing step may comprise contacting a plurality of T1R receptors or dimers of the invention with a test compound and quantitatively measuring the interaction of the compound with T1R receptors or dimers.

Also contemplated by the invention are methods for predicting the taste perception in a mammal generated by one or more molecules or combinations of molecules yielding unknown taste perception in a mammal, such as a cat, by providing values $X_1$ to $X_n$ representative of the quantitative stimulation of each of n T1R receptors of the invention, where n is greater than or equal to 2, for one or more molecules or combinations of molecules yielding known taste perception in a mammal; and generating from the values a quantitative representation of taste perception in a mammal for the one or more molecules or combinations of molecules yielding known taste perception in a mammal, providing values $X_1$ to $X_n$ representative of the quantitative stimulation of each of n T1R receptors of the invention, where n is greater than or equal to 2, for one or more molecules or combinations of molecules yielding unknown taste perception in a mammal; and generating from said values a quantitative representation of taste perception in a mammal for the one or more molecules or combinations of molecules yielding unknown taste perception in a mammal, and predicting the taste perception in a mammal generated by one or more molecules or combinations of molecules yielding unknown taste perception in a mammal by comparing the quantitative representation of taste perception in a mammal for the one or more molecules or combinations of molecules yielding unknown taste perception in a mammal to the quantitative representation of taste perception in a mammal for the one or more molecules or combinations of molecules yielding known taste perception in a mammal.

In another embodiment, novel molecules or combinations of molecules are generated which elicit a predetermined taste perception in a mammal by determining a value of taste perception in a mammal such as a cat for a known molecule or combinations of molecules as described above; determining a value of taste perception in a mammal for one or more unknown molecules or combinations of molecules as described above; comparing the value of taste perception in a mammal for one or more unknown compositions to the value of taste perception in a mammal for one or more known compositions; selecting a molecule or combination of molecules that elicits a predetermined taste perception in a mammal; and combining two or more unknown molecules or combinations of molecules to form a molecule or combination of molecules that elicits a predetermined taste perception in a mammal. The combining step yields a single molecule or a combination of molecules that elicits a predetermined taste perception in a mammal.

Treatment Methods

The invention provides methods of treatment of T1R receptor-associated disorders by administering to a subject or patient an effective amount of a compound that modulates the T1R receptor. In some aspects of the invention, the compounds or pharmaceutical compositions of the invention are administered to a patient having an increased risk of or having a disorder associated with the T1R receptor. The patient may be, for example, avian, feline, canine, bovine, ovine, porcine, equine, rodent, simian, or human.

Kits

A kit of the invention comprises a carrier means being compartmentalized to receive in close confinement one or more container means such as vials, tubes, and the like, each of the container means comprising an element to be used in the methods of the invention. For example, one of the container means may comprise the a polynucleotide encoding a T1R receptor of the invention, a T1R receptor of the invention, or an antibody thereto. The kit may also have one or more conventional kit components, including, but not limited to, instructions, test tubes, Eppendorf™ tubes, labels, reagents helpful for quantification of marker gene expression, etc.

EXAMPLES

The following examples are meant to be illustrative of the present invention and are not intended to limit the scope thereof.

Cloning and Characterization of the Feline T1R3 Receptor

The discovery of feline taste receptor, T1R3, was achieved by using a molecular strategy termed "overgo" (Thomas, et al., *Genome Res.*, 12:1277-1285 (2002); Vollrath, D., *DNA markers for physical mapping* In Genome analysis: A Laboratory manual, Vol. 4, ed. B. Birren, et al., pp. 187-215, 1999). Cold Spring Harbor Laboratory Press, Cold Spring Harbor, N.Y.). This strategy involves the use of the shortest DNA probes among the many kinds of probes used in bacterial artificial chromosome (BAC) library screening. These probes are comprised of two DNA sequences (e.g., 22 mers) with a complementary 8 base overlap. They can be designed by computer program available online, for example, through the Washington University School of Medicine Genome Sequencing Center, and are readily synthesized.

Overgo probes were designed from conserved regions of the chromosome 1 marker, "disheveled 1" (DVL1) and the G protein-coupled receptor, T1R3, by aligning DVL1 and T1R3 genomic sequences from several species. The overlapping sequences of the seven DVL1 overgo probes used in the present invention were as follows:

catOV1a ACTTTGAGAACATGAGTAATGACG (SEQ ID NO:21)

catOV1b AGTACCCGGACTGCGTCGTCATTA (SEQ ID NO:22)

catOV2a CACTAGGGTCATCCTTGCTTTCAG (SEQ ID NO:23)

catOV2b AGTCAGGGTGATGGGCCTGAAAGC (SEQ ID NO:24)

Ov8-OVa ATGTGGTGGACTGGCTGTACCATC (SEQ ID NO:25)

Ov8-OVb TTGAAGCCCTCCACGTGATGGTAC (SEQ ID NO:26)

Ov9a CACACGGTGAACAAGATCACCTTC (SEQ ID NO:27)

Ov9b AGTAGCACTGCTCGGAGAAGGTGA (SEQ ID NO:28)

Ov10A ATCTACCACATGGACGAGGAGGAG (SEQ ID NO:29)

Ov10b TGACCAGGTACGGCGTCTCCTCCT (SEQ ID NO:30)

Ov11a AGCGCGTCACGCTGGCCGACTTCA (SEQ ID NO:31)

Ov11b TTGCTGAGCACGTTCTTGAAGTCG (SEQ ID NO:32)

Ov12a CACGCCTACAAATTCTTCTTTAAG (SEQ ID NO:33)

Ov12b AGTCCTGGTCCATGGACTTAAAGA. (SEQ ID NO:34)

The overlapping sequences of the twelve T1R3 overgo probes used in the present invention were as follows:

t1r3-OV1a CTTCCACTCCTGCTGCTACGACTG (SEQ ID NO:35)

t1r3-OV1b TGCCTCGCAGTCCACGCAGTCGTA (SEQ ID NO:36)

t1r3-OV2a AGGTGCGCCGCGTCAAGGGCTTCC (SEQ ID NO:37)

t1r3-OV2b TCGTAGCAGCAGGAGTGGAAGCCC (SEQ ID NO:38)

t1r3-OV3a GTTCCTGGCATGGGGGGAGCCGGC (SEQ ID NO:39)

t1r3-OV3b GAGCAGCACAAGCACAGCCGGCTC (SEQ ID NO:40)

t1r3-OV4a ACAGCCCACTAGTTCAGGCCGCAG (SEQ ID NO:41)

t1r3-OV4b CAGGCCCGGGGTCCCCCTGCGGCC (SEQ ID NO:42)

t1r3-OV5a CCCACTGGTTCAGGCCTCGGGGGG (SEQ ID NO:43)

t1r3-OV5b AAAGCAGGCCAGGGGCCCCCCCGA (SEQ ID NO:44)

t1r3-OV6a AGGCGCTGGTGCACTGCCGCACAC (SEQ ID NO:45)

t1r3-OV6b AAGCTGACCCAGGAGCGTGTGCGG (SEQ ID NO:46)

t1r3-OV7a ACAGAGGCACTGGTGCACTGCCGC (SEQ ID NO:47)

t1r3-OV7b TGATCCAGGAGTGCACGCGGCAGT (SEQ ID NO:48)

t1r3-OV8a ACCAATGCCACGCTGGCCTTTCTC (SEQ ID NO:49)

t1r3-OV8b AAGTGCCCAGGAAGCAGAGAAAGG (SEQ ID NO:50)

t1r3-OV9a TGGTACATGCTGCCAATGCCACGC (SEQ ID NO:51)

t1r3-OV9b AAGCAGAGGAAAGCCAGCGTGGCA (SEQ ID NO:52)

t1r3-OV10a TACAACCGTGCCCGTGGCCTCACC (SEQ ID NO:53)

t1r3-OV10b AGGCCAGCATGGCGAAGGTGAGGC (SEQ ID NO:54)

t1r3-OV11a TCATCACCTGGGTCTCCTTTGTGC (SEQ ID NO:55)

t1r3-OV11b ACATTGGCCAGGAGGGGCACAAAG (SEQ ID NO:56)

t1r3-OV12a TGCAGATGGGTGCCCTCCTGCTCT (SEQ ID NO:57)

t1r3-OV12b AGGATGCCCAGCACACAGAGCAGG. (SEQ ID NO:58)

The single-stranded overhangs were filled in with $^{32}P$ labeled dATP and dCTP, and the overgo probes hybridized with BAC libraries.

The overgo strategy is considered to be more versatile than a PCR-based strategy by those skilled in the art of comparative physical mapping for the following reasons: (1) overgo probes are short (e.g., 36 mers or 40 mers), making the probability of good alignment from among many species more favorable; (2) overgo probes are more specific to the target genes compared with traditional cDNA and genomic DNA probes used by PCR; and (3) although overgo probes are short, they are not as restricted as traditional PCR probes, which cannot tolerate even a few mismatches, because they can be used in hybridization approaches with BACs or other libraries.

Screening a feline genomic BAC library. Seven DVL1 overgo probes (SEQ ID NOS:21-34) were used in screening a feline genomic BAC library. Probes were radioactively labeled by the random hexa-nucleotide method (Feinberg & Vogelstein, *Analytical Biochemistry,* (1983)). Hybridization and washing of membranes followed standard protocols (Church & Gilbert, *PNAS U.S.A.,* 81:1991-1995 (1984)). Thirty-nine positive BAC clones were identified. Several BAC ends were sequenced. One clone containing homologous sequence to human chromosome 1p36, BAC 552J19, was identified using bioinformatics tools.

Production of a shotgun library for BAC 552J19 and identification of a single clone containing feline T1R3. BAC DNA from 552J19 was prepared by using Qiagen Large Construct Kit. DNA was then digested by the restriction enzyme Sau3A1 and subcloned into pGEM+3Z (Promega) vector. After transformants were arrayed to a nylon membrane, two separate hybridizations were performed using seven DVL1 and twelve T1R3 overgo probes (SEQ ID NOS:35-58). Two clones positive for DVL1 and four clones positive for T1R3 were found. These clones were confirmed by sequencing. Because DVL1 is the neighboring gene of T1R3 in human and mouse, it is likely this also is the case in cat; therefore, the DVL1 positive clones verified that the BAC 552J19 is the correct BAC, that is, it is the one containing feline T1R3.

Cloning and Characterization of the Feline T1R1 and T1R2 Receptors

Eludication of the cat T1R1 and cat T1R2 receptors also was accomplished using an overgo strategy. Overgo probes from conserved coding regions were designed by aligning T1R1 and T1R2 sequences from many different species, including human, mouse, rat, cow, and pig. The single-stranded overhangs (14 bases) were filled in with $^{32}P$-labeled dATP and dCTP, and the overgo probes hybridized with BAC libraries. The overlapping sequences of the six cat T1R1 overgo probes were as follows:

t1r1_1-OVa TAAACAACTCCACGGCCCTGCTGC (SEQ ID NO:65)

t1r1_1-OVb CCCAGGGTGATGTTGGGCAGCAGG (SEQ ID NO:66)

t1r1_2-OVa GCTGTGTATGCGGTGGCCCATGGC (SEQ ID NO:67)

t1r1_2-OVb CCAGGAGCTGGTGGAGGCCATGGG (SEQ ID NO:68)

t1r1_3-OVa TGCTGACCAACCTGACTGGCAAGG (SEQ ID NO:69)

t1r1_3-OVb TCTGAGGCGACCCACACCTTGCCA (SEQ ID NO:70)

t1r1_4-OVa CCAGTTCAGCTAAACATAAATGAG (SEQ ID NO:7i)

t1r1_4-OVb GCCACTGGATTTTGGTCTCATTTA (SEQ ID NO:72)

-continued

```
t1r1_5-OVa AGCTAACACGCTGCTGCTGCTGCT  (SEQ ID NO:73)

t1r1_5-OVb AGCAGTCCCAAGCAGCAGCAGCAG  (SEQ ID NO:74)

t1r1_6-OVa TGTGTCACCTTCAGCCTGCTCTTC  (SEQ ID NO:75)

t1r1_6-OVb TCCAGGACACGAAGTTGAAGAGCA. (SEQ ID NO:76)
```

The overlapping sequences of the seven cat T1R2 overgo probes were as follows:

```
t1r2_1-OVa TACTTCGGCCCCAAGTGCTACATG  (SEQ ID NO:77)

t1r2_1-OVb CCGGGTAGAAGAGGATCATGTAGC  (SEQ ID NO:78)
```

-continued

```
t1r2_2-OVa TGGTCACCATCGTGGACCTCTTGG  (SEQ ID NO:79)

t1r2_2-OVb AGGTTGAGCACAGTGACCAAGAGG  (SEQ ID NO:80)

t1r2_3-OVa ACCAACTACAACGAGGCCAAGTTC  (SEQ ID NO:81)

t1r2_3-OVb TCATGCTGAGGGTGATGAACTTGG  (SEQ ID NO:82)

t1r2_4-OVa TCCGAGTCCTGGGCCATCGACCCG  (SEQ ID NO:83)

t1r2_4-OVb TGAGGTTGTGCAGGACCGGGTCGA  (SEQ ID NO:84)

t1r2_5-OVa TACAACCTCATGCAGGCCATGCGC  (SEQ ID NO:85)

t1r2_5-OVb TCTCCTCCACCGCGAAGCGCATGG  (SEQ ID NO:86)

t1r2_6-OVa ATCACCATCCAGAGCGTGCCCATC  (SEQ ID NO:87)

t1r2_6-OVb ACTCACTGAAGCCCGGGATGGGCA  (SEQ ID NO:88)

t1r2_7-OVa ACCACCACGTCGAGGCCATGGTGC  (SEQ ID NO:89)

t1r2_7-OVb AAGTGCAGCATCAGCTGCACCATG. (SEQ ID NO:90)
```

Screening a feline genomic BAC library. The T1R1 and T1R2 overgo probes were used to screen a feline genomic BAC library. Probes were radioactively labeled by the random hexa-nucleotide method (Feinberg & Vogelstein, *Analytical Biochemistry,* 132(1):6-13 (1983)). Hybridization and washing of membranes followed standard protocols (Church & Gilbert, *PNAS U.S.A.,* 81:1991-1995 (1984)). Six positive BAC clones for cat T1R1 and eight positive BAC clones for cat T1R2 were identified.

Production of shotgun libraries for BACs containing cat T1R1 and T1R2, and identification of small insert clones containing feline T1R1 and T1R2. Two BACs (150M6 and 233G22) containing cat T1R1 and three BACs (93C1, 240H9 and 400B1) containing cat T1R2 were used to prepare BAC DNAs using Qiagen Large Construct Kit. BAC DNAs were digested using the enzyme Sau3AI and the digested BAC DNA fragments were subcloned into pGEM+3Z (Promega) vector. After transformants were arrayed to a nylon membrane, two separate hybridizations were performed using pooled six T1R1 and seven T1R2 overgo probes. By sequencing positive clones from shotgun libraries and by using a chromosome walking strategy, the full coding region of the cat T1R1 and exon 3 to exon 6 of cat T1R2 were obtained.

Elucidation of exon 1 and exon 2 of the cat T1R2 by PCR strategy. Since exon 1 and exon 2 of cat T1R2 were not present in the three BACs selected above, PCR was performed using degenerate primers designed from T1R2 alignments from different species (human, rodents, and dog) and cat genomic DNA as template.

Degenerate Primers for Cat T1R2 exon1 and exon2:

| | | | PCR product size |
|---|---|---|---|
| Dex1f1: | 5' TCRGACTTCTACCTGCCTGGRGA 3' | (SEQ ID NO:91) | 85 bp |
| Dex1r1: | 5' CTTCACGTTGGCATGGAGGG 3' | (SEQ ID NO:92) | |
| Dex1f2: | 5' TACCTCCTGGGTGGCCTCTTC 3' | (SEQ ID NO:93) | 66 bp |
| Dex1r2: | 5' TCTTGCACwkGGGCACCTGC 3' | (SEQ ID NO:94) | |
| Dex2f1: | 5' AGGTGtTGGGCTACAACCTsAT 3' | (SEQ ID NO:95) | 206 bp |
| Dex2r1: | 5' GGGCAkGTAGTGGCTGTAGTC 3' | (SEQ ID ND:95) | |
| Dex2f2: | 5' GGCTACAACCTsATGCAGGCCA 3' | (SEQ ID ND:97) | 220 bp |
| Dex2r2: | 5' GAGTTGTCAGGGCCAATGACCG 3'. | (SEQ ID ND:98) | |

The PCR products were confirmed by sequencing. The feline BAC library was then re-screened using PCR products and four new BACs were retrieved (4O545, 2J533, 4F220 and 24D448). Using a chromosome walking strategy, the complete sequence of exon 1 and exon 2 from these four BAC clones were obtained.

Results

More than 3 kb of genomic sequences containing the open reading frame for domestic cat taste receptor, T1R3, were obtained. Approximately 10 kb of genomic sequence containing the open reading frame (ORF) for cat T1R1 and approximately 38 kb of genomic sequence containing the open reading frame for cat T1R2 were obtained. FIGS. 6A-D show the genomic sequence of cat T1R1 (SEQ ID NO:59) obtained from BAC sequencing. FIGS. 7A-E show the genomic sequence of cat T1R2 (SEQ ID NO:62) obtained from BAC sequencing. The letter "N" denotes gaps between exons or unknown sequences. FIGS. 1A-1I show the multiple sequence alignment of the cDNAs encoding T1R receptors of domestic cat (T1R1, SEQ ID NO:60; T1R2, SEQ ID NO:63; and T1R3, SEQ ID NO:99) with known nucleotide sequences of receptors of the T1R family from human (T1R1, SEQ ID NO:8; T1R2, SEQ ID NO:5; T1R3, SEQ ID NO:11), mouse (T1R1, SEQ ID NO:6; T1R2, SEQ ID NO:3; T1R3, SEQ ID NO:9), and rat (T1R1, SEQ ID NO:7; T1R2, SEQ ID NO:4; T1R3, SEQ ID NO:10). An asterisk (*) indicates a conserved nucleotide position among the sequences. A heart (♥) indicates the stop codon of feline T1R2.

FIGS. 2A-D show the deduced amino acid sequences of the feline T1R taste receptors (T1R1, SEQ ID NO:61; T1R2, SEQ ID NO:64; and T1R3, SEQ ID NO:2) aligned with the amino acid sequences of members of the T1R receptor family from human (T1R1, SEQ ID NO:17; T1R2, SEQ ID NO:20; T1R3, SEQ ID NO:12), rat (T1R1, SEQ ID NO:16; T1R2, SEQ ID NO:19; T1R3, SEQ ID NO:14), and mouse (T1R1, SEQ ID NO:15; T1R2, SEQ ID NO:18; T1R3, SEQ ID NO:13). An asterisk (*) indicates a conserved nucleotide position among the sequences. A colon (:) indicates an observed conserved amino acid substitution. A period (.) indicates an observed semi-conserved amino acid substitution. The cat T1R1 is very similar to human and rodents in terms of gene structure; however, cat T1R2 predicts a shorter protein of 391 amino acids compared with the human T1R2, which has 839 amino acids. This prediction of a short T1R2 is the result of a stop codon TAA in exon 3. The deduced amino acid sequence for cat T1R3 (SEQ ID NO:2) contains four additional amino acids at positions 11-14 relative to the homologous T1R3 receptors of mouse (SEQ ID NO:13), human (SEQ ID NO:12), and rat (SEQ ID NO:14). The deduced sequence for cat reveals a threonine in position 64, a position equivalent to amino acid 60 in mouse, and a leucine at position 59, a position equivalent to position 55 in mouse. In mouse, amino acid substitutions of a threonine at position 60 and an alanine at position 55, both positions located within the putative extracellular N-terminal domain of the polypeptide, are present in strains of mice demonstrating low preference for the sweet stimulus saccharin (Bachmanov et al., *Chem. Senses,* 26:925-933 (2001)). Leucine is a conservative substitution for alanine. Accordingly, the amino acid sequence differences of cat and mouse T1R3 receptor may account for functional differences that lead to different taste preferences between the two species.

FIG. 3 illustrates a phylogenetic tree showing the relatedness of the domestic cat T1R receptor family to the T1R family of receptors including human, rat, and mouse T1R1, T1R2, and T1R3. The T1R receptors of the rat and mouse are closely related, while the T1R receptors of human and cat diverge from rat and mouse. Interestingly, the sweet stimuli to which the rat and mouse respond are very similar, whereas those that stimulate the human and those that stimulate the cat differ from one another and from those for rat and mouse. For example, humans are unique in their ability to taste most high-intensity sweeteners, while cats find many amino acids attractive but are unable to taste most carbohydrate and high-intensity sweeteners. The cat T1R2 diverges from that of human, mouse, and rat, which is consistent with the fact that cat does not show preference for the carbohydrate sweeteners.

Figure 4:
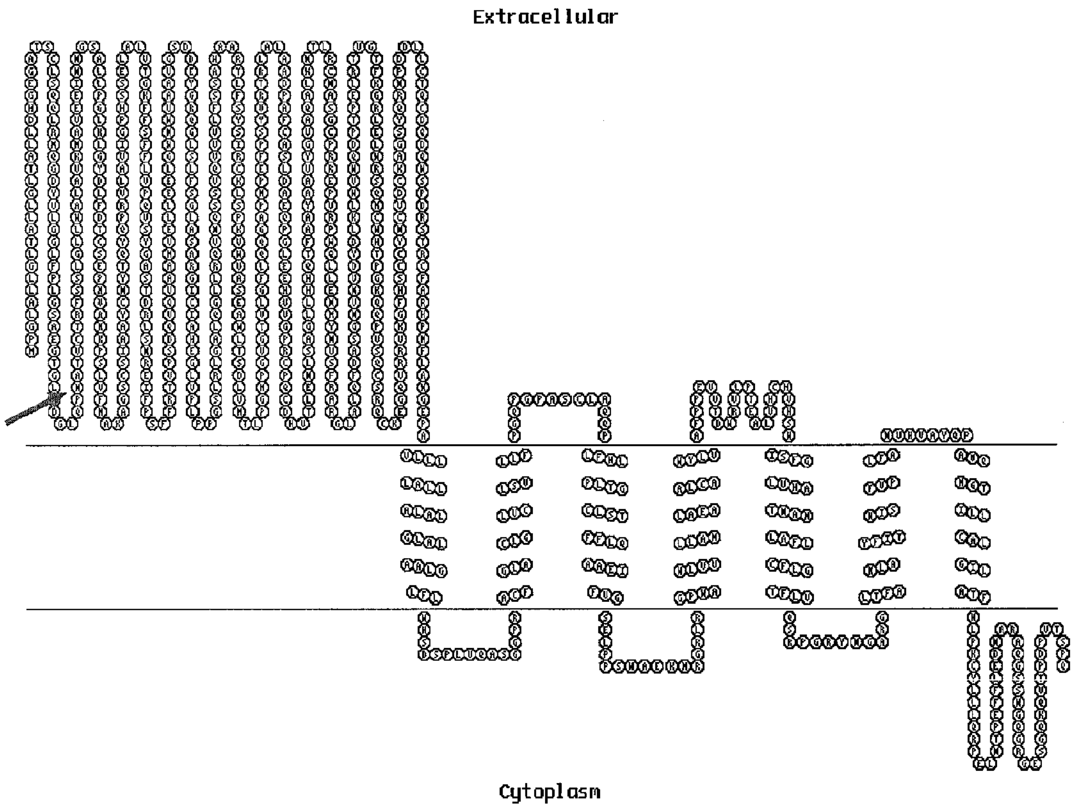
FIG. 4 illustrates the predicted conformation of cat T1R3 receptor. The cat T1R3 receptor is a seven-transmembrane domain receptor. The structure of the feline T1R3 receptor was generated through use of the protein modeling program publicly available through the European Bioinformatics Institute of the European Molecular Biology Laboratory.

FIG. 4 illustrates the predicted conformation of cat T1R3 receptor. The cat T1R3 receptor is a seven-transmembrane domain receptor. The structure of the feline T1R3 receptor was generated through use of the protein modeling program available online through the European Bioinformatics Institute.

FIG. 5A shows the predicted conformation of cat T1R1, indicating that the receptor is a 7-transmembrane-type receptor. FIG. 5B illustrates the predicted conformation of cat T1R2. Since feline T1R2 is a short protein (391 amino acids), a 7 transmembrane domain protein is not predicted. Without seven transmembrane domains, the cat T1R2 receptor may not interact appropriately with a dimerization partner, such as T1R3, and/or the plasma membrane, thereby resulting in the cat's inability to taste sweet carbohydrates. The cat T1R2 may have another function.

Table 4 shows the percent homology among the members of the T1R family in relation to the cat T1R taste receptors. The portion of Table 1 to the left of the diagonal (in bold type) shows the percent homology based on the open reading frame of the nucleotide sequences obtained from FIG. 1 for the T1R family among human, cat, rat and mouse. The upper portion to the right of the diagonal (in italic type) shows the percent homology of the T1R members based on the amino acid sequences of FIG. 2. Cat T1R1 shows 84% nucleotide sequence homology with human T1R1, 78% with rat T1R1 and 79% with mouse T1R1. At the amino acid level, cat T1R1 shows 81% homology with human T1R1, 74% with rat, and 74% with mouse. Cat T1R1 shows generally low homology with the other known members of the T1R family, T1R2 and T1R3, from human, rat and mouse. The same range of relatively low homology is present among the human, rat and mouse T1R1, T1R2 and T1R3 receptors from the same species. Cat T1R2 shows 72% nucleotide sequence homology with human T1R2, 61% with rat T1R2 and 64% with mouse T1R2. At the amino acid level, cat T1R2 shows 58% homology with human T1R2, 52% with rat, and 53% with mouse. Since cat T1R2 has a shorter protein (391aa) due to a stop codon in exon 3, cat T1R2 shows much lower homology with T1R2 in other species than the homology for T1R1 and T1R3 among different species, which indicates that cat T1R2 is very different from that of the other species. This is also consistent with the behavioral responses showing that cats do not show preference for carbohydrate sweeteners. This indicates that cat T1R2 may not be functional, freeing it from selective pressure. Therefore mutations in cat T1R2 most likely have accumulated. Cat T1R2 shows generally low homology with the other members of the T1R family, T1R1 and T1R3, from human, rat and mouse. The same range of relatively low homology is present among the human, rat, and mouse T1R2 and the T1R1 and T1R3 receptors from the same species.

TABLE 4

Percent Homology Among Diverse Species for T1Rs

| Species | Mouse T1R1 | Mouse T1R2 | Mouse T1R3 | Rat T1R1 | Rat T1R2 | Rat T1R3 | Human T1R1 | Human T1R2 | Human T1R3 | Cat T1R1 | Cat T1R2 | Cat T1R3 |
|---|---|---|---|---|---|---|---|---|---|---|---|---|
| Mouse T1R1 | | *36* | *30* | *90* | *36* | *30* | *73* | *37* | *30* | *74* | *30* | *30* |
| Mouse T1R2 | **55** | | *28* | *36* | *91* | *28* | *34* | *69* | *28* | *36* | *53* | *28* |
| Mouse T1R3 | **33** | **15** | | *31* | *28* | *92* | *30* | *27* | *72* | *30* | *25* | *72* |
| Rat T1R1 | **91** | **55** | **33** | | *37* | *31* | *73* | *37* | *31* | *74* | *26* | *31* |
| Rat T1R2 | **55** | **91** | **15** | **57** | | *28* | *34* | *71* | *29* | *36* | *52* | *28* |
| Rat T1R3 | **33** | **21** | **93** | **32** | **15** | | *31* | *27* | *73* | *30* | *26* | *72* |
| Human T1R1 | **79** | **56** | **35** | **79** | **56** | **35** | | *35* | *31* | *81* | *29* | *31* |

TABLE 4-continued

| Percent Homology Among Diverse Species for T1Rs | | | | | | | | | | | | |
|---|---|---|---|---|---|---|---|---|---|---|---|---|
| Species | Mouse T1R1 | Mouse T1R2 | Mouse T1R3 | Rat T1R1 | Rat T1R2 | Rat T1R3 | Human T1R1 | Human T1R2 | Human T1R3 | Cat T1R1 | Cat T1R2 | Cat T1R3 |
| Human T1R2 | **57** | **78** | **17** | **56** | **78** | **17** | **57** | | *28* | *36* | *58* | *28* |
| Human T1R3 | **41** | **39** | **73** | **39** | **36** | **75** | **40** | **38** | | *29* | *23* | *73* |
| Cat T1R1 | **79** | **54** | **35** | **78** | **56** | **35** | **84** | **56** | **53** | | *28* | *30* |
| Cat T1R2 | **42** | **64** | **22** | **41** | **61** | **22** | **44** | **72** | **48** | **44** | | *29* |
| Cat T1R3 | **33** | **34** | **74** | **36** | **36** | **75** | **53** | **39** | **79** | **53** | **39** | |

Note:
Upper right cells (italics) contain deduced amino acid homology; lower left cells (bold) contain nucleotide homology.

What is claimed:

1. An isolated T1R receptor polypeptide comprising:

a) an amino acid sequence of SEQ ID NO:61; or b) a fragment of at least 40 contiguous amino acids of SEQ ID NO:61.

2. An isolated and purified T1R1 receptor polypeptide comprising the amino acid sequence of SEQ ID NO:61.

3. An isolated T1R receptor comprising at least one extracellular domain of a feline T1R receptor, said extracellular domain comprising amino acids 1-563, amino acids 624-635, amino acids 701-726, or amino acids 781-792 of SEQ ID NO:61.

4. An isolated T1R receptor comprising at least one transmembrane domain of a feline T1R receptor, said transmembrane domain comprising acids 564-589, amino acids 604-623, amino acids 636-660, amino acids 681-700, amino acids 727-748, amino acids 761-780, or amino acids 793-817 of SEQ ID NO:61.

5. An isolated T1R receptor comprising an intracellular domain of a feline T1R receptor, said intracellular domain comprising amino acids 590-603, amino acids 661-680, amino acids 749-760, or amino acids 818-841 of SEQ ID NO:61.

6. An isolated T1R receptor dimer comprising a polypeptide comprising the amino acid sequence of SEQ ID NO:61.

7. The T1R receptor dimer of claim 6 wherein said dimer is a heterodimer.

8. The T1R receptor dimer of claim 6 further comprising a polypeptide comprising the amino acid sequence of SEQ ID NO:2.

9. A chimeric T1R receptor comprising at least one extracellular domain of a feline T1R receptor, said extracellular domain comprising amino acids 1-563, amino acids 624-635, amino acids 701-726, or amino acids 781-792 of SEQ ID NO:61.

10. A chimeric T1R receptor comprising at least one transmembrane domain of a feline T1R receptor, said transmembrane domain comprising acids 564-589, amino acids 604-623, amino acids 636-660, amino acids 681-700, amino acids 727-748, amino acids 761-780, or amino acids 793-817 of SEQ ID NO:61.

11. A chimeric T1R receptor comprising an intracellular domain of a feline T1R receptor, said intracellular domain comprising amino acids 590-603, amino acids 661-680, amino acids 749-760, or amino acids 818-841 of SEQ ID NO:61.

* * * * *

SEQUENCE LISTING

<160> NUMBER OF SEQ ID NOS: 99

<210> SEQ ID NO 1
<211> LENGTH: 2569
<212> TYPE: DNA
<213> ORGANISM: Felis catus

<400> SEQUENCE: 1
atgcccggcc tcgctctcct gggcctcacg gctctcctgg gcctcacggc tctcttggac 60
cacggggagg gcgcaacgtc ctgcttgtca cagcagctca ggatgcaggg ggactatgtg 120
ctgggtgggc tcttccctct gggctctgcc gagggtacag gtcttggcga cgggctgcag 180
cccaatgcca ccgtgtgcac caggttctcg tctctgggcc tgctctgggc gctggccgtg 240
aagatggcgg tggaggagat caacaacggg tcggccctgc tgcccgggct gcacctgggc 300
tatgacctct ttgacacgtg ttcagagccc atggtggcca tgaagcccag cctcgtgttc 360
atggccaaag caggcagctg cagcattgcc gcctactgca attacacaca gtaccagccc 420
cgcgtgctgg ccgtcatcgg gccccactcg tctgagctcg ccctcgtcac cggcaagttc 480
ttcagcttct tccttgtgcc tcaggtcagc tacggcgcca gcaccgaccg gctgagcaac 540
cgggagatct tcccgtcctt cttccgcacg gtgcccagcg accaggtgca ggtggcggcc 600
atggtggagc tgctggagga gctcggctgg aactgggtgg cggcggtggg tagtgacgac 660
gagtatggcc ggcagggcct gagcctcttc tccggcctgg ccagcgccag ggcatctgc 720 atcgcgcatg agggcctggt gccactgccg ccaggcagcc tgcggctggg cgccctacag 780
ggcctgctgc gccaggtgaa ccagagcagc gtgcaggtgg tggtgctgtt ctcctccgcc 840
cacgcggccc gcaccctctt cagctacagc atccgctgca agctctcacc caaggtgtgg 900
gtggccagcg aggcctggct gacctcagac ctggtcatga cgctgcccgg catgcctggg 960
gtgggcaccg tgctgggctt cctgcagcag ggcgccccga tgccggagtt cccatcctac 1020
gtgcggaccc gcctggccct ggccgctgac cctgccttct gcgcctcgct ggacgctgaa 1080
cagccaggcc tggaggagca cgtggtgggg ccacgctgcc cccaatgtga ccacgtcacg 1140
ctagagaacc tatctgcggg gctgctgcac caccagacct tcgctgccta cgcggctgtg 1200
tatggcgtgg cccaagccct tcacaacaca ctgcgctgca atgcctcggg ctgccccagg 1260
cgggagcctg tgcggccctg gcagctccta gagaacatgt acaacgtgag cttccgtgct 1320
cgcggcctgg cactgcagtt cgacgccagc gggaacgtga acgtggatta cgacctgaaa 1380

```
ctgtgggtgt ggcaggaccc gacgcccgag ctgcgcaccg taggcacctt caagggccgc   1440

ctggagctct ggcgctctca gatgtgctgg cacacgccgg ggaagcagca gcccgtgtcc   1500

cagtgctccc ggcagtgcaa ggaaggccag gtgcgccgcg tgaagggctt ccactcttgc   1560

tgttacaact gcgtggactg caaggcgggc agttatcagc gcaacccaga tgacctcctc   1620

tgcacccagt gtgaccagga ccagtggtcc ccagaccgga gcacacgctg cttcgcccgc   1680

aagcccatgt tcctggcatg gggggagcca gctgtgctgc tactgctcgc gctgctggct   1740

ctggcgctgg gcctggcgct ggcagccctg gggctcttcc tctggcactc ggacagcccg   1800

ctggttcagg cctcaggtgg gccacgggcc tgctttggcc tggcttgcct gggcctggtc   1860

tgcctcagtg tcctcctgtt ccctggccag ccaggccctg ccagctgcct ggcccagcag   1920

ccactgttcc acctcccact cactggctgc ctgagcacgt tttcctgca agcggccgag   1980

atatttgtgg ggtcggagct gccaccaagc tgggctgaga agatgcgtgg ccgcctgcgg   2040

gggccctggg cctggctggt ggtgctgctt gctatgctgg cagaagccgc attgtgtgcc   2100

tggtacctgg tagccttccc gccagaggtg gtgacggact ggcgggtact gcccacagag   2160

gcgctggtgc actgccacgt gcactcctgg atcagcttcg gcctggtgca tgccactaac   2220

gccatgctgg ccttcctctg cttcctgggc actttcctgg tgcagagccg gccaggccgc   2280

tacaatggtg cccgcggcct cacctttgcc atgctggcct acttcatcac ctggatctcc   2340

tttgtgcccc tctttgccaa tgtgcacgtg gcctaccagc ctgccgtgca gatgggcacc   2400

atcctcctct gtgccctggg tatcctagcc accttccacc tgcccaagtg ctacctgctg   2460

ctgcagcggc cggagctcaa cacccctgag ttcttcctgg aagacaatgc cagagcacag   2520

ggcagcagtt gggggcaggg gaggggagaa tcggggcaaa aacaagtga               2569
```

<210> SEQ ID NO 2
<211> LENGTH: 865
<212> TYPE: PRT
<213> ORGANISM: Felis catus

<400> SEQUENCE: 2

```
Met Pro Gly Leu Ala Leu Leu Gly Leu Thr Ala Leu Leu Gly Leu Thr
1               5                   10                  15

Ala Leu Leu Asp His Gly Glu Gly Ala Thr Ser Cys Leu Ser Gln Gln
            20                  25                  30

Leu Arg Met Gln Gly Asp Tyr Val Leu Gly Gly Leu Phe Pro Leu Gly
        35                  40                  45

Ser Ala Glu Gly Thr Gly Leu Gly Asp Gly Leu Gln Pro Asn Ala Thr
    50                  55                  60

Val Cys Thr Arg Phe Ser Ser Leu Gly Leu Leu Trp Ala Leu Ala Val
65                  70                  75                  80

Lys Met Ala Val Glu Glu Ile Asn Asn Gly Ser Ala Leu Leu Pro Gly
                85                  90                  95

Leu His Leu Gly Tyr Asp Leu Phe Asp Thr Cys Ser Glu Pro Met Val
            100                 105                 110

Ala Met Lys Pro Ser Leu Val Phe Met Ala Lys Ala Gly Ser Cys Ser
        115                 120                 125

Ile Ala Ala Tyr Cys Asn Tyr Thr Gln Tyr Gln Pro Arg Val Leu Ala
    130                 135                 140

Val Ile Gly Pro His Ser Ser Glu Leu Ala Leu Val Thr Gly Lys Phe
145                 150                 155                 160

Phe Ser Phe Phe Leu Val Pro Gln Val Ser Tyr Gly Ala Ser Thr Asp
```

```
                165                 170                 175

Arg Leu Ser Asn Arg Glu Ile Phe Pro Ser Phe Phe Arg Thr Val Pro
            180                 185                 190

Ser Asp Gln Val Gln Val Ala Ala Met Val Glu Leu Leu Glu Glu Leu
        195                 200                 205

Gly Trp Asn Trp Val Ala Ala Val Gly Ser Asp Asp Glu Tyr Gly Arg
    210                 215                 220

Gln Gly Leu Ser Leu Phe Ser Gly Leu Ala Ser Ala Arg Gly Ile Cys
225                 230                 235                 240

Ile Ala His Glu Gly Leu Val Pro Leu Pro Pro Gly Ser Leu Arg Leu
                245                 250                 255

Gly Ala Leu Gln Gly Leu Leu Arg Gln Val Asn Gln Ser Ser Val Gln
            260                 265                 270

Val Val Val Leu Phe Ser Ser Ala His Ala Ala Arg Thr Leu Phe Ser
        275                 280                 285

Tyr Ser Ile Arg Cys Lys Leu Ser Pro Lys Val Trp Val Ala Ser Glu
    290                 295                 300

Ala Trp Leu Thr Ser Asp Leu Val Met Thr Leu Pro Gly Met Pro Gly
305                 310                 315                 320

Val Gly Thr Val Leu Gly Phe Leu Gln Gln Gly Ala Pro Met Pro Glu
                325                 330                 335

Phe Pro Ser Tyr Val Arg Thr Arg Leu Ala Leu Ala Ala Asp Pro Ala
            340                 345                 350

Phe Cys Ala Ser Leu Asp Ala Glu Gln Pro Gly Leu Glu Glu His Val
        355                 360                 365

Val Gly Pro Arg Cys Pro Gln Cys Asp His Val Thr Leu Glu Asn Leu
    370                 375                 380

Ser Ala Gly Leu Leu His His Gln Thr Phe Ala Ala Tyr Ala Ala Val
385                 390                 395                 400

Tyr Gly Val Ala Gln Ala Leu His Asn Thr Leu Arg Cys Asn Ala Ser
                405                 410                 415

Gly Cys Pro Arg Arg Glu Pro Val Arg Pro Trp Gln Leu Leu Glu Asn
            420                 425                 430

Met Tyr Asn Val Ser Phe Arg Ala Arg Gly Leu Ala Leu Gln Phe Asp
        435                 440                 445

Ala Ser Gly Asn Val Asn Val Asp Tyr Asp Leu Lys Leu Trp Val Trp
    450                 455                 460

Gln Asp Pro Thr Pro Glu Leu Arg Thr Val Gly Thr Phe Lys Gly Arg
465                 470                 475                 480

Leu Glu Leu Trp Arg Ser Gln Met Cys Trp His Thr Pro Gly Lys Gln
                485                 490                 495

Gln Pro Val Ser Gln Cys Ser Arg Gln Cys Lys Glu Gly Gln Val Arg
            500                 505                 510

Arg Val Lys Gly Phe His Ser Cys Cys Tyr Asn Cys Val Asp Cys Lys
        515                 520                 525

Ala Gly Ser Tyr Gln Arg Asn Pro Asp Asp Leu Leu Cys Thr Gln Cys
    530                 535                 540

Asp Gln Asp Gln Trp Ser Pro Asp Arg Ser Thr Arg Cys Phe Ala Arg
545                 550                 555                 560

Lys Pro Met Phe Leu Ala Trp Gly Glu Pro Ala Val Leu Leu Leu Leu
                565                 570                 575

Ala Leu Leu Ala Leu Ala Leu Gly Leu Ala Leu Ala Ala Leu Gly Leu
            580                 585                 590
```

```
Phe Leu Trp His Ser Asp Ser Pro Leu Val Gln Ala Ser Gly Gly Pro
        595                 600                 605

Arg Ala Cys Phe Gly Leu Ala Cys Leu Gly Leu Val Cys Leu Ser Val
    610                 615                 620

Leu Leu Phe Pro Gly Gln Pro Gly Pro Ala Ser Cys Leu Ala Gln Gln
625                 630                 635                 640

Pro Leu Phe His Leu Pro Leu Thr Gly Cys Leu Ser Thr Phe Phe Leu
                645                 650                 655

Gln Ala Ala Glu Ile Phe Val Gly Ser Glu Leu Pro Pro Ser Trp Ala
            660                 665                 670

Glu Lys Met Arg Gly Arg Leu Arg Gly Pro Trp Ala Trp Leu Val Val
        675                 680                 685

Leu Leu Ala Met Leu Ala Glu Ala Ala Leu Cys Ala Trp Tyr Leu Val
    690                 695                 700

Ala Phe Pro Pro Glu Val Val Thr Asp Trp Arg Val Leu Pro Thr Glu
705                 710                 715                 720

Ala Leu Val His Cys His Val His Ser Trp Ile Ser Phe Gly Leu Val
                725                 730                 735

His Ala Thr Asn Ala Met Leu Ala Phe Leu Cys Phe Leu Gly Thr Phe
            740                 745                 750

Leu Val Gln Ser Arg Pro Gly Arg Tyr Asn Gly Ala Arg Gly Leu Thr
        755                 760                 765

Phe Ala Met Leu Ala Tyr Phe Ile Thr Trp Ile Ser Phe Val Pro Leu
    770                 775                 780

Phe Ala Asn Val His Val Ala Tyr Gln Pro Ala Val Gln Met Gly Thr
785                 790                 795                 800

Ile Leu Leu Cys Ala Leu Gly Ile Leu Ala Thr Phe His Leu Pro Lys
                805                 810                 815

Cys Tyr Leu Leu Leu Gln Arg Pro Glu Leu Asn Thr Pro Glu Phe Phe
            820                 825                 830

Leu Glu Asp Asn Ala Arg Ala Gln Gly Ser Ser Trp Gly Gln Gly Arg
        835                 840                 845

Gly Glu Ser Gly Gln Lys Gln Val Thr Pro Asp Pro Val Thr Ser Pro
    850                 855                 860

Gln
865


<210> SEQ ID NO 3
<211> LENGTH: 2532
<212> TYPE: DNA
<213> ORGANISM: Mus musculus

<400> SEQUENCE: 3

atgggacccc aggcgaggac actccatttg ctgtttctcc tgctgcatgc tctgcctaag      60

ccagtcatgc tggtagggaa ctccgacttt cacctggctg gggactacct cctgggtggc     120

ctctttaccc tccatgccaa cgtgaagagc gtctctcacc tcagctacct gcaggtgccc     180

aagtgcaatg agtacaacat gaaggtcttg ggctacaacc tcatgcaggc catgcgattc     240

gccgtggagg aaatcaacaa ctgtagctct ctgctgcccg gcgtgctgct cggctacgag     300

atggtggatg tctgctacct ctccaacaat atccagcctg ggctctactt cctgtcacag     360

atagatgact tcctgcccat cctcaaagac tacagccagt acaggcccca agtggtggcc     420

gtcattggcc cagacaactc tgagtccgcc atcaccgtgt ccaacattct ctcctacttc     480

ctcgtgccac aggtcacata tagcgccatc accgacaagc tgcgagacaa gcggcgcttc     540
```

-continued

```
cctgccatgc tgcgcactgt gcccagcgcc acccaccaca tcgaggccat ggtgcaactg    600

atggttcact tccagtggaa ctggatcgtg gtgctggtga gcgatgacga ttatggccga    660

gagaacagcc acctgctgag ccagcgtctg accaacactg gcgatatctg cattgccttc    720

caggaggttc tgcctgtacc agaacccaac caggccgtga ggcctgagga gcaggaccaa    780

ctggacaaca tcctggacaa gctgcggcgg acctcggcgc gtgtggtggt gatattctcg    840

ccagagctga gcctgcacaa cttcttccgc gaggtgctgc gctggaactt cacaggcttt    900

gtgtggattg cctctgagtc ctgggccatc gaccctgttc tacacaacct cacagagctg    960

cgccacacgg gcactttcct gggcgtcacc atccagaggg tgtccatccc tggcttcagc   1020

cagttccgag tgcgccacga caagccagag tatcccatgc ctaacgagac cagcctgagg   1080

actacctgta accaggactg tgacgcctgc atgaacatca ccgagtcctt taacaacgtt   1140

ctcatgcttt cgggggagcg tgtggtctac agtgtgtact cggccgtcta cgcggtagcc   1200

cacaccctcc acagactcct ccactgcaac caggtccgct gcaccaagca aatcgtctat   1260

ccatggcagc tactcaggga gatctggcat gtcaacttca cgctcctggg caaccagctc   1320

ttcttcgacg aacaagggga catgccgatg ctcctggaca tcatccagtg gcaatggggc   1380

ctgagccaga accccttcca aagcatcgcc tcctactccc ccaccgagac gaggctgacc   1440

tacattagca atgtgtcctg gtacaccccc aacaacacgg tccccatatc catgtgttct   1500

aagagttgcc agcctgggca aatgaaaaaa cccataggcc tccacccgtg ctgcttcgag   1560

tgtgtggact gtccgccggg cacctacctc aaccgatcag tagatgagtt taactgtctg   1620

tcctgcccgg gttccatgtg gtcttacaag aacaacatcg cttgcttcaa gcggcggctg   1680

gccttcctgg agtggcacga agtgcccact atcgtggtga ccatcctggc cgccctgggc   1740

ttcatcagta cgctggccat tctgctcatc ttctggagac atttccagac gcccatggtg   1800

cgctcggcgg gcggccccat gtgcttcctg atgctggtgc ccctgctgct ggcgttcggg   1860

atggtccccg tgtatgtggg cccccccacg gtcttctcct gtttctgccg ccaggctttc   1920

ttcaccgttt gcttctccgt ctgcctctcc tgcatcacgg tgcgctcctt ccagattgtg   1980

tgcgtcttca agatggccag acgcctgcca agcgcctacg gtttctggat gcgttaccac   2040

gggccctacg tctttgtggc cttcatcacg gccgtcaagg tggccctggt ggcaggcaac   2100

atgctggcca ccaccatcaa ccccattggc cggaccgacc ccgatgaccc caatatcata   2160

atcctctcct gccaccctaa ctaccgcaac gggctactct tcaacaccag catggacttg   2220

ctgctgtccg tgctgggttt cagcttcgcg tacgtgggca aggaactgcc caccaactac   2280

aacgaagcca agttcatcac cctcagcatg accttctcct tcacctcctc catctccctc   2340

tgcacgttca tgtctgtcca cgatggcgtg ctggtcacca tcatggatct cctggtcact   2400

gtgctcaact ttctggccat cggcttgggg tactttggcc ccaagtgtta catgatcctt   2460

ttctacccgg agcgcaacac ttcagcttat ttcaatagca tgattcaggg ctacacgatg   2520

aggaagagct ag                                                       2532
```

<210> SEQ ID NO 4
<211> LENGTH: 2529
<212> TYPE: DNA
<213> ORGANISM: Rattus rattus

<400> SEQUENCE: 4

```
atgggtcccc aggcaaggac actctgcttg ctgtctctcc tgctgcatgt tctgcctaag     60

ccaggcaagc tggtagagaa ctctgacttc cacctggccg ggactacct cctgggtggc    120
```

-continued

```
ctctttaccc tccatgccaa cgtgaagagc atctcccacc tcagctacct gcaggtgccc    180
aagtgcaatg agttcaccat gaaggtgttg ggctacaacc tcatgcaggc catgcgtttc    240
gctgtggagg agatcaacaa ctgtagctcc ctgctacccg gcgtgctgct cggctacgag    300
atggtggatg tctgttacct ctccaacaat atccaccctg ggctctactt cctggcacag    360
gacgacgacc tcctgcccat cctcaaagac tacagccagt acatgcccca cgtggtggct    420
gtcattggcc ccgacaactc tgagtccgcc attaccgtgt ccaacattct ctctcatttc    480
ctcatcccac agatcacata cagcgccatc tccgacaagc tgcgggacaa gcggcacttc    540
cctagcatgc tacgcacagt gcccagcgcc acccaccaca tcgaggccat ggtgcagctg    600
atggttcact tccaatggaa ctggattgtg gtgctggtga gcgacgacga ttacggccgc    660
gagaacagcc acctgttgag ccagcgtctg accaaaaacga gcgacatctg cattgccttc    720
caggaggttc tgcccatacc tgagtccagc caggtcatga ggtccgagga gcagagacaa    780
ctggacaaca tcctggacaa gctgcggcgg acctcggcgc gcgtcgtggt ggtgttctcg    840
cccgagctga gcctgtatag cttctttcac gaggtgctcc gctggaactt cacgggtttt    900
gtgtggatcg cctctgagtc ctgggctatc gacccagttc tgcataacct cacggagctg    960
cgccacacgg gtacttttct gggcgtcacc atccagaggg tgtccatccc tggcttcagt   1020
cagttccgag tgcgccgtga caagccaggg tatcccgtgc ctaacacgac caacctgcgg   1080
acgacctgca accaggactg tgacgcctgc ttgaacacca ccaagtcctt caacaacatc   1140
cttatacttt cgggggagcg cgtggtctac agcgtgtact cggcagttta cgcggtggcc   1200
catgccctcc acagactcct cggctgtaac cgggtccgct gcaccaagca aaaggtctac   1260
ccgtggcagc tactcaggga gatctggcac gtcaacttca cgctcctggg taaccggctc   1320
ttctttgacc aacaagggga catgccgatg ctcttggaca tcatccagtg gcagtgggac   1380
ctgagccaga atcccttcca aagcatcgcc tcctattctc ccaccagcaa gaggctaacc   1440
tacattaaca atgtgtcctg gtacaccccc aacaacacgg tccctgtctc catgtgttcc   1500
aagagctgcc agccagggca aatgaaaaag tctgtgggcc tccacccttg ttgcttcgag   1560
tgcttggatt gtatgccagg cacctacctc aaccgctcag cagatgagtt taactgtctg   1620
tcctgcccgg gttccatgtg gtcctacaag aacgacatca cttgcttcca gcggcggcct   1680
accttcctgg agtggcacga agtgcccacc atcgtggtgg ccatactggc tgccctgggc   1740
ttcttcagta cactggccat tcttttcatc ttctggagac atttccagac acccatggtg   1800
cgctcggccg gtggccccat gtgcttcctg atgctcgtgc ccctgctgct ggcgtttggg   1860
atggtgcccg tgtatgtggg gccccccacg gtcttctcat gcttctgccg acaggctttc   1920
ttcaccgtct gcttctccat ctgcctatcc tgcatcaccg tgcgctcctt ccagatcgtg   1980
tgtgtcttca agatggccag acgcctgcca agtgcctaca gtttttggat gcgttaccac   2040
gggccctatg tcttcgtggc cttcatcacg gccatcaagg tggccctggt ggtgggcaac   2100
atgctggcca ccaccatcaa ccccattggc cggaccgacc cggatgaccc caacatcatg   2160
atcctctcgt gccaccctaa ctaccgcaac gggctactgt tcaacaccag catggacttg   2220
ctgctgtctg tgctgggttt cagcttcgct tacatgggca aggagctgcc caccaactac   2280
aacgaagcca agttcatcac tctcagcatg accttctcct tcacctcctc catctccctc   2340
tgcaccttca tgtctgtgca cgacggcgtg ctggtcacca tcatggacct cctggtcact   2400
gtgctcaact tcctggccat cggcttggga tactttggcc ccaagtgtta catgatcctt   2460
ttctacccgg agcgcaacac ctcagcctat ttcaatagca tgatccaggg ctacaccatg   2520
```

aggaagagc 2529

<210> SEQ ID NO 5
<211> LENGTH: 2520
<212> TYPE: DNA
<213> ORGANISM: Homo sapiens

<400> SEQUENCE: 5
atggggccca gggcaaagac catctgctcc ctgttcttcc tcctatgggt cctggctgag 60
ccggctgaga actcggactt ctacctgcct ggggattacc tcctgggtgg cctcttctcc 120
ctccatgcca acatgaaggg cattgttcac cttaacttcc tgcaggtgcc catgtgcaag 180
gagtatgaag tgaaggtgat aggctacaac ctcatgcagg ccatgcgctt cgcggtggag 240
gagatcaaca atgacagcag cctgctgcct ggtgtgctgc tgggctatga gatcgtggat 300
gtgtgctaca tctccaacaa tgtccagccg gtgctctact tcctggcaca cgaggacaac 360
ctccttccca tccaagagga ctacagtaac tacatttccc gtgtggtggc tgtcattggc 420
cctgacaact ccgagtctgt catgactgtg gccaacttcc tctccctatt tctccttcca 480
cagatcacct acagcgccat cagcgatgag ctgcgagaca aggtgcgctt cccggctttg 540
ctgcgtacca cacccagcgc cgaccaccac gtcgaggcca tggtgcagct gatgctgcac 600
ttccgctgga actggatcat tgtgctggtg agcagcgaca cctatggccg cgacaatggc 660
cagctgcttg gcgagcgcgt ggcccggcgc gacatctgca tcgccttcca ggagacgctg 720
cccacactgc agcccaacca gaacatgacg tcagaggagc gccagcgcct ggtgaccatt 780
gtggacaagc tgcagcagag cacagcgcgc gtcgtggtcg tgttctcgcc cgacctgacc 840
ctgtaccact tcttcaatga ggtgctgcgc cagaacttca cgggcgccgt gtggatcgcc 900
tccgagtcct gggccatcga cccggtcctg cacaacctca cggagctggg ccacttgggc 960
accttcctgg gcatcaccat ccagagcgtg cccatcccgg gcttcagtga gttccgcgag 1020
tggggcccac aggctgggcc gccacccctc agcaggacca gccagagcta tacctgcaac 1080
caggagtgcg acaactgcct gaacgccacc ttgtccttca acaccattct caggctctct 1140
ggggagcgtg tcgtctacag cgtgtactct gcggtctatg ctgtggccca tgccctgcac 1200
agcctcctcg gctgtgacaa aagcacctgc accaagaggg tggtctaccc ctggcagctg 1260
cttgaggaga tctggaaggt caacttcact ctcctggacc accaaatctt cttcgacccg 1320
caaggggacg tggctctgca cttggagatt gtccagtggc aatgggaccg gagccagaat 1380
cccttccaga gcgtcgcctc ctactacccc ctgcagcgac agctgaagaa catccaagac 1440
atctcctggc acaccgtcaa caacacgatc cctatgtcca tgtgttccaa gaggtgccag 1500
tcagggcaaa agaagaagcc tgtgggcatc cacgtctgct gcttcgagtg catcgactgc 1560
cttcccggca ccttcctcaa ccacactgaa gatgaatatg aatgccaggc ctgcccgaat 1620
aacgagtggt cctaccagag tgagacctcc tgcttcaagc ggcagctggt cttcctggaa 1680
tggcatgagg cacccaccat cgctgtggcc ctgctggccg ccctgggctt cctcagcacc 1740
ctggccatcc tggtgatatt ctggaggcac ttccagacac ccatagttcg ctcggctggg 1800
ggccccatgt gcttcctgat gctgacactg ctgctggtgg catacatggt ggtcccggtg 1860
tacgtggggc cgcccaaggt ctccacctgc ctctgccgcc aggccctctt tcccctctgc 1920
ttcacaattt gcatctcctg tatcgccgtg cgttctttcc agatcgtctg cgccttcaag 1980
atggccagcc gcttcccacg cgcctacagc tactgggtcc gctaccaggg gccctacgtc 2040
tctatggcat ttatcacggt actcaaaatg gtcattgtgg taattggcat gctggccacg 2100

-continued ggcctcagtc ccaccacccg tactgacccc gatgacccca agatcacaat tgtctcctgt 2160
aaccccaact accgcaacag cctgctgttc aacaccagcc tggacctgct gctctcagtg 2220
gtgggtttca gcttcgccta catgggcaaa gagctgccca ccaactacaa cgaggccaag 2280
ttcatcaccc tcagcatgac cttctatttc acctcatccg tctccctctg caccttcatg 2340
tctgcctaca gcggggtgct ggtcaccatc gtggacctct tggtcactgt gctcaacctc 2400
ctggccatca gcctgggcta cttcggcccc aagtgctaca tgatcctctt ctacccggag 2460
cgcaacacgc ccgcctactt caacagcatg atccagggct acaccatgag gagggactag 2520

<210> SEQ ID NO 6
<211> LENGTH: 2529
<212> TYPE: DNA
<213> ORGANISM: Mus musculus

<400> SEQUENCE: 6
atgcttttct gggcagctca cctgctgctc agcctgcagc tggccgttgc ttactgctgg 60
gctttcagct gccaaaggac agaatcctct ccaggtttca gcctccctgg ggacttcctc 120
ctggcaggcc tgttctccct ccatgctgac tgtctgcagg tgagacacag acctctggtg 180
acaagttgtg acaggtctga cagcttcaac ggccatggct atcacctctt ccaagccatg 240
cggttcaccg ttgaggagat aaacaactcc acagctctgc ttcccaacat caccctgggg 300
tatgaactgt atgacgtgtg ctcagagtct tccaatgtct atgccaccct gagggtgctc 360
gcccagcaag ggacaggcca cctagagatg cagagagatc ttcgcaacca ctcctccaag 420
gtggtggcac tcattgggcc tgataacact gaccacgctg tcaccactgc tgccctgctg 480 agccctttc tgatgcccct ggtcagctat gaggcgagca gcgtgatcct cagtgggaag 540
cgcaagttcc cgtccttctt gcgcaccatc cccagcgata agtaccaggt ggaagtcata 600
gtgcggctgc tgcagagctt cggctgggtc tggatctcgc tcgttggcag ctatggtgac 660
tacgggcagc tgggcgtaca ggcgctggag gagctggcca ctccacgggg catctgcgtc 720
gccttcaagg acgtggtgcc tctctccgcc caggcgggtg acccaaggat gcagcgcatg 780
atgctgcgtc tggctcgagc caggaccacc gtggtcgtgg tcttctctaa ccggcacctg 840
gctggagtgt tcttcaggtc tgtggtgctg gccaacctga ctggcaaagt gtggatcgcc 900
tccgaagact gggccatctc cacgtacatc accaatgtgc ccgggatcca gggcattggg 960
acggtgctgg gggtggccat ccagcagaga caagtccctg gcctgaagga gtttgaagag 1020
tcctatgtcc aggcagtgat gggtgctccc agaacttgcc cagaggggtc ctggtgcggc 1080
actaaccagc tgtgcaggga gtgtcacgct ttcacgacat ggaacatgcc cgagcttgga 1140
gccttctcca tgagcgctgc ctacaatgtg tatgaggctg tgtatgctgt ggcccacggc 1200
ctccaccagc tcctgggatg tacctctggg acctgtgcca gaggcccagt ctacccctgg 1260
cagcttcttc agcagatcta caaggtgaat ttccttctac ataagaagac tgtagcattc 1320
gatgacaagg gggaccctct aggttattat gacatcatcg cctgggactg gaatggacct 1380
gaatggacct ttgaggtcat tggttctgcc tcactgtctc cagttcatct agacataaat 1440
aagacaaaaa tccagtggca cgggaagaac aatcaggtgc ctgtgtcagt gtgtaccagg 1500
gactgtctcg aagggcacca caggttggtc atgggttccc accactgctg cttcgagtgc 1560
atgccctgtg aagctgggac atttctcaac acgagtgagc ttcacacctg ccagccttgt 1620
ggaacagaag aatgggcccc tgaggggagc tcagcctgct tctcacgcac cgtggagttc 1680
ttggggtggc atgaacccat ctctttggtg ctattagcag ctaacacgct attgctgctg 1740

```
ctgctgattg ggactgctgg cctgtttgcc tggcgtcttc acacgcctgt tgtgaggtca   1800

gctgggggta ggctgtgctt cctcatgctg ggttccttgg tagctgggag ttgcagcctc   1860

tacagcttct tcgggaagcc cacggtgccc gcgtgcttgc tgcgtcagcc cctcttttct   1920

ctcgggtttg ccattttcct ctcctgtctg acaatccgct ccttccaact ggtcatcatc   1980

ttcaagtttt ctaccaaggt acccacattc taccacactt gggcccaaaa ccatggtgcc   2040

ggaatattcg tcattgtcag ctccacggtc catttgttcc tctgtctcac gtggcttgca   2100

atgtggaccc cacggcccac cagggagtac cagcgcttcc cccatctggt gattcttgag   2160

tgcacagagg tcaactctgt gggcttcctg gtggctttcg cacacaacat cctcctctcc   2220

atcagcacct ttgtctgcag ctacctgggt aaggaactgc cggagaacta taacgaagcc   2280

aaatgtgtca ccttcagcct gctcctccac ttcgtatcct ggatcgcttt cttcaccatg   2340

tccagcattt accagggcag ctacctaccc gcggtcaatg tgctggcagg gctggccact   2400

ctgagtggcg gcttcagcgg ctatttcctc cctaaatgct acgtgattct ctgccgtcca   2460

gaactcaaca acacagaaca ctttcaggcc tccatccagg actacacgag gcgctgcggc   2520

actacctga                                                           2529
```

<210> SEQ ID NO 7
<211> LENGTH: 2520
<212> TYPE: DNA
<213> ORGANISM: Rattus rattus

<400> SEQUENCE: 7

```
atgctcttct gggctgctca cctgctgctc agcctgcagt tggtctactg ctgggctttc     60

agctgccaaa ggacagagtc ctctccaggc ttcagccttc ctggggactt cctccttgca    120

ggtctgttct ccctccatgg tgactgtctg caggtgagac acagacctct ggtgacaagt    180

tgtgacaggc ccgacagctt caacggccat ggctaccacc tcttccaagc catgcggttc    240

actgttgagg agataaacaa ctcctcggcc ctgcttccca acatcaccct ggggtatgag    300

ctgtacgacg tgtgctcaga atctgccaat gtgtatgcca ccctgagggt gcttgccctg    360

caagggcccc gccacataga gatacagaaa gaccttcgca accactcctc caaggtggtg    420

gccttcatcg ggcctgacaa cactgaccac gctgtcacta ccgctgcctt gctgggtcct    480

ttcctgatgc ccctggtcag ctatgaggca agcagcgtgg tactcagtgc caagcgcaag    540

ttcccgtctt tccttcgtac cgtccccagt gaccggcacc aggtggaggt catggtgcag    600

ctgctgcaga gttttgggtg ggtgtggatc tcgctcattg gcagctacgg tgattacggg    660

cagctgggtg tgcaggcgct ggaggagctg gccgtgcccc ggggcatctg cgtcgccttc    720

aaggacatcg tgcctttctc tgcccgggtg ggtgacccga ggatgcagag catgatgcag    780

catctggctc aggccaggac caccgtggtt gtggtcttct ctaaccggca cctggctaga    840

gtgttcttca ggtccgtggt gctggccaac ctgactggca aagtgtgggt cgcctcagaa    900

gactgggcca tctccacgta catcaccagc gtgactggga tccaaggcat tgggacggtg    960

ctcggtgtgg ccgtccagca gagacaagtc cctgggctga aggagtttga ggagtcttat   1020

gtcagggctg taacagctgc tcccagcgct tgcccggagg ggtcctggtg cagcactaac   1080

cagctgtgcc gggagtgcca cacgttcacg actcgtaaca tgcccacgct tggagccttc   1140

tccatgagtg ccgcctacag agtgtatgag gctgtgtacg ctgtggccca cggcctccac   1200

cagctcctgg gatgtacttc tgagatctgt tccagaggcc cagtctaccc ctggcagctt   1260

cttcagcaga tctacaaggt gaattttctt ctacatgaga atactgtggc atttgatgac   1320
```

```
aacggggaca ctctaggtta ctacgacatc atcgcctggg actggaatgg acctgaatgg   1380

acctttgaga tcattggctc tgcctcactg tctccagttc atctggacat aaataagaca   1440

aaaatccagt ggcacgggaa gaacaatcag gtgcctgtgt cagtgtgtac cacggactgt   1500

ctggcagggc accacagggt ggttgtgggt tcccaccact gctgctttga gtgtgtgccc   1560

tgcgaagctg ggaccttttct caacatgagt gagcttcaca tctgccagcc ttgtggaaca   1620

gaagaatggg cacccaagga gagcactact tgcttcccac gcacggtgga gttcttggct   1680

tggcatgaac ccatctcttt ggtgctaata gcagctaaca cgctattgct gctgctgctg   1740

gttgggactg ctggcctgtt tgcctggcat tttcacacac ctgtagtgag gtcagctggg   1800

ggtaggctgt gcttcctcat gctgggttcc ctggtggccg gaagttgcag cttctatagc   1860

ttcttcgggg agcccacggt gcccgcgtgc ttgctgcgtc agcccctctt ttctctcggg   1920

tttgccatct tcctctcctg cctgacaatc cgctccttcc aactggtcat catcttcaag   1980

ttttctacca aggtgcccac attctaccgt acctgggccc aaaaccatgg tgcaggtcta   2040

ttcgtcattg tcagctccac ggtccatttg ctcatctgtc tcacatggct tgtaatgtgg   2100

accccacgac ccaccaggga ataccagcgc ttcccccatc tggtgattct cgagtgcaca   2160

gaggtcaact ctgtaggctt cctgttggct ttcacccaca acattctcct ctccatcagt   2220

accttcgtct gcagctacct gggtaaggaa ctgccagaga actataatga agccaaatgt   2280

gtcaccttca gcctgctcct caacttcgta tcctggatcg ccttcttcac catggccagc   2340

atttaccagg gcagctacct gcctgcggtc aatgtgctgg cagggctgac cacactgagc   2400

ggcggcttca gcggttactt cctcccccaag tgctatgtga ttctctgccg tccagaactc   2460

aacaatacag aacactttca ggcctccatc caggactaca cgaggcgctg cggcactacc   2520
```

<210> SEQ ID NO 8
<211> LENGTH: 2526
<212> TYPE: DNA
<213> ORGANISM: Homo sapiens

<400> SEQUENCE: 8

```
atgctgctct gcacggctcg cctggtcggc ctgcagcttc tcatttcctg ctgctgggcc     60

tttgcctgcc atagcacgga gtcttctcct gacttcaccc tccccggaga ttacctcctg    120

gcaggcctgt tccctctcca ttctggctgt ctgcaggtga ggcacagacc cgaggtgacc    180

ctgtgtgaca ggtcttgtag cttcaatgag catggctacc acctcttcca ggctatgcgg    240

cttggggttg aggagataaa caactccacg gccctgctgc ccaacatcac cctggggtac    300

cagctgtatg atgtgtgttc tgactctgcc aatgtgtatg ccacgctgag agtgctctcc    360

ctgccagggc aacaccacat agagctccaa ggagaccttc tccactattc ccctacggtg    420

ctggcagtga ttgggcctga cagcaccaac cgtgctgcca ccacagccgc cctgctgagc    480

cctttcctgg tgcccatgat tagctatgcg gccagcagcg agacgctcag cgtgaagcgg    540

cagtatccct ctttcctgcg caccatcccc aatgacaagt accaggtgga gaccatggtg    600

ctgctgctgc agaagttcgg gtggacctgg atctctctgg ttggcagcag tgacgactat    660

gggcagctag ggtgcaggc actggagaac caggccactg gtcaggggat ctgcattgct    720

ttcaaggaca tcatgccctt ctctgcccag gtgggcgatg agaggatgca gtgcctcatg    780

cgccacctgg cccaggccgg ggccaccgtc gtggttgttt tttccagccg gcagttggcc    840

agggtgtttt tcgagtccgt ggtgctgacc aacctgactg gcaaggtgtg ggtcgcctca    900

gaagcctggg ccctctccag gcacatcact ggggtgcccg ggatccagcg cattgggatg    960
```

-continued gtgctgggcg tggccatcca gaagagggct gtccctggcc tgaaggcgtt tgaagaagcc 1020
tatgcccggg cagacaagaa ggcccctagg ccttgccaca agggctcctg gtgcagcagc 1080
aatcagctct gcagagaatg ccaagctttc atggcacaca cgatgcccaa gctcaaagcc 1140
ttctccatga gttctgccta caacgcatac cgggctgtgt atgcggtggc ccatggcctc 1200
caccagctcc tgggctgtgc ctctggagct tgttccaggg gccgagtcta cccctggcag 1260
cttttggagc agatccacaa ggtgcatttc cttctacaca aggacactgt ggcgtttaat 1320
gacaacagag atcccctcag tagctataac ataattgcct gggactggaa tggacccaag 1380
tggaccttca cggtcctcgg ttcctccaca tggtctccag ttcagctaaa cataaatgag 1440
accaaaatcc agtggcacgg aaaggacaac caggtgccta agtctgtgtg ttccagcgac 1500
tgtcttgaag ggcaccagcg agtggttacg ggtttccatc actgctgctt tgagtgtgtg 1560
ccctgtgggg ctgggacctt cctcaacaag agtgacctct acagatgcca gccttgtggg 1620
aaagaagagt gggcacctga gggaagccag acctgcttcc cgcgcactgt ggtgtttttg 1680
gctttgcgtg agcacacctc ttgggtgctg ctggcagcta acacgctgct gctgctgctg 1740
ctgcttggga ctgctggcct gtttgcctgg cacctagaca cccctgtggt gaggtcagca 1800
gggggccgcc tgtgctttct tatgctgggc tccctggcag caggtagtgg cagcctctat 1860
ggcttctttg gggaacccac aaggcctgcg tgcttgctac gccaggccct ctttgccctt 1920
ggtttcacca tcttcctgtc ctgcctgaca gttcgctcat tccaactaat catcatcttc 1980
aagttttcca ccaaggtacc tacattctac cacgcctggg tccaaaacca cggtgctggc 2040
ctgtttgtga tgatcagctc agcggcccag ctgcttatct gtctaacttg gctggtggtg 2100
tggaccccac tgcctgctag ggaataccag cgcttccccc atctggtgat gcttgagtgc 2160
acagagacca actccctggg cttcatactg gccttcctct acaatggcct cctctccatc 2220
agtgcctttg cctgcagcta cctgggtaag gacttgccag agaactacaa cgaggccaaa 2280
tgtgtcacct tcagcctgct cttcaacttc gtgtcctgga tcgccttctt caccacggcc 2340
agcgtctacg acggcaagta cctgcctgcg gccaacatga tggctgggct gagcagcctg 2400
agcagcggct tcggtgggta ttttctgcct aagtgctacg tgatcctctg ccgcccagac 2460
ctcaacagca cagagcactt ccaggcctcc attcaggact acacgaggcg ctgcggctcc 2520
acctga 2526

<210> SEQ ID NO 9
<211> LENGTH: 2577
<212> TYPE: DNA
<213> ORGANISM: Mus musculus

<400> SEQUENCE: 9
atgccagctt tggctatcat gggtctcagc ctggctgctt tcctggagct tgggatgggg 60
gcctctttgt gtctgtcaca gcaattcaag gcacaagggg actacatact gggcgggcta 120
tttcccctgg gctcaaccga ggaggccact ctcaaccaga gaacacaacc caacagcatc 180
ccgtgcaaca ggttctcacc ccttggtttg ttcctggcca tggctatgaa gatggctgtg 240
gaggagatca acaatggatc tgccttgctc cctgggctgc ggctgggcta tgacctattt 300
gacacatgct ccgagccagt ggtcaccatg aaatccagtc tcatgttcct ggccaaggtg 360
ggcagtcaaa gcattgctgc ctactgcaac tacacacagt accaaccccg tgtgctggct 420
gtcatcggcc cccactcatc agagcttgcc ctcattacag gcaagttctt cagcttcttc 480
ctcatgccac aggtcagcta tagtgccagc atggatcggc taagtgaccg ggaaacgttt 540

-continued

```
ccatccttct tccgcacagt gcccagtgac cgggtgcagc tgcaggcagt tgtgactctg    600

ttgcagaact tcagctggaa ctgggtggcc gccttaggga gtgatgatga ctatggccgg    660

gaaggtctga gcatcttttc tagtctggcc aatgcacgag gtatctgcat cgcacatgag    720

ggcctggtgc cacaacatga cactagtggc caacagttgg gcaaggtgct ggatgtacta    780

cgccaagtga accaaagtaa agtacaagtg gtggtgctgt ttgcctctgc ccgtgctgtc    840

tactcccttt ttagttacag catccatcat ggcctctcac ccaaggtatg ggtggccagt    900

gagtcttggc tgacatctga cctggtcatg acacttccca atattgcccg tgtgggcact    960

gtgcttgggt tttgcagcg gggtgcccta ctgcctgaat ttcccatta tgtggagact    1020

caccttgccc tggccgctga cccagcattc tgtgcctcac tgaatgcgga gttggatctg   1080

gaggaacatg tgatggggca acgctgtcca cggtgtgacg acatcatgct gcagaaccta   1140

tcatctgggc tgttgcagaa cctatcagct gggcaattgc accaccaaat atttgcaacc   1200

tatgcagctg tgtacagtgt ggctcaagcc cttcacaaca ccctacagtg caatgtctca   1260

cattgccacg tatcagaaca tgttctaccc tggcagctcc tggagaacat gtacaatatg   1320

agtttccatg ctcgagactt gacactacag tttgatgctg aagggaatgt agacatggaa   1380

tatgacctga agatgtgggt gtggcagagc cctacacctg tattacatac tgtgggcacc   1440

ttcaacggca cccttcagct gcagcagtct aaaatgtact ggccaggcaa ccaggtgcca   1500

gtctcccagt gttcccgcca gtgcaaagat ggccaggttc gccgagtaaa gggctttcat   1560

tcctgctgct atgactgcgt ggactgcaag gcgggcagct accggaagca tccagatgac   1620

ttcacctgta ctccatgtaa ccaggaccag tggtccccag agaaaagcac agcctgctta   1680

cctcgcaggc ccaagtttct ggcttggggg gagccagttg tgctgtcact cctcctgctg   1740

ctttgcctgg tgctgggtct agcactggct gctctggggc tctctgtcca ccactgggac   1800

agccctcttg tccaggcctc aggtggctca cagttctgct ttggcctgat ctgcctaggc   1860

ctcttctgcc tcagtgtcct tctgttccca gggcggccaa gctctgccag ctgccttgca   1920

caacaaccaa tggctcacct ccctctcaca ggctgcctga gcacactctt cctgcaagca   1980

gctgagacct ttgtggagtc tgagctgcca ctgagctggg caaactggct atgcagctac   2040

cttcggggac tctgggcctg gctagtggta ctgttggcca cttttgtgga ggcagcacta   2100

tgtgcctggt atttgatcgc tttcccacca gaggtggtga cagactggtc agtgctgccc   2160

acagaggtac tggagcactg ccacgtgcgt tcctgggtca gcctgggctt ggtgcacatc   2220

accaatgcaa tgttagcttt cctctgcttt ctgggcactt tcctggtaca gagccagcct   2280

ggccgctaca accgtgcccg tggtctcacc ttcgccatgc tagcttattt catcacctgg   2340

gtctcttttg tgcccctcct ggccaatgtg caggtggcct accagccagc tgtgcagatg   2400

ggtgctatcc tagtctgtgc cctgggcatc ctggtcacct tccacctgcc caagtgctat   2460

gtgcttcttt ggctgccaaa gctcaacacc caggagttct tcctgggaag gaatgccaag   2520

aaagcagcag atgagaacag tggcggtggt gaggcagctc agggacacaa tgaatga      2577
```

```
<210> SEQ ID NO 10
<211> LENGTH: 2577
<212> TYPE: DNA
<213> ORGANISM: Rattus rattus

<400> SEQUENCE: 10

atgccgggtt tggctatctt gggcctcagt ctggctgctt tcctggagct tgggatgggg      60

tcctctttgt gtctgtcaca gcaattcaag gcacaagggg actatatatt gggtggacta    120
```

-continued

```
tttcccctgg gcacaactga ggaggccact ctcaaccaga gaacacagcc caacggcatc    180
ctatgtacca ggttctcgcc ccttggtttg ttcctggcca tggctatgaa gatggctgta    240
gaggagatca acaatggatc tgccttgctc cctgggctgc gactgggcta tgacctgttt    300
gacacatgct cagagccagt ggtcaccatg aagcccagcc tcatgttcat ggccaaggtg    360
ggaagtcaaa gcattgctgc ctactgcaac tacacacagt accaaccccg tgtgctggct    420
gtcattggtc cccactcatc agagcttgcc ctcattacag gcaagttctt cagcttcttc    480
ctcatgccac aggtcagcta tagtgccagc atggatcggc taagtgaccg ggaaacattt    540
ccatccttct tccgcacagt gcccagtgac cgggtgcagc tgcaggccgt tgtgacactg    600
ttgcagaatt tcagctggaa ctgggtggct gccttaggta gtgatgatga ctatggccgg    660
gaaggtctga gcatcttttc tggtctggcc aactcacgag gtatctgcat tgcacacgag    720
ggcctggtgc cacaacatga cactagtggc caacaattgg gcaaggtggt ggatgtgcta    780
cgccaagtga accaaagcaa agtacaggtg gtggtgctgt ttgcatctgc ccgtgctgtc    840
tactcccttt ttagctacag catccttcat gacctctcac ccaaggtatg ggtggccagt    900
gagtcctggc tgacctctga cctggtcatg acacttccca atattgcccg tgtgggcact    960
gttcttgggt ttctgcagcg cggtgcccta ctgcctgaat ttcccattta tgtggagact   1020
cgccttgccc tagctgctga cccaacattc tgtgcctccc tgaaagctga gttggatctg   1080
gaggagcgcg tgatggggcc acgctgttca caatgtgact acatcatgct acagaacctg   1140
tcatctgggc tgatgcagaa cctatcagct gggcagttgc accaccaaat atttgcaacc   1200
tatgcagctg tgtacagtgt ggctcaggcc cttcacaaca ccctgcagtg caatgtctca   1260
cattgccaca catcagagcc tgttcaaccc tggcagctcc tggagaacat gtacaatatg   1320
agtttccgtg ctcgagactt gacactgcag tttgatgcca aagggagtgt agacatggaa   1380
tatgacctga agatgtgggt gtggcagagc cctacacctg tactacatac tgtaggcacc   1440
ttcaacggca cccttcagct gcagcactcg aaaatgtatt ggccaggcaa ccaggtgcca   1500
gtctcccagt gctcccggca gtgcaaagat ggccaggtgc gcagagtaaa gggctttcat   1560
tcctgctgct atgactgtgt ggactgcaag gcagggagct accggaagca tccagatgac   1620
ttcacctgta ctccatgtgg caaggatcag tggtccccag aaaaaagcac aacctgctta   1680
cctcgcaggc ccaagtttct ggcttggggg gagccagctg tgctgtcact tctcctgctg   1740
ctttgcctgg tgctgggcct gacactggct gccctggggc tctttgtcca ctactgggac   1800
agccctcttg ttcaggcctc aggtgggtca ctgttctgct ttggcctgat ctgcctaggc   1860
ctcttctgcc tcagtgtcct tctgttccca ggacgaccac gctctgccag ctgccttgcc   1920
caacaaccaa tggctcacct ccctctcaca ggctgcctga gcacactctt cctgcaagca   1980
gccgagatct ttgtggagtc tgagctgcca ctgagttggg caaactggct ctgcagctac   2040
cttcggggcc cctgggcttg gctggtggta ctgctggcca ctcttgtgga ggctgcacta   2100
tgtgcctggt acttgatggc tttccctcca gaggtggtga cagattggca ggtgctgccc   2160
acggaggtac tggaacactg ccgcatgcgt tcctgggtca gcctgggctt ggtgcacatc   2220
accaatgcag tgttagcttt cctctgcttt ctgggcactt tcctggtaca gagccagcct   2280
ggtcgctata accgtgcccg tggcctcacc ttcgccatgc tagcttattt catcatctgg   2340
gtctcttttg tgcccctcct ggctaatgtg caggtggcct accagccagc tgtgcagatg   2400
ggtgctatct tattctgtgc cctgggcatc ctggccacct tccacctgcc caaatgctat   2460
gtacttctgt ggctgccaga gctcaacacc caggagttct tcctgggaag gagccccaag   2520
```

-continued gaagcatcag atgggaatag tggtagtagt gaggcaactc ggggacacag tgaatga 2577

<210> SEQ ID NO 11
<211> LENGTH: 2559
<212> TYPE: DNA
<213> ORGANISM: Homo sapiens

<400> SEQUENCE: 11
atgctgggcc ctgctgtcct gggcctcagc ctctgggctc tcctgcaccc tgggacgggg 60
gccccattgt gcctgtcaca gcaacttagg atgaaggggg actacgtgct gggggggctg 120 ttcccccctgg gcgaggccga ggaggctggc ctccgcagcc ggacacggcc cagcagccct 180
gtgtgcacca ggttctcctc aaacggcctg ctctgggcac tggccatgaa aatggccgtg 240
gaggagatca acaacaagtc ggatctgctg cccgggctgc gcctgggcta cgacctcttt 300
gatacgtgct cggagcctgt ggtggccatg aagcccagcc tcatgttcct ggccaaggca 360
ggcagccgcg acatcgccgc ctactgcaac tacacgcagt accagccccg tgtgctggct 420
gtcatcgggc cccactcgtc agagctcgcc atggtcaccg gcaagttctt cagcttcttc 480
ctcatgcccc aggtcagcta cggtgctagc atggagctgc tgagcgcccg ggagaccttc 540
ccctccttct tccgcaccgt gcccagcgac cgtgtgcagc tgacggccgc cgcggagctg 600
ctgcaggagt tcggctggaa ctgggtggcc gccctgggca gcgacgacga gtacggccgg 660
cagggcctga gcatcttctc ggccctggcc gcggcacgcg gcatctgcat cgcgcacgag 720
ggcctggtgc cgctgccccg tgccgatgac tcgcggctgg ggaaggtgca ggacgtcctg 780
caccaggtga accagagcag cgtgcaggtg gtgctgctgt tcgcctccgt gcacgccgcc 840
cacgccctct tcaactacag catcagcagc aggctctcgc ccaaggtgtg ggtggccagc 900
gaggcctggc tgacctctga cctggtcatg ggctgcccg gcatggccca gatgggcacg 960
gtgcttggct tcctccagag gggtgcccag ctgcacgagt tcccccagta cgtgaagacg 1020
cacctggccc tggccaccga cccggccttc tgctctgccc tgggcgagag ggagcagggt 1080
ctggaggagg acgtggtggg ccagcgctgc ccgcagtgtg actgcatcac gctgcagaac 1140
gtgagcgcag ggctaaatca ccaccagacg ttctctgtct acgcagctgt gtatagcgtg 1200
gcccaggccc tgcacaacac tcttcagtgc aacgcctcag gctgccccgc gcaggacccc 1260
gtgaagccct ggcagctcct ggagaacatg tacaacctga ccttccacgt gggcgggctg 1320
ccgctgcggt tcgacagcag cggaaacgtg gacatggagt acgacctgaa gctgtgggtg 1380
tggcagggct cagtgcccag gctccacgac gtgggcaggt tcaacggcag cctcaggaca 1440
gagcgcctga agatccgctg gcacacgtct gacaaccaga agcccgtgtc ccggtgctcg 1500
cggcagtgcc aggagggcca ggtgcgccgg gtcaaggggt tccactcctg ctgctacgac 1560
tgtgtggact gcgaggcggg cagctaccgg caaaacccag acgacatcgc ctgcaccttt 1620
tgtggccagg atgagtggtc cccggagcga agcacacgct gcttccgccg caggtctcgg 1680
ttcctggcat ggggcgagcc ggctgtgctg ctgctgctcc tgctgctgag cctggcgctg 1740
ggccttgtgc tggctgcttt ggggctgttc gttcaccatc gggacagccc actggttcag 1800
gcctcggggg ggcccctggc ctgctttggc ctggtgtgcc tgggcctggt ctgcctcagc 1860
gtcctcctgt tccctggcca gcccagccct gcccgatgcc tggcccagca gcccttgtcc 1920
cacctcccgc tcacgggctg cctgagcaca ctcttcctgc aggcggccga gatcttcgtg 1980
gagtcagaac tgcctctgag ctgggcagac cggctgagtg gctgcctgcg ggggccctgg 2040
gcctggctgg tggtgctgct ggccatgctg gtggaggtcg cactgtgcac ctggtacctg 2100

-continued

```
gtggccttcc cgccggaggt ggtgacggac tggcacatgc tgcccacgga ggcgctggtg   2160

cactgccgca cacgctcctg ggtcagcttc ggcctagcgc acgccaccaa tgccacgctg   2220

gcctttctct gcttcctggg cactttcctg gtgcggagcc agccgggccg ctacaaccgt   2280

gcccgtggcc tcacctttgc catgctggcc tacttcatca cctgggtctc ctttgtgccc   2340

ctcctggcca atgtgcaggt ggtcctcagg cccgccgtgc agatgggcgc cctcctgctc   2400

tgtgtcctgg gcatcctggc tgccttccac ctgcccaggt gttacctgct catgcggcag   2460

ccagggctca acacccccga gttcttcctg ggagggggcc ctggggatgc ccaaggccag   2520

aatgacggga acacaggaaa tcaggggaaa catgagtga                          2559


<210> SEQ ID NO 12
<211> LENGTH: 852
<212> TYPE: PRT
<213> ORGANISM: Homo sapiens

<400> SEQUENCE: 12

Met Leu Gly Pro Ala Val Leu Gly Leu Ser Leu Trp Ala Leu Leu His
1               5                   10                  15

Pro Gly Thr Gly Ala Pro Leu Cys Leu Ser Gln Gln Leu Arg Met Lys
            20                  25                  30

Gly Asp Tyr Val Leu Gly Gly Leu Phe Pro Leu Gly Glu Ala Glu Glu
        35                  40                  45

Ala Gly Leu Arg Ser Arg Thr Arg Pro Ser Ser Pro Val Cys Thr Arg
    50                  55                  60

Phe Ser Ser Asn Gly Leu Leu Trp Ala Leu Ala Met Lys Met Ala Val
65                  70                  75                  80

Glu Glu Ile Asn Asn Lys Ser Asp Leu Leu Pro Gly Leu Arg Leu Gly
                85                  90                  95

Tyr Asp Leu Phe Asp Thr Cys Ser Glu Pro Val Val Ala Met Lys Pro
            100                 105                 110

Ser Leu Met Phe Leu Ala Lys Ala Gly Ser Arg Asp Ile Ala Ala Tyr
        115                 120                 125

Cys Asn Tyr Thr Gln Tyr Gln Pro Arg Val Leu Ala Val Ile Gly Pro
    130                 135                 140

His Ser Ser Glu Leu Ala Met Val Thr Gly Lys Phe Phe Ser Phe Phe
145                 150                 155                 160

Leu Met Pro Gln Val Ser Tyr Gly Ala Ser Met Glu Leu Leu Ser Ala
                165                 170                 175

Arg Glu Thr Phe Pro Ser Phe Phe Arg Thr Val Pro Ser Asp Arg Val
            180                 185                 190

Gln Leu Thr Ala Ala Ala Glu Leu Leu Gln Glu Phe Gly Trp Asn Trp
        195                 200                 205

Val Ala Ala Leu Gly Ser Asp Asp Glu Tyr Gly Arg Gln Gly Leu Ser
    210                 215                 220

Ile Phe Ser Ala Leu Ala Ala Ala Arg Gly Ile Cys Ile Ala His Glu
225                 230                 235                 240

Gly Leu Val Pro Leu Pro Arg Ala Asp Asp Ser Arg Leu Gly Lys Val
                245                 250                 255

Gln Asp Val Leu His Gln Val Asn Gln Ser Ser Val Gln Val Val Leu
            260                 265                 270

Leu Phe Ala Ser Val His Ala Ala His Ala Leu Phe Asn Tyr Ser Ile
        275                 280                 285

Ser Ser Arg Leu Ser Pro Lys Val Trp Val Ala Ser Glu Ala Trp Leu
    290                 295                 300
```

-continued

```
Thr Ser Asp Leu Val Met Gly Leu Pro Gly Met Ala Gln Met Gly Thr
305                 310                 315                 320

Val Leu Gly Phe Leu Gln Arg Gly Ala Gln Leu His Glu Phe Pro Gln
                325                 330                 335

Tyr Val Lys Thr His Leu Ala Leu Ala Thr Asp Pro Ala Phe Cys Ser
            340                 345                 350

Ala Leu Gly Glu Arg Glu Gln Gly Leu Glu Glu Asp Val Val Gly Gln
        355                 360                 365

Arg Cys Pro Gln Cys Asp Cys Ile Thr Leu Gln Asn Val Ser Ala Gly
    370                 375                 380

Leu Asn His His Gln Thr Phe Ser Val Tyr Ala Ala Val Tyr Ser Val
385                 390                 395                 400

Ala Gln Ala Leu His Asn Thr Leu Gln Cys Asn Ala Ser Gly Cys Pro
                405                 410                 415

Ala Gln Asp Pro Val Lys Pro Trp Gln Leu Leu Glu Asn Met Tyr Asn
            420                 425                 430

Leu Thr Phe His Val Gly Gly Leu Pro Leu Arg Phe Asp Ser Ser Gly
        435                 440                 445

Asn Val Asp Met Glu Tyr Asp Leu Lys Leu Trp Val Trp Gln Gly Ser
    450                 455                 460

Val Pro Arg Leu His Asp Val Gly Arg Phe Asn Gly Ser Leu Arg Thr
465                 470                 475                 480

Glu Arg Leu Lys Ile Arg Trp His Thr Ser Asp Asn Gln Lys Pro Val
                485                 490                 495

Ser Arg Cys Ser Arg Gln Cys Gln Glu Gly Gln Val Arg Arg Val Lys
            500                 505                 510

Gly Phe His Ser Cys Cys Tyr Asp Cys Val Asp Cys Glu Ala Gly Ser
        515                 520                 525

Tyr Arg Gln Asn Pro Asp Asp Ile Ala Cys Thr Phe Cys Gly Gln Asp
    530                 535                 540

Glu Trp Ser Pro Glu Arg Ser Thr Arg Cys Phe Arg Arg Arg Ser Arg
545                 550                 555                 560

Phe Leu Ala Trp Gly Glu Pro Ala Val Leu Leu Leu Leu Leu Leu Leu
                565                 570                 575

Ser Leu Ala Leu Gly Leu Val Leu Ala Ala Leu Gly Leu Phe Val His
            580                 585                 590

His Arg Asp Ser Pro Leu Val Gln Ala Ser Gly Gly Pro Leu Ala Cys
        595                 600                 605

Phe Gly Leu Val Cys Leu Gly Leu Val Cys Leu Ser Val Leu Leu Phe
    610                 615                 620

Pro Gly Gln Pro Ser Pro Ala Arg Cys Leu Ala Gln Gln Pro Leu Ser
625                 630                 635                 640

His Leu Pro Leu Thr Gly Cys Leu Ser Thr Leu Phe Leu Gln Ala Ala
                645                 650                 655

Glu Ile Phe Val Glu Ser Glu Leu Pro Leu Ser Trp Ala Asp Arg Leu
            660                 665                 670

Ser Gly Cys Leu Arg Gly Pro Trp Ala Trp Leu Val Val Leu Leu Ala
        675                 680                 685

Met Leu Val Glu Val Ala Leu Cys Thr Trp Tyr Leu Val Ala Phe Pro
    690                 695                 700

Pro Glu Val Val Thr Asp Trp His Met Leu Pro Thr Glu Ala Leu Val
705                 710                 715                 720

His Cys Arg Thr Arg Ser Trp Val Ser Phe Gly Leu Ala His Ala Thr
```

```
                725                 730                 735

Asn Ala Thr Leu Ala Phe Leu Cys Phe Leu Gly Thr Phe Leu Val Arg
            740                 745                 750

Ser Gln Pro Gly Arg Tyr Asn Arg Ala Arg Gly Leu Thr Phe Ala Met
        755                 760                 765

Leu Ala Tyr Phe Ile Thr Trp Val Ser Phe Val Pro Leu Leu Ala Asn
    770                 775                 780

Val Gln Val Val Leu Arg Pro Ala Val Gln Met Gly Ala Leu Leu Leu
785                 790                 795                 800

Cys Val Leu Gly Ile Leu Ala Ala Phe His Leu Pro Arg Cys Tyr Leu
                805                 810                 815

Leu Met Arg Gln Pro Gly Leu Asn Thr Pro Glu Phe Phe Leu Gly Gly
            820                 825                 830

Gly Pro Gly Asp Ala Gln Gly Gln Asn Asp Gly Asn Thr Gly Asn Gln
        835                 840                 845

Gly Lys His Glu
    850


<210> SEQ ID NO 13
<211> LENGTH: 858
<212> TYPE: PRT
<213> ORGANISM: Mus musculus

<400> SEQUENCE: 13

Met Pro Ala Leu Ala Ile Met Gly Leu Ser Leu Ala Ala Phe Leu Glu
1               5                   10                  15

Leu Gly Met Gly Ala Ser Leu Cys Leu Ser Gln Gln Phe Lys Ala Gln
            20                  25                  30

Gly Asp Tyr Ile Leu Gly Gly Leu Phe Pro Leu Gly Ser Thr Glu Glu
        35                  40                  45

Ala Thr Leu Asn Gln Arg Thr Gln Pro Asn Ser Ile Pro Cys Asn Arg
    50                  55                  60

Phe Ser Pro Leu Gly Leu Phe Leu Ala Met Ala Met Lys Met Ala Val
65                  70                  75                  80

Glu Glu Ile Asn Asn Gly Ser Ala Leu Leu Pro Gly Leu Arg Leu Gly
                85                  90                  95

Tyr Asp Leu Phe Asp Thr Cys Ser Glu Pro Val Val Thr Met Lys Ser
            100                 105                 110

Ser Leu Met Phe Leu Ala Lys Val Gly Ser Gln Ser Ile Ala Ala Tyr
        115                 120                 125

Cys Asn Tyr Thr Gln Tyr Gln Pro Arg Val Leu Ala Val Ile Gly Pro
    130                 135                 140

His Ser Ser Glu Leu Ala Leu Ile Thr Gly Lys Phe Phe Ser Phe Phe
145                 150                 155                 160

Leu Met Pro Gln Val Ser Tyr Ser Ala Ser Met Asp Arg Leu Ser Asp
                165                 170                 175

Arg Glu Thr Phe Pro Ser Phe Phe Arg Thr Val Pro Ser Asp Arg Val
            180                 185                 190

Gln Leu Gln Ala Val Val Thr Leu Leu Gln Asn Phe Ser Trp Asn Trp
        195                 200                 205

Val Ala Ala Leu Gly Ser Asp Asp Asp Tyr Gly Arg Glu Gly Leu Ser
    210                 215                 220

Ile Phe Ser Ser Leu Ala Asn Ala Arg Gly Ile Cys Ile Ala His Glu
225                 230                 235                 240

Gly Leu Val Pro Gln His Asp Thr Ser Gly Gln Gln Leu Gly Lys Val
```

-continued

```
                245                 250                 255

Leu Asp Val Leu Arg Gln Val Asn Gln Ser Lys Val Gln Val Val Val
            260                 265                 270

Leu Phe Ala Ser Ala Arg Ala Val Tyr Ser Leu Phe Ser Tyr Ser Ile
        275                 280                 285

His His Gly Leu Ser Pro Lys Val Trp Val Ala Ser Glu Ser Trp Leu
    290                 295                 300

Thr Ser Asp Leu Val Met Thr Leu Pro Asn Ile Ala Arg Val Gly Thr
305                 310                 315                 320

Val Leu Gly Phe Leu Gln Arg Gly Ala Leu Leu Pro Glu Phe Ser His
                325                 330                 335

Tyr Val Glu Thr His Leu Ala Leu Ala Ala Asp Pro Ala Phe Cys Ala
            340                 345                 350

Ser Leu Asn Ala Glu Leu Asp Leu Glu Glu His Val Met Gly Gln Arg
        355                 360                 365

Cys Pro Arg Cys Asp Asp Ile Met Leu Gln Asn Leu Ser Ser Gly Leu
    370                 375                 380

Leu Gln Asn Leu Ser Ala Gly Gln Leu His His Gln Ile Phe Ala Thr
385                 390                 395                 400

Tyr Ala Ala Val Tyr Ser Val Ala Gln Ala Leu His Asn Thr Leu Gln
                405                 410                 415

Cys Asn Val Ser His Cys His Val Ser Glu His Val Leu Pro Trp Gln
            420                 425                 430

Leu Leu Glu Asn Met Tyr Asn Met Ser Phe His Ala Arg Asp Leu Thr
        435                 440                 445

Leu Gln Phe Asp Ala Glu Gly Asn Val Asp Met Glu Tyr Asp Leu Lys
    450                 455                 460

Met Trp Val Trp Gln Ser Pro Thr Pro Val Leu His Thr Val Gly Thr
465                 470                 475                 480

Phe Asn Gly Thr Leu Gln Leu Gln Gln Ser Lys Met Tyr Trp Pro Gly
                485                 490                 495

Asn Gln Val Pro Val Ser Gln Cys Ser Arg Gln Cys Lys Asp Gly Gln
            500                 505                 510

Val Arg Arg Val Lys Gly Phe His Ser Cys Cys Tyr Asp Cys Val Asp
        515                 520                 525

Cys Lys Ala Gly Ser Tyr Arg Lys His Pro Asp Asp Phe Thr Cys Thr
    530                 535                 540

Pro Cys Asn Gln Asp Gln Trp Ser Pro Glu Lys Ser Thr Ala Cys Leu
545                 550                 555                 560

Pro Arg Arg Pro Lys Phe Leu Ala Trp Gly Glu Pro Val Val Leu Ser
                565                 570                 575

Leu Leu Leu Leu Leu Cys Leu Val Leu Gly Leu Ala Leu Ala Ala Leu
            580                 585                 590

Gly Leu Ser Val His His Trp Asp Ser Pro Leu Val Gln Ala Ser Gly
        595                 600                 605

Gly Ser Gln Phe Cys Phe Gly Leu Ile Cys Leu Gly Leu Phe Cys Leu
    610                 615                 620

Ser Val Leu Leu Phe Pro Gly Arg Pro Ser Ser Ala Ser Cys Leu Ala
625                 630                 635                 640

Gln Gln Pro Met Ala His Leu Pro Leu Thr Gly Cys Leu Ser Thr Leu
                645                 650                 655

Phe Leu Gln Ala Ala Glu Thr Phe Val Glu Ser Glu Leu Pro Leu Ser
            660                 665                 670
```

```
Trp Ala Asn Trp Leu Cys Ser Tyr Leu Arg Gly Leu Trp Ala Trp Leu
        675                 680                 685

Val Val Leu Leu Ala Thr Phe Val Glu Ala Ala Leu Cys Ala Trp Tyr
    690                 695                 700

Leu Ile Ala Phe Pro Pro Glu Val Val Thr Asp Trp Ser Val Leu Pro
705                 710                 715                 720

Thr Glu Val Leu Glu His Cys His Val Arg Ser Trp Val Ser Leu Gly
                725                 730                 735

Leu Val His Ile Thr Asn Ala Met Leu Ala Phe Leu Cys Phe Leu Gly
            740                 745                 750

Thr Phe Leu Val Gln Ser Gln Pro Gly Arg Tyr Asn Arg Ala Arg Gly
        755                 760                 765

Leu Thr Phe Ala Met Leu Ala Tyr Phe Ile Thr Trp Val Ser Phe Val
    770                 775                 780

Pro Leu Leu Ala Asn Val Gln Val Ala Tyr Gln Pro Ala Val Gln Met
785                 790                 795                 800

Gly Ala Ile Leu Val Cys Ala Leu Gly Ile Leu Val Thr Phe His Leu
                805                 810                 815

Pro Lys Cys Tyr Val Leu Leu Trp Leu Pro Lys Leu Asn Thr Gln Glu
            820                 825                 830

Phe Phe Leu Gly Arg Asn Ala Lys Lys Ala Ala Asp Glu Asn Ser Gly
        835                 840                 845

Gly Gly Glu Ala Ala Gln Gly His Asn Glu
    850                 855


<210> SEQ ID NO 14
<211> LENGTH: 858
<212> TYPE: PRT
<213> ORGANISM: Rattus rattus

<400> SEQUENCE: 14

Met Pro Gly Leu Ala Ile Leu Gly Leu Ser Leu Ala Ala Phe Leu Glu
1               5                   10                  15

Leu Gly Met Gly Ser Ser Leu Cys Leu Ser Gln Gln Phe Lys Ala Gln
            20                  25                  30

Gly Asp Tyr Ile Leu Gly Gly Leu Phe Pro Leu Gly Thr Thr Glu Glu
        35                  40                  45

Ala Thr Leu Asn Gln Arg Thr Gln Pro Asn Gly Ile Leu Cys Thr Arg
    50                  55                  60

Phe Ser Pro Leu Gly Leu Phe Leu Ala Met Ala Met Lys Met Ala Val
65                  70                  75                  80

Glu Glu Ile Asn Asn Gly Ser Ala Leu Leu Pro Gly Leu Arg Leu Gly
                85                  90                  95

Tyr Asp Leu Phe Asp Thr Cys Ser Glu Pro Val Val Thr Met Lys Pro
            100                 105                 110

Ser Leu Met Phe Met Ala Lys Val Gly Ser Gln Ser Ile Ala Ala Tyr
        115                 120                 125

Cys Asn Tyr Thr Gln Tyr Gln Pro Arg Val Leu Ala Val Ile Gly Pro
    130                 135                 140

His Ser Ser Glu Leu Ala Leu Ile Thr Gly Lys Phe Phe Ser Phe Phe
145                 150                 155                 160

Leu Met Pro Gln Val Ser Tyr Ser Ala Ser Met Asp Arg Leu Ser Asp
                165                 170                 175

Arg Glu Thr Phe Pro Ser Phe Phe Arg Thr Val Pro Ser Asp Arg Val
            180                 185                 190
```

-continued

Gln Leu Gln Ala Val Val Thr Leu Leu Gln Asn Phe Ser Trp Asn Trp
195 200 205

Val Ala Ala Leu Gly Ser Asp Asp Asp Tyr Gly Arg Glu Gly Leu Ser
210 215 220

Ile Phe Ser Gly Leu Ala Asn Ser Arg Gly Ile Cys Ile Ala His Glu
225 230 235 240

Gly Leu Val Pro Gln His Asp Thr Ser Gly Gln Gln Leu Gly Lys Val
245 250 255

Val Asp Val Leu Arg Gln Val Asn Gln Ser Lys Val Gln Val Val Val
260 265 270

Leu Phe Ala Ser Ala Arg Ala Val Tyr Ser Leu Phe Ser Tyr Ser Ile
275 280 285

Leu His Asp Leu Ser Pro Lys Val Trp Val Ala Ser Glu Ser Trp Leu
290 295 300

Thr Ser Asp Leu Val Met Thr Leu Pro Asn Ile Ala Arg Val Gly Thr
305 310 315 320

Val Leu Gly Phe Leu Gln Arg Gly Ala Leu Leu Pro Glu Phe Ser His
325 330 335

Tyr Val Glu Thr Arg Leu Ala Leu Ala Ala Asp Pro Thr Phe Cys Ala
340 345 350

Ser Leu Lys Ala Glu Leu Asp Leu Glu Glu Arg Val Met Gly Pro Arg
355 360 365

Cys Ser Gln Cys Asp Tyr Ile Met Leu Gln Asn Leu Ser Ser Gly Leu
370 375 380

Met Gln Asn Leu Ser Ala Gly Gln Leu His His Gln Ile Phe Ala Thr
385 390 395 400

Tyr Ala Ala Val Tyr Ser Val Ala Gln Ala Leu His Asn Thr Leu Gln
405 410 415

Cys Asn Val Ser His Cys His Thr Ser Glu Pro Val Gln Pro Trp Gln
420 425 430

Leu Leu Glu Asn Met Tyr Asn Met Ser Phe Arg Ala Arg Asp Leu Thr
435 440 445

Leu Gln Phe Asp Ala Lys Gly Ser Val Asp Met Glu Tyr Asp Leu Lys
450 455 460

Met Trp Val Trp Gln Ser Pro Thr Pro Val Leu His Thr Val Gly Thr
465 470 475 480

Phe Asn Gly Thr Leu Gln Leu Gln His Ser Lys Met Tyr Trp Pro Gly
485 490 495

Asn Gln Val Pro Val Ser Gln Cys Ser Arg Gln Cys Lys Asp Gly Gln
500 505 510

Val Arg Arg Val Lys Gly Phe His Ser Cys Cys Tyr Asp Cys Val Asp
515 520 525

Cys Lys Ala Gly Ser Tyr Arg Lys His Pro Asp Asp Phe Thr Cys Thr
530 535 540

Pro Cys Gly Lys Asp Gln Trp Ser Pro Glu Lys Ser Thr Thr Cys Leu
545 550 555 560

Pro Arg Arg Pro Lys Phe Leu Ala Trp Gly Glu Pro Ala Val Leu Ser
565 570 575

Leu Leu Leu Leu Leu Cys Leu Val Leu Gly Leu Thr Leu Ala Ala Leu
580 585 590

Gly Leu Phe Val His Tyr Trp Asp Ser Pro Leu Val Gln Ala Ser Gly
595 600 605

Gly Ser Leu Phe Cys Phe Gly Leu Ile Cys Leu Gly Leu Phe Cys Leu
610 615 620

```
Ser Val Leu Leu Phe Pro Gly Arg Pro Arg Ser Ala Ser Cys Leu Ala
625                 630                 635                 640

Gln Gln Pro Met Ala His Leu Pro Leu Thr Gly Cys Leu Ser Thr Leu
                645                 650                 655

Phe Leu Gln Ala Ala Glu Ile Phe Val Glu Ser Glu Leu Pro Leu Ser
            660                 665                 670

Trp Ala Asn Trp Leu Cys Ser Tyr Leu Arg Gly Pro Trp Ala Trp Leu
        675                 680                 685

Val Val Leu Leu Ala Thr Leu Val Glu Ala Ala Leu Cys Ala Trp Tyr
    690                 695                 700

Leu Met Ala Phe Pro Pro Glu Val Val Thr Asp Trp Gln Val Leu Pro
705                 710                 715                 720

Thr Glu Val Leu Glu His Cys Arg Met Arg Ser Trp Val Ser Leu Gly
                725                 730                 735

Leu Val His Ile Thr Asn Ala Val Leu Ala Phe Leu Cys Phe Leu Gly
            740                 745                 750

Thr Phe Leu Val Gln Ser Gln Pro Gly Arg Tyr Asn Arg Ala Arg Gly
        755                 760                 765

Leu Thr Phe Ala Met Leu Ala Tyr Phe Ile Ile Trp Val Ser Phe Val
    770                 775                 780

Pro Leu Leu Ala Asn Val Gln Val Ala Tyr Gln Pro Ala Val Gln Met
785                 790                 795                 800

Gly Ala Ile Leu Phe Cys Ala Leu Gly Ile Leu Ala Thr Phe His Leu
                805                 810                 815

Pro Lys Cys Tyr Val Leu Leu Trp Leu Pro Glu Leu Asn Thr Gln Glu
            820                 825                 830

Phe Phe Leu Gly Arg Ser Pro Lys Glu Ala Ser Asp Gly Asn Ser Gly
        835                 840                 845

Ser Ser Glu Ala Thr Arg Gly His Ser Glu
    850                 855


<210> SEQ ID NO 15
<211> LENGTH: 842
<212> TYPE: PRT
<213> ORGANISM: Mus musculus

<400> SEQUENCE: 15

Met Leu Phe Trp Ala Ala His Leu Leu Leu Ser Leu Gln Leu Ala Val
1               5                   10                  15

Ala Tyr Cys Trp Ala Phe Ser Cys Gln Arg Thr Glu Ser Ser Pro Gly
            20                  25                  30

Phe Ser Leu Pro Gly Asp Phe Leu Leu Ala Gly Leu Phe Ser Leu His
        35                  40                  45

Ala Asp Cys Leu Gln Val Arg His Arg Pro Leu Val Thr Ser Cys Asp
    50                  55                  60

Arg Ser Asp Ser Phe Asn Gly His Gly Tyr His Leu Phe Gln Ala Met
65                  70                  75                  80

Arg Phe Thr Val Glu Glu Ile Asn Asn Ser Thr Ala Leu Leu Pro Asn
                85                  90                  95

Ile Thr Leu Gly Tyr Glu Leu Tyr Asp Val Cys Ser Glu Ser Ser Asn
            100                 105                 110

Val Tyr Ala Thr Leu Arg Val Leu Ala Gln Gln Gly Thr Gly His Leu
        115                 120                 125

Glu Met Gln Arg Asp Leu Arg Asn His Ser Ser Lys Val Val Ala Leu
    130                 135                 140
```

```
Ile Gly Pro Asp Asn Thr Asp His Ala Val Thr Thr Ala Ala Leu Leu
145                 150                 155                 160

Ser Pro Phe Leu Met Pro Leu Val Ser Tyr Glu Ala Ser Ser Val Ile
                165                 170                 175

Leu Ser Gly Lys Arg Lys Phe Pro Ser Phe Leu Arg Thr Ile Pro Ser
            180                 185                 190

Asp Lys Tyr Gln Val Glu Val Ile Val Arg Leu Leu Gln Ser Phe Gly
        195                 200                 205

Trp Val Trp Ile Ser Leu Val Gly Ser Tyr Gly Asp Tyr Gly Gln Leu
    210                 215                 220

Gly Val Gln Ala Leu Glu Glu Leu Ala Thr Pro Arg Gly Ile Cys Val
225                 230                 235                 240

Ala Phe Lys Asp Val Val Pro Leu Ser Ala Gln Ala Gly Asp Pro Arg
                245                 250                 255

Met Gln Arg Met Met Leu Arg Leu Ala Arg Ala Arg Thr Thr Val Val
            260                 265                 270

Val Val Phe Ser Asn Arg His Leu Ala Gly Val Phe Phe Arg Ser Val
        275                 280                 285

Val Leu Ala Asn Leu Thr Gly Lys Val Trp Ile Ala Ser Glu Asp Trp
    290                 295                 300

Ala Ile Ser Thr Tyr Ile Thr Asn Val Pro Gly Ile Gln Gly Ile Gly
305                 310                 315                 320

Thr Val Leu Gly Val Ala Ile Gln Gln Arg Gln Val Pro Gly Leu Lys
                325                 330                 335

Glu Phe Glu Glu Ser Tyr Val Gln Ala Val Met Gly Ala Pro Arg Thr
            340                 345                 350

Cys Pro Glu Gly Ser Trp Cys Gly Thr Asn Gln Leu Cys Arg Glu Cys
        355                 360                 365

His Ala Phe Thr Thr Trp Asn Met Pro Glu Leu Gly Ala Phe Ser Met
    370                 375                 380

Ser Ala Ala Tyr Asn Val Tyr Glu Ala Val Tyr Ala Val Ala His Gly
385                 390                 395                 400

Leu His Gln Leu Leu Gly Cys Thr Ser Gly Thr Cys Ala Arg Gly Pro
                405                 410                 415

Val Tyr Pro Trp Gln Leu Leu Gln Gln Ile Tyr Lys Val Asn Phe Leu
            420                 425                 430

Leu His Lys Lys Thr Val Ala Phe Asp Asp Lys Gly Asp Pro Leu Gly
        435                 440                 445

Tyr Tyr Asp Ile Ile Ala Trp Asp Trp Asn Gly Pro Glu Trp Thr Phe
    450                 455                 460

Glu Val Ile Gly Ser Ala Ser Leu Ser Pro Val His Leu Asp Ile Asn
465                 470                 475                 480

Lys Thr Lys Ile Gln Trp His Gly Lys Asn Asn Gln Val Pro Val Ser
                485                 490                 495

Val Cys Thr Arg Asp Cys Leu Glu Gly His His Arg Leu Val Met Gly
            500                 505                 510

Ser His His Cys Cys Phe Glu Cys Met Pro Cys Glu Ala Gly Thr Phe
        515                 520                 525

Leu Asn Thr Ser Glu Leu His Thr Cys Gln Pro Cys Gly Thr Glu Glu
    530                 535                 540

Trp Ala Pro Glu Gly Ser Ser Ala Cys Phe Ser Arg Thr Val Glu Phe
545                 550                 555                 560

Leu Gly Trp His Glu Pro Ile Ser Leu Val Leu Leu Ala Ala Asn Thr
```

```
                565                 570                 575

Leu Leu Leu Leu Leu Leu Ile Gly Thr Ala Gly Leu Phe Ala Trp Arg
            580                 585                 590

Leu His Thr Pro Val Val Arg Ser Ala Gly Gly Arg Leu Cys Phe Leu
        595                 600                 605

Met Leu Gly Ser Leu Val Ala Gly Ser Cys Ser Leu Tyr Ser Phe Phe
    610                 615                 620

Gly Lys Pro Thr Val Pro Ala Cys Leu Leu Arg Gln Pro Leu Phe Ser
625                 630                 635                 640

Leu Gly Phe Ala Ile Phe Leu Ser Cys Leu Thr Ile Arg Ser Phe Gln
                645                 650                 655

Leu Val Ile Ile Phe Lys Phe Ser Thr Lys Val Pro Thr Phe Tyr His
            660                 665                 670

Thr Trp Ala Gln Asn His Gly Ala Gly Ile Phe Val Ile Val Ser Ser
        675                 680                 685

Thr Val His Leu Phe Leu Cys Leu Thr Trp Leu Ala Met Trp Thr Pro
    690                 695                 700

Arg Pro Thr Arg Glu Tyr Gln Arg Phe Pro His Leu Val Ile Leu Glu
705                 710                 715                 720

Cys Thr Glu Val Asn Ser Val Gly Phe Leu Val Ala Phe Ala His Asn
                725                 730                 735

Ile Leu Leu Ser Ile Ser Thr Phe Val Cys Ser Tyr Leu Gly Lys Glu
            740                 745                 750

Leu Pro Glu Asn Tyr Asn Glu Ala Lys Cys Val Thr Phe Ser Leu Leu
        755                 760                 765

Leu His Phe Val Ser Trp Ile Ala Phe Phe Thr Met Ser Ser Ile Tyr
    770                 775                 780

Gln Gly Ser Tyr Leu Pro Ala Val Asn Val Leu Ala Gly Leu Ala Thr
785                 790                 795                 800

Leu Ser Gly Gly Phe Ser Gly Tyr Phe Leu Pro Lys Cys Tyr Val Ile
                805                 810                 815

Leu Cys Arg Pro Glu Leu Asn Asn Thr Glu His Phe Gln Ala Ser Ile
            820                 825                 830

Gln Asp Tyr Thr Arg Arg Cys Gly Thr Thr
        835                 840


<210> SEQ ID NO 16
<211> LENGTH: 840
<212> TYPE: PRT
<213> ORGANISM: Rattus rattus

<400> SEQUENCE: 16

Met Leu Phe Trp Ala Ala His Leu Leu Leu Ser Leu Gln Leu Val Tyr
1               5                   10                  15

Cys Trp Ala Phe Ser Cys Gln Arg Thr Glu Ser Ser Pro Gly Phe Ser
            20                  25                  30

Leu Pro Gly Asp Phe Leu Leu Ala Gly Leu Phe Ser Leu His Gly Asp
        35                  40                  45

Cys Leu Gln Val Arg His Arg Pro Leu Val Thr Ser Cys Asp Arg Pro
    50                  55                  60

Asp Ser Phe Asn Gly His Gly Tyr His Leu Phe Gln Ala Met Arg Phe
65                  70                  75                  80

Thr Val Glu Glu Ile Asn Asn Ser Ser Ala Leu Leu Pro Asn Ile Thr
                85                  90                  95

Leu Gly Tyr Glu Leu Tyr Asp Val Cys Ser Glu Ser Ala Asn Val Tyr
```

-continued

```
            100                 105                 110

Ala Thr Leu Arg Val Leu Ala Leu Gln Gly Pro Arg His Ile Glu Ile
        115                 120                 125

Gln Lys Asp Leu Arg Asn His Ser Ser Lys Val Val Ala Phe Ile Gly
    130                 135                 140

Pro Asp Asn Thr Asp His Ala Val Thr Thr Ala Ala Leu Leu Gly Pro
145                 150                 155                 160

Phe Leu Met Pro Leu Val Ser Tyr Glu Ala Ser Ser Val Val Leu Ser
                165                 170                 175

Ala Lys Arg Lys Phe Pro Ser Phe Leu Arg Thr Val Pro Ser Asp Arg
            180                 185                 190

His Gln Val Glu Val Met Val Gln Leu Leu Gln Ser Phe Gly Trp Val
        195                 200                 205

Trp Ile Ser Leu Ile Gly Ser Tyr Gly Asp Tyr Gly Gln Leu Gly Val
    210                 215                 220

Gln Ala Leu Glu Glu Leu Ala Val Pro Arg Gly Ile Cys Val Ala Phe
225                 230                 235                 240

Lys Asp Ile Val Pro Phe Ser Ala Arg Val Gly Asp Pro Arg Met Gln
                245                 250                 255

Ser Met Met Gln His Leu Ala Gln Ala Arg Thr Thr Val Val Val Val
            260                 265                 270

Phe Ser Asn Arg His Leu Ala Arg Val Phe Phe Arg Ser Val Val Leu
        275                 280                 285

Ala Asn Leu Thr Gly Lys Val Trp Val Ala Ser Glu Asp Trp Ala Ile
    290                 295                 300

Ser Thr Tyr Ile Thr Ser Val Thr Gly Ile Gln Gly Ile Gly Thr Val
305                 310                 315                 320

Leu Gly Val Ala Val Gln Gln Arg Gln Val Pro Gly Leu Lys Glu Phe
                325                 330                 335

Glu Glu Ser Tyr Val Arg Ala Val Thr Ala Ala Pro Ser Ala Cys Pro
            340                 345                 350

Glu Gly Ser Trp Cys Ser Thr Asn Gln Leu Cys Arg Glu Cys His Thr
        355                 360                 365

Phe Thr Thr Arg Asn Met Pro Thr Leu Gly Ala Phe Ser Met Ser Ala
    370                 375                 380

Ala Tyr Arg Val Tyr Glu Ala Val Tyr Ala Val Ala His Gly Leu His
385                 390                 395                 400

Gln Leu Leu Gly Cys Thr Ser Glu Ile Cys Ser Arg Gly Pro Val Tyr
                405                 410                 415

Pro Trp Gln Leu Leu Gln Gln Ile Tyr Lys Val Asn Phe Leu Leu His
            420                 425                 430

Glu Asn Thr Val Ala Phe Asp Asp Asn Gly Asp Thr Leu Gly Tyr Tyr
        435                 440                 445

Asp Ile Ile Ala Trp Asp Trp Asn Gly Pro Glu Trp Thr Phe Glu Ile
    450                 455                 460

Ile Gly Ser Ala Ser Leu Ser Pro Val His Leu Asp Ile Asn Lys Thr
465                 470                 475                 480

Lys Ile Gln Trp His Gly Lys Asn Asn Gln Val Pro Val Ser Val Cys
                485                 490                 495

Thr Thr Asp Cys Leu Ala Gly His His Arg Val Val Val Gly Ser His
            500                 505                 510

His Cys Cys Phe Glu Cys Val Pro Cys Glu Ala Gly Thr Phe Leu Asn
        515                 520                 525
```

```
Met Ser Glu Leu His Ile Cys Gln Pro Cys Gly Thr Glu Glu Trp Ala
    530                 535                 540

Pro Lys Glu Ser Thr Thr Cys Phe Pro Arg Thr Val Glu Phe Leu Ala
545                 550                 555                 560

Trp His Glu Pro Ile Ser Leu Val Leu Ile Ala Ala Asn Thr Leu Leu
                565                 570                 575

Leu Leu Leu Leu Val Gly Thr Ala Gly Leu Phe Ala Trp His Phe His
            580                 585                 590

Thr Pro Val Val Arg Ser Ala Gly Gly Arg Leu Cys Phe Leu Met Leu
        595                 600                 605

Gly Ser Leu Val Ala Gly Ser Cys Ser Phe Tyr Ser Phe Phe Gly Glu
    610                 615                 620

Pro Thr Val Pro Ala Cys Leu Leu Arg Gln Pro Leu Phe Ser Leu Gly
625                 630                 635                 640

Phe Ala Ile Phe Leu Ser Cys Leu Thr Ile Arg Ser Phe Gln Leu Val
                645                 650                 655

Ile Ile Phe Lys Phe Ser Thr Lys Val Pro Thr Phe Tyr Arg Thr Trp
            660                 665                 670

Ala Gln Asn His Gly Ala Gly Leu Phe Val Ile Val Ser Ser Thr Val
        675                 680                 685

His Leu Leu Ile Cys Leu Thr Trp Leu Val Met Trp Thr Pro Arg Pro
    690                 695                 700

Thr Arg Glu Tyr Gln Arg Phe Pro His Leu Val Ile Leu Glu Cys Thr
705                 710                 715                 720

Glu Val Asn Ser Val Gly Phe Leu Leu Ala Phe Thr His Asn Ile Leu
                725                 730                 735

Leu Ser Ile Ser Thr Phe Val Cys Ser Tyr Leu Gly Lys Glu Leu Pro
            740                 745                 750

Glu Asn Tyr Asn Glu Ala Lys Cys Val Thr Phe Ser Leu Leu Leu Asn
        755                 760                 765

Phe Val Ser Trp Ile Ala Phe Phe Thr Met Ala Ser Ile Tyr Gln Gly
    770                 775                 780

Ser Tyr Leu Pro Ala Val Asn Val Leu Ala Gly Leu Thr Thr Leu Ser
785                 790                 795                 800

Gly Gly Phe Ser Gly Tyr Phe Leu Pro Lys Cys Tyr Val Ile Leu Cys
                805                 810                 815

Arg Pro Glu Leu Asn Asn Thr Glu His Phe Gln Ala Ser Ile Gln Asp
            820                 825                 830

Tyr Thr Arg Arg Cys Gly Thr Thr
        835                 840


<210> SEQ ID NO 17
<211> LENGTH: 841
<212> TYPE: PRT
<213> ORGANISM: Homo sapiens

<400> SEQUENCE: 17

Met Leu Leu Cys Thr Ala Arg Leu Val Gly Leu Gln Leu Leu Ile Ser
1               5                   10                  15

Cys Cys Trp Ala Phe Ala Cys His Ser Thr Glu Ser Ser Pro Asp Phe
            20                  25                  30

Thr Leu Pro Gly Asp Tyr Leu Leu Ala Gly Leu Phe Pro Leu His Ser
        35                  40                  45

Gly Cys Leu Gln Val Arg His Arg Pro Glu Val Thr Leu Cys Asp Arg
    50                  55                  60
```

-continued

Ser Cys Ser Phe Asn Glu His Gly Tyr His Leu Phe Gln Ala Met Arg
65 70 75 80

Leu Gly Val Glu Glu Ile Asn Asn Ser Thr Ala Leu Leu Pro Asn Ile
85 90 95

Thr Leu Gly Tyr Gln Leu Tyr Asp Val Cys Ser Asp Ser Ala Asn Val
100 105 110

Tyr Ala Thr Leu Arg Val Leu Ser Leu Pro Gly Gln His His Ile Glu
115 120 125

Leu Gln Gly Asp Leu Leu His Tyr Ser Pro Thr Val Leu Ala Val Ile
130 135 140

Gly Pro Asp Ser Thr Asn Arg Ala Ala Thr Thr Ala Ala Leu Leu Ser
145 150 155 160

Pro Phe Leu Val Pro Met Ile Ser Tyr Ala Ala Ser Ser Glu Thr Leu
165 170 175

Ser Val Lys Arg Gln Tyr Pro Ser Phe Leu Arg Thr Ile Pro Asn Asp
180 185 190

Lys Tyr Gln Val Glu Thr Met Val Leu Leu Leu Gln Lys Phe Gly Trp
195 200 205

Thr Trp Ile Ser Leu Val Gly Ser Ser Asp Asp Tyr Gly Gln Leu Gly
210 215 220

Val Gln Ala Leu Glu Asn Gln Ala Thr Gly Gln Gly Ile Cys Ile Ala
225 230 235 240

Phe Lys Asp Ile Met Pro Phe Ser Ala Gln Val Gly Asp Glu Arg Met
245 250 255

Gln Cys Leu Met Arg His Leu Ala Gln Ala Gly Ala Thr Val Val Val
260 265 270

Val Phe Ser Ser Arg Gln Leu Ala Arg Val Phe Phe Glu Ser Val Val
275 280 285

Leu Thr Asn Leu Thr Gly Lys Val Trp Val Ala Ser Glu Ala Trp Ala
290 295 300

Leu Ser Arg His Ile Thr Gly Val Pro Gly Ile Gln Arg Ile Gly Met
305 310 315 320

Val Leu Gly Val Ala Ile Gln Lys Arg Ala Val Pro Gly Leu Lys Ala
325 330 335

Phe Glu Glu Ala Tyr Ala Arg Ala Asp Lys Lys Ala Pro Arg Pro Cys
340 345 350

His Lys Gly Ser Trp Cys Ser Ser Asn Gln Leu Cys Arg Glu Cys Gln
355 360 365

Ala Phe Met Ala His Thr Met Pro Lys Leu Lys Ala Phe Ser Met Ser
370 375 380

Ser Ala Tyr Asn Ala Tyr Arg Ala Val Tyr Ala Val Ala His Gly Leu
385 390 395 400

His Gln Leu Leu Gly Cys Ala Ser Gly Ala Cys Ser Arg Gly Arg Val
405 410 415

Tyr Pro Trp Gln Leu Leu Glu Gln Ile His Lys Val His Phe Leu Leu
420 425 430

His Lys Asp Thr Val Ala Phe Asn Asp Asn Arg Asp Pro Leu Ser Ser
435 440 445

Tyr Asn Ile Ile Ala Trp Asp Trp Asn Gly Pro Lys Trp Thr Phe Thr
450 455 460

Val Leu Gly Ser Ser Thr Trp Ser Pro Val Gln Leu Asn Ile Asn Glu
465 470 475 480

Thr Lys Ile Gln Trp His Gly Lys Asp Asn Gln Val Pro Lys Ser Val
485 490 495

```
Cys Ser Ser Asp Cys Leu Glu Gly His Gln Arg Val Val Thr Gly Phe
            500                 505                 510

His His Cys Cys Phe Glu Cys Val Pro Cys Gly Ala Gly Thr Phe Leu
        515                 520                 525

Asn Lys Ser Asp Leu Tyr Arg Cys Gln Pro Cys Gly Lys Glu Glu Trp
    530                 535                 540

Ala Pro Glu Gly Ser Gln Thr Cys Phe Pro Arg Thr Val Val Phe Leu
545                 550                 555                 560

Ala Leu Arg Glu His Thr Ser Trp Val Leu Leu Ala Ala Asn Thr Leu
                565                 570                 575

Leu Leu Leu Leu Leu Leu Gly Thr Ala Gly Leu Phe Ala Trp His Leu
            580                 585                 590

Asp Thr Pro Val Val Arg Ser Ala Gly Gly Arg Leu Cys Phe Leu Met
        595                 600                 605

Leu Gly Ser Leu Ala Ala Gly Ser Gly Ser Leu Tyr Gly Phe Phe Gly
    610                 615                 620

Glu Pro Thr Arg Pro Ala Cys Leu Leu Arg Gln Ala Leu Phe Ala Leu
625                 630                 635                 640

Gly Phe Thr Ile Phe Leu Ser Cys Leu Thr Val Arg Ser Phe Gln Leu
                645                 650                 655

Ile Ile Ile Phe Lys Phe Ser Thr Lys Val Pro Thr Phe Tyr His Ala
            660                 665                 670

Trp Val Gln Asn His Gly Ala Gly Leu Phe Val Met Ile Ser Ser Ala
        675                 680                 685

Ala Gln Leu Leu Ile Cys Leu Thr Trp Leu Val Val Trp Thr Pro Leu
    690                 695                 700

Pro Ala Arg Glu Tyr Gln Arg Phe Pro His Leu Val Met Leu Glu Cys
705                 710                 715                 720

Thr Glu Thr Asn Ser Leu Gly Phe Ile Leu Ala Phe Leu Tyr Asn Gly
                725                 730                 735

Leu Leu Ser Ile Ser Ala Phe Ala Cys Ser Tyr Leu Gly Lys Asp Leu
            740                 745                 750

Pro Glu Asn Tyr Asn Glu Ala Lys Cys Val Thr Phe Ser Leu Leu Phe
        755                 760                 765

Asn Phe Val Ser Trp Ile Ala Phe Phe Thr Thr Ala Ser Val Tyr Asp
    770                 775                 780

Gly Lys Tyr Leu Pro Ala Ala Asn Met Met Ala Gly Leu Ser Ser Leu
785                 790                 795                 800

Ser Ser Gly Phe Gly Gly Tyr Phe Leu Pro Lys Cys Tyr Val Ile Leu
                805                 810                 815

Cys Arg Pro Asp Leu Asn Ser Thr Glu His Phe Gln Ala Ser Ile Gln
            820                 825                 830

Asp Tyr Thr Arg Arg Cys Gly Ser Thr
        835                 840


<210> SEQ ID NO 18
<211> LENGTH: 843
<212> TYPE: PRT
<213> ORGANISM: Mus musculus

<400> SEQUENCE: 18

Met Gly Pro Gln Ala Arg Thr Leu His Leu Leu Phe Leu Leu Leu His
1               5                   10                  15

Ala Leu Pro Lys Pro Val Met Leu Val Gly Asn Ser Asp Phe His Leu
            20                  25                  30
```

```
Ala Gly Asp Tyr Leu Leu Gly Gly Leu Phe Thr Leu His Ala Asn Val
        35                  40                  45

Lys Ser Val Ser His Leu Ser Tyr Leu Gln Val Pro Lys Cys Asn Glu
    50                  55                  60

Tyr Asn Met Lys Val Leu Gly Tyr Asn Leu Met Gln Ala Met Arg Phe
65                  70                  75                  80

Ala Val Glu Glu Ile Asn Asn Cys Ser Ser Leu Leu Pro Gly Val Leu
                85                  90                  95

Leu Gly Tyr Glu Met Val Asp Val Cys Tyr Leu Ser Asn Asn Ile Gln
            100                 105                 110

Pro Gly Leu Tyr Phe Leu Ser Gln Ile Asp Asp Phe Leu Pro Ile Leu
        115                 120                 125

Lys Asp Tyr Ser Gln Tyr Arg Pro Gln Val Val Ala Val Ile Gly Pro
    130                 135                 140

Asp Asn Ser Glu Ser Ala Ile Thr Val Ser Asn Ile Leu Ser Tyr Phe
145                 150                 155                 160

Leu Val Pro Gln Val Thr Tyr Ser Ala Ile Thr Asp Lys Leu Arg Asp
                165                 170                 175

Lys Arg Arg Phe Pro Ala Met Leu Arg Thr Val Pro Ser Ala Thr His
            180                 185                 190

His Ile Glu Ala Met Val Gln Leu Met Val His Phe Gln Trp Asn Trp
        195                 200                 205

Ile Val Val Leu Val Ser Asp Asp Asp Tyr Gly Arg Glu Asn Ser His
    210                 215                 220

Leu Leu Ser Gln Arg Leu Thr Asn Thr Gly Asp Ile Cys Ile Ala Phe
225                 230                 235                 240

Gln Glu Val Leu Pro Val Pro Glu Pro Asn Gln Ala Val Arg Pro Glu
                245                 250                 255

Glu Gln Asp Gln Leu Asp Asn Ile Leu Asp Lys Leu Arg Arg Thr Ser
            260                 265                 270

Ala Arg Val Val Val Ile Phe Ser Pro Glu Leu Ser Leu His Asn Phe
        275                 280                 285

Phe Arg Glu Val Leu Arg Trp Asn Phe Thr Gly Phe Val Trp Ile Ala
    290                 295                 300

Ser Glu Ser Trp Ala Ile Asp Pro Val Leu His Asn Leu Thr Glu Leu
305                 310                 315                 320

Arg His Thr Gly Thr Phe Leu Gly Val Thr Ile Gln Arg Val Ser Ile
                325                 330                 335

Pro Gly Phe Ser Gln Phe Arg Val Arg His Asp Lys Pro Glu Tyr Pro
            340                 345                 350

Met Pro Asn Glu Thr Ser Leu Arg Thr Thr Cys Asn Gln Asp Cys Asp
        355                 360                 365

Ala Cys Met Asn Ile Thr Glu Ser Phe Asn Asn Val Leu Met Leu Ser
    370                 375                 380

Gly Glu Arg Val Val Tyr Ser Val Tyr Ser Ala Val Tyr Ala Val Ala
385                 390                 395                 400

His Thr Leu His Arg Leu Leu His Cys Asn Gln Val Arg Cys Thr Lys
                405                 410                 415

Gln Ile Val Tyr Pro Trp Gln Leu Leu Arg Glu Ile Trp His Val Asn
            420                 425                 430

Phe Thr Leu Leu Gly Asn Gln Leu Phe Phe Asp Glu Gln Gly Asp Met
        435                 440                 445

Pro Met Leu Leu Asp Ile Ile Gln Trp Gln Trp Gly Leu Ser Gln Asn
```

```
    450                 455                 460

Pro Phe Gln Ser Ile Ala Ser Tyr Ser Pro Thr Glu Thr Arg Leu Thr
465                 470                 475                 480

Tyr Ile Ser Asn Val Ser Trp Tyr Thr Pro Asn Asn Thr Val Pro Ile
                485                 490                 495

Ser Met Cys Ser Lys Ser Cys Gln Pro Gly Gln Met Lys Lys Pro Ile
            500                 505                 510

Gly Leu His Pro Cys Cys Phe Glu Cys Val Asp Cys Pro Pro Gly Thr
        515                 520                 525

Tyr Leu Asn Arg Ser Val Asp Glu Phe Asn Cys Leu Ser Cys Pro Gly
    530                 535                 540

Ser Met Trp Ser Tyr Lys Asn Asn Ile Ala Cys Phe Lys Arg Arg Leu
545                 550                 555                 560

Ala Phe Leu Glu Trp His Glu Val Pro Thr Ile Val Val Thr Ile Leu
                565                 570                 575

Ala Ala Leu Gly Phe Ile Ser Thr Leu Ala Ile Leu Leu Ile Phe Trp
            580                 585                 590

Arg His Phe Gln Thr Pro Met Val Arg Ser Ala Gly Gly Pro Met Cys
        595                 600                 605

Phe Leu Met Leu Val Pro Leu Leu Leu Ala Phe Gly Met Val Pro Val
    610                 615                 620

Tyr Val Gly Pro Pro Thr Val Phe Ser Cys Phe Cys Arg Gln Ala Phe
625                 630                 635                 640

Phe Thr Val Cys Phe Ser Val Cys Leu Ser Cys Ile Thr Val Arg Ser
                645                 650                 655

Phe Gln Ile Val Cys Val Phe Lys Met Ala Arg Arg Leu Pro Ser Ala
            660                 665                 670

Tyr Gly Phe Trp Met Arg Tyr His Gly Pro Tyr Val Phe Val Ala Phe
        675                 680                 685

Ile Thr Ala Val Lys Val Ala Leu Val Ala Gly Asn Met Leu Ala Thr
    690                 695                 700

Thr Ile Asn Pro Ile Gly Arg Thr Asp Pro Asp Asp Pro Asn Ile Ile
705                 710                 715                 720

Ile Leu Ser Cys His Pro Asn Tyr Arg Asn Gly Leu Leu Phe Asn Thr
                725                 730                 735

Ser Met Asp Leu Leu Leu Ser Val Leu Gly Phe Ser Phe Ala Tyr Val
            740                 745                 750

Gly Lys Glu Leu Pro Thr Asn Tyr Asn Glu Ala Lys Phe Ile Thr Leu
        755                 760                 765

Ser Met Thr Phe Ser Phe Thr Ser Ser Ile Ser Leu Cys Thr Phe Met
    770                 775                 780

Ser Val His Asp Gly Val Leu Val Thr Ile Met Asp Leu Leu Val Thr
785                 790                 795                 800

Val Leu Asn Phe Leu Ala Ile Gly Leu Gly Tyr Phe Gly Pro Lys Cys
                805                 810                 815

Tyr Met Ile Leu Phe Tyr Pro Glu Arg Asn Thr Ser Ala Tyr Phe Asn
            820                 825                 830

Ser Met Ile Gln Gly Tyr Thr Met Arg Lys Ser
        835                 840
```

<210> SEQ ID NO 19
<211> LENGTH: 843
<212> TYPE: PRT
<213> ORGANISM: Rattus rattus -continued

<400> SEQUENCE: 19

```
Met Gly Pro Gln Ala Arg Thr Leu Cys Leu Leu Ser Leu Leu Leu His
1               5                   10                  15

Val Leu Pro Lys Pro Gly Lys Leu Val Glu Asn Ser Asp Phe His Leu
            20                  25                  30

Ala Gly Asp Tyr Leu Leu Gly Gly Leu Phe Thr Leu His Ala Asn Val
        35                  40                  45

Lys Ser Ile Ser His Leu Ser Tyr Leu Gln Val Pro Lys Cys Asn Glu
    50                  55                  60

Phe Thr Met Lys Val Leu Gly Tyr Asn Leu Met Gln Ala Met Arg Phe
65                  70                  75                  80

Ala Val Glu Glu Ile Asn Asn Cys Ser Ser Leu Leu Pro Gly Val Leu
                85                  90                  95

Leu Gly Tyr Glu Met Val Asp Val Cys Tyr Leu Ser Asn Asn Ile His
            100                 105                 110

Pro Gly Leu Tyr Phe Leu Ala Gln Asp Asp Asp Leu Leu Pro Ile Leu
        115                 120                 125

Lys Asp Tyr Ser Gln Tyr Met Pro His Val Val Ala Val Ile Gly Pro
    130                 135                 140

Asp Asn Ser Glu Ser Ala Ile Thr Val Ser Asn Ile Leu Ser His Phe
145                 150                 155                 160

Leu Ile Pro Gln Ile Thr Tyr Ser Ala Ile Ser Asp Lys Leu Arg Asp
                165                 170                 175

Lys Arg His Phe Pro Ser Met Leu Arg Thr Val Pro Ser Ala Thr His
            180                 185                 190

His Ile Glu Ala Met Val Gln Leu Met Val His Phe Gln Trp Asn Trp
        195                 200                 205

Ile Val Val Leu Val Ser Asp Asp Asp Tyr Gly Arg Glu Asn Ser His
    210                 215                 220

Leu Leu Ser Gln Arg Leu Thr Lys Thr Ser Asp Ile Cys Ile Ala Phe
225                 230                 235                 240

Gln Glu Val Leu Pro Ile Pro Glu Ser Ser Gln Val Met Arg Ser Glu
                245                 250                 255

Glu Gln Arg Gln Leu Asp Asn Ile Leu Asp Lys Leu Arg Arg Thr Ser
            260                 265                 270

Ala Arg Val Val Val Val Phe Ser Pro Glu Leu Ser Leu Tyr Ser Phe
        275                 280                 285

Phe His Glu Val Leu Arg Trp Asn Phe Thr Gly Phe Val Trp Ile Ala
    290                 295                 300

Ser Glu Ser Trp Ala Ile Asp Pro Val Leu His Asn Leu Thr Glu Leu
305                 310                 315                 320

Arg His Thr Gly Thr Phe Leu Gly Val Thr Ile Gln Arg Val Ser Ile
                325                 330                 335

Pro Gly Phe Ser Gln Phe Arg Val Arg Arg Asp Lys Pro Gly Tyr Pro
            340                 345                 350

Val Pro Asn Thr Thr Asn Leu Arg Thr Thr Cys Asn Gln Asp Cys Asp
        355                 360                 365

Ala Cys Leu Asn Thr Thr Lys Ser Phe Asn Asn Ile Leu Ile Leu Ser
    370                 375                 380

Gly Glu Arg Val Val Tyr Ser Val Tyr Ser Ala Val Tyr Ala Val Ala
385                 390                 395                 400

His Ala Leu His Arg Leu Leu Gly Cys Asn Arg Val Arg Cys Thr Lys
                405                 410                 415
```

```
Gln Lys Val Tyr Pro Trp Gln Leu Leu Arg Glu Ile Trp His Val Asn
            420                 425                 430

Phe Thr Leu Leu Gly Asn Arg Leu Phe Phe Asp Gln Gln Gly Asp Met
        435                 440                 445

Pro Met Leu Leu Asp Ile Ile Gln Trp Gln Trp Asp Leu Ser Gln Asn
    450                 455                 460

Pro Phe Gln Ser Ile Ala Ser Tyr Ser Pro Thr Ser Lys Arg Leu Thr
465                 470                 475                 480

Tyr Ile Asn Asn Val Ser Trp Tyr Thr Pro Asn Asn Thr Val Pro Val
                485                 490                 495

Ser Met Cys Ser Lys Ser Cys Gln Pro Gly Gln Met Lys Lys Ser Val
            500                 505                 510

Gly Leu His Pro Cys Cys Phe Glu Cys Leu Asp Cys Met Pro Gly Thr
        515                 520                 525

Tyr Leu Asn Arg Ser Ala Asp Glu Phe Asn Cys Leu Ser Cys Pro Gly
    530                 535                 540

Ser Met Trp Ser Tyr Lys Asn Asp Ile Thr Cys Phe Gln Arg Arg Pro
545                 550                 555                 560

Thr Phe Leu Glu Trp His Glu Val Pro Thr Ile Val Val Ala Ile Leu
                565                 570                 575

Ala Ala Leu Gly Phe Phe Ser Thr Leu Ala Ile Leu Phe Ile Phe Trp
            580                 585                 590

Arg His Phe Gln Thr Pro Met Val Arg Ser Ala Gly Gly Pro Met Cys
        595                 600                 605

Phe Leu Met Leu Val Pro Leu Leu Leu Ala Phe Gly Met Val Pro Val
    610                 615                 620

Tyr Val Gly Pro Pro Thr Val Phe Ser Cys Phe Cys Arg Gln Ala Phe
625                 630                 635                 640

Phe Thr Val Cys Phe Ser Ile Cys Leu Ser Cys Ile Thr Val Arg Ser
                645                 650                 655

Phe Gln Ile Val Cys Val Phe Lys Met Ala Arg Arg Leu Pro Ser Ala
            660                 665                 670

Tyr Ser Phe Trp Met Arg Tyr His Gly Pro Tyr Val Phe Val Ala Phe
        675                 680                 685

Ile Thr Ala Ile Lys Val Ala Leu Val Val Gly Asn Met Leu Ala Thr
    690                 695                 700

Thr Ile Asn Pro Ile Gly Arg Thr Asp Pro Asp Asp Pro Asn Ile Met
705                 710                 715                 720

Ile Leu Ser Cys His Pro Asn Tyr Arg Asn Gly Leu Leu Phe Asn Thr
                725                 730                 735

Ser Met Asp Leu Leu Leu Ser Val Leu Gly Phe Ser Phe Ala Tyr Met
            740                 745                 750

Gly Lys Glu Leu Pro Thr Asn Tyr Asn Glu Ala Lys Phe Ile Thr Leu
        755                 760                 765

Ser Met Thr Phe Ser Phe Thr Ser Ser Ile Ser Leu Cys Thr Phe Met
    770                 775                 780

Ser Val His Asp Gly Val Leu Val Thr Ile Met Asp Leu Leu Val Thr
785                 790                 795                 800

Val Leu Asn Phe Leu Ala Ile Gly Leu Gly Tyr Phe Gly Pro Lys Cys
                805                 810                 815

Tyr Met Ile Leu Phe Tyr Pro Glu Arg Asn Thr Ser Ala Tyr Phe Asn
            820                 825                 830

Ser Met Ile Gln Gly Tyr Thr Met Arg Lys Ser
        835                 840
```

<210> SEQ ID NO 20
<211> LENGTH: 839
<212> TYPE: PRT
<213> ORGANISM: Homo sapiens

<400> SEQUENCE: 20

```
Met Gly Pro Arg Ala Lys Thr Ile Cys Ser Leu Phe Phe Leu Leu Trp
1               5                   10                  15

Val Leu Ala Glu Pro Ala Glu Asn Ser Asp Phe Tyr Leu Pro Gly Asp
            20                  25                  30

Tyr Leu Leu Gly Gly Leu Phe Ser Leu His Ala Asn Met Lys Gly Ile
        35                  40                  45

Val His Leu Asn Phe Leu Gln Val Pro Met Cys Lys Glu Tyr Glu Val
    50                  55                  60

Lys Val Ile Gly Tyr Asn Leu Met Gln Ala Met Arg Phe Ala Val Glu
65                  70                  75                  80

Glu Ile Asn Asn Asp Ser Ser Leu Leu Pro Gly Val Leu Leu Gly Tyr
                85                  90                  95

Glu Ile Val Asp Val Cys Tyr Ile Ser Asn Asn Val Gln Pro Val Leu
            100                 105                 110

Tyr Phe Leu Ala His Glu Asp Asn Leu Leu Pro Ile Gln Glu Asp Tyr
        115                 120                 125

Ser Asn Tyr Ile Ser Arg Val Val Ala Val Ile Gly Pro Asp Asn Ser
    130                 135                 140

Glu Ser Val Met Thr Val Ala Asn Phe Leu Ser Leu Phe Leu Leu Pro
145                 150                 155                 160

Gln Ile Thr Tyr Ser Ala Ile Ser Asp Glu Leu Arg Asp Lys Val Arg
                165                 170                 175

Phe Pro Ala Leu Leu Arg Thr Thr Pro Ser Ala Asp His His Val Glu
            180                 185                 190

Ala Met Val Gln Leu Met Leu His Phe Arg Trp Asn Trp Ile Ile Val
        195                 200                 205

Leu Val Ser Ser Asp Thr Tyr Gly Arg Asp Asn Gly Gln Leu Leu Gly
    210                 215                 220

Glu Arg Val Ala Arg Arg Asp Ile Cys Ile Ala Phe Gln Glu Thr Leu
225                 230                 235                 240

Pro Thr Leu Gln Pro Asn Gln Asn Met Thr Ser Glu Glu Arg Gln Arg
                245                 250                 255

Leu Val Thr Ile Val Asp Lys Leu Gln Gln Ser Thr Ala Arg Val Val
            260                 265                 270

Val Val Phe Ser Pro Asp Leu Thr Leu Tyr His Phe Phe Asn Glu Val
        275                 280                 285

Leu Arg Gln Asn Phe Thr Gly Ala Val Trp Ile Ala Ser Glu Ser Trp
    290                 295                 300

Ala Ile Asp Pro Val Leu His Asn Leu Thr Glu Leu Gly His Leu Gly
305                 310                 315                 320

Thr Phe Leu Gly Ile Thr Ile Gln Ser Val Pro Ile Pro Gly Phe Ser
                325                 330                 335

Glu Phe Arg Glu Trp Gly Pro Gln Ala Gly Pro Pro Pro Leu Ser Arg
            340                 345                 350

Thr Ser Gln Ser Tyr Thr Cys Asn Gln Glu Cys Asp Asn Cys Leu Asn
        355                 360                 365

Ala Thr Leu Ser Phe Asn Thr Ile Leu Arg Leu Ser Gly Glu Arg Val
    370                 375                 380
```

```
Val Tyr Ser Val Tyr Ser Ala Val Tyr Ala Val Ala His Ala Leu His
385                 390                 395                 400

Ser Leu Leu Gly Cys Asp Lys Ser Thr Cys Thr Lys Arg Val Val Tyr
                405                 410                 415

Pro Trp Gln Leu Leu Glu Glu Ile Trp Lys Val Asn Phe Thr Leu Leu
            420                 425                 430

Asp His Gln Ile Phe Phe Asp Pro Gln Gly Asp Val Ala Leu His Leu
        435                 440                 445

Glu Ile Val Gln Trp Gln Trp Asp Arg Ser Gln Asn Pro Phe Gln Ser
    450                 455                 460

Val Ala Ser Tyr Tyr Pro Leu Gln Arg Gln Leu Lys Asn Ile Gln Asp
465                 470                 475                 480

Ile Ser Trp His Thr Val Asn Asn Thr Ile Pro Met Ser Met Cys Ser
                485                 490                 495

Lys Arg Cys Gln Ser Gly Gln Lys Lys Lys Pro Val Gly Ile His Val
            500                 505                 510

Cys Cys Phe Glu Cys Ile Asp Cys Leu Pro Gly Thr Phe Leu Asn His
        515                 520                 525

Thr Glu Asp Glu Tyr Glu Cys Gln Ala Cys Pro Asn Asn Glu Trp Ser
    530                 535                 540

Tyr Gln Ser Glu Thr Ser Cys Phe Lys Arg Gln Leu Val Phe Leu Glu
545                 550                 555                 560

Trp His Glu Ala Pro Thr Ile Ala Val Ala Leu Leu Ala Ala Leu Gly
                565                 570                 575

Phe Leu Ser Thr Leu Ala Ile Leu Val Ile Phe Trp Arg His Phe Gln
            580                 585                 590

Thr Pro Ile Val Arg Ser Ala Gly Gly Pro Met Cys Phe Leu Met Leu
        595                 600                 605

Thr Leu Leu Leu Val Ala Tyr Met Val Val Pro Val Tyr Val Gly Pro
    610                 615                 620

Pro Lys Val Ser Thr Cys Leu Cys Arg Gln Ala Leu Phe Pro Leu Cys
625                 630                 635                 640

Phe Thr Ile Cys Ile Ser Cys Ile Ala Val Arg Ser Phe Gln Ile Val
                645                 650                 655

Cys Ala Phe Lys Met Ala Ser Arg Phe Pro Arg Ala Tyr Ser Tyr Trp
            660                 665                 670

Val Arg Tyr Gln Gly Pro Tyr Val Ser Met Ala Phe Ile Thr Val Leu
        675                 680                 685

Lys Met Val Ile Val Val Ile Gly Met Leu Ala Thr Gly Leu Ser Pro
    690                 695                 700

Thr Thr Arg Thr Asp Pro Asp Asp Pro Lys Ile Thr Ile Val Ser Cys
705                 710                 715                 720

Asn Pro Asn Tyr Arg Asn Ser Leu Leu Phe Asn Thr Ser Leu Asp Leu
                725                 730                 735

Leu Leu Ser Val Val Gly Phe Ser Phe Ala Tyr Met Gly Lys Glu Leu
            740                 745                 750

Pro Thr Asn Tyr Asn Glu Ala Lys Phe Ile Thr Leu Ser Met Thr Phe
        755                 760                 765

Tyr Phe Thr Ser Ser Val Ser Leu Cys Thr Phe Met Ser Ala Tyr Ser
    770                 775                 780

Gly Val Leu Val Thr Ile Val Asp Leu Leu Val Thr Val Leu Asn Leu
785                 790                 795                 800

Leu Ala Ile Ser Leu Gly Tyr Phe Gly Pro Lys Cys Tyr Met Ile Leu
```

```
                805                 810                 815

Phe Tyr Pro Glu Arg Asn Thr Pro Ala Tyr Phe Asn Ser Met Ile Gln
            820                 825                 830

Gly Tyr Thr Met Arg Arg Asp
        835
```

<210> SEQ ID NO 21
<211> LENGTH: 24
<212> TYPE: DNA
<213> ORGANISM: Artificial Sequence
<220> FEATURE:
<223> OTHER INFORMATION: Overgo probe

<400> SEQUENCE: 21
actttgagaa catgagtaat gacg 24

<210> SEQ ID NO 22
<211> LENGTH: 24
<212> TYPE: DNA
<213> ORGANISM: Artificial Sequence
<220> FEATURE:
<223> OTHER INFORMATION: Overgo probe

<400> SEQUENCE: 22
agtacccgga ctgcgtcgtc atta 24

<210> SEQ ID NO 23
<211> LENGTH: 24
<212> TYPE: DNA
<213> ORGANISM: Artificial Sequence
<220> FEATURE:
<223> OTHER INFORMATION: Overgo probe

<400> SEQUENCE: 23
cactagggtc atccttgctt tcag 24

<210> SEQ ID NO 24
<211> LENGTH: 24
<212> TYPE: DNA
<213> ORGANISM: Artificial Sequence
<220> FEATURE:
<223> OTHER INFORMATION: Overgo probe

<400> SEQUENCE: 24
agtcagggtg atgggcctga aagc 24

<210> SEQ ID NO 25
<211> LENGTH: 24
<212> TYPE: DNA
<213> ORGANISM: Artificial Sequence
<220> FEATURE:
<223> OTHER INFORMATION: Overgo probe

<400> SEQUENCE: 25
atgtggtgga ctggctgtac catc 24

<210> SEQ ID NO 26
<211> LENGTH: 24
<212> TYPE: DNA
<213> ORGANISM: Artificial Sequence
<220> FEATURE:
<223> OTHER INFORMATION: Overgo probe

<400> SEQUENCE: 26
ttgaagccct ccacgtgatg gtac 24

<210> SEQ ID NO 27
<211> LENGTH: 24
<212> TYPE: DNA
<213> ORGANISM: Artificial Sequence
<220> FEATURE:
<223> OTHER INFORMATION: Overgo probe

<400> SEQUENCE: 27
cacacggtga acaagatcac cttc 24

<210> SEQ ID NO 28
<211> LENGTH: 24
<212> TYPE: DNA
<213> ORGANISM: Artificial Sequence
<220> FEATURE:
<223> OTHER INFORMATION: Overgo probe

<400> SEQUENCE: 28
agtagcactg ctcggagaag gtga 24

<210> SEQ ID NO 29
<211> LENGTH: 24
<212> TYPE: DNA
<213> ORGANISM: Artificial Sequence
<220> FEATURE:
<223> OTHER INFORMATION: Overgo probe

<400> SEQUENCE: 29
atctaccaca tggacgagga ggag 24

<210> SEQ ID NO 30
<211> LENGTH: 24
<212> TYPE: DNA
<213> ORGANISM: Artificial Sequence
<220> FEATURE:
<223> OTHER INFORMATION: Overgo probe

<400> SEQUENCE: 30
tgaccaggta cggcgtctcc tcct 24

<210> SEQ ID NO 31
<211> LENGTH: 24
<212> TYPE: DNA
<213> ORGANISM: Artificial Sequence
<220> FEATURE:
<223> OTHER INFORMATION: Overgo probe

<400> SEQUENCE: 31
agcgcgtcac gctggccgac ttca 24

<210> SEQ ID NO 32
<211> LENGTH: 24
<212> TYPE: DNA
<213> ORGANISM: Artificial Sequence
<220> FEATURE:
<223> OTHER INFORMATION: Overgo probe

<400> SEQUENCE: 32
ttgctgagca cgttcttgaa gtcg 24

<210> SEQ ID NO 33
<211> LENGTH: 24
<212> TYPE: DNA
<213> ORGANISM: Artificial Sequence
<220> FEATURE:
<223> OTHER INFORMATION: Overgo probe

<400> SEQUENCE: 33
cacgcctaca aattcttctt taag 24

<210> SEQ ID NO 34
<211> LENGTH: 24
<212> TYPE: DNA
<213> ORGANISM: Artificial Sequence
<220> FEATURE:
<223> OTHER INFORMATION: Overgo probe

<400> SEQUENCE: 34
agtcctggtc catggactta aaga 24

<210> SEQ ID NO 35
<211> LENGTH: 24
<212> TYPE: DNA
<213> ORGANISM: Artificial Sequence
<220> FEATURE:
<223> OTHER INFORMATION: Overgo probe

<400> SEQUENCE: 35
cttccactcc tgctgctacg actg 24

<210> SEQ ID NO 36
<211> LENGTH: 24
<212> TYPE: DNA
<213> ORGANISM: Artificial Sequence
<220> FEATURE:
<223> OTHER INFORMATION: Overgo probe

<400> SEQUENCE: 36
tgcctcgcag tccacgcagt cgta 24

<210> SEQ ID NO 37
<211> LENGTH: 24
<212> TYPE: DNA
<213> ORGANISM: Artificial Sequence
<220> FEATURE:
<223> OTHER INFORMATION: Overgo probe

<400> SEQUENCE: 37
aggtgcgccg cgtcaagggc ttcc 24

<210> SEQ ID NO 38
<211> LENGTH: 24
<212> TYPE: DNA
<213> ORGANISM: Artificial Sequence
<220> FEATURE:
<223> OTHER INFORMATION: Overgo probe

<400> SEQUENCE: 38
tcgtagcagc aggagtggaa gccc 24

<210> SEQ ID NO 39
<211> LENGTH: 24
<212> TYPE: DNA
<213> ORGANISM: Artificial Sequence
<220> FEATURE:
<223> OTHER INFORMATION: Overgo probe

<400> SEQUENCE: 39
gttcctggca tggggggagc cggc 24

<210> SEQ ID NO 40
<211> LENGTH: 24
<212> TYPE: DNA

<213> ORGANISM: Artificial Sequence
<220> FEATURE:
<223> OTHER INFORMATION: Overgo probe

<400> SEQUENCE: 40
gagcagcaca agcacagccg gctc 24

<210> SEQ ID NO 41
<211> LENGTH: 24
<212> TYPE: DNA
<213> ORGANISM: Artificial Sequence
<220> FEATURE:
<223> OTHER INFORMATION: Overgo probe

<400> SEQUENCE: 41
acagcccact agttcaggcc gcag 24

<210> SEQ ID NO 42
<211> LENGTH: 24
<212> TYPE: DNA
<213> ORGANISM: Artificial Sequence
<220> FEATURE:
<223> OTHER INFORMATION: Overgo probe

<400> SEQUENCE: 42
caggcccggg gtccccctgc ggcc 24

<210> SEQ ID NO 43
<211> LENGTH: 24
<212> TYPE: DNA
<213> ORGANISM: Artificial Sequence
<220> FEATURE:
<223> OTHER INFORMATION: Overgo probe

<400> SEQUENCE: 43
cccactggtt caggcctcgg gggg 24

<210> SEQ ID NO 44
<211> LENGTH: 24
<212> TYPE: DNA
<213> ORGANISM: Artificial Sequence
<220> FEATURE:
<223> OTHER INFORMATION: Overgo probe

<400> SEQUENCE: 44
aaagcaggcc aggggccccc ccga 24

<210> SEQ ID NO 45
<211> LENGTH: 24
<212> TYPE: DNA
<213> ORGANISM: Artificial Sequence
<220> FEATURE:
<223> OTHER INFORMATION: Overgo probe

<400> SEQUENCE: 45
aggcgctggt gcactgccgc acac 24

<210> SEQ ID NO 46
<211> LENGTH: 24
<212> TYPE: DNA
<213> ORGANISM: Artificial Sequence
<220> FEATURE:
<223> OTHER INFORMATION: Overgo probe

<400> SEQUENCE: 46
aagctgaccc aggagcgtgt gcgg 24

<210> SEQ ID NO 47
<211> LENGTH: 24
<212> TYPE: DNA
<213> ORGANISM: Artificial Sequence
<220> FEATURE:
<223> OTHER INFORMATION: Overgo probe

<400> SEQUENCE: 47
acagaggcac tggtgcactg ccgc 24

<210> SEQ ID NO 48
<211> LENGTH: 24
<212> TYPE: DNA
<213> ORGANISM: Artificial Sequence
<220> FEATURE:
<223> OTHER INFORMATION: Overgo probe

<400> SEQUENCE: 48
tgatccagga gtgcacgcgg cagt 24

<210> SEQ ID NO 49
<211> LENGTH: 24
<212> TYPE: DNA
<213> ORGANISM: Artificial Sequence
<220> FEATURE:
<223> OTHER INFORMATION: Overgo probe

<400> SEQUENCE: 49
accaatgcca cgctggcctt tctc 24

<210> SEQ ID NO 50
<211> LENGTH: 24
<212> TYPE: DNA
<213> ORGANISM: Artificial Sequence
<220> FEATURE:
<223> OTHER INFORMATION: Overgo probe

<400> SEQUENCE: 50
aagtgcccag gaagcagaga aagg 24

<210> SEQ ID NO 51
<211> LENGTH: 24
<212> TYPE: DNA
<213> ORGANISM: Artificial Sequence
<220> FEATURE:
<223> OTHER INFORMATION: Overgo probe

<400> SEQUENCE: 51
tggtacatgc tgccaatgcc acgc 24

<210> SEQ ID NO 52
<211> LENGTH: 24
<212> TYPE: DNA
<213> ORGANISM: Artificial Sequence
<220> FEATURE:
<223> OTHER INFORMATION: Overgo probe

<400> SEQUENCE: 52
aagcagagga aagccagcgt ggca 24

<210> SEQ ID NO 53
<211> LENGTH: 24
<212> TYPE: DNA
<213> ORGANISM: Artificial Sequence
<220> FEATURE:
<223> OTHER INFORMATION: Overgo probe

<400> SEQUENCE: 53
tacaaccgtg cccgtggcct cacc 24

<210> SEQ ID NO 54
<211> LENGTH: 24
<212> TYPE: DNA
<213> ORGANISM: Artificial Sequence
<220> FEATURE:
<223> OTHER INFORMATION: Overgo probe

<400> SEQUENCE: 54
aggccagcat ggcgaaggtg aggc 24

<210> SEQ ID NO 55
<211> LENGTH: 24
<212> TYPE: DNA
<213> ORGANISM: Artificial Sequence
<220> FEATURE:
<223> OTHER INFORMATION: Overgo probe

<400> SEQUENCE: 55
tcatcacctg ggtctccttt gtgc 24

<210> SEQ ID NO 56
<211> LENGTH: 24
<212> TYPE: DNA
<213> ORGANISM: Artificial Sequence
<220> FEATURE:
<223> OTHER INFORMATION: Overgo probe

<400> SEQUENCE: 56
acattggcca ggaggggcac aaag 24

<210> SEQ ID NO 57
<211> LENGTH: 24
<212> TYPE: DNA
<213> ORGANISM: Artificial Sequence
<220> FEATURE:
<223> OTHER INFORMATION: Overgo probe

<400> SEQUENCE: 57
tgcagatggg tgccctcctg ctct 24

<210> SEQ ID NO 58
<211> LENGTH: 24
<212> TYPE: DNA
<213> ORGANISM: Artificial Sequence
<220> FEATURE:
<223> OTHER INFORMATION: Overgo probe

<400> SEQUENCE: 58
aggatgccca gcacacagag cagg 24

<210> SEQ ID NO 59
<211> LENGTH: 9049
<212> TYPE: DNA
<213> ORGANISM: Felis catus
<220> FEATURE:
<221> NAME/KEY: misc_feature
<222> LOCATION: (14)..(14)
<223> OTHER INFORMATION: n is a, c, g, or t
<220> FEATURE:
<221> NAME/KEY: misc_feature
<222> LOCATION: (47)..(47)
<223> OTHER INFORMATION: n is a, c, g, or t
<220> FEATURE:
<221> NAME/KEY: misc_feature
<222> LOCATION: (56)..(56)

<223> OTHER INFORMATION: n is a, c, g, or t
<220> FEATURE:
<221> NAME/KEY: misc_feature
<222> LOCATION: (67)..(67)
<223> OTHER INFORMATION: n is a, c, g, or t
<220> FEATURE:
<221> NAME/KEY: misc_feature
<222> LOCATION: (2113)..(2113)
<223> OTHER INFORMATION: n is a, c, g, or t
<220> FEATURE:
<221> NAME/KEY: misc_feature
<222> LOCATION: (2121)..(2121)
<223> OTHER INFORMATION: n is a, c, g, or t
<220> FEATURE:
<221> NAME/KEY: misc_feature
<222> LOCATION: (2125)..(2132)
<223> OTHER INFORMATION: n is a, c, g, or t
<220> FEATURE:
<221> NAME/KEY: misc_feature
<222> LOCATION: (2138)..(2138)
<223> OTHER INFORMATION: n is a, c, g, or t
<220> FEATURE:
<221> NAME/KEY: misc_feature
<222> LOCATION: (4198)..(4198)
<223> OTHER INFORMATION: n is a, c, g, or t
<220> FEATURE:
<221> NAME/KEY: misc_feature
<222> LOCATION: (4232)..(4232)
<223> OTHER INFORMATION: n is a, c, g, or t
<220> FEATURE:
<221> NAME/KEY: misc_feature
<222> LOCATION: (4237)..(4237)
<223> OTHER INFORMATION: n is a, c, g, or t
<220> FEATURE:
<221> NAME/KEY: misc_feature
<222> LOCATION: (4256)..(4256)
<223> OTHER INFORMATION: n is a, c, g, or t
<220> FEATURE:
<221> NAME/KEY: misc_feature
<222> LOCATION: (4264)..(4264)
<223> OTHER INFORMATION: n is a, c, g, or t
<220> FEATURE:
<221> NAME/KEY: misc_feature
<222> LOCATION: (4272)..(4272)
<223> OTHER INFORMATION: n is a, c, g, or t
<220> FEATURE:
<221> NAME/KEY: misc_feature
<222> LOCATION: (4298)..(4298)
<223> OTHER INFORMATION: n is a, c, g, or t
<220> FEATURE:
<221> NAME/KEY: misc_feature
<222> LOCATION: (4328)..(4328)
<223> OTHER INFORMATION: n is a, c, g, or t
<220> FEATURE:
<221> NAME/KEY: misc_feature
<222> LOCATION: (4341)..(4341)
<223> OTHER INFORMATION: n is a, c, g, or t
<220> FEATURE:
<221> NAME/KEY: misc_feature
<222> LOCATION: (4343)..(4343)
<223> OTHER INFORMATION: n is a, c, g, or t
<220> FEATURE:
<221> NAME/KEY: misc_feature
<222> LOCATION: (4354)..(4354)
<223> OTHER INFORMATION: n is a, c, g, or t
<220> FEATURE:
<221> NAME/KEY: misc_feature
<222> LOCATION: (4386)..(4386)
<223> OTHER INFORMATION: n is a, c, g, or t
<220> FEATURE:
<221> NAME/KEY: misc_feature
<222> LOCATION: (4389)..(4390)
<223> OTHER INFORMATION: n is a, c, g, or t
<220> FEATURE:
<221> NAME/KEY: misc_feature
<222> LOCATION: (4399)..(4456)
<223> OTHER INFORMATION: n is a, c, g, or t

<400> SEQUENCE: 59

-continued

```
ctggaaaaaa aggngaaccc aggatgattc accccaaaat ttcagtntca gaaaantgag      60
gactggnagg aggtcaactt aaagtcagtt tcatttggta aactgaggcc caggtaaaaa     120
gttctaaaac ccacagctcc cttccatatt ctgtccccca gagaagcagt gtccctgcct     180
tcctctgacc cctgcccctc aagacgcctg ggctcccttt ctgagccggg tgaagccgca     240
ggcaccagag cgagaacaga acccacaacc atccagaggg aggggcagcg gccaccacct     300
ggcttgcacc tgtgccttca ccctgcccag ttcctgagta ggaccgcagg cccggaaggc     360
caaggcaaac agcctggttc ctacgactgg gttccagccc cacccctggc acaggcgtga     420
agttgggaag catctgggca gccgctgtct attctattta aacagccgag ctggtcagag     480
ggtgctggct ggccatgcca ggcacaggac ggactggcca gcatgtcact cccggcggct     540
cacctggtcg gcctgcagct ctccctctcc tgctgctggg ctctcagctg ccacagcaca     600
gagacgtctg ccgacttcag cctccctggg gattacctcc tcgcaggtct gttccctctg     660
cactctgact gtccgggcgt gaggcaccgg cccacggtga ccctctgtga caggtgagtg     720
aggggtcccg tgcctctagg acctctgccc atcctctgtc ctcctcagtg aggatccttg     780
ggttgttgat tgagtggagt tagggccttt tagagagctg agactctaga agctaaacca     840
cgtgttgctt tacctgtctt ccaccctgag gatcacacgt taagtgttct taccagtcaa     900
aattgaatat gtatcaaaca aaaataaatg gccttccatg ctgaaataac aaaaaacaga     960
cacgcatgga gaacctactt tgtggggcgc ctgggtggcc cagtcggtta agtgtctgcc    1020
tcttcgtttt ggctcaggtc atgacctcgg ggttcatgag ttcgagcccc gcgtcagctc    1080
cgtgatgagc ctggagcccg cttggaattc cctccccacc cccacccccc gctcatgcca    1140
gctcgagctc tcgctcactc tctcaaaata aacttaagag gggcgcctgg gtggcgcagt    1200
cagttaagcg tccgacttca gccaggtcac gatcagcaca ttatttcctg gaccttccat    1260
tctcctttcg ctgtacagag cttaacgtaa actccctggc aagacctcct ttctgatttt    1320
agaaaggcca gcttattggt ttggttcctg taatagctta aaaatagaat ccagctgtat    1380
caggaaacat ttaaaaaatg tatcaaggaa gacctataac agtaaaaata tttttaaatc    1440
ccagagtgtt ttcataaaga cacaggatta cattactcaa ttattttttaa agggtttttg   1500
aaaagccgtg tttcacttgc catggctaat gattataggc atccgaatga gcctgtggct    1560
atgacttcag tctgttcggt ggaaatgact ctgatgtcat aaactgactc ggcttcgctg    1620
acaggaaagt cgtacagaag aaaagctgtt cgagcccata tgttggttgc gctcaatgtc    1680
aggaaggggc gacgtaatgt gtgcagaaat gggcagctgt cgagagtgaa gaaattggga    1740
agttggcacg gaagagggga ccgagtccga gaaggctgct ggataaagca gagcttttgc    1800
agaagagaag ggccggctgc tgtccctatc ctggtggcgg aaccacttag aaacaaggcg    1860
tcagaattag agacttcggt tcatgcaggg agggcggccc aggggggtgg cgtccttgga    1920
aactctggta agtttgagat tgatcccagg ggtcgtggga tggagcctcg catgagactc    1980
tacactgatc gatgagaagc agaagcccct tgtctgtgag gaaggggaca cgagcagttg    2040
gcacactaaa acgcaaggac acgtttctac gagaaaacgg tacatctgtc tgcgacacag    2100
aaagatcccc ggnaccagtc ntcgnnnnnn nnttccgntg ggattccagt cagcagttcc    2160
cgagaggcac tgaggaacac aggccctcac cacgttcaca agtgtcctga tgagagggat    2220
actaggtaaa cgaggttcga caggtgtggt ggttaatttt atacatcaac ctggctaggg    2280
tacggtgccc agttgtttgg ccaaacacca gtctagatgg ggctgtgaag gttaacattt    2340
aaaccaacag ggtgagtaaa gcagatcgct ttccattgtg tgggtgggcc tcatccaatc    2400
```

-continued agttgaagac cttaaaagaa aagattgagg tccccccaaa aaggaagaaa ttctgccttc 2460
gaactcaaca ctgcagcttt gaccactgag agcatttcca gcctgccctg caaacgccag 2520
actcaccagc cccacaatca tgtgaaccaa ttccttaaaa taaacttctc tttctctctc 2580
tctatccaac tggttctgtt tctctgcaga accctgactc acgcagcagg tttccctgct 2640
acaggacttc atcagccttt caaccctaat atgctcatcc agggaggaat ggtttgtggt 2700
ttctccaagt tgtaaccgcc cctccccccc cgcccccgcc cccccaaagg cctgttaaca 2760
cagctgagtg tatggtacag ggcccacagt gaggtcatgg tggtagggga cgggacagat 2820
gccctcagag tttcctttct acccttcccc ccacccccga cgccaagagg gtctcggcaa 2880
ggccttgctc ctctgagctc tcagctgggc tttctctaca ggcccgacag cttcaacggt 2940
cacggctacc acctcttcca ggccatgcgg tttggcatcg aggagataaa caactccacg 3000
gccctcctgc cgaacgtcac cctgggatac cagctgtacg acgtgtgctc ggagtctgcc 3060
aacgtgtatg ccacactaaa cgtgctctcc ctgctgggga cacatcacgt agagatccga 3120
gcagaccctt cccactattc gcctgccgcc ctggctgtca ttgggcctga caccaccaac 3180
cacgcagcca ccactgcagc cctgctgagc cccttcctgg tgcccctggt gagctggagc 3240
ccgggggcct gtccatctcc cctgccggca ggtccagtgt gggctgaggg ggtggggggg 3300
tgggcaagag ctgccatgcc cactctgagt ctcctgggtg gtcacattgc agggggccct 3360
gccccccttca cagtccccgc cccagcatcc cttcctcccc aagtgctgca tccagacctc 3420
cctgcctcaa tgtcctgaga aaaaccgtct cctttgaaac tgctgccctt tgctctgccc 3480
cctccattcc atctcctctg tgaagaacgg aacacccttt gtttcccacc tcacacactt 3540
gtccacttct ccccgccctc ctccttccgg tcttccttcc ctccctccca gctcaggctc 3600
agaggtgtgg tccccctccc cctccaatgc cgtcctcctg ggcctcaccc tctcctctgc 3660
tcgtaggcct gtcctaggct tcctcctccg cctataagct ggctttaccc ctctctgtct 3720
tccaggcacc tgtggtctta gcgctgccct ctctctgaac ctcgttccgt ggaaacttgt 3780
gcactgagct ctctcttctt gtttgcttct ccctctcatc acttgcttcc cgggcccctg 3840
ccctgactgc tgcaccacca ctcctgctct tgtgatctcc agggctttct agatctccag 3900
gtccagcaaa tgcttttcag cccttctttg cttgacatga cgactttgtg acaaatttga 3960
ccagtccttc agtgacgctc ttgcctcggc atttatgacc tgccacctcc ctctcacttg 4020
tggtacctcc ttctcagtct cctttggaga atctcctccc cccctcttct gaaaaagtgg 4080
atgattcccc gagtgcagga ccactccctt tcccaggcag gtgctgggag caaacaactt 4140
tccctactct tcaagaatct ttctggctgg tctaaaaata agttgatgtg acacaganaa 4200
aaggaaaagt caaatcacgt atgtacaggg anctacnaaa cacgaaaggt caaganagga 4260
aagngaggct anctgctatc tgaactatga acaagggnag gggtaaattc aaggaaagaa 4320
gaaatcanag aaagaagagg nanggtataa aagntgctgg ccatcaaaaa tggaaggaag 4380
aattanaann gattggagnn nnnnnnnnnn nnnnnnnnnn nnnnnnnnnn nnnnnnnnnn 4440
nnnnnnnnnn nnnnnncttt ttcccgtcac cggtggccag ggttaaattc aggctgccaa 4500
gctgtttttt gggatgactc cagcagtctc ctagggagtt cttcctgact ctggtcttga 4560
gccttttcta acacattctt cactgaaatc agatacaccc ctgaaacaca agtctgggca 4620
gattacctct ctgcctagac atttaagggg ctccccaggg cctgcagata aagaccaagt 4680
atcttagcta tcttggtgcc aggagtaagg cctcctgccc tgaccagaca cgcctacttt 4740
tgtgctcctt cttccggctt ccaacctcct gggtcagttc tctcactggg tgtagctttt 4800

-continued

```
gttctcttcc ccttcttctc ccacaaacct cccccctgggt ttctgcctct tctttagatg   4860
tagctggtcg gcctcctagt ccaccagagc tgtccttgag agccagggct gggaccatgt   4920
ctccctcctc ctcgggtccc cgcgcccagc acagggccag cacttggagg ctctgagttg   4980
aggccaaggc cactgaagtc gctgaactga acccccccc cggcccccct ccgcagatca   5040
gctacgaggc cagcagcgtg acgctcggag tgaagcggca ttacccctcg tttctgcgca   5100
ccatccccag cgacaagcac caggtggagg ccatggtgct gctgctgcag agcttcgggt   5160
gggtctggat ctcggtggtc ggcagcgacg gcgactacgg gcagctgggg gtgcaggcgc   5220
tggaggagca ggccacccag cagggcatct gcgttgcctt caaggacatc atccccttct   5280
ctgcccggcc gggcgacgag aggatgcaga gcatcatgca ccacctggcc cgagcgagga   5340
ccaccgttgt ggtcgttttc tccagcaggc agctggccag ggtgttcttt gagtcggtgg   5400
tgctggccaa cctgactgcc aaggtgtgga tcgcctcaga agactgggcc atctctagac   5460
acatcagcaa tgtgcccggg atccagggca ttggcacggt gctgggtgtg gccatccagc   5520
agaggcttgt ccctggcctg aaggagtttg aagaggccta tgtccaggca gataaggggg   5580
cccctgggcc ttgctccagg acctccgagt gcagcagcaa ccagctctgt agagagtgtc   5640
gggctttcac ggcagagcag atgcccacgc tcggggcatt ctccatgagc tctgcttata   5700
acgcctaccg ggcagtctac gcagtggccc atggcctcca ccagctcctg ggctgtgcct   5760
ctggagcctg ttccagggac cgagtctacc cctggcaggt aaggtagccc agaccccggc   5820
accctgaaac ggggtgcttt cctaaggcaa acagagtgat ccctctctgg ccaactgagt   5880
gctgggggtg gggacaaag gccacccatc agaaggctaa ttccttctct tgggcttcac   5940
ttctctgacc tcggcccctc ccaccaccat gctccagacc cagggctaaa aatctctggg   6000
aaacgggcct ttttagaagc ttcctctcac tcaggaggcc agttgggagg gtcgaggggc   6060
ttccttggaa gggagggggc tctgaatttc cagacagact gaaaccaccc aaatagaagc   6120
atttgcttcc taagccttcc gggtctggga gagttgagga ggagcagcct gcgtcatctg   6180
tggctgctcc atgatccccg tttatctcag cttctggagc agatccgcaa ggtgaatttc   6240
ctcctacaca aggacaccgt gaggtttaat gacaacgggg accctctcag tggctacgac   6300
ataattgcct gggactggag tggccccaag tggaacttca gggtcattgg ctcctccatg   6360
tggcctccag ttcagctgga cataaataaa accaaaatcc ggtggcacgg gaaggacaac   6420
caggtaatgg agccatggtc actcaccaag tcaccgcctt acgggcagcc tggagcctga   6480
agtcactgtc gacacagctc acacggagca ggagggggcc ccgggtgcca ggccaacgtg   6540
gctctatcca gccctgccag ggaagcccca cagaccgcac ccagatggcc ggctgcagct   6600
ggtatacaca accaggggct gtgccctggg agtgagctgt gagggcagat gcacggagac   6660
tcccattcgc catgtgagca tcccttgact tgggccactc catgtggttc cagaacacct   6720
gtggcttctt gcaggtgcca aagtctgtgt gctccagcga ctgcctcgaa gggcaccagc   6780
gagtgatttc gggtttctac cactgttgct ttgagtgtgt gccctgtgag gccgggagct   6840
tcctcaacaa gagcggtgag tgtccaaatg agtgggagaa tgactgggca ctcccagggt   6900
ctgtatggca gatgagggga tctcccttgg gccacgcacg tgcagaacca gagccttgct   6960
ccctctgttg ccagttgagg tacaggttgt agaatatttg ccaccagact gagttctgat   7020
gaagcagaaa ccaacaacca gttgaaatcc tcaggtcccc tacgtctttt actagagggc   7080
tcctgatgca atccctgcag atgcaatctt atcctaaatt caaccttttt atgcgaacag   7140
atgtagttat gttcccttgt cccctcccat gctgtctgtg tgaagtccct tccgtcgccc   7200
```

-continued ctgccaaaga cagccagcac cttggacagc ttggccttga tgcagatact attgtatccg 7260
cagacaagaa acatagcata ctccacccag tgatggtgca aggtcaagat cagagagcaa 7320
actcaggtag ctaagggctc agcccagagc tggactctgt gagccacgtt ctttcctttt 7380
actatctctg tgggcgtgag aacacatctc ttctgttctc agagagtcag agaaaccaca 7440
gaatggcagc acagataggg ggctttgggt aatggaagcg ctggggagat gaaaatgccc 7500
ttcctttggg gctggttgct cctgttggat catagcctca ctggcatgtg ggcagagcta 7560
ccagagtaag gccctctcta aggatctctc ggtttgcaag ccccttctgg gatcataagc 7620
catacagaac ctacccaagg gtctccagaa tctgcaatta acacaggcat ctggaggaaa 7680
cacttggccg cggggcccca ctcagggcta ccccctatct cgctgtgtgc agtaggagcc 7740
cggcttctgg ggtacagcgc tcccagcacc ttgcaggcct acatggcttc ccttcctcat 7800
tcctgctctg ctcatctagg ctctcaggag ccccctccac ctttttcttc cagacctcca 7860
cagctgccag ccttgtggga aagaagagtg ggcacccgcg ggaagtgaaa cctgctttcc 7920
acgcaccgtg gtgtttttga cttggcacga gaccatctct tgggtgctgc tggcagctaa 7980
tacgttgctg ctgctgctgg tgactgggac tgctggcctg tttgcctggc acttagacac 8040
ccctgtggtg aagtccgctg gggccgact gtgcttcttc atgctaggct ccctggcagg 8100
gggcagctgt gggctctacg gctttttggg ggagcccacg ctgcccacat gcttgttgcg 8160
ccaaagcctc cttgccctgg gttttgccat cttcctgtcc tgcctgacca tccgctcctt 8220
ccaactggtc ttcatcttca agttttctgc caaggtaccc accttctacc gtgcctgggt 8280
ccaaaaccac ggtcctggcc tatttgtggt gatcagctca atggcccagc tgctcatctg 8340
tctaacttgg ctggcggtgt ggaccccact gcccaccagg gagtaccagc gcttccctca 8400
gctggtggtg cttgattgca cagaggccaa ctcaccgggc ttcatgttgg ctttcgccta 8460
caatggcctc ctgtccgtca gcgcctttgc ctgcagctac ctgggcaagg acctgccaga 8520
gaactacaac gaggccaaat gtgtcacttt tagtctgctg ctcaacttcg tgtcctggat 8580
tgccttcttc accacggcca gcgtctacca gggcaagtac ttgcccgcgg tcaacgtgct 8640
ggcggcgctg agcagcctga gtggcggctt cagcggttat ttcctcccca agtgctacgt 8700
gatcctgtgc cgcccaaaat ttaacagcac acagcacttc caggcctcca tccaggagta 8760
cacgaggcgc tgcggctcca cctgaccagt ggggcgggca gggcctagcc ggggaggtgg 8820
ggggtggggg gtgaaggggt agaaggtggg gtaggggcgc ctcccctgcc ctgagggtcg 8880
aaggtcgagc gaggcgagcg ggccccgcgc cctccgggag gccttttgga ctcctgtctt 8940
ggctcgggta gtgtacgctc acgggagtcc agtccaggct ccgagctgcc aataaagcgg 9000
tgaaacatgc gtcctggctg ctctagctgt ctgaaccgag ggtggggcg 9049

<210> SEQ ID NO 60
<211> LENGTH: 2526
<212> TYPE: DNA
<213> ORGANISM: Felis catus

<400> SEQUENCE: 60
atgtcactcc cggcggctca cctggtcggc ctgcagctct ccctctcctg ctgctgggct 60
ctcagctgcc acagcacaga gacgtctgcc gacttcagcc tccctgggga ttacctcctc 120
gcaggtctgt tccctctgca ctctgactgt ccgggcgtga ggcaccggcc cacggtgacc 180
ctctgtgaca ggcccgacag cttcaacggt cacggctacc acctcttcca ggccatgcgg 240
tttggcatcg aggagataaa caactccacg gccctcctgc cgaacgtcac cctgggatac 300

```
cagctgtacg acgtgtgctc ggagtctgcc aacgtgtatg ccacactaaa cgtgctctcc    360
ctgctgggga cacatcacgt agagatccga gcagaccctt cccactattc gcctgccgcc    420
ctggctgtca ttgggcctga caccaccaac cacgcagcca ccactgcagc cctgctgagc    480
cccttcctgg tgcccctgat cagctacgag gccagcagcg tgacgctcgg agtgaagcgg    540
cattacccct cgtttctgcg caccatcccc agcgacaagc accaggtgga ggccatggtg    600
ctgctgctgc agagcttcgg gtgggtctgg atctcggtgg tcggcagcga cggcgactac    660
gggcagctgg gggtgcaggc gctggaggag caggccaccc agcagggcat ctgcgttgcc    720
ttcaaggaca tcatcccctt ctctgcccgg ccgggcgacg agaggatgca gagcatcatg    780
caccacctgg cccgagcgag gaccaccgtt gtggtcgttt tctccagcag gcagctggcc    840
agggtgttct ttgagtcggt ggtgctggcc aacctgactg ccaaggtgtg gatcgcctca    900
gaagactggg ccatctctag acacatcagc aatgtgcccg ggatccaggg cattggcacg    960
gtgctgggtg tggccatcca gcagaggctt gtccctggcc tgaaggagtt tgaagaggcc   1020
tatgtccagg cagataaggg ggcccctggg ccttgctcca ggacctccga gtgcagcagc   1080
aaccagctct gtagagagtg tcgggctttc acggcagagc agatgcccac gctcggggca   1140
ttctccatga gctctgctta taacgcctac cgggcagtct acgcagtggc ccatggcctc   1200
caccagctcc tgggctgtgc ctctggagcc tgttccaggg accgagtcta cccctggcag   1260
cttctggagc agatccgcaa ggtgaatttc ctcctacaca aggacaccgt gaggtttaat   1320
gacaacgggg accctctcag tggctacgac ataattgcct gggactggag tggccccaag   1380
tggaacttca gggtcattgg ctcctccatg tggcctccag ttcagctgga cataaataaa   1440
accaaaatcc ggtggcacgg gaaggacaac caggtgccaa agtctgtgtg ctccagcgac   1500
tgcctcgaag ggcaccagcg agtgatttcg ggtttctacc actgttgctt tgagtgtgtg   1560
ccctgtgagg ccgggagctt cctcaacaag agcgacctcc acagctgcca gccttgtggg   1620
aaagaaaagt gggcacccgc gggaagtgaa acctgctttc cacgcaccgt ggtgtttttg   1680
acttggcacg agaccatctc ttgggtgctg ctggcagcta atacgttgct gctgctgctg   1740
gtgactggga ctgctggcct gtttgcctgg cacttagaca cccctgtggt gaagtccgct   1800
gggggccgac tgtgcttctt catgctaggc tccctggcag gggggcagctg tgggctctac   1860
ggctttttg gggagcccac gctgcccaca tgcttgttgc gccaaagcct ccttgccctg   1920
ggttttgcca tcttcctgtc ctgcctgacc atccgctcct tccaactggt cttcatcttc   1980
aagttttctg ccaaggtacc caccttctac cgtgcctggg tccaaaacca cggtcctggc   2040
ctatttgtgg tgatcagctc aatggcccag ctgctcatct gtctaacttg gctggcggtg   2100
tggaccccac tgcccaccag ggagtaccag cgcttccctc agctggtggt gcttgattgc   2160
acagaggcca actcaccggg cttcatgttg gctttcgcct acaatggcct cctgtccgtc   2220
agcgcctttg cctgcagcta cctgggcaag gacctgccag agaactacaa cgaggccaaa   2280
tgtgtcactt ttagtctgct gctcaacttc gtgtcctgga ttgccttctt caccacggcc   2340
agcgtctacc agggcaagta cttgcccgcg gtcaacgtgc tggcggcgct gagcagcctg   2400
agtggcggct tcagcggtta tttcctcccc aagtgctacg tgatcctgtg ccgcccaaaa   2460
tttaacagca cacagcactt ccaggcctcc atccaggagt acacgaggcg ctgcggctcc   2520
acctga                                                              2526
```

<210> SEQ ID NO 61
<211> LENGTH: 841
<212> TYPE: PRT

```
<213> ORGANISM: Felis catus

<400> SEQUENCE: 61

Met Ser Leu Pro Ala Ala His Leu Val Gly Leu Gln Leu Ser Leu Ser
1               5                   10                  15

Cys Cys Trp Ala Leu Ser Cys His Ser Thr Glu Thr Ser Ala Asp Phe
            20                  25                  30

Ser Leu Pro Gly Asp Tyr Leu Leu Ala Gly Leu Phe Pro Leu His Ser
        35                  40                  45

Asp Cys Pro Gly Val Arg His Arg Pro Thr Val Thr Leu Cys Asp Arg
    50                  55                  60

Pro Asp Ser Phe Asn Gly His Gly Tyr His Leu Phe Gln Ala Met Arg
65                  70                  75                  80

Phe Gly Ile Glu Glu Ile Asn Asn Ser Thr Ala Leu Leu Pro Asn Val
                85                  90                  95

Thr Leu Gly Tyr Gln Leu Tyr Asp Val Cys Ser Glu Ser Ala Asn Val
            100                 105                 110

Tyr Ala Thr Leu Asn Val Leu Ser Leu Leu Gly Thr His His Val Glu
        115                 120                 125

Ile Arg Ala Asp Pro Ser His Tyr Ser Pro Ala Ala Leu Ala Val Ile
    130                 135                 140

Gly Pro Asp Thr Thr Asn His Ala Ala Thr Thr Ala Ala Leu Leu Ser
145                 150                 155                 160

Pro Phe Leu Val Pro Leu Ile Ser Tyr Glu Ala Ser Ser Val Thr Leu
                165                 170                 175

Gly Val Lys Arg His Tyr Pro Ser Phe Leu Arg Thr Ile Pro Ser Asp
            180                 185                 190

Lys His Gln Val Glu Ala Met Val Leu Leu Leu Gln Ser Phe Gly Trp
        195                 200                 205

Val Trp Ile Ser Val Val Gly Ser Asp Gly Asp Tyr Gly Gln Leu Gly
    210                 215                 220

Val Gln Ala Leu Glu Glu Gln Ala Thr Gln Gln Gly Ile Cys Val Ala
225                 230                 235                 240

Phe Lys Asp Ile Ile Pro Phe Ser Ala Arg Pro Gly Asp Glu Arg Met
                245                 250                 255

Gln Ser Ile Met His His Leu Ala Arg Ala Arg Thr Thr Val Val Val
            260                 265                 270

Val Phe Ser Ser Arg Gln Leu Ala Arg Val Phe Phe Glu Ser Val Val
        275                 280                 285

Leu Ala Asn Leu Thr Ala Lys Val Trp Ile Ala Ser Glu Asp Trp Ala
    290                 295                 300

Ile Ser Arg His Ile Ser Asn Val Pro Gly Ile Gln Gly Ile Gly Thr
305                 310                 315                 320

Val Leu Gly Val Ala Ile Gln Gln Arg Leu Val Pro Gly Leu Lys Glu
                325                 330                 335

Phe Glu Glu Ala Tyr Val Gln Ala Asp Lys Gly Ala Pro Gly Pro Cys
            340                 345                 350

Ser Arg Thr Ser Glu Cys Ser Ser Asn Gln Leu Cys Arg Glu Cys Arg
        355                 360                 365

Ala Phe Thr Ala Glu Gln Met Pro Thr Leu Gly Ala Phe Ser Met Ser
    370                 375                 380

Ser Ala Tyr Asn Ala Tyr Arg Ala Val Tyr Ala Val Ala His Gly Leu
385                 390                 395                 400

His Gln Leu Leu Gly Cys Ala Ser Gly Ala Cys Ser Arg Asp Arg Val
```

-continued

```
                405                 410                 415

Tyr Pro Trp Gln Leu Leu Glu Gln Ile Arg Lys Val Asn Phe Leu Leu
            420                 425                 430

His Lys Asp Thr Val Arg Phe Asn Asp Asn Gly Asp Pro Leu Ser Gly
        435                 440                 445

Tyr Asp Ile Ile Ala Trp Asp Trp Ser Gly Pro Lys Trp Asn Phe Arg
    450                 455                 460

Val Ile Gly Ser Ser Met Trp Pro Pro Val Gln Leu Asp Ile Asn Lys
465                 470                 475                 480

Thr Lys Ile Arg Trp His Gly Lys Asp Asn Gln Val Pro Lys Ser Val
                485                 490                 495

Cys Ser Ser Asp Cys Leu Glu Gly His Gln Arg Val Ile Ser Gly Phe
            500                 505                 510

Tyr His Cys Cys Phe Glu Cys Val Pro Cys Glu Ala Gly Ser Phe Leu
        515                 520                 525

Asn Lys Ser Asp Leu His Ser Cys Gln Pro Cys Gly Lys Glu Lys Trp
    530                 535                 540

Ala Pro Ala Gly Ser Glu Thr Cys Phe Pro Arg Thr Val Val Phe Leu
545                 550                 555                 560

Thr Trp His Glu Thr Ile Ser Trp Val Leu Leu Ala Ala Asn Thr Leu
                565                 570                 575

Leu Leu Leu Leu Val Thr Gly Thr Ala Gly Leu Phe Ala Trp His Leu
            580                 585                 590

Asp Thr Pro Val Val Lys Ser Ala Gly Gly Arg Leu Cys Phe Phe Met
        595                 600                 605

Leu Gly Ser Leu Ala Gly Gly Ser Cys Gly Leu Tyr Gly Phe Phe Gly
    610                 615                 620

Glu Pro Thr Leu Pro Thr Cys Leu Leu Arg Gln Ser Leu Leu Ala Leu
625                 630                 635                 640

Gly Phe Ala Ile Phe Leu Ser Cys Leu Thr Ile Arg Ser Phe Gln Leu
                645                 650                 655

Val Phe Ile Phe Lys Phe Ser Ala Lys Val Pro Thr Phe Tyr Arg Ala
            660                 665                 670

Trp Val Gln Asn His Gly Pro Gly Leu Phe Val Val Ile Ser Ser Met
        675                 680                 685

Ala Gln Leu Leu Ile Cys Leu Thr Trp Leu Ala Val Trp Thr Pro Leu
    690                 695                 700

Pro Thr Arg Glu Tyr Gln Arg Phe Pro Gln Leu Val Val Leu Asp Cys
705                 710                 715                 720

Thr Glu Ala Asn Ser Pro Gly Phe Met Leu Ala Phe Ala Tyr Asn Gly
                725                 730                 735

Leu Leu Ser Val Ser Ala Phe Ala Cys Ser Tyr Leu Gly Lys Asp Leu
            740                 745                 750

Pro Glu Asn Tyr Asn Glu Ala Lys Cys Val Thr Phe Ser Leu Leu Leu
        755                 760                 765

Asn Phe Val Ser Trp Ile Ala Phe Phe Thr Thr Ala Ser Val Tyr Gln
    770                 775                 780

Gly Lys Tyr Leu Pro Ala Val Asn Val Leu Ala Ala Leu Ser Ser Leu
785                 790                 795                 800

Ser Gly Gly Phe Ser Gly Tyr Phe Leu Pro Lys Cys Tyr Val Ile Leu
                805                 810                 815

Cys Arg Pro Lys Phe Asn Ser Thr Gln His Phe Gln Ala Ser Ile Gln
            820                 825                 830
```

Glu Tyr Thr Arg Arg Cys Gly Ser Thr
        835                 840

<210> SEQ ID NO 62
<211> LENGTH: 10607
<212> TYPE: DNA
<213> ORGANISM: Felis catus
<220> FEATURE:
<221> NAME/KEY: misc_feature
<222> LOCATION: (1604)..(1683)
<223> OTHER INFORMATION: n is a, c, g, or t
<220> FEATURE:
<221> NAME/KEY: misc_feature
<222> LOCATION: (2470)..(2516)
<223> OTHER INFORMATION: n is a, c, g, or t
<220> FEATURE:
<221> NAME/KEY: misc_feature
<222> LOCATION: (2537)..(2537)
<223> OTHER INFORMATION: n is a, c, g, or t
<220> FEATURE:
<221> NAME/KEY: misc_feature
<222> LOCATION: (2560)..(2560)
<223> OTHER INFORMATION: n is a, c, g, or t
<220> FEATURE:
<221> NAME/KEY: misc_feature
<222> LOCATION: (2574)..(2574)
<223> OTHER INFORMATION: n is a, c, g, or t
<220> FEATURE:
<221> NAME/KEY: misc_feature
<222> LOCATION: (2580)..(2580)
<223> OTHER INFORMATION: n is a, c, g, or t
<220> FEATURE:
<221> NAME/KEY: misc_feature
<222> LOCATION: (2599)..(2599)
<223> OTHER INFORMATION: n is a, c, g, or t
<220> FEATURE:
<221> NAME/KEY: misc_feature
<222> LOCATION: (2850)..(2850)
<223> OTHER INFORMATION: n is a, c, g, or t
<220> FEATURE:
<221> NAME/KEY: misc_feature
<222> LOCATION: (5784)..(5830)
<223> OTHER INFORMATION: n is a, c, g, or t
<220> FEATURE:
<221> NAME/KEY: misc_feature
<222> LOCATION: (7512)..(7553)
<223> OTHER INFORMATION: n is a, c, g, or t
<220> FEATURE:
<221> NAME/KEY: misc_feature
<222> LOCATION: (8626)..(8626)
<223> OTHER INFORMATION: n is a, c, g, or t
<220> FEATURE:
<221> NAME/KEY: misc_feature
<222> LOCATION: (10453)..(10453)
<223> OTHER INFORMATION: n is a, c, g, or t
<220> FEATURE:
<221> NAME/KEY: misc_feature
<222> LOCATION: (10491)..(10491)
<223> OTHER INFORMATION: n is a, c, g, or t
<220> FEATURE:
<221> NAME/KEY: misc_feature
<222> LOCATION: (10501)..(10501)
<223> OTHER INFORMATION: n is a, c, g, or t
<220> FEATURE:
<221> NAME/KEY: misc_feature
<222> LOCATION: (10511)..(10511)
<223> OTHER INFORMATION: n is a, c, g, or t
<220> FEATURE:
<221> NAME/KEY: misc_feature
<222> LOCATION: (10545)..(10545)
<223> OTHER INFORMATION: n is a, c, g, or t
<220> FEATURE:
<221> NAME/KEY: misc_feature
<222> LOCATION: (10558)..(10558)
<223> OTHER INFORMATION: n is a, c, g, or t
<220> FEATURE:
<221> NAME/KEY: misc_feature
<222> LOCATION: (10574)..(10574)
<223> OTHER INFORMATION: n is a, c, g, or t
<220> FEATURE:
<221> NAME/KEY: misc_feature
<222> LOCATION: (10599)..(10599)
<223> OTHER INFORMATION: n is a, c, g, or t

<400> SEQUENCE: 62

```
ttagctgctg aaacgctgct ttttagcaaa aggccgtgac ctcatgatgt tatacgtcgt     60

ggagattgag aaccaggtcc tagcatctga ctatgtgctt tgagtcccca cttttgctgg    120

ttgtgcaacc cagggtgagc ttcgtaagct tctctgtgcc tcagttttct catctgtgga    180

atggggccgg tcatagtccc cgttattgtg atcatcgagc aagatggtga atggcgagca    240

cacagcatga tgcctagttc ttactggaac acctgtcctg ggtcaggggc tgtatataaa    300

gtactacctg ccaggatcaa cttgatccgg ttctattctg tctcctgggt gagtatctgt    360

gccctttact cccagatgtt ggaaatgtca ggggcatgag acctgtcctt aaccgagtgg    420

cagaaggtta agtttgtgtc cgagatagca ggacatgctt tctctacctc cgcagggcgt    480

tctcccagac cccccagggc ccaccatgcc ctgctaggaa gggatcatcc taattctagc    540

ctcttcttcc gccccagagt tctgaagctt ctccacctgt ccaggtgttt ccccacccct    600

tcagccacgg caagaccgtc actatgtaaa tgtctgtgca aatcccctgg tgtcaagctg    660

ccagctctct gatgaggcag ggccacctcc ggggacccct cacttcccag ccatgggacc    720

ccgggccagg gaagtctgct gcttcatcat cctgccgcgg ctcctggctg agccggctga    780

gaactcagac ttctacttgg ctggggatta cttcctcggc ggcctcttca ccctccatgc    840

caacgtgaag ggcatcgtcc acctcaacct cctgcaggtg ccccagtgca aggagtgagt    900

cgccaatgtg gggctggaag tggcgacggg ggcggagtgg gaagcctggg ctggtcctgt    960

gctcctcagg ggaccacgcc aggaccaagg gctcaaaatg ctcttcctca ttcattgcca   1020

acctctcatc ccgcattatc ccccaccggcc tgcagggaga ccccatgcag ttcatgttac  1080

caaaatcttt ggcaattgta ttctgaaata tggagagctg gttgtcccgc cgtgtgtctt   1140

aataaataaa gagttacagg gtacttgagc ctggaggggt tgtagagacc acccccacct   1200

actttgtcaa gtggggaact cctactgagt ccgtgtcaag tccaagtcta gacaccgggg   1260

gttatgcctt tggaaggcag aaatgtggtt tttcggtagc aggttctcag actggagggg   1320

aaggtttgca tttctctagg gctgtggtta ggtgggaagg ggtgcttcca ggaccagaag   1380

ggatttcctc cactcacctt gtcccctgtg agccctgggg gtggctgcat cactcaaggt   1440

tgggtgagac acctttgtgc aagtgcgaag gctgggatgg cggacccagc gtgggatgat   1500

gagatagtga cttgctgcag agagggtgaa ggcgtcctgt gagagaggga gagaaaaaag   1560

tctgtgacgt cggggaagat cacatgctgg cttgagaatg acgnnnnnnn nnnnnnnnnn   1620

nnnnnnnnnn nnnnnnnnnn nnnnnnnnnn nnnnnnnnnn nnnnnnnnnn nnnnnnnnnn   1680

nnngatgtgg aggtgatrgt gatggcggtg attgtgacgg tggtatcggt gatggtggtc   1740

acagacaacg cagttatagt gatggcagtg gtgataggaa tagtaggtgg tgatggtcat   1800

tctggagatg tggcaggtga caacgatgag atgaaaatgc cagaatcttc tggagtggct   1860

ccttcttgag ccactcctcg gctttcctat ggcaggcaga ggggactccc cggctctcct   1920

gtcccttccc cctctcactc tggacctgcc tctcacccca ccccacatgg ctcccccagg   1980

tatgaaataa aggtgttggg ctacgatctc atgcaggcca tgtgctttgc aggggaggag   2040

atcaatagcc agagcagcct gctgcctggc gtgctgctgg gctacaaaat ggtggatgtc   2100

agctacatct ccaacaatgt ccagcccgtg ctccacttcc cggcaaagga ggactgttcc   2160

ttgcccatcc aggaggacta cagccactgt gtgccccgtg tggtggctgt cattggtcct   2220
```

-continued

```
ggcaactctg agtccactgt gactgtggcc cgcttcctct ctctcttcct ccttccacag   2280
gggaggcccc tgggtcctgg ggtaaggagc tggggggcag aggagtggtt atccaggggg   2340
ctcacttccc cccaccggtc ctgggggtag gaggaggcag gaagtagggt cagaatgtca   2400
accccaatcc trggaaggca gcccagccac gtggttaaga gctcaggctt ggaggcagac   2460
agacckgggn nnnnnnnnnn nnnnnnnnnn nnnnnnnnnn nnnnnnnnnn nnnnnngcct   2520
tcagagagat catcctntca agggggccct tattcctttn cccctgggag cccntcagtn   2580
cccaccactt tctgcagcnc ccattcgggt ctccgattcc tccaatccac tcactcgctg   2640
tgtggctctg gataagtgac tgtccctctc tgaacctcag cgtcctcatc tgcaaagtgg   2700
agacataaca gcacatcaga aggtcgcgag aataggggcg cctgggaggc tcagtcggtt   2760
aagcatccga ttctgggtcg cggctcaggt catgatctcc cggttcgtga gttcaagccc   2820
cgcatcgggc tgtgtgctga cagcacagan cctgcttggg attctgtctt cccttctctc   2880
tgcccctcac ctgcttttgc tctctctctc tcaaaataaa taaataaact ttttaaaaaa   2940
aaggaaggta gtgagaaaaa agcgggtgac agagatggag agggctccac gcggtacctg   3000
gcatgctgcg agccctcaga acccgttagc gacggaagtg acctgtgtgc gtcgtcacca   3060
ccatcccagc aggccttgag gcttcgaccc tgcctccccc gcaaagctca cagtctccga   3120
ggctccgggc cacgtccccc gggcgtcctg tctgtgtccc tcgaaccccg cccagccctg   3180
ccgcaccgtg agctagtcag cgcctgctgg gttcgtgact ctctccgcca ttgtgcaccc   3240
tggggctggg gccacaccca ggggctccgg ttaatttaga tgctttcttt ctctgccatc   3300
tgcttacccc cgagcttggt tagagagcct gactttgctg ggagtctcca gaacgtcccg   3360
ggacctccca gcaaccagca tctttattct ccctccttag aactgatgtg tgcagtcgct   3420
gtgcctctgc agctcagagc aggggtggtt cctgtgaact ggggccaggg gtggtttcct   3480
ggagggggca aggcaccgac tagccctcga agaaggagcc gggcttggct gaggtgggac   3540
agggggagag catgaggttt tcggccagct ttctgtgcct gggaaccccc tctccccaca   3600
accctggatc ccagaggcct taacgggccc cagctgtaac agactcgtct gtgtcgagca   3660
ttccacagta ggtgtcccca ggctccctcg gggccaccaa aggaccacaa cgacattacg   3720
cggacagggt ctcagattcc gatgggtccc ctgtttgctg gaaccatctc cctttggaaa   3780
tttacagctc tcttttctgg cagtaacccc gccccttggt gctgggtacg aagggggcac   3840
ccagagcggg gctcacccag cagcgctgac tgctgcgttg tcgggctaac gggtattaac   3900
cgcctccctc gccgctccca ttctcttagc tgctgaaacg ctgcttttta gcaaaggccg   3960
tgacctcatg atgttatacg tcgtggagat tgagaaccag gtcctagcat ctgactatgt   4020
gctttgagtc cccacttttg ctggttgtgc aacccagggt gagcttcgta agcttctctg   4080
tgcctcagtt ttctcatctg tggaatgtgt gagggggaga cctcagtttc aagcggggtg   4140
gccaggaggg cctttctgac aactggacaa cgacctgagg gagaggaagg agtgagggag   4200
ctatgtgggt gcctagaaga gcgctccgga agagggggca gcgaatgcag aggccggcag   4260
gagcctggtg cgttggctga accggtgagc agccccggga ccaggcggga cagtaggaga   4320
agatgaagcc agagaggtga gggccggggt cagtggtgga gccccttggg ggccactgaa   4380
ggactctggc tgtcctcgag tgacattagg agctgttggg gagttttgag ctgaggagta   4440
aggtgacgga caagtggtcg cagaggccac ccggctgcca cgaacagcag cagagacagc   4500
caaggggaag ggtgggggc tgtggtgacc ccgggagggt ggtgatggtg gcccggtgag   4560
gccctagctc acgctggcgg ccctccgctc tccggcagat cacctacagc gccatcagtg   4620
```

-continued

```
acgagctacg ggacaagcag cgcttcccgg cccttctgcc cacagcgccg ggcgccgatc   4680
accagatcga ggccatggtg cagctgatgt tgtacttccg ccggaactgg atcatcgcgc   4740
tggtgagcag cggcgactgc ggccgcgacg acagccagct gctcagcgat cgcccggccg   4800
gcggcgacac ctgcatcgcc ttccgggaga cgctgcccat gccccagccc aaccaggcgg   4860
tgacgcagtg ggagcgccgg cgcctgaagg ccatcgtgga cgagcagcag cggcagagct   4920
ctgcgcgcgt cgtggtcctg ctgtcgccaa agctggtcct gcacaacttc ttccgcgagg   4980
tgctccgcca gaacctcacg ggcgtcgtgc ggatcgcctc cgagtcctgg gccatcgacc   5040
cggtcctgca cgacaggccc acgcgctgca cagcctcctg ggctgcaccc agaccagcag   5100
ctccgggtcg tctatccctg gcaggtgagg ccccacccac ggagagtcgg ggccacacac   5160
gcaggcgccg ccacagccct gagtggttgc catggagacc actgccctgc tctagcgtcc   5220
ccctctctgg ccgggtcctg ggcaaactgg cgggagaggc caggggacgt accctgtccc   5280
cagacacata aagccagaag tgcttcatgg tgacaaaact ccttttttta cattaatgta   5340
atcctcgcca tccaagatag cctgtcccgg caggagattt gggtgaagtt tcctggaagg   5400
aggcctggca ggcagtgggc cccctgggcc ccctgccgtt tctccagggt ggcggccttg   5460
ggggaggact tctgtgttca gctctctgag gctctgcttt gggtttatgc atcttctctc   5520
gtcccaggtc tggacgattc agaggagtaa ggaggcaagg agtcgcctgg attcagacct   5580
ggaatttaaa tctgtatttt tctgatctgc gtgcacaccc gcgcgtgcac acacacacac   5640
ctaaccacga agtttatgta ggtagaagat tttactgagg gggcgcctgg gtggctcagt   5700
cggttaagcg tccgacttca gccaggtcac gatctcgcgg tctgtgagtt cgagccccgc   5760
gtcaggctct gggctgatgg ctcnnnnnnn nnnnnnnnnn nnnnnnnnnn nnnnnnnnnn   5820
nnnnnnnnnn agcaccccga gggcccgggg gagggcacct gagcccgtaa agggaaacag   5880
gagtggcctc tgaacccagg tgataggtct ccgctggatg gcagacgtga ctcccacggg   5940
agcaggaata atgtcgacac atcggccgga aggggagcac ttcctggtgt gcagtcattg   6000
tgctaagctc ccaacattgg gaaactcatg cgttgcttca gagcccggga gacagggttt   6060
ttgttgtcct actttacaga agaggagact ggagctcacg gggggttgggc gacaggcccg   6120
aggctcagag caggtggcag agctggtgcc tgaacccagg tgtgtctgac tacagagccg   6180
gggctcccag ccgctgcctc ccgggtgacc acatctgcgg tctcattgcc cccttgtagg   6240
gatgtggaca cccagtctcg tggggtagtc actctccccc ggatcgagcc cgacttcttt   6300
ttttttttt aattttttt tcaacgttta tttattttg ggacagagag agacagagca   6360
tgaatgggcg aggggcagag agagagggag acacagaatc ggaaacaggc tccaggctcc   6420
gagccatcag cccagagcct gatgcggggc tcgaactcac ggaccgcgag atcgtgacct   6480
ggctgaagtc ggacacttac ccgaatgcgc cacccagggg cccagatcga gcccgacttc   6540
tgacgccagc gtcgcttcct ttccctgtgg cctcccagct gcttcaggaa atctggaagg   6600
tcaacttcac cctcctgggc caccagatct tttttgacca gcgaggggac ctactcatgc   6660
gcctggagat catccaggga cggtgggacc tgagccagaa cctttctgga gcgtcgcctc   6720
ctactgcccg gtgctacgac ggctgagggc catccgtgac gtctcctggc acacggccaa   6780
caacacggtc agctctcgga gggctggtgg ggggctggga cctgggtctg ggcactggct   6840
cgtgcagggg tggcaagggc cctgtggacc tgagatccat tatcgagcac tgatgtcatc   6900
cctatttgtg ggtgtccctc ctcccattga ctaagcactg tggaagtcta gagctttctg   6960
gatcctcagg acccaggggc tcagggggct gcacaaagtg aacgttaggt ggacacgtgt   7020
```

-continued

```
gtgctaagga cttcaattct catgtcaacc ctaggaaata gagagtactg ttcctcctgt   7080
ctttggggtt gggaaactgg aggcacagag ggggtcgcgt gacccataaa aggccacaca   7140
gctttcgcat gtctctatac acagcattca gtctacatcc catcgattag tactcgcgtt   7200
ttggggacag tagctgtgcc ttcacctgtg tctgacatct gtcagtctga aagctccttt   7260
gttttaccct cttagcttac aagctgtcag aatggccgcg atgtggggaa ggtagagact   7320
cagcctcgtg gggaaggggg gaggtggggg gacctaaaag ttcaaagagc cagggcacct   7380
gggtggctca gtcagttaag catccgactc tggatctcag ctcagtcttg atctcaggtc   7440
gtgagtttag acccctgtgt agggctccgt gctgggcgcg cagcctactt aaaaataata   7500
aaaacaaaag cnnnnnnnnn nnnnnnnnnn nnnnnnnnnn nnnnnnnnnn nnngatcccc   7560
gtgtccatgt gttccaagga ctgccagcct gggcaaagga agaagcccgt gggtattcat   7620
ccctgctgct tcgagtgtct cgactgcctt ccgggcacct tcctcaacca aactgcagat   7680
gggactcaca gacccacacc cctgccctgc cctgccctgc cccgccctgg ggctcccagg   7740
gcccttcatc tttggcaggg tctctggagt ctcatccagg ggacacaggt gtccaaaggc   7800
cagggaccat gttttgactc cgcttgtatc tccctaaccg ctggtgtaag aaaaatcttc   7860
aatgctgtga gggcgtgggg gtgggagaag gaacagccct caaccaggcg aggctgtaac   7920
tgatcccctc tgcacacaca tgtagctgag ggcccagggg ggtcaggcca gagaatgtcc   7980
accggatgaa cgaacgaatg aatgaatgaa cgaacgaaca aacacacaaa tgaatgaatg   8040
tctctgtccg tagaagaaat gtttctggca gacagggcta ggatctaatt tctctctgtg   8100
gcctcccgag tgcctcgtgt agttcggagc atataatgtt tgctcagtga atgtttattg   8160
agtgacatcc ttgatgagaa gaattgacat ctccccctat agatcataaa ctccaggaaa   8220
ggggggacaa tgtcatccct ccagtgttta ccacagttca ccgttggggc cgaattattt   8280
ttttttcatg acttcacaga ttagtaacta agcggttctg tacatctacc gatcagagta   8340
cttacgacgt gcccagcaga gcccagggca cagggtaggt gctcaacaaa agtttgtttg   8400
caattgatca gtagccggaa gtcagggggc tcggttttat ccacgtctgt gctctccatc   8460
tcagatgcct atcacagtgg gtggcgctca aaaagaaact tgaataaacg gtcgaatgtc   8520
catctcacca gagggtacgg tcttggaagg gaggcattac ggttgccagg ctctgagtca   8580
aggggacctt ggaccacatc ctgcctctgt aactggtttt gtaacngcct ggaggagcct   8640
cagatgccac atctgtgaaa tggggttgca gtgaggatct gatgggccgg tggatacgag   8700
ggacgcagtg agaggtgcta cgaccgcagg catcgccctt ggctcgcccc ctccctaccc   8760
ctacagccgg ccgggtgcag gtgcagagga tgtgggtgcc gggaaggtgg gtgtatctga   8820
tggaactgct gtgggctctt gcagacgagt ttggctgccg gccctgcccg agttgcgggt   8880
ggtcccggag gaacgacgct tcgtgcttca agcggcggct ggcctccctt gaatgacgcg   8940
aggcacccgc cgtcgctgtg gccgtgctgt ccatcctggg ctccctctgc accctggcca   9000
tcctggtgat cttctggagg caccgccacg cgcccatggt tcgctcggcc gggggcccca   9060
ggtgcttccc gatgccgatg cccctgctgt ataggtgacg gtctccatgt acatcgggca   9120
gcccgcgttt ttcatgtgcc tcggccacca gaccctcttc accctctgct tcaccgtctg   9180
tatctcccgt gtcaccgtgc gctctttcca gatcgtccgc gtcttcaaca tggccaggcg   9240
cctcccgcgt gcctacggct actgggtccg ctaccacggg ccctgtgtct tcgtggcgtc   9300
cttcacggtg ctcaagatgg tcatcgtggc gggcaacgtg ctggccgcga ccgccgagcc   9360
cgccgcccgc cccgaccccg atgaccccaa gatcgcggtt ctcgcctgca actaccacaa   9420
```

cgtgctcctg ttcgacacca gcctggaccc gcttctgtcc gtggcgggct tcggcttcgc 9480
ctacgtgggc aaggagctgc ccaccaccca caacgaggcc aagttcttca ccttccgcat 9540
gaccttctac ttcacctctt ccatctccct ctgtaccttc atgtctgtct acgagggggt 9600
cctggtcacc atcctgcacc tcgtggtggc agtgctcaac cttctgggcg ctttggcccc 9660
tgggctactt cggccccaag tgctgcgtgg tcctcttcta cccggatcac aacacgcccg 9720
tctacttcag cagcatgatt cagggctaca ccaccgggaa ggactagcac tgccccctgg 9780
ctgcccaggg ggccagaggg ctcggtactg ggagatggag accaggggtg gggctggggg 9840
tggtggtgac tcattcagcc cctgctggga gcagggacac caccccgccc tactctctga 9900
tttggcctcc ccctccaggt tctctgcacc ctggccgttt ttacccaccc gctggtggat 9960
gcctaaaaat acgctttccc tgcagccgtt tggcttgcca ggcactgcca cccatgctag 10020
ggaaaggagc cggggtgacc tccctatggg tctccaagac agagatggag cgaagcagcc 10080
cacagtcgcc atctggtggt cacagcgggt gtccgcaggt tccggctccg ggcagccatg 10140
ctggaaggct gggctggggc tggtgttggg ggacatctgc ccggcatcat tcactccctg 10200
cccacgtgtc tgcgcctcac ctcccagact cccccgcccc ccagcttggg acccagcttg 10260
ggacccagct tctctgagtc atggctgcgc ataggggctg cttcataaat gcttatgaat 10320
aaacctccct tgggtgaaac gaaggcgttt ccttcttgtt tccagaggtt tccccccctcc 10380 ccccccgtc gccccaagaa agaagactgg gatcagagac ctcagcttcc atttccgcgt 10440
tgccacttct ganccgtgta ctttgggcca attctattta ctgtttcgga ncctacacgg 10500
nccctttcct naaataggaa caataaacca ggggcacctt tgacncactg tgtagtancc 10560
aatttgacga taantttttt taaaagatta aattaatcng ataaatt 10607

<210> SEQ ID NO 63
<211> LENGTH: 1176
<212> TYPE: DNA
<213> ORGANISM: Felis catus

<400> SEQUENCE: 63
atgggacccc gggccaggga agtctgctgc ttcatcatcc tgccgcggct cctggctgag 60
ccggctgaga actcagactt ctacttggct ggggattact tcctcggcgg cctcttcacc 120
ctccatgcca acgtgaaggg catcgtccac ctcaacctcc tgcaggtgcc ccagtgcaag 180
gagtatgaaa taaaggtgtt gggctacgat ctcatgcagg ccatgtgctt tgcaggggag 240
gagatcaata gccagagcag cctgctgcct ggcgtgctgc tgggctacaa aatggtggat 300
gtcagctaca tctccaacaa tgtccagccc gtgctccact tcccggcaaa ggaggactgt 360
tccttgccca tccaggagga ctacagccac tgtgtgcccc gtgtggtggc tgtcattggt 420
cctggcaact ctgagtccac tgtgactgtg gcccgcttcc tctctctctt cctccttcca 480
cagatcacct acagcgccat cagtgacgag ctacgggaca agcagcgctt cccggccctt 540
ctgcccacag cgccgggcgc cgatcaccag atcgaggcca tggtgcagct gatgttgtac 600
ttccgccgga actggatcat cgcgctggtg agcagcggcg actgcggccg cgacgacagc 660
cagctgctca gcgatcgccc ggccggcggc gacacctgca tcgccttccg ggagacgctg 720
cccatgcccc agcccaacca ggcggtgacg cagtgggagc gccggcgcct gaaggccatc 780
gtggacgagc agcagcggca gagctctgcg cgcgtcgtgg tcctgctgtc gccaaagctg 840
gtcctgcaca acttcttccg cgaggtgctc cgccagaacc tcacgggcgt cgtgcggatc 900
gcctccgagt cctgggccat cgacccggtc ctgcacgaca ggcccacgcg ctgcacagcc 960

```
tcctgggctg cacccagacc agcagctccg ggtcgtctat ccctggcagg tgaggcccca   1020

cccacggaga gtcggggcca cacacgcagg cgccgccaca gccctgagtg gttgccatgg   1080

agaccactgc cctgctctag cgtccccctc tctggccggg tcctgggcaa actggcggga   1140

gaggccaggg gacgtaccct gtccccagac acataa                             1176


<210> SEQ ID NO 64
<211> LENGTH: 391
<212> TYPE: PRT
<213> ORGANISM: Felis catus

<400> SEQUENCE: 64

Met Gly Pro Arg Ala Arg Glu Val Cys Cys Phe Ile Ile Leu Pro Arg
1               5                   10                  15

Leu Leu Ala Glu Pro Ala Glu Asn Ser Asp Phe Tyr Leu Ala Gly Asp
            20                  25                  30

Tyr Phe Leu Gly Gly Leu Phe Thr Leu His Ala Asn Val Lys Gly Ile
        35                  40                  45

Val His Leu Asn Leu Leu Gln Val Pro Gln Cys Lys Glu Tyr Glu Ile
    50                  55                  60

Lys Val Leu Gly Tyr Asp Leu Met Gln Ala Met Cys Phe Ala Gly Glu
65                  70                  75                  80

Glu Ile Asn Ser Gln Ser Ser Leu Leu Pro Gly Val Leu Leu Gly Tyr
                85                  90                  95

Lys Met Val Asp Val Ser Tyr Ile Ser Asn Asn Val Gln Pro Val Leu
            100                 105                 110

His Phe Pro Ala Lys Glu Asp Cys Ser Leu Pro Ile Gln Glu Asp Tyr
        115                 120                 125

Ser His Cys Val Pro Arg Val Val Ala Val Ile Gly Pro Gly Asn Ser
    130                 135                 140

Glu Ser Thr Val Thr Val Ala Arg Phe Leu Ser Leu Phe Leu Leu Pro
145                 150                 155                 160

Gln Ile Thr Tyr Ser Ala Ile Ser Asp Glu Leu Arg Asp Lys Gln Arg
                165                 170                 175

Phe Pro Ala Leu Leu Pro Thr Ala Pro Gly Ala Asp His Gln Ile Glu
            180                 185                 190

Ala Met Val Gln Leu Met Leu Tyr Phe Arg Arg Asn Trp Ile Ile Ala
        195                 200                 205

Leu Val Ser Ser Gly Asp Cys Gly Arg Asp Asp Ser Gln Leu Leu Ser
    210                 215                 220

Asp Arg Pro Ala Gly Gly Asp Thr Cys Ile Ala Phe Arg Glu Thr Leu
225                 230                 235                 240

Pro Met Pro Gln Pro Asn Gln Ala Val Thr Gln Trp Glu Arg Arg Arg
                245                 250                 255

Leu Lys Ala Ile Val Asp Glu Gln Gln Arg Gln Ser Ser Ala Arg Val
            260                 265                 270

Val Val Leu Leu Ser Pro Lys Leu Val Leu His Asn Phe Phe Arg Glu
        275                 280                 285

Val Leu Arg Gln Asn Leu Thr Gly Val Val Arg Ile Ala Ser Glu Ser
    290                 295                 300

Trp Ala Ile Asp Pro Val Leu His Asp Arg Pro Thr Arg Cys Thr Ala
305                 310                 315                 320

Ser Trp Ala Ala Pro Arg Pro Ala Ala Pro Gly Arg Leu Ser Leu Ala
                325                 330                 335
```

Gly Glu Ala Pro Pro Thr Glu Ser Arg Gly His Thr Arg Arg Arg Arg
340 345 350

His Ser Pro Glu Trp Leu Pro Trp Arg Pro Leu Pro Cys Ser Ser Val
355 360 365

Pro Leu Ser Gly Arg Val Leu Gly Lys Leu Ala Gly Glu Ala Arg Gly
370 375 380

Arg Thr Leu Ser Pro Asp Thr
385 390

<210> SEQ ID NO 65
<211> LENGTH: 24
<212> TYPE: DNA
<213> ORGANISM: Artificial Sequence
<220> FEATURE:
<223> OTHER INFORMATION: Synthetic Construct

<400> SEQUENCE: 65
taaacaactc cacggccctg ctgc 24

<210> SEQ ID NO 66
<211> LENGTH: 24
<212> TYPE: DNA
<213> ORGANISM: Artificial Sequence
<220> FEATURE:
<223> OTHER INFORMATION: Synthetic Construct

<400> SEQUENCE: 66
cccagggtga tgttgggcag cagg 24

<210> SEQ ID NO 67
<211> LENGTH: 24
<212> TYPE: DNA
<213> ORGANISM: Artificial Sequence
<220> FEATURE:
<223> OTHER INFORMATION: Synthetic Construct

<400> SEQUENCE: 67
gctgtgtatg cggtggccca tggc 24

<210> SEQ ID NO 68
<211> LENGTH: 24
<212> TYPE: DNA
<213> ORGANISM: Artificial Sequence
<220> FEATURE:
<223> OTHER INFORMATION: Synthetic Construct

<400> SEQUENCE: 68
ccaggagctg gtggaggcca tggg 24

<210> SEQ ID NO 69
<211> LENGTH: 24
<212> TYPE: DNA
<213> ORGANISM: Artificial Sequence
<220> FEATURE:
<223> OTHER INFORMATION: Synthetic Construct

<400> SEQUENCE: 69
tgctgaccaa cctgactggc aagg 24

<210> SEQ ID NO 70
<211> LENGTH: 24
<212> TYPE: DNA
<213> ORGANISM: Artificial Sequence
<220> FEATURE:
<223> OTHER INFORMATION: Synthetic Construct

<400> SEQUENCE: 70
tctgaggcga cccacacctt gcca 24

<210> SEQ ID NO 71
<211> LENGTH: 24
<212> TYPE: DNA
<213> ORGANISM: Artificial Sequence
<220> FEATURE:
<223> OTHER INFORMATION: Synthetic Construct

<400> SEQUENCE: 71
ccagttcagc taaacataaa tgag 24

<210> SEQ ID NO 72
<211> LENGTH: 24
<212> TYPE: DNA
<213> ORGANISM: Artificial Sequence
<220> FEATURE:
<223> OTHER INFORMATION: Synthetic Construct

<400> SEQUENCE: 72
gccactggat tttggtctca ttta 24

<210> SEQ ID NO 73
<211> LENGTH: 24
<212> TYPE: DNA
<213> ORGANISM: Artificial Sequence
<220> FEATURE:
<223> OTHER INFORMATION: Synthetic Construct

<400> SEQUENCE: 73
agctaacacg ctgctgctgc tgct 24

<210> SEQ ID NO 74
<211> LENGTH: 24
<212> TYPE: DNA
<213> ORGANISM: Artificial Sequence
<220> FEATURE:
<223> OTHER INFORMATION: Synthetic Construct

<400> SEQUENCE: 74
agcagtccca agcagcagca gcag 24

<210> SEQ ID NO 75
<211> LENGTH: 24
<212> TYPE: DNA
<213> ORGANISM: Artificial Sequence
<220> FEATURE:
<223> OTHER INFORMATION: Synthetic Construct

<400> SEQUENCE: 75
tgtgtcacct tcagcctgct cttc 24

<210> SEQ ID NO 76
<211> LENGTH: 24
<212> TYPE: DNA
<213> ORGANISM: Artificial Sequence
<220> FEATURE:
<223> OTHER INFORMATION: Synthetic Construct

<400> SEQUENCE: 76
tccaggacac gaagttgaag agca 24

<210> SEQ ID NO 77
<211> LENGTH: 24
<212> TYPE: DNA

<213> ORGANISM: Artificial Sequence
<220> FEATURE:
<223> OTHER INFORMATION: Synthetic Construct

<400> SEQUENCE: 77
tacttcggcc ccaagtgcta catg 24

<210> SEQ ID NO 78
<211> LENGTH: 24
<212> TYPE: DNA
<213> ORGANISM: Artificial Sequence
<220> FEATURE:
<223> OTHER INFORMATION: Synthetic Construct

<400> SEQUENCE: 78
ccgggtagaa gaggatcatg tagc 24

<210> SEQ ID NO 79
<211> LENGTH: 24
<212> TYPE: DNA
<213> ORGANISM: Artificial Sequence
<220> FEATURE:
<223> OTHER INFORMATION: Synthetic Construct

<400> SEQUENCE: 79
tggtcaccat cgtggacctc ttgg 24

<210> SEQ ID NO 80
<211> LENGTH: 24
<212> TYPE: DNA
<213> ORGANISM: Artificial Sequence
<220> FEATURE:
<223> OTHER INFORMATION: Synthetic Construct

<400> SEQUENCE: 80
aggttgagca cagtgaccaa gagg 24

<210> SEQ ID NO 81
<211> LENGTH: 24
<212> TYPE: DNA
<213> ORGANISM: Artificial Sequence
<220> FEATURE:
<223> OTHER INFORMATION: Synthetic Construct

<400> SEQUENCE: 81
accaactaca acgaggccaa gttc 24

<210> SEQ ID NO 82
<211> LENGTH: 24
<212> TYPE: DNA
<213> ORGANISM: Artificial Sequence
<220> FEATURE:
<223> OTHER INFORMATION: Synthetic Construct

<400> SEQUENCE: 82
tcatgctgag ggtgatgaac ttgg 24

<210> SEQ ID NO 83
<211> LENGTH: 24
<212> TYPE: DNA
<213> ORGANISM: Artificial Sequence
<220> FEATURE:
<223> OTHER INFORMATION: Synthetic Construct

<400> SEQUENCE: 83
tccgagtcct gggccatcga cccg 24

<210> SEQ ID NO 84
<211> LENGTH: 24
<212> TYPE: DNA
<213> ORGANISM: Artificial Sequence
<220> FEATURE:
<223> OTHER INFORMATION: Synthetic Construct

<400> SEQUENCE: 84
tgaggttgtg caggaccggg tcga 24

<210> SEQ ID NO 85
<211> LENGTH: 24
<212> TYPE: DNA
<213> ORGANISM: Artificial Sequence
<220> FEATURE:
<223> OTHER INFORMATION: Synthetic Construct

<400> SEQUENCE: 85
tacaacctca tgcaggccat gcgc 24

<210> SEQ ID NO 86
<211> LENGTH: 24
<212> TYPE: DNA
<213> ORGANISM: Artificial Sequence
<220> FEATURE:
<223> OTHER INFORMATION: Synthetic Construct

<400> SEQUENCE: 86
tctcctccac cgcgaagcgc atgg 24

<210> SEQ ID NO 87
<211> LENGTH: 24
<212> TYPE: DNA
<213> ORGANISM: Artificial Sequence
<220> FEATURE:
<223> OTHER INFORMATION: Synthetic Construct

<400> SEQUENCE: 87
atcaccatcc agagcgtgcc catc 24

<210> SEQ ID NO 88
<211> LENGTH: 24
<212> TYPE: DNA
<213> ORGANISM: Artificial Sequence
<220> FEATURE:
<223> OTHER INFORMATION: Synthetic Construct

<400> SEQUENCE: 88
actcactgaa gcccgggatg ggca 24

<210> SEQ ID NO 89
<211> LENGTH: 24
<212> TYPE: DNA
<213> ORGANISM: Artificial Sequence
<220> FEATURE:
<223> OTHER INFORMATION: Synthetic Construct

<400> SEQUENCE: 89
accaccacgt cgaggccatg gtgc 24

<210> SEQ ID NO 90
<211> LENGTH: 24
<212> TYPE: DNA
<213> ORGANISM: Artificial Sequence
<220> FEATURE:
<223> OTHER INFORMATION: Synthetic Construct

<400> SEQUENCE: 90
aagtgcagca tcagctgcac catg 24

<210> SEQ ID NO 91
<211> LENGTH: 23
<212> TYPE: DNA
<213> ORGANISM: Artificial Sequence
<220> FEATURE:
<223> OTHER INFORMATION: Synthetic Construct

<400> SEQUENCE: 91
tcrgacttct acctgcctgg rga 23

<210> SEQ ID NO 92
<211> LENGTH: 20
<212> TYPE: DNA
<213> ORGANISM: Artificial Sequence
<220> FEATURE:
<223> OTHER INFORMATION: Synthetic Construct

<400> SEQUENCE: 92
cttcacgttg gcatggaggg 20

<210> SEQ ID NO 93
<211> LENGTH: 21
<212> TYPE: DNA
<213> ORGANISM: Artificial Sequence
<220> FEATURE:
<223> OTHER INFORMATION: Synthetic Construct

<400> SEQUENCE: 93
tacctcctgg gtggcctctt c 21

<210> SEQ ID NO 94
<211> LENGTH: 20
<212> TYPE: DNA
<213> ORGANISM: Artificial Sequence
<220> FEATURE:
<223> OTHER INFORMATION: Synthetic Construct

<400> SEQUENCE: 94
tcttgcacwk gggcacctgc 20

<210> SEQ ID NO 95
<211> LENGTH: 22
<212> TYPE: DNA
<213> ORGANISM: Artificial Sequence
<220> FEATURE:
<223> OTHER INFORMATION: Synthetic Construct

<400> SEQUENCE: 95
aggtgttggg ctacaaccts at 22

<210> SEQ ID NO 96
<211> LENGTH: 21
<212> TYPE: DNA
<213> ORGANISM: Artificial Sequence
<220> FEATURE:
<223> OTHER INFORMATION: Synthetic Construct

<400> SEQUENCE: 96
gggcakgtag tggctgtagt c 21

<210> SEQ ID NO 97
<211> LENGTH: 22
<212> TYPE: DNA

<213> ORGANISM: Artificial Sequence
<220> FEATURE:
<223> OTHER INFORMATION: Synthetic Construct

<400> SEQUENCE: 97
ggctacaacc tsatgcaggc ca 22

<210> SEQ ID NO 98
<211> LENGTH: 22
<212> TYPE: DNA
<213> ORGANISM: Artificial Sequence
<220> FEATURE:
<223> OTHER INFORMATION: Synthetic Construct

<400> SEQUENCE: 98
gagttgtcag ggccaatgac cg 22

<210> SEQ ID NO 99
<211> LENGTH: 2598
<212> TYPE: DNA
<213> ORGANISM: Felis catus

<400> SEQUENCE: 99
atgcccggcc tcgctctcct gggcctcacg gctctcctgg gcctcacggc tctcttggac 60
cacggggagg gcgcaacgtc ctgcttgtca cagcagctca ggatgcaggg ggactatgtg 120
ctgggtgggc tcttccctct gggctctgcc gagggtacag gtcttggcga cgggctgcag 180
cccaatgcca ccgtgtgcac caggttctcg tctctgggcc tgctctgggc gctggccgtg 240
aagatggcgg tggaggagat caacaacggg tcggccctgc tgcccgggct gcacctgggc 300
tatgacctct ttgacacgtg ttcagagccc atggtggcca tgaagcccag cctcgtgttc 360
atggccaaag caggcagctg cagcattgcc gcctactgca attacacaca gtaccagccc 420
cgcgtgctgg ccgtcatcgg gccccactcg tctgagctcg ccctcgtcac cggcaagttc 480
ttcagcttct tccttgtgcc tcaggtcagc tacggcgcca gcaccgaccg gctgagcaac 540
cgggagatct tcccgtcctt cttccgcacg gtgcccagcg accaggtgca ggtggcggcc 600
atggtggagc tgctggagga gctcggctgg aactgggtgg cggcggtggg tagtgacgac 660
gagtatggcc ggcagggcct gagcctcttc tccggcctgg ccagcgccag ggcatctgc 720 atcgcgcatg agggcctggt gccactgccg ccaggcagcc tgcggctggg cgccctacag 780
ggcctgctgc gccaggtgaa ccagagcagc gtgcaggtgg tggtgctgtt ctcctccgcc 840
cacgcggccc gcaccctctt cagctacagc atccgctgca agctctcacc caaggtgtgg 900
gtggccagcg aggcctggct gacctcagac ctggtcatga cgctgcccgg catgcctggg 960
gtgggcaccg tgctgggctt cctgcagcag ggcgccccga tgccggagtt cccatcctac 1020
gtgcggaccc gcctggccct ggccgctgac cctgccttct gcgcctcgct ggacgctgaa 1080
cagccaggcc tggaggagca cgtggtgggg ccacgctgcc cccaatgtga ccacgtcacg 1140
ctagagaacc tatctgcggg gctgctgcac caccagacct tcgctgccta cgcggctgtg 1200
tatggcgtgg cccaagccct tcacaacaca ctgcgctgca atgcctcggg ctgccccagg 1260
cgggagcctg tgcggccctg gcagctccta gagaacatgt acaacgtgag cttccgtgct 1320
cgcggcctgg cactgcagtt cgacgccagc gggaacgtga acgtggatta cgacctgaaa 1380
ctgtgggtgt ggcaggaccc gacgcccgag ctgcgcaccg taggcacctt caagggccgc 1440
ctggagctct ggcgctctca gatgtgctgg cacacgccgg ggaagcagca gcccgtgtcc 1500
cagtgctccc ggcagtgcaa ggaaggccag gtgcgccgcg tgaagggctt ccactcttgc 1560

-continued

```
tgttacaact gcgtggactg caaggcgggc agttatcagc gcaacccaga tgacctcctc   1620

tgcacccagt gtgaccagga ccagtggtcc ccagaccgga gcacacgctg cttcgcccgc   1680

aagcccatgt tcctggcatg gggggagcca gctgtgctgc tactgctcgc gctgctggct   1740

ctggcgctgg gcctggcgct ggcagccctg gggctcttcc tctggcactc ggacagcccg   1800

ctggttcagg cctcaggtgg gccacgggcc tgctttggcc tggcttgcct gggcctggtc   1860

tgcctcagtg tcctcctgtt ccctggccag ccaggccctg ccagctgcct ggcccagcag   1920

ccactgttcc acctcccact cactggctgc ctgagcacgt ttttcctgca agcggccgag   1980

atatttgtgg ggtcggagct gccaccaagc tgggctgaga agatgcgtgg ccgcctgcgg   2040

gggccctggg cctggctggt ggtgctgctt gctatgctgg cagaagccgc attgtgtgcc   2100

tggtacctgg tagccttccc gccagaggtg gtgacggact ggcgggtact gcccacagag   2160

gcgctggtgc actgccacgt gcactcctgg atcagcttcg gcctggtgca tgccactaac   2220

gccatgctgg ccttcctctg cttcctgggc actttcctgg tgcagagccg gccaggccgc   2280

tacaatggtg cccgcggcct cacctttgcc atgctggcct acttcatcac ctggatctcc   2340

tttgtgcccc tctttgccaa tgtgcacgtg gcctaccagc ctgccgtgca gatgggcacc   2400

atcctcctct gtgccctggg tatcctagcc accttccacc tgcccaagtg ctacctgctg   2460

ctgcagcggc cggagctcaa cacccctgag ttcttcctgg aagacaatgc cagagcacag   2520

ggcagcagtt gggggcaggg gaggggagaa tcggggcaaa aacaagtgac acccgatcca   2580

gtgacctcac cgcagtga                                                 2598
```